United States Patent
Blum et al.

(10) Patent No.: US 9,708,274 B2
(45) Date of Patent: Jul. 18, 2017

(54) SULFOXIMINE SUBSTITUTED QUINAZOLINES FOR PHARMACEUTICAL COMPOSITIONS

(71) Applicant: EVOTEC INTERNATIONAL GMBH, Hamburg (DE)

(72) Inventors: Andreas Blum, Warthausen (DE); Dirk Gottschling, Mittelbiberach (DE); Armin Heckel, Biberach an der Riss (DE); Joerg P. Hehn, Biberach an der Riss (DE); Bernhard Schmid, Ingoldingen (DE); Dieter Wiedenmayer, Biberach an der Riss (DE)

(73) Assignee: EVOTEC INTERNATIONAL GMBH (DE)

(*) Notice: Subject to any disclaimer, the term of this patent is extended or adjusted under 35 U.S.C. 154(b) by 0 days.

(21) Appl. No.: 14/802,235

(22) Filed: Jul. 17, 2015

(65) Prior Publication Data

US 2015/0361055 A1 Dec. 17, 2015

Related U.S. Application Data

(62) Division of application No. 14/315,399, filed on Jun. 26, 2014, now Pat. No. 9,139,577.

(30) Foreign Application Priority Data

Jun. 28, 2013 (EP) ..................................... 13174337

(51) Int. Cl.
| | | |
|---|---|---|
| C07D 239/94 | (2006.01) |
| C07D 413/14 | (2006.01) |
| A61K 31/517 | (2006.01) |
| C07D 409/12 | (2006.01) |
| C07D 401/12 | (2006.01) |
| C07D 413/12 | (2006.01) |
| C07D 411/12 | (2006.01) |
| C07D 409/14 | (2006.01) |
| C07D 495/10 | (2006.01) |
| C07D 403/12 | (2006.01) |
| A61K 45/06 | (2006.01) |
| A61K 31/541 | (2006.01) |
| C07D 401/14 | (2006.01) |
| C07D 405/12 | (2006.01) |
| C07D 417/04 | (2006.01) |
| C07D 417/14 | (2006.01) |
| A61K 31/5377 | (2006.01) |

(52) U.S. Cl.
CPC .......... *C07D 239/94* (2013.01); *A61K 31/517* (2013.01); *A61K 31/5377* (2013.01); *A61K 31/541* (2013.01); *A61K 45/06* (2013.01); *C07D 401/12* (2013.01); *C07D 401/14* (2013.01); *C07D 403/12* (2013.01); *C07D 405/12* (2013.01); *C07D 409/12* (2013.01); *C07D 409/14* (2013.01); *C07D 411/12* (2013.01); *C07D 413/12* (2013.01); *C07D 413/14* (2013.01); *C07D 417/04* (2013.01); *C07D 417/14* (2013.01); *C07D 495/10* (2013.01)

(58) Field of Classification Search
CPC .................................................... C07D 413/14
See application file for complete search history.

(56) References Cited

U.S. PATENT DOCUMENTS

2011/0212939 A1  9/2011 Bertram et al.

FOREIGN PATENT DOCUMENTS

| WO | 2007009236 A1 | 1/2007 |
|---|---|---|
| WO | 2007134457 | 11/2007 |
| WO | 2007143824 A1 | 12/2007 |
| WO | 2008141843 A1 | 11/2008 |
| WO | 2009054983 | 4/2009 |
| WO | 2009054984 A1 | 4/2009 |
| WO | 2010004347 A1 | 1/2010 |
| WO | 2011104340 A1 | 9/2011 |
| WO | 2014072244 | 5/2014 |

OTHER PUBLICATIONS

International Search Report and Written Opinion mailing date Aug. 27, 2014 for PCTEP2014/063123.
McMahon, The Oncologist, "VEGF Receptor Signaling in Tumor Angiogenesis", 2000, vol. 3.
Pinedo, The Oncologist, "Translational Research: The Role of VEGF in Tumor Angiogenesis", 2000.

*Primary Examiner* — Paul V Ward
(74) *Attorney, Agent, or Firm* — J.A. Lindeman & Co., PLLC

(57) ABSTRACT

This invention relates to novel sulfoximine substituted quinazoline derivatives of formula I

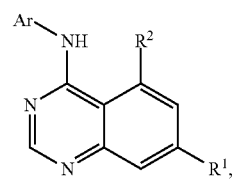

wherein Ar, $R^1$ and $R^2$ are as defined in the description and claims, and their use as MNK1 (MNK1a or MNK1b) and/or MNK2 (MNK2a or MNK2b) kinase inhibitors, pharmaceutical compositions containing the same, and methods of using the same as agents for treatment or amelioration of MNK1 (MNK1a or MNK1b) and/or MNK2 (MNK2a or MNK2b) mediated disorders.

10 Claims, No Drawings

```
                        SEQUENCE LISTING

<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term CONH2

<400> SEQUENCE: 1

Thr Ala Thr Lys Ser Gly Ser Thr Thr Lys Asn Arg
1               5                   10

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 2

His His His His His His
1               5
```

SULFOXIMINE SUBSTITUTED QUINAZOLINES FOR PHARMACEUTICAL COMPOSITIONS

SEQUENCE LISTING

The instant application contains a Sequence Listing which has been submitted electronically in ASCII format and is hereby incorporated by reference in its entirety. Said ASCII copy, created on Aug. 21, 2015, is named 01-2934-US-2_SL.txt and is 942 bytes in size.

FIELD OF THE INVENTION

This invention relates to sulfoximine substituted quinazoline derivatives and their use as MNK1 (MNK1a or MNK1b) and/or MNK2 (MNK2a or MNK2b) kinase inhibitors, pharmaceutical compositions containing them and their use in the treatment or amelioration of MNK1 (MNK1a or MNK1b) and/or MNK2 (MNK2a or MNK2b) mediated disorders.

Moreover, the present invention relates to the use of sulfoximine substituted quinazoline derivatives of the invention for the production of pharmaceutical compositions for the prophylaxis and/or treatment of diseases which can be influenced by the inhibition of the kinase activity of MNK1 (MNK1a or MNK1b) and/or MNK2 (MNK2a or MNK2b) or further variants thereof. Particularly, the present invention relates to the use of sulfoximine substituted quinazoline derivatives of the invention for the production of pharmaceutical compositions for the prophylaxis and/or therapy of metabolic diseases, such as diabetes, hyperlipidemia and obesity, hematopoietic disorders, neurodegenerative diseases, kidney damage, inflammatory disorders, and cancer and their consecutive complications and disorders associated therewith.

BACKGROUND OF THE INVENTION

Metabolic diseases are diseases caused by an abnormal metabolic process and may either be congenital due to an inherited enzyme abnormality or acquired due to a disease of an endocrine organ or failure of a metabolically important organ such as the liver or the pancreas.

The present invention is more particularly directed to the treatment and/or prophylaxis of in particular metabolic diseases of the lipid and carbohydrate metabolism and the consecutive complications and disorders associated therewith.

Lipid disorders cover a group of conditions which cause abnormalities in the level and metabolism of plasma lipids and lipoproteins. Thus, hyperlipidemias are of particular clinical relevance since they constitute an important risk factor for the development of atherosclerosis and subsequent vascular diseases such as coronary heart disease.

Diabetes mellitus is defined as a chronic hyperglycemia associated with resulting damages to organs and dysfunctions of metabolic processes. Depending on its etiology, one differentiates between several forms of diabetes, which are either due to an absolute (lacking or decreased insulin secretion) or to a relative lack of insulin. Diabetes mellitus Type I (IDDM, insulin-dependent diabetes mellitus) generally occurs in adolescents under 20 years of age. It is assumed to be of auto-immune etiology, leading to an insulitis with the subsequent destruction of the beta cells of the islets of Langerhans which are responsible for the insulin synthesis. In addition, in latent autoimmune diabetes in adults (LADA; Diabetes Care. 8: 1460-1467, 2001) beta cells are being destroyed due to autoimmune attack. The amount of insulin produced by the remaining pancreatic islet cells is too low, resulting in elevated blood glucose levels (hyperglycemia). Diabetes mellitus Type II generally occurs at an older age. It is above all associated with a resistance to insulin in the liver and the skeletal muscles, but also with a defect of the islets of Langerhans. High blood glucose levels (and also high blood lipid levels) in turn lead to an impairment of beta cell function and to an increase in beta cell apoptosis.

Diabetes is a very disabling disease, because today's common anti-diabetic drugs do not control blood sugar levels well enough to completely prevent the occurrence of high and low blood sugar levels. Out of range blood sugar levels are toxic and cause long-term complications for example retinopathy, renopathy, neuropathy and peripheral vascular disease. There is also a host of related conditions, such as obesity, hypertension, heart disease and hyperlipidemia, for which persons with diabetes are substantially at risk.

Obesity is associated with an increased risk of follow-up diseases such as cardiovascular diseases, hypertension, diabetes, hyperlipidemia and an increased mortality. Diabetes (insulin resistance) and obesity are part of the "metabolic syndrome" which is defined as the linkage between several diseases (also referred to as syndrome X, insulin-resistance syndrome, or deadly quartet). These often occur in the same patients and are major risk factors for development of diabetes type II and cardiovascular disease. It has been suggested that the control of lipid levels and glucose levels is required to treat diabetes type II, heart disease, and other occurrences of metabolic syndrome (see e.g., Diabetes 48: 1836-1841, 1999; JAMA 288: 2209-2716, 2002).

In one embodiment of the present invention the compounds and compositions of the present invention are useful for the treatment and/or prophylaxis of metabolic diseases of the carbohydrate metabolism and their consecutive complications and disorders such as impaired glucose tolerance, diabetes (preferably diabetes type II), diabetic complications such as diabetic gangrene, diabetic arthropathy, diabetic osteopenia, diabetic glomerosclerosis, diabetic nephropathy, diabetic dermopathy, diabetic neuropathy, diabetic cataract and diabetic retinopathy, diabetic maculopathy, diabetic feet syndrome, diabetic coma with or without ketoacidosis, diabetic hyperosmolar coma, hypoglycemic coma, hyperglycemic coma, diabetic acidosis, diabetic ketoacidosis, intracapillary glomerulonephrosis, Kimmelstiel-Wilson syndrome, diabetic amyotrophy, diabetic autonomic neuropathy, diabetic mononeuropathy, diabetic polyneuropathy, diabetic angiopathies, diabetic peripheral angiopathy, diabetic ulcer, diabetic arthropathy, or obesity in diabetes.

In a further embodiment the compounds and compositions of the present invention are useful for the treatment and/or prophylaxis of metabolic diseases of the lipid metabolism (i.e. lipid disorders) and their consecutive complications and disorders such as hypercholesterolemia, familial hypercholesterolemia, Fredrickson's hyperlipoproteinemia, hyperbetalipoproteinemia, hyperlipidemia, low-density-lipoprotein-type [LDL] hyperlipoproteinemia, pure hyperglyceridemia, endogenous hyperglyceridemia, isolated hypercholesterolemia, isolated hypertroglyceridemia, cardiovascular diseases such as hypertension, ischemia, varicose veins, retinal vein occlusion, atherosclerosis, angina pectoris, myocardial infarction, stenocardia, pulmonary hypertension, congestive heart failure, glomerulopaty, tubulointestitial disorders, renal failure, angiostenosis, or cerebrovascular disorders, such as cerebral apoplexy.

In a further embodiment of the present invention the compounds and compositions of the present invention are useful for the treatment and/or prophylaxis of hematopoetic disorders and their consecutive complications and disorders such as acute myeloid leukemia (AML), Morbus Hodgkin, Non-Hodgkin's lymphoma; hematopoetic disease, acute non-lymphocytic leukemia (ANLL), myeloproliferative disease acute promyelocytic leukemia (APL), acute myelomonocytic leukemia (AMMoL), multiple myeloma, polycythemia vera, lymphoma, acute lymphocytic leukemia (ALL), chronic lymphocytic leukemia (CCL), Wilm's tumor, or Ewing's Sarcoma.

In a further embodiment of the present invention the compounds and compositions of the present invention are useful for the treatment and/or prophylaxis of cancer and consecutive complications and disorders such as cancer of the upper gastrointestinal tract, pancreatic carcinoma, breast cancer, colon cancer, ovarian carcinoma, cervix carcinoma, endometrial cancer, brain tumor, testicular cancer, laryngeal carcinoma, osteocarcinoma, prostatic cancer, retinoblastoma, liver carcinoma, lung cancer, neuroblastoma, renal carcinoma, thyroid carcinoma, esophageal cancer, soft tissue sarcoma, skin cancer, osteosarcoma, rhabdomyosarcoma, bladder cancer, metastatic cancer, cachexia, or pain.

Certain anti-cancer drugs such as cisplatin are linked to serious side effects such as nephrotoxicity or ototoxicity, which can be dose limiting. Activation of MNKs has been linked to these side effects. In a further embodiment of the present invention, the compounds and compositions of the present invention are useful for the treatment and/or prophylaxis of ear or kidney damage, in particular for the prevention or treatment of ear and kidney drug induced damage.

Furthermore, the present invention relates to the use of the compounds according to the invention for the production of pharmaceutical compositions for the prophylaxis and/or therapy of cytokine related diseases.

Such diseases include inflammatory diseases, autoimmune diseases, destructive bone disorders, proliferative disorders, infectious diseases, neurodegenerative diseases, allergies, or other conditions associated with proinflammatory cytokines. Allergic and inflammatory diseases such as acute or chronic inflammation, chronic inflammatory arthritis, rheumatoid arthritis, psoriasis, COPD, inflammatory bowel disease, asthma and septic shock and their consecutive complications and disorders associated therewith.

Inflammatory diseases like rheumatoid arthritis, inflammatory lung diseases like COPD, inflammatory bowel disease and psoriasis afflict one in three people in the course of their lives. Not only do those diseases impose immense health care costs, but also they are often crippling and debilitating.

Although inflammation is the unifying pathogenic process of these inflammatory diseases below, the current treatment approach is complex and is generally specific for any one disease. Many of the current therapies available today only treat the symptoms of the disease and not the underlying cause of inflammation.

The compositions of the present invention are useful for the treatment and/or prophylaxis of inflammatory diseases and consecutive complications and disorders. such as chronic or acute inflammation, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythrodermic psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis. oesophagitis, gastritis, peritonitis, hepatitis, cholelithiasis, cholecystitis, glomerulonephritis, goodpasture's disease, crescentic glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies.

Moreover, cytokines are also believed to be implicated in the production and development of various cardiovascular and cerebrovascular disorders such as congestive heart disease, myocardial infarction, the formation of atherosclerotic plaques, hypertension, platelet aggregation, angina, stroke, Alzheimer's disease, reperfusion injury, vascular injury including restenosis and peripheral vascular disease, and, for example, various disorders of bone metabolism such as osteoporosis (including senile and postmenopausal osteoporosis), Paget's disease, bone metastases, hypercalcaemia, hyperparathyroidism, osteosclerosis, osteoporosis and periodontitis, and the abnormal changes in bone metabolism which may accompany rheumatoid arthritis and osteoarthritis.

Excessive cytokine production has also been implicated in mediating certain complications of bacterial, fungal and/or viral infections such as endotoxic shock, septic shock and toxic shock syndrome and in mediating certain complications of CNS surgery or injury such as neurotrauma and ischaemic stroke.

Excessive cytokine production has, moreover, been implicated in mediating or exacerbating the development of diseases involving cartilage or muscle resorption, pulmonary fibrosis, cirrhosis, renal fibrosis, the cachexia found in certain chronic diseases such as malignant disease and acquired immune deficiency syndrome (AIDS), tumour invasiveness and tumour metastasis and multiple sclerosis. The treatment and/or prophylaxis of these diseases are also contemplated by the present invention Additionally, the inventive compositions may be used to treat inflammation associated with autoimmune diseases including, but not limited to, systemic lupus erythematosis, Addison's disease, autoimmune polyglandular disease (also known as autoimmune polyglandular syndrome), glomerulonephritis, rheumatoid arthritis scleroderma, chronic thyroiditis, Graves' disease, autoimmune gastritis, diabetes, autoimmune hemolytic anemia, glomerulonephritis, rheumatoid arthritis autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, and graft vs. host disease.

In a further embodiment the compositions of the present invention may be used for the treatment and prevention of infectious diseases such as sepsis, septic shock, Shigellosis, and *Helicobacter pylori* and viral diseases including herpes simplex type 1 (HSV-1), herpes simplex type 2 (HSV-2), cytomegalovirus, Epstein-Barr, human immunodeficiency virus (HIV), acute hepatitis infection (including hepatitis A, hepatits B, and hepatitis C), HIV infection and CMV retinitis, AIDS or malignancy, malaria, mycobacterial infection and meningitis. These also include viral infections, by influenza virus, varicella-zoster virus (VZV), Epstein-Barr virus, human herpesvirus-6 (HHV-6), human herpesvirus-7 (HHV-7), human herpesvirus-8 (HHV-8), Poxvirus, Vacciniavirus, Monkeypoxvirus, pseudorabies and rhinotracheitis.

The compositions of the present invention may also be used topically in the treatment or prophylaxis of topical disease states mediated by or exacerbated by excessive cytokine production, such as inflamed joints, eczema, psoriasis and other inflammatory skin conditions such as sunburn; inflammatory eye conditions including conjunctivitis; pyresis, pain and other conditions associated with inflammation.

Periodontal disease has also been implemented in cytokine production, both topically and systemically. Hence, use of compositions of the present invention to control the inflammation associated with cytokine production in such peroral diseases such as gingivitis and periodontitis is another aspect of the present invention.

Finally, the compositions of the present invention may also be used to treat or prevent neurodegenerative disease selected from Alzheimer's disease, Parkinson's disease, amyotrophic lateral sclerosis, Huntington's disease, frontotemporal lobar dementia, spinocerebellar ataxia, dementia with Lewy bodies, cerebral ischemia or neurodegenerative disease caused by traumatic injury, glutamate neurotoxicity or hypoxia.

In a preferred embodiment the compositions of the present invention may be used to treat or prevent a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

Protein kinases are important enzymes involved in the regulation of many cellular functions. The LK6-serine/threonine-kinase gene of *Drosophila melanogaster* was described as a short-lived kinase which can associate with microtubules (J. Cell Sci. 1997, 110(2): 209-219). Genetic analysis in the development of the compound eye of *Drosophila* suggested a role in the modulation of the RAS signal pathway (Genetics 2000 156(3): 1219-1230). The closest human homologues of *Drosophila* LK6-kinase are the MAP-kinase interacting kinase 2 (MNK2, e.g. the variants MNK2a and MNK2b) and MAP-kinase interacting kinase 1 (MNK1) and variants thereof. These kinases are mostly localized in the cytoplasm. MNKs are phosphorylated by the p42 MAP kinases Erk1 and Erk2 and the p38-MAP kinases. This phosphorylation is triggered in a response to growth factors, phorbol esters and oncogenes such as Ras and Mos, and by stress signaling molecules and cytokines. The phosphorylation of MNK proteins stimulates their kinase activity towards eukaryotic initiation factor 4E (eIF4E) (EMBO J. 16: 1909-1920, 1997; Mol Cell Biol 19, 1871-1880, 1990; Mol Cell Biol 21, 743-754, 2001). Simultaneous disruption of both, the MNK1 and MNK2 gene in mice diminishes basal and stimulated eIF4E phosphorylation (Mol Cell Biol 24, 6539-6549, 2004). Phosphorylation of eIF4E results in a regulation of the protein translation (Mol Cell Biol 22: 5500-5511, 2001).

There are different hypotheses describing the mode of the stimulation of the protein translation by MNK proteins. Most publications describe a positive stimulatory effect on the cap-dependent protein translation upon activation of MAP kinase-interacting kinases. Thus, the activation of MNK proteins can lead to an indirect stimulation or regulation of the protein translation, e.g. by the effect on the cytosolic phospholipase 2 alpha (BBA 1488:124-138, 2000).

WO 03/037362 discloses a link between human MNK genes, particularly the variants of the human MNK2 genes, and diseases which are associated with the regulation of body weight or thermogenesis. It is postulated that human MNK genes, particularly the MNK2 variants are involved in diseases such as e.g. metabolic diseases including obesity, eating disorders, cachexia, diabetes mellitus, hypertension, coronary heart disease, hypercholesterolemia, dyslipidemia, osteoarthritis, biliary stones, cancer of the genitals and sleep apnea, and in diseases connected with the ROS defense, such as e.g. diabetes mellitus and cancer. WO 03/03762 moreover discloses the use of nucleic acid sequences of the MAP kinase-interacting kinase (MNK) gene family and amino acid sequences encoding these and the use of these sequences or of effectors of MNK nucleic acids or polypeptides, particularly MNK inhibitors and activators in the diagnosis, prophylaxis or therapy of diseases associated with the regulation of body weight or thermogenesis.

WO 02/103361 describes the use of kinases 2a and 2b (MNK2a and MNK2b) interacting with the human MAP kinase in assays for the identification of pharmacologically active ingredients, particularly useful for the treatment of diabetes mellitus type 2. Moreover, WO 02/103361 discloses also the prophylaxis and/or therapy of diseases associated with insulin resistance, by modulation of the expression or the activity of MNK2a or MNK2b. Apart from peptides, peptidomimetics, amino acids, amino acid analogues, polynucleotides, polynucleotide analogues, nucleotides and nucleotide analogues, 4-hydroxybenzoic acid methyl ester are described as a substance which binds the human MNK2 protein.

First evidence for a role of MNKs in inflammation was provided by studies demonstrating activation of MNK1 by proinflammatory stimuli. The cytokines TNFα and IL-1β trigger the activation of MNK1 in vitro (Fukunaga and Hunter, EMBO J 16(8): 1921-1933, 1997) and induce the phosphorylation of the MNK-specific substrate eIF4E in vivo (Ueda et al., Mol Cell Biol 24(15): 6539-6549, 2004). In addition, administration of lipopolysaccharide (LPS), a potent stimulant of the inflammatory response, induces activation of MNK1 and MNK2 in mice, concomitant with a phosphorylation of their substrate eIF4E (Ueda et al., Mol Cell Biol 24(15): 6539-6549, 2004).

Furthermore, MNK1 has been shown to be involved in regulating the production of proinflammatory cytokines.

MNK1 enhances expression of the chemokine RANTES (Nikolcheva et al., J Clin Invest 110, 119-126, 2002). RANTES is a potent chemo-tractant of monocytes, eosinophils, basophiles and, natural killer cells. It activates and induces proliferation of T lymphocytes, mediates degranulation of basophils and induces the respiratory burst in eosinophils (Conti and DiGioacchino, Allergy Asthma Proc 22(3):133-7, 2001).

WO 2005/00385 and Buxade et al., Immunity 23: 177-189, August 2005 both disclose a link between MNKs and the control of TNFα biosynthesis. The proposed mechanism is mediated by a regulatory AU-rich element (ARE) in the TNFα mRNA. Buxade et al. demonstrate proteins binding and controlling ARE function to be phosphorylated by MNK1 and MNK2. Specifically MNK-mediated phosphorylation of the ARE-binding protein hnRNP A1 has been suggested to enhance translation of the TNFα mRNA.

TNFα is not the only cytokine regulated by an ARE. Functional AREs are also found in the transcripts of several interleukins, interferones and chemokines (Khabar, J lnterf Cytokine Res 25: 1-10, 2005). The MNK-mediated phosphorylation of ARE-binding proteins has thus the potential to control biosynthesis of cytokines in addition to that of TNFα.

Current evidence demonstrates MNKs as down stream targets of inflammatory signalling as well as mediators of the inflammatory response. Their involvement in the production of TNFα, RANTES, and potentially additional cytokines suggests inhibition of MNKs as strategy for anti-inflammatory therapeutic intervention.

MNK1 and MNK2 (including all splice forms) phosphorylate the translation factor eIF4E on Serine 209. MNK1/2 double knockout mice completely lack phosphorylation on Serine 209, indicating that MNK kinase are the only kinases able to phosphorylate this site in vivo (Ueda et al., Mol Cell Biol. 2004; 24(15):6539-49). eIF4E is overexpressed in a wide range of human malignancies, and high eIF4E expression is frequently associated with more aggressive disease and poor prognosis. Furthermore, eIF4E can act as an oncogene when assayed in standard assays for oncogenic activity (e.g. Ruggero et al., Nat Med. 2004 May; 10(5): 484-6). eIF4E excerts its oncogenic activity by stimulating the translation of oncogenes such as c-myc and cyclinD1 (Culjkovic et al., J Cell Biol. 2006; 175(3):415-26), by increasing the expression of pro-survival factors such as MCP-1 (Wendel et al., Genes Dev. 2007; 21(24):3232-7) and by positively regulating pathways of drug resistance (Wendel et al., Nature 2004; 428(6980):332-7; Graff et el., Cancer Res. 2008; 68(3):631-4; De Benedetti and Graff, Oncogene 2004; 23(18):3189-99; Barnhart and Simon, J Clin Invest. 2007; 117(9):2385-8). Suppression of eIF4E expression by antisense oligonucleotides has shown promise in preclinical experiments with human tumor cells (Graff et al., J Clin Invest. 2007; 117(9):2638-48). It has been shown that phosphorylation on Ser209 is strictly required for the oncogenic activity of eIF4E in vitro and in vivo (Topisirovic et al., Cancer Res. 2004; 64(23):8639-42; Wendel et al., Genes Dev. 2007; 21(24):3232-7). Thus, inhibition of MNK1 and MNK2 is expected to have beneficial effects in human malignancies.

Inhibitors of MNK (referred to as CGP57380 and CGP052088) have been described (cf. Mol. Cell. Biol. 21, 5500, 2001; Mol Cell Biol Res Comm 3, 205, 2000; Genomics 69, 63, 2000). CGP052088 is a staurosporine derivative having an $IC_{50}$ of 70 nM for inhibition of in vitro kinase activity of MNK1. CGP57380 is a low molecular weight selective, non-cytotoxic inhibitor of MNK2 (MNK2a or MNK2b) or of MNK1: The addition of CGP57380 to cell culture cells, transfected with MNK2 (MNK2a or MNK2b) or MNK1 showed a strong reduction of phosphorylated eIF4E.

WO 2007/147874 describes pyridine and pyrazine derivatives as MNK kinase inhibitors. WO 2007/104053 describes 8-heteroarylpurines as MNK2 inhibitors WO 2006/066937 discloses pyrazolopyrimidine compounds, and WO 2006/136402 discloses certain thienopyrimidine compounds, both useful as MNK inhibitors.

DE 10 2007 024 470 and WO 2008/141843 disclose sulfoximine-substituted quinoline and/or quinazoline derivatives which are claimed to act as erythropoietin-producing hepatoma amplified sequence-receptor kinase inhibitors.

AIM OF THE PRESENT INVENTION

The aim of the present invention is to provide new compounds, in particular new sulfoximine substituted quinazoline derivatives, which are MNK1 and/or MNK2 inhibitors.

Another aim of the present invention is to provide new compounds, in particular new sulfoximine substituted quinazoline derivatives, which are potent and selective MNK1 and/or MNK2 inhibitors.

A further aim of the present invention is to provide new compounds, in particular new sulfoximine substituted quinazoline derivatives, which have an inhibiting effect on the kinase activity of MNK1 (MNK1a or MNK1b) and/or MNK2 (MNK2a or MNK2b) and/or variants thereof in vitro and/or in vivo and possess suitable pharmacological and pharmacokinetic properties to use them as medicaments.

A further aim of the present invention is to provide effective MNK1 and/or MNK2 inhibitors, in particular for the treatment of metabolic disorders, for example metabolic diseases, inflammatory diseases, cancer, neurodegenerative diseases and their consecutive complication and disorders.

Still a further aim of the present invention is to provide effective MNK1 and/or MNK2 inhibitors, in particular for the treatment of metabolic disorders, for example diabetes, dyslipidemia and/or obesity and their consecutive complication and disorders.

A further aim of the present invention is to provide methods for treating a disease or condition mediated by the inhibition of the kinase activity of MNK1 (MNK1a or MNK1b) and/or MNK2 (MNK2a or MNK2b) and/or variants thereof in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of new compounds, in particular sulfoximine substituted quinazoline derivatives.

A further aim of the present invention is to provide starting and/or intermediate compounds suitable in methods for the synthesis of new compounds.

Further aims of the present invention become apparent to the one skilled in the art by the description hereinbefore and in the following and by the examples.

OBJECT OF THE INVENTION

It has now been found that the compounds according to the invention described in more detail hereinafter have surprising and particularly advantageous properties, in particular as MNK1 and/or MNK2 inhibitors.

The present invention concerns compounds of the general formula I:

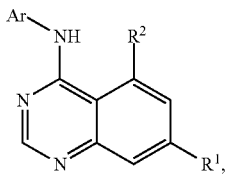

wherein
Ar is selected from the group Ar-G1 consisting of:

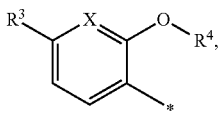

wherein X is CH or N;
R³ is H, halogen, CN or —C(=O)—NH₂; and
R⁴ is selected from the group R⁴-G1 consisting of:

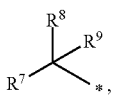

wherein R⁷ is selected from a group consisting of H, CN, $C_{1-6}$-alkyl, —O—($C_{1-3}$-alkyl), $C_{2-4}$-alkynyl, $C_{3-7}$-cycloalkyl heterocyclyl, —($C_{1-3}$-alkyl)-heterocyclyl, —($C_{1-3}$-alkyl)-O-heterocyclyl aryl, —($C_{1-3}$-alkyl)-aryl, 5- or 6-membered heteroaryl, —($C_{1-3}$-alkyl)-heteroaryl, —COOH, —(C=O)—O—($C_{1-6}$-alkyl), —(C=O)—N=S(=O)($C_{1-3}$-alkyl)₂ and —(C=O)—NR$^{N1}$R$^{N2}$;
wherein R$^{N1}$ is H or $C_{1-3}$-alkyl; and
R$^{N2}$ is selected from a group consisting of H, $C_{1-6}$-alkyl, $C_{2-5}$-alkynyl, $C_{3-7}$-cycloalkyl, heterocyclyl, —($C_{1-3}$-alkyl)-heterocyclyl, —($C_{1-3}$-alkyl)-aryl and —SO₂—($C_{1-3}$-alkyl);
or R$^{N1}$ and R$^{N2}$ together with the N-atom to which they are attached form a azetidinyl, pyrrolidinyl, piperidinyl, 4-oxo-piperidinyl, piperazinyl, morpholinyl, thiomorpholinyl, 1-oxo-thiomorpholinyl, 1,1-dioxo-thiomorpholinyl or 1-imino-1,4-thiazinane 1-oxide ring, which may be substituted with one OH, $C_{1-3}$-alkyl or —O—$C_{1-3}$-alkyl; and
wherein in the definition of R⁴, each heterocyclyl is selected from a group consisting of 4-, 5- or 6-membered saturated monocyclic ring systems containing 1, 2 or 3 heteroatoms independently of each other selected from the group consisting on O, S, N and NH, wherein one —CH₂— group may be replaced by a —C(=O)— group and wherein each heterocyclyl group is optionally substituted with $C_{1-3}$-alkyl;
wherein in the definition of R⁴, each aryl is phenyl or naphthyl;
wherein in the definition of R⁴, each heteroaryl is selected from a group consisting of 5- or 6-membered monocyclic heteroaromatic ring systems containing 1, 2 or 3 heteroatoms independently of each other selected from the group consisting on O, S, N and NH and is optionally substituted with $C_{1-3}$-alkyl;
wherein in the definition of R⁴, each alkyl is optionally substituted with 1 or more F or with one or two substituents independently selected from the group consisting of CN, OH, —O—($C_{1-3}$-alkyl), —O-tetrahydrofuranyl, NH₂, —NH—(C=O)—($C_{1-3}$-alkyl), —NH—(C=O)—NH—($C_{1-3}$-alkyl) or —NH—SO₂—($C_{1-3}$-alkyl); and
wherein in the definition of R⁴, each cycloalkyl is optionally substituted with 1 or more F or one CN, OH, CF₃, —O—($C_{1-3}$-alkyl) or =O; and
R⁸ and R⁹ are independently of each other selected from the group consisting of:
H and $C_{1-3}$-alkyl optionally substituted with 1-3 F or one OH or NH₂;
R¹ is selected from the group R¹-G1 consisting of:

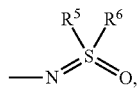

wherein R⁵ is selected from the group consisting of:
a) $C_{1-5}$-alkyl, which is optionally substituted with —O—($C_{1-3}$-alkyl), cycloalkyl, —O-heterocyclyl, $C_{3-7}$-cycloalkyl, heterocyclyl or phenyl,
wherein each alkyl group is optionally substituted with one or more F; and
b) $C_{2-3}$-alkenyl, $C_{2-3}$-alkynyl, $C_{3-7}$-cycloalkyl, heterocyclyl, heteroaryl, and aryl; and
R⁶ is $C_{1-3}$-alkyl which is optionally substituted with one or more F,
or wherein R⁵ and R⁶ together with the sulfur atom to which they are attached form a 3 to 7-membered saturated or partly unsaturated heterocycle that further to the sulfur atom may contain one additional heteroatom selected from the group consisting of O, S and NR$^N$,
wherein R$^N$ is H, $C_{1-3}$-alkyl, —C(=O)—($C_{1-3}$-alkyl), —C(=O)—O—($C_{1-4}$-alkyl), —C(=O)—($C_{1-3}$-alkyl)-O—($C_{1-4}$-alkyl), —C(=O)—NH₂, —C(=O)—NH($C_{1-3}$-alkyl), —C(=O)—N($C_{1-3}$-alkyl)₂ or —SO₂($C_{1-4}$-alkyl);
and wherein R⁵, R⁶ and the heterocycles formed by R⁵ and R⁶ together with the sulfur atom to which they are attached may each be independently substituted with halogen, CN, OH, NH₂, —NH($C_{1-4}$-alkyl), —N($C_{1-4}$-alkyl)₂, —NH—C(=O)—($C_{1-4}$-alkyl), —NH—C(=O)—O—($C_{1-4}$-alkyl), —NH—C(=O)—NH₂, —NH—C(=O)—NH—($C_{1-4}$-alkyl), —NH—C(=O)—N($C_{1-4}$-alkyl)₂, —N($C_{1-4}$-alkyl)-C(=O)—($C_{1-4}$-alkyl), —N($C_{1-4}$-alkyl)-C(=O)—O—($C_{1-4}$-alkyl), —N($C_{1-4}$-alkyl)-C(=O)—NH₂, —N($C_{1-4}$-alkyl)-O(=O)—NH—($C_{1-4}$-alkyl), —N($C_{1-4}$-alkyl)-C(=O)—N($C_{1-4}$-alkyl)₂, —O—($C_{1-4}$-alkyl), $C_{1-6}$-alkyl, $C_{3-7}$-cycloalkyl, heterocylcyl, heteroaryl, —C(=O)—NH₂, —C(=O)—NH($C_{1-4}$-alkyl), —C(=O)—N($C_{1-4}$-alkyl)₂, —COOH, —C(=O)—O—($C_{1-4}$-alkyl), —($C_{1-4}$-alkyl)-NH—C(=O)—($C_{1-4}$-alkyl); —SO—($C_{1-4}$-alkyl) or —SO₂—($C_{1-4}$-alkyl); and
R² is selected from the group R²-G1 consisting of halogen, CN, OH, NH₂, $C_{1-3}$-alkyl, $C_{2-3}$-alkenyl, $C_{2-3}$-alkynyl, $C_{3-5}$-cycloalkyl, —O—($C_{1-3}$-alkyl), —O-cyclopropyl and —S—$C_{1-3}$-alkyl, wherein each alkyl group is optionally substituted with one or more F; and wherein, if not otherwise specified, each alkyl group in the above definitions is linear or branched and may be substituted with one to three F;

including any tautomers and stereoisomers thereof,
or a salt thereof
or a solvate or hydrate thereof.

If not specified otherwise, any alkyl moiety mentioned in this application may be straight-chained or branched and may be substituted with one to three F.

In a further aspect the present invention relates to processes for preparing a compound of general formula I and to new intermediate compounds in these processes.

A further aspect of the invention relates to a salt of the compounds of general formula I according to this invention, in particular to a pharmaceutically acceptable salt thereof.

In a further aspect this invention relates to a pharmaceutical composition, comprising one or more compounds of general formula I or one or more pharmaceutically acceptable salts thereof according to the invention, optionally together with one or more inert carriers and/or diluents.

In a further aspect this invention relates to a method for treating diseases or conditions which are influenced by the inhibition of the kinase activity of MNK1 (MNK1a or MNK1b) and/or MNK2 (MNK2a or MNK2b) and/or variants thereof in a patient in need thereof characterized in that a compound of general formula I or a pharmaceutically acceptable salt thereof is administered to the patient.

According to another aspect of the invention, there is provided a method for treating a metabolic disease or disorder in a patient in need thereof characterized in that a compound of general formula I or a pharmaceutically acceptable salt thereof is administered to the patient.

According to another aspect of the invention, there is provided the use of a compound of the general formula I or a pharmaceutically acceptable salt thereof for the manufacture of a medicament for a therapeutic method as described hereinbefore and hereinafter.

According to another aspect of the invention, there is provided a compound of the general formula I or a pharmaceutically acceptable salt thereof for use in a therapeutic method as described hereinbefore and hereinafter.

In a further aspect this invention relates to a method for treating a disease or condition influenced by the inhibition of the kinase activity of MNK1 (MNK1a or MNK1b) and/or MNK2 (MNK2a or MNK2b) and/or variants thereof in a patient that includes the step of administering to the patient in need of such treatment a therapeutically effective amount of a compound of the general formula I or a pharmaceutically acceptable salt thereof in combination with a therapeutically effective amount of one or more additional therapeutic agents.

In a further aspect this invention relates to a use of a compound of the general formula I or a pharmaceutically acceptable salt thereof in combination with one or more additional therapeutic agents for the treatment of diseases or conditions which are influenced by the inhibition of the kinase activity of MNK1 (MNK1a or MNK1b) and/or MNK2 (MNK2a or MNK2b) and/or variants thereof.

In a further aspect this invention relates to a pharmaceutical composition which comprises a compound according to general formula I or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION OF THE INVENTION

Unless otherwise stated, the groups, residues and substituents, particularly Ar, X, $R^1$, $R^2$, $R^3$, $R^4$, $R^5$, $R^6$, $R^7$, $R^8$, $R^9$, $R^{N1}$ and $R^{N2}$ are defined as above and hereinafter. If residues, substituents, or groups occur several times in a compound, they may have the same or different meanings. Some preferred meanings of individual groups and substituents of the compounds according to the invention will be given hereinafter. Any and each of these definitions may be combined with each other.

Ar:
Ar-G1:
According to one embodiment, the group Ar is selected from the group Ar-G1 as defined hereinbefore and hereinafter.

Ar-G2:
According to another embodiment, the group Ar is selected from the group Ar-G2 consisting of:

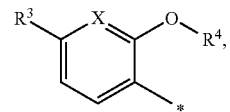

wherein X is CH or N;
$R^3$ is H, F, Cl, Br, CN or —C(=O)—$NH_2$; and
$R^4$ is as defined hereinbefore or hereinafter.

Ar-G3:
According to another embodiment, the group Ar is selected from the group Ar-G3 consisting of:

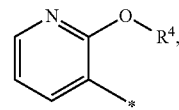

wherein $R^4$ is as defined hereinbefore or hereinafter.

Ar-G4:
According to another embodiment, the group Ar is selected from the group Ar-G4 consisting of:

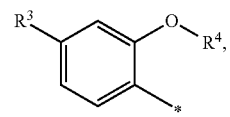

wherein $R^3$ is F, Cl, Br, CN or —C(=O)—$NH_2$; and
$R^4$ is as defined hereinbefore or hereinafter.

Ar-G5:
According to another embodiment, the group Ar is selected from the group Ar-G5 consisting of:

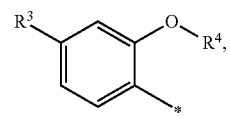

wherein $R^3$ is F, Cl, CN or —C(=O)—$NH_2$; and
$R^4$ is as defined hereinbefore or hereinafter.

Ar-G5a:

According to another embodiment, the group Ar is selected from the group Ar-G5a consisting of:

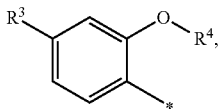

wherein $R^3$ is F, CN or —C(=O)—NH$_2$; and
$R^4$ is as defined hereinbefore or hereinafter.

Ar-G6:

According to another embodiment, the group Ar is selected from the group Ar-G6 consisting of:

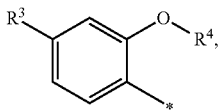

wherein $R^3$ is F or Cl; and
$R^4$ is as defined hereinbefore or hereinafter.

Ar-G6a:

According to another embodiment, the group Ar is selected from the group Ar-G6a consisting of:

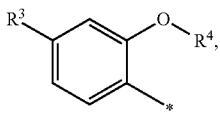

wherein $R^3$ is F; and
$R^4$ is as defined hereinbefore or hereinafter.

Ar-G6b:

According to another embodiment, the group Ar is selected from the group Ar-G6b consisting of:

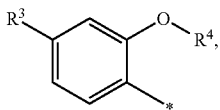

wherein $R^3$ is Cl; and
$R^4$ is as defined hereinbefore or hereinafter.

$R^4$:

$R^4$-G1:

According to one embodiment, the group $R^4$ is selected from the group $R^4$-G1 as defined hereinbefore and hereinafter.

$R^4$-G1a:

According to another embodiment, the group $R^4$ is selected from the group $R^4$-G1a consisting of:

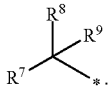

wherein $R^7$ is selected from a group consisting of H, CN, $C_{1-6}$-alkyl, —O—($C_{1-3}$-alkyl), $C_{2-4}$-alkynyl, $C_{3-7}$-cycloalkyl heterocyclyl, —($C_{1-3}$-alkyl)-heterocyclyl, —($C_{1-3}$-alkyl)-O-heterocyclyl aryl, —($C_{1-3}$-alkyl)-aryl, 5- or 6-membered heteroaryl, —($C_{1-3}$-alkyl)-heteroaryl, —COOH, —(C=O)—O—($C_{1-6}$-alkyl), —(C=O)—N=S(=O)($C_{1-3}$-alkyl)$_2$ and —(C=O)—NR$^{N1}$R$^{N2}$;

wherein $R^{N1}$ is H or $C_{1-3}$-alkyl; and
$R^{N2}$ is selected from a group consisting of H, $C_{1-6}$-alkyl, $C_{2-5}$-alkynyl, $C_{3-7}$-cycloalkyl, heterocyclyl, —($C_{1-3}$-alkyl)-heterocyclyl, —($C_{1-3}$-alkyl)-aryl and —SO$_2$—($C_{1-3}$-alkyl);

or $R^{N1}$ and $R^{N2}$ together with the N-atom to which they are attached form a azetidinyl, pyrrolidinyl, piperidinyl, 4-oxo-piperidinyl, piperazinyl, morpholinyl, thiomorpholinyl, 1-oxo-thiomorpholinyl, 1,1-dioxo-thiomorpholinyl or 1-imino-1,4-thiazinane 1-oxide ring, which may be substituted with one OH, $C_{1-3}$-alkyl or —O—$C_{1-3}$-alkyl; and wherein in the definition of $R^4$, each heterocyclyl is selected from a group consisting of 2-oxo-pyrrolidinyl, 2-oxo-piperidinyl, 2-oxo-oxazolidinyl, oxetanyl, tetrahydrofuranyl, tetrahydropyranyl, [1,4]-dioxanyl and is optionally substituted with $C_{1-3}$-alkyl;

wherein in the definition of $R^4$, each aryl is phenyl or naphthyl;

wherein in the definition of $R^4$, each heteroaryl is selected from a group consisting of pyrazolyl, imidazolyl, oxazolyl, isoxazolyl, oxadiazolyl, thiazolyl, thiadiazolyl, pyridinyl, pyrimidinyl, pyrazinyl and pyridazinyl and is optionally substituted with $C_{1-3}$-alkyl;

wherein in the definition of $R^4$, each alkyl is optionally substituted with 1 or more F or with one or two substituents independently selected from the group consisting of CN, OH, —O—($C_{1-3}$-alkyl), —O-tetrahydrofuranyl, NH$_2$, —NH—(C=O)—($C_{1-3}$-alkyl), —NH—(C=O)—NH—($C_{1-3}$-alkyl) or —NH—SO$_2$—($C_{1-3}$-alkyl); and wherein in the definition of $R^4$, each cycloalkyl is optionally substituted with 1 or more F or one CN, OH, CF$_3$, —O—($C_{1-3}$-alkyl) or =O; and $R^4$-G2:

According to another embodiment, the group $R^4$ is selected from the group $R^4$-G2 consisting of:

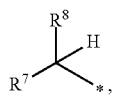

wherein $R^7$ is selected from a group consisting of CN; $C_{1-6}$-alkyl; —O—($C_{1-3}$-alkyl); $C_{2-4}$-alkynyl; $C_{3-7}$-cycloalkyl heterocyclyl; —($C_{1-3}$-alkyl)-heterocyclyl; —($C_{1-3}$-alkyl)-O-heterocyclyl aryl; —($C_{1-3}$-alkyl)-aryl; 5- or 6-membered heteroaryl; —($C_{1-3}$-alkyl)-heteroaryl; —COOH; —(C=O)—O—($C_{1-6}$-alkyl); —(C=O)—N=S(=O)($C_{1-3}$-alkyl)$_2$ and —(C=O)—NR$^{N1}$R$^{N2}$;

wherein $R^{N1}$ is H or $C_{1-3}$-alkyl; and
$R^{N2}$ is selected from a group consisting of H, $C_{1-6}$-alkyl, $C_{2-5}$-alkynyl, $C_{3-7}$-cycloalkyl, -heterocyclyl, —($C_{1-3}$-alkyl)-heterocyclyl and —($C_{1-3}$-alkyl)-aryl or $R^{N1}$ and $R^{N2}$ together with the N-atom to which they are attached form a azetidinyl, pyrrolidinyl, piperidinyl, 4-oxo-piperidinyl, piperazinyl, morpholinyl, thiomorpholinyl or 1-oxo-thiomorpholinyl ring, which may be substituted with one OH, $C_{1-3}$-alkyl or —O—$C_{1-3}$-alkyl; and wherein in the definition of $R^4$, each heterocyclyl is selected from a group consisting of 2-oxo-pyrrolidinyl, 2-oxo-piperidinyl, 2-oxo-oxazolidinyl, oxetanyl, tetrahydrofuranyl, tetrahydropyranyl and [1,4]-dioxanyl and is optionally substituted with $C_{1-3}$-alkyl;

wherein in the definition of $R^4$, each aryl is phenyl;

wherein in the definition of $R^4$, each heteroaryl is selected from a group consisting of pyrazolyl, imidazolyl, oxazolyl, isoxazolyl, oxadiazolyl, thiazolyl, thiadiazolyl, pyridinyl, pyrimidinyl, pyrazinyl and pyridazinyl and is optionally substituted with $C_{1-3}$-alkyl;

wherein in the definition of $R^4$, each alkyl is optionally substituted with 1-3 F or with one or two substituents independently selected from the group consisting of CN, OH, —O—($C_{1-3}$-alkyl), —O-tetrahydrofuranyl, $NH_2$, —NH—(C═O)—($C_{1-3}$-alkyl), —NH—(C═O)—NH—($C_{1-3}$-alkyl) or —NH—$SO_2$—($C_{1-3}$-alkyl); and wherein in the definition of $R^4$, each cycloalkyl is optionally substituted with 1-3 F or one CN, OH, $CF_3$ or ═O; and $R^8$ is selected from the group consisting of H and $C_{1-3}$-alkyl optionally substituted with 1-3 F or one OH or $NH_2$.

Preferably, $R^8$ is H, $CH_3$, $CH_2F$, $CF_3$ or $CH_2CH_3$.

$R^4$-G2a:

According to another embodiment, the group $R^4$ is selected from the group $R^4$-G2a consisting of:

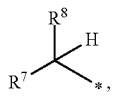

wherein $R^7$ is selected from a group consisting of CN, $C_{1-6}$-alkyl, $C_{3-7}$-cycloalkyl heterocyclyl, phenyl, 5- or 6-membered heteroaryl, —(C═O)—N═S(═O)($C_{1-3}$-alkyl)$_2$ and —(C═O)—$NR^{N1}R^{N2}$;

wherein $R^{N1}$ is H or $C_{1-3}$-alkyl; and $R^{N2}$ is selected from a group consisting of H, $C_{1-6}$-alkyl, $C_{2-5}$-alkynyl, $C_{3-7}$-cycloalkyl, heterocyclyl, —($C_{1-3}$-alkyl)-heterocyclyl and —($C_{1-3}$-alkyl)-phenyl;

or $R^{N1}$ and $R^{N2}$ together with the N-atom to which they are attached form a azetidinyl, pyrrolidinyl, piperidinyl, 4-oxo-piperidinyl, piperazinyl, morpholinyl, thiomorpholinyl or 1-oxo-thiomorpholinyl ring, which may be substituted with one OH, $C_{1-3}$-alkyl or —O—$C_{1-3}$-alkyl; and wherein in the definition of $R^4$, each heterocyclyl is selected from a group consisting of 2-oxo-pyrrolidinyl, 2-oxo-piperidinyl, 2-oxo-oxazolidinyl, oxetanyl, tetrahydrofuranyl, tetrahydropyranyl and [1,4]-dioxanyl and is optionally substituted with $C_{1-3}$-alkyl;

wherein in the definition of $R^4$, each heteroaryl is selected from a group consisting of pyrazolyl, imidazolyl, oxazolyl, isoxazolyl, oxadiazolyl, thiazolyl, thiadiazolyl, pyridinyl, pyrimidinyl, pyrazinyl and pyridazinyl and is optionally substituted with $C_{1-3}$-alkyl;

wherein in the definition of $R^4$, each alkyl is optionally substituted with 1-3 F or with one or two substituents independently selected from the group consisting of CN, OH, —O—($C_{1-3}$-alkyl), —O-tetrahydrofuranyl, $NH_2$, —NH—(C═O)—($C_{1-3}$-alkyl), —NH—(C═O)—NH—($C_{1-3}$-alkyl) or —NH—$SO_2$—($C_{1-3}$-alkyl); and wherein in the definition of $R^4$, each cycloalkyl is optionally substituted with 1-3 F or one CN, OH, $CF_3$ or ═O; and $R^8$ is selected from the group consisting of H and $C_{1-3}$-alkyl optionally substituted with 1-3 F or one OH or $NH_2$.

Preferably, $R^8$ is H, $CH_3$, $CH_2F$, $CF_3$ or $CH_2CH_3$.

$R^4$-G3:

According to another embodiment, the group $R^4$ is selected from the group $R^4$-G3 consisting of:

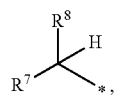

wherein $R^7$ is selected from a group consisting of CN; $C_{1-4}$-alkyl optionally substituted with 1-3 F or with one $NH_2$ or —NH—(C═O)—NH—$CH_3$; $C_{2-3}$-alkynyl; cyclopropyl optionally substituted with one $CF_3$; 2-oxo-pyrrolidinyl; 2-oxo-piperidinyl; 2-oxo-oxazolidinyl; tetrahydrofuranyl; tetrahydropyranyl; isoxazolyl optionally substituted with $CH_3$; pyridinyl; —$CH_2$-imidazolyl optionally substituted with $CH_3$; —(C═O)—O—($C_{1-3}$-alkyl), —(C═O)—N═S(═O)($C_{1-3}$-alkyl)$_2$ and —(C═O)—$NR^{N1}R^{N2}$;

wherein $R^{N1}$ is H or $CH_3$ or $CH_2CH_3$ and $R^{N2}$ is selected from a group consisting of $C_{1-4}$-alkyl optionally substituted with 1-3 F or one CN, OH, —O—$CH_3$; $C_{2-4}$-alkynyl; $C_{3-6}$-cycloalkyl optionally substituted with OH; oxetanyl; tetrahydrofuranyl; and tetrahydropyranyl;

or $R^{N1}$ and $R^{N2}$ together with the N-atom to which they are attached form a piperidinyl ring; and wherein in the definition of $R^4$, each alkyl is optionally substituted with 1-3 F; and $R^8$ is selected from the group consisting of H and $C_{1-3}$-alkyl optionally substituted with 1-3 F.

Preferably, $R^8$ is H, $CH_3$ and $CH_2F$.

$R^4$-G4:

According to another embodiment, the group $R^4$ is selected from the group $R^4$-G4 consisting of:

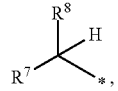

wherein $R^7$ is selected from a group consisting of:
a) heterocyclyl selected from a group consisting of 2-oxo-pyrrolidinyl, 2-oxo-piperidinyl, 2-oxo-oxazolidinyl, oxetanyl, tetrahydrofuranyl, tetrahydropyranyl and [1,4]-dioxanyl, wherein each heterocyclyl group is optionally substituted with $C_{1-3}$-alkyl;

b) heteroaryl selected from a group consisting of pyrazolyl, imidazolyl, oxazolyl, isoxazolyl, oxadiazolyl, thiazolyl, thiadiazolyl, pyridinyl, pyrimidinyl, pyrazinyl and pyridazinyl and is optionally substituted with $C_{1-3}$-alkyl;
c) —(C=O)—N=S(=O)($C_{1-3}$-alkyl)$_2$ and
d) —(C=O)—NR$^{N1}$R$^{N2}$;
wherein R$^{N1}$ is H or CH$_3$ or CH$_2$CH$_3$ and
R$^{N2}$ is selected from a group consisting of $C_{1-4}$-alkyl optionally substituted with 1-3 F or one CN, OH, —O—CH$_3$; $C_{2-4}$-alkynyl; $C_{3-6}$-cycloalkyl optionally substituted with OH; oxetanyl; tetrahydrofuranyl; and tetrahydropyranyl];
or R$^{N1}$ and R$^{N2}$ together with the N-atom to which they are attached form a piperidinyl ring; and
wherein in the definition of R$^4$, each alkyl is optionally substituted with 1-3 F; and
R$^8$ is selected from the group consisting of H and $C_{1-3}$-alkyl optionally substituted with 1-3 F.

Preferably, R$^8$ is CH$_3$.

R$^4$-G4a:

According to another embodiment, the group R$^4$ is selected from the group R$^4$-G4a consisting of:

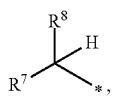

wherein R$^7$ is selected from a group consisting of 2-oxo-pyrrolidinyl; 2-oxo-piperidinyl; 2-oxo-oxazolidinyl; tetrahydrofuranyl; tetrahydropyranyl; isoxazolyl optionally substituted with CH$_3$; pyridinyl; —CH$_2$-imidazolyl optionally substituted with CH$_3$; —(C=O)—N=S(=O)($C_{1-3}$-alkyl)$_2$, and —(C=O)—NR$^{N1}$R$^{N2}$;
wherein R$^{N1}$ is H or CH$_3$ or CH$_2$CH$_3$ and
R$^{N2}$ is selected from a group consisting of $C_{1-4}$-alkyl optionally substituted with 1-3 F or one CN, OH, —O—CH$_3$; $C_{2-4}$-alkynyl; $C_{3-6}$-cycloalkyl optionally substituted with OH; oxetanyl; tetrahydrofuranyl; and tetrahydropyranyl;
or R$^{N1}$ and R$^{N2}$ together with the N-atom to which they are attached form a piperidinyl ring; and
wherein in the definition of R$^4$, each alkyl is optionally substituted with 1-3 F; and
R$^8$ is selected from the group consisting of H and $C_{1-3}$-alkyl optionally substituted with 1-3 F.

Preferably, R$^8$ is CH$_3$.

R$^4$-G5:

According to another embodiment, the group R$^4$ is selected from the group R$^4$-G5 consisting of:

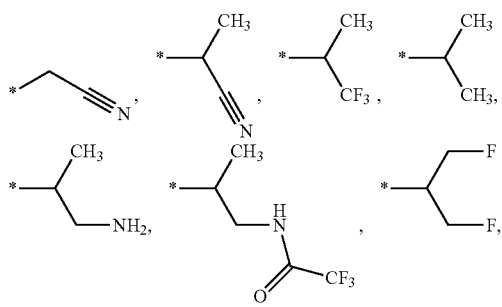

-continued
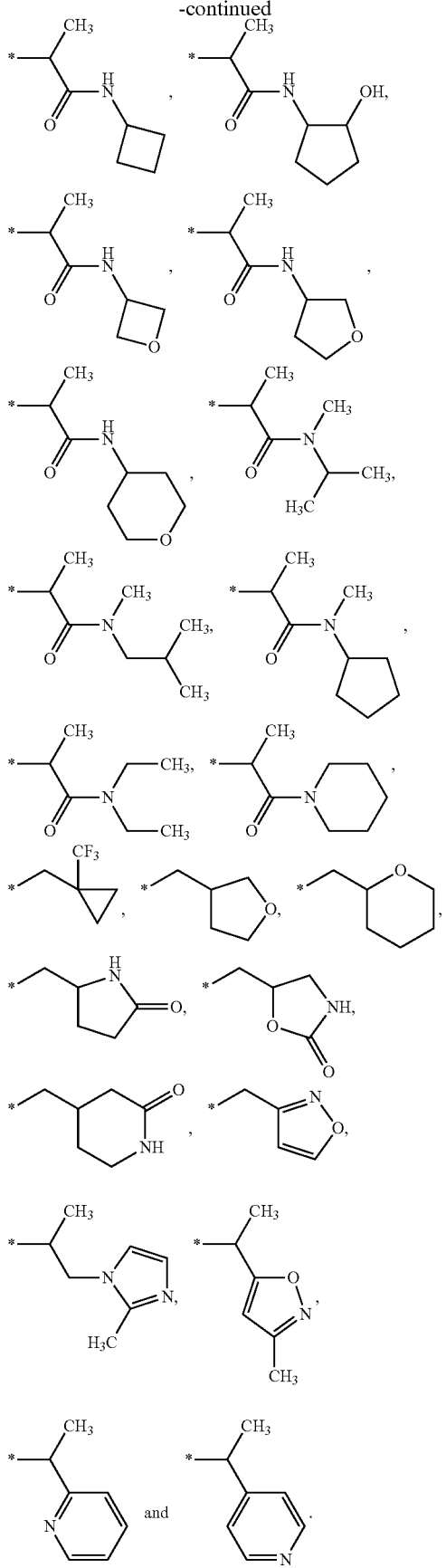
$R^4$-G5a:
According to another embodiment, the group $R^4$ is selected from the group $R^4$-G5a consisting of:

-continued
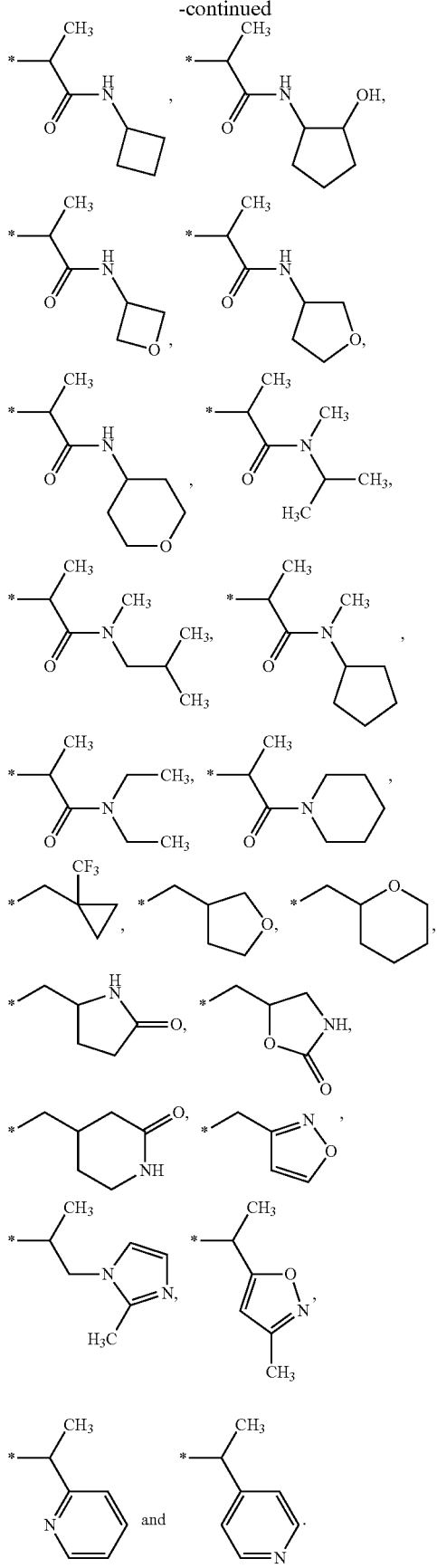
R⁴-G6:
According to another embodiment, the group $R^4$ is selected from the group $R^4$-G6 consisting of:
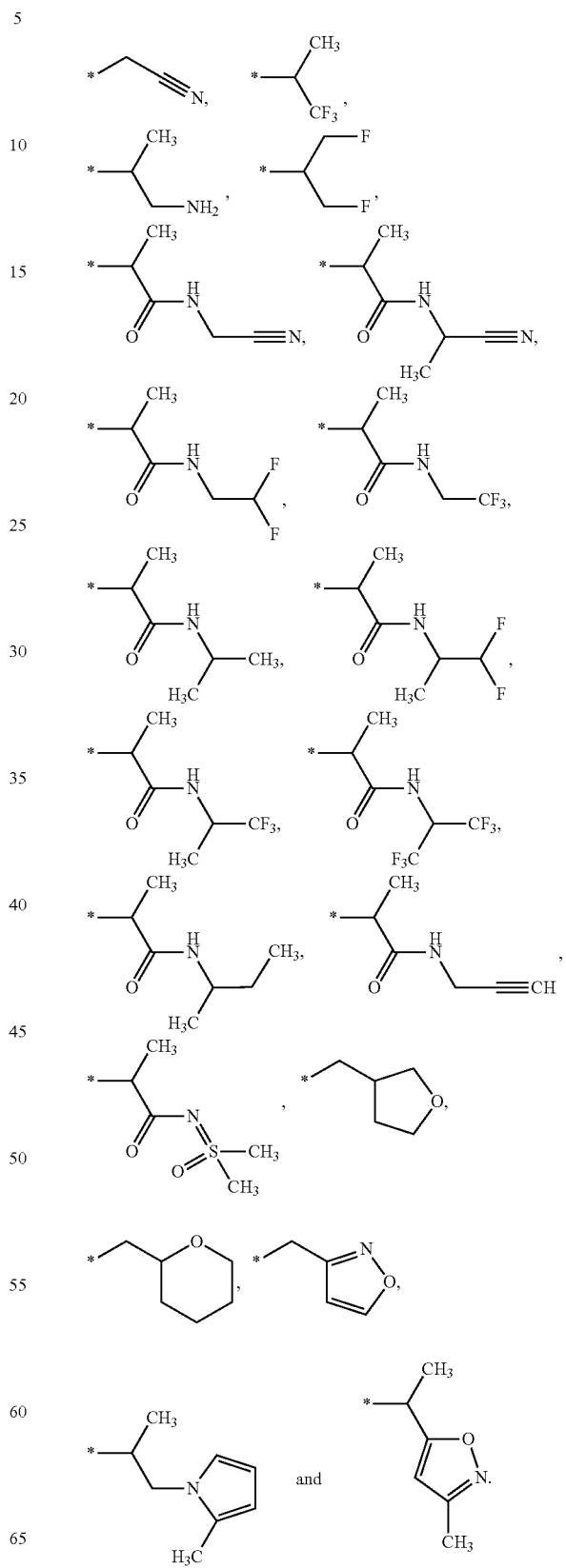

$R^4$-G6a:

According to another embodiment, the group $R^4$ is selected from the group $R^4$-G6a consisting of:

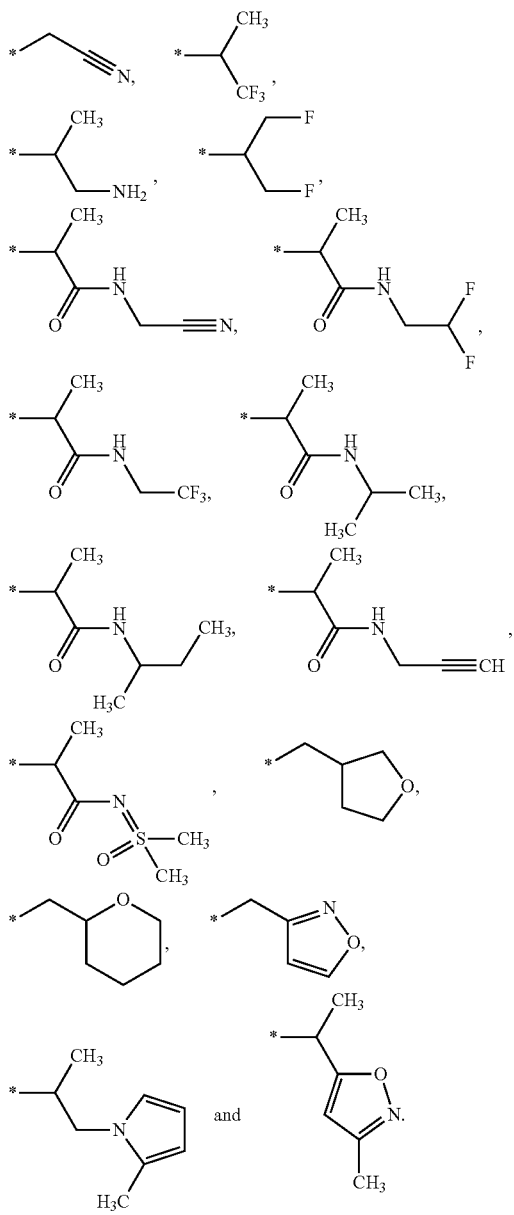

$R^4$-G7-I:

According to another embodiment, the group $R^4$ is selected from the group $R^4$-G7-I consisting of:

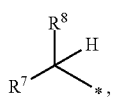

wherein $R^7$ is selected from a group consisting of $C_{1-6}$-alkyl; $C_{3-7}$-cycloalkyl and heterocyclyl: —($C_{1-3}$-alkyl)-heterocyclyl: —($C_{1-3}$-alkyl)-O-heterocyclyl: —($C_{1-3}$-alkyl)-aryl; —($C_{1-3}$-alkyl)-heteroaryl;

wherein each heterocyclyl is selected from a group consisting of 2-oxo-pyrrolidinyl, 2-oxo-piperidinyl, 2-oxo-oxazolidinyl, oxetanyl, tetrahydrofuranyl, tetrahydropyranyl and [1,4]-dioxanyl and is optionally substituted with $C_{1-3}$-alkyl;

wherein each aryl is phenyl;

wherein each heteroaryl is selected from a group consisting of pyrazolyl, imidazolyl, oxazolyl, isoxazolyl, oxadiazolyl, thiazolyl, thiadiazolyl, pyridinyl, pyrimidinyl, pyrazinyl and pyridazinyl and is optionally substituted with $C_{1-3}$-alkyl;

wherein each alkyl is optionally substituted with 1-3 F or with one or two substituents independently selected from the group consisting of CN, OH, —O—($C_{1-3}$-alkyl), —O-tetrahydrofuranyl, $NH_2$, —NH—(C=O)—($C_{1-3}$-alkyl), —NH—(C=O)—NH—($C_{1-3}$-alkyl) or —NH—$SO_2$—($C_{1-3}$-alkyl); and wherein each cycloalkyl is optionally substituted with 1-3 F or one CN, OH, $CF_3$ or =O; and $R^8$ is selected from the group consisting of H and $C_{1-3}$-alkyl optionally substituted with 1-3 F or one OH or $NH_2$.

Preferably, $R^8$ is H, $CH_3$, $CH_2F$, $CF_3$ or $CH_2CH_3$.

$R^4$-G7-Ia:

According to another embodiment, the group $R^4$ is selected from the group $R^4$-G7-Ia consisting of:

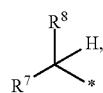

wherein $R^7$ is selected from a group consisting of $C_{1-6}$-alkyl; $C_{3-7}$-cycloalkyl and heterocyclyl;

wherein each heterocyclyl is selected from a group consisting of 2-oxo-pyrrolidinyl, 2-oxo-piperidinyl, 2-oxo-oxazolidinyl, oxetanyl, tetrahydrofuranyl, tetrahydropyranyl and [1,4]-dioxanyl and is optionally substituted with $C_{1-3}$-alkyl;

wherein each alkyl is optionally substituted with 1-3 F or with one or two substituents independently selected from the group consisting of CN, OH, —O—($C_{1-3}$-alkyl), —O-tetrahydrofuranyl, $NH_2$, —NH—(C=O)—($C_{1-3}$-alkyl), —NH—(C=O)—NH—($C_{1-3}$-alkyl) or —NH—$SO_2$—($C_{1-3}$-alkyl); and wherein each cycloalkyl is optionally substituted with 1-3 F or one CN, OH, $CF_3$ or =O; and $R^8$ is selected from the group consisting of H and $C_{1-3}$-alkyl optionally substituted with 1-3 F or one OH or $NH_2$.

Preferably, $R^8$ is H, $CH_3$, $CH_2F$, $CF_3$ or $CH_2CH_3$.

$R^4$-G7-Ib:

According to another embodiment, the group $R^4$ is selected from the group $R^4$-G7-Ib consisting of:

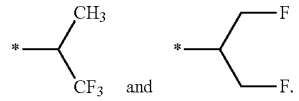

$R^4$-G7-II:

According to another embodiment, the group $R^4$ is selected from the group $R^4$-G7-II consisting of:

wherein $R^7$ is selected from a group consisting of phenyl and; 5- or 6-membered heteroaryl;
  wherein said heteroaryl is selected from a group consisting of pyrazolyl, imidazolyl, oxazolyl, isoxazolyl, oxadiazolyl, thiazolyl, thiadiazolyl, pyridinyl, pyrimidinyl, pyrazinyl and pyridazinyl and is optionally substituted with $C_{1-3}$-alkyl; and
  wherein each alkyl is optionally substituted with 1-3 F; and
$R^8$ is selected from the group consisting of H and $C_{1-3}$-alkyl optionally substituted with 1-3 F or one OH or $NH_2$.
  Preferably, $R^8$ is H, $CH_3$, $CH_2F$, $CF_3$ or $CH_2CH_3$.
$R^4$-G7-IIa:
  According to another embodiment, the group $R^4$ is selected from the group $R^4$-G7-IIa consisting of:

wherein $R^7$ is 5- or 6-membered heteroaryl;
  wherein said heteroaryl is selected from a group consisting of isoxazolyl and pyridinyl, and is optionally substituted with $C_{1-3}$-alkyl; and
  wherein said alkyl substituent is optionally substituted with 1-3 F; and
$R^8$ is selected from the group consisting of H and $C_{1-3}$-alkyl optionally substituted with 1-3 F or one OH or $NH_2$.
  Preferably, $R^8$ is H, $CH_3$, $CH_2F$, $CF_3$ or $CH_2CH_3$.
$R^4$-G7-IIb:
  According to another embodiment, the group $R^4$ is selected from the group $R^4$-G7-IIb consisting of:

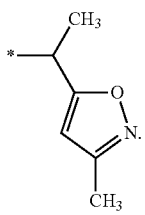

$R^4$-G7-III:
  According to another embodiment, the group $R^4$ is selected from the group $R^4$-G7-III consisting of:

wherein $R^7$ is selected from a group consisting of CN; $-(C=O)-N=S(=O)(C_{1-3}\text{-alkyl})_2$ and $-(C=O)-NR^{N1}R^{N2}$;
  wherein $R^{N1}$ is H or $C_{1-3}$-alkyl; and
  $R^{N2}$ is selected from a group consisting of H, $C_{1-6}$-alkyl, $C_{2-5}$-alkynyl, $C_{3-7}$-cycloalkyl, heterocyclyl, $-(C_{1-3}\text{-alkyl})$-heterocyclyl and $-(C_{1-3}\text{-alkyl})$-aryl;
  or $R^{N1}$ and $R^{N2}$ together with the N-atom to which they are attached form a azetidinyl, pyrrolidinyl, piperidinyl, 4-oxo-piperidinyl, piperazinyl, morpholinyl, thiomorpholinyl or 1-oxo-thiomorpholinyl ring, which may be substituted with one OH, $C_{1-3}$-alkyl or $-O-C_{1-3}$-alkyl; and
  wherein in the definition of $R^4$, each heterocyclyl is selected from a group consisting of 2-oxo-pyrrolidinyl, 2-oxo-piperidinyl, 2-oxo-oxazolidinyl, oxetanyl, tetrahydrofuranyl, tetrahydropyranyl and [1,4]-dioxanyl and is optionally substituted with $C_{1-3}$-alkyl;
  wherein in the definition of $R^4$, each aryl is phenyl;
  wherein in the definition of $R^4$, each alkyl is optionally substituted with 1-3 F or with one or two substituents independently selected from the group consisting of CN, OH, $-O-(C_{1-3}\text{-alkyl})$, $-O$-tetrahydrofuranyl, $NH_2$, $-NH-(C=O)-(C_{1-3}\text{-alkyl})$, $-NH-(C=O)-NH-(C_{1-3}\text{-alkyl})$ or $-NH-SO_2-(C_{1-3}\text{-alkyl})$; and
  wherein in the definition of $R^4$, each cycloalkyl is optionally substituted with 1-3 F or one CN, OH, $CF_3$ or $=O$; and
$R^8$ is selected from the group consisting of H and $C_{1-3}$-alkyl optionally substituted with 1-3 F or one OH or $NH_2$.
  Preferably, $R^8$ is H, $CH_3$, $CH_2F$, $CF_3$ or $CH_2CH_3$.
$R^4$-G7-IIIa:
  According to another embodiment, the group $R^4$ is selected from the group $R^4$-G7-IIIa consisting of:

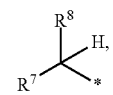

wherein $R^7$ is selected from a group consisting of CN; $-(C=O)-N=S(=O)(C_{1-2}\text{-alkyl})_2$ and $-(C=O)-NR^{N1}R^{N2}$;
  wherein $R^{N1}$ is H or $CH_3$; and
  $R^{N2}$ is selected from a group consisting of H, $C_{1-6}$-alkyl, $C_{2-5}$-alkynyl, $C_{3-7}$-cycloalkyl and heterocyclyl;
  or $R^{N1}$ and $R^{N2}$ together with the N-atom to which they are attached form a azetidinyl, pyrrolidinyl, piperidinyl, 4-oxo-piperidinyl or piperazinyl, ring, which may be substituted with one OH, $C_{1-3}$-alkyl or $-O-C_{1-3}$-alkyl; and
  wherein in the definition of $R^4$, each heterocyclyl is selected from a group consisting of 2-oxo-pyrrolidinyl, 2-oxo-piperidinyl, 2-oxo-oxazolidinyl, oxetanyl, tetrahydrofuranyl, tetrahydropyranyl and [1,4]-dioxanyl and is optionally substituted with $C_{1-3}$-alkyl;
  wherein in the definition of $R^4$, each alkyl is optionally substituted with 1-3 F or with one or two substituents independently selected from the group consisting of CN, OH, $-O-(C_{1-3}\text{-alkyl})$; and
  wherein in the definition of $R^4$, each cycloalkyl is optionally substituted with 1-3 F or one OH; and
$R^8$ is selected from the group consisting of H and $C_{1-3}$-alkyl optionally substituted with 1-3 F or one OH or $NH_2$.
  Preferably, $R^8$ is H, $CH_3$, $CH_2F$, $CF_3$ or $CH_2CH_3$.
  Preferably, $R^{N1}$ is H.
$R^4$-G7-IIIb:
  According to another embodiment, the group $R^4$ is selected from the group $R^4$-G7-IIIb consisting of:

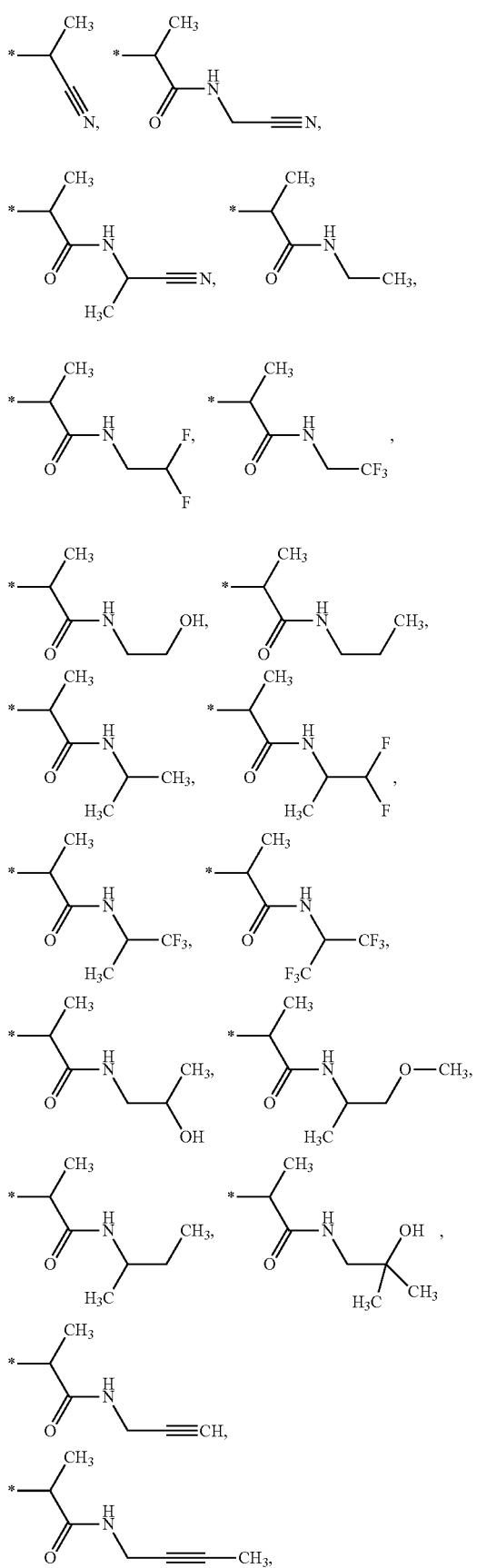
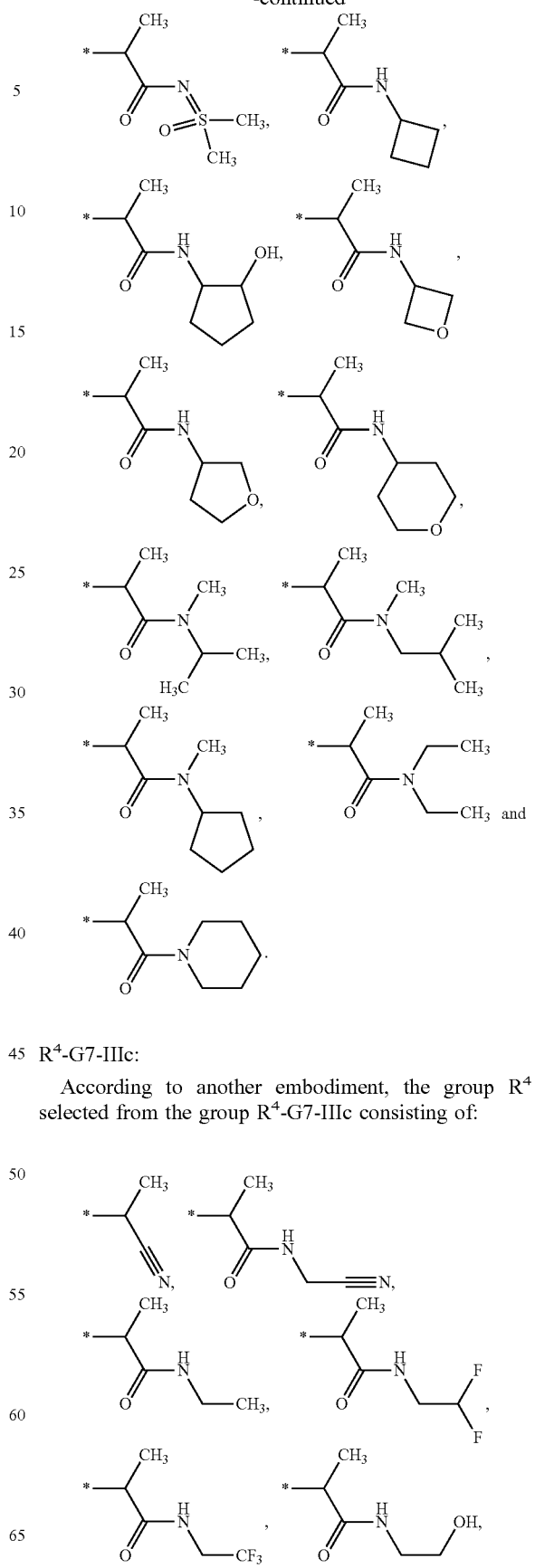
-continued
R⁴-G7-IIIc:
According to another embodiment, the group $R^4$ is selected from the group R⁴-G7-IIIc consisting of:

-continued

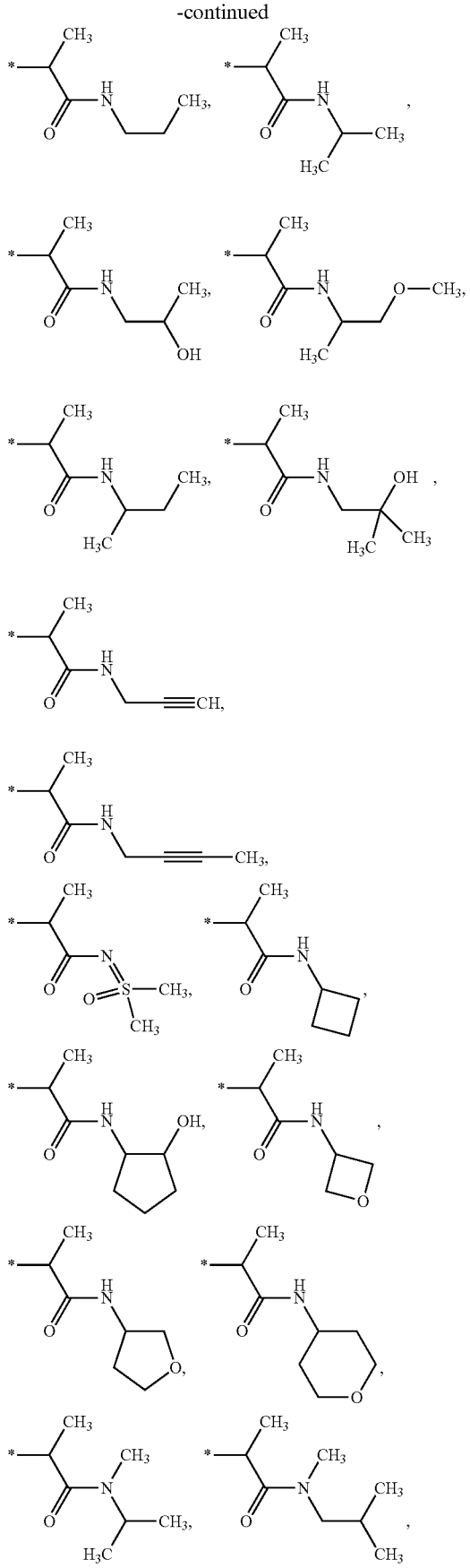

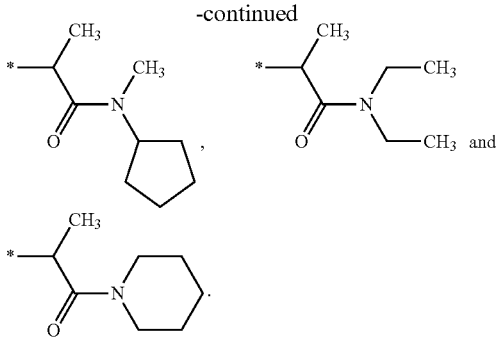

$R^1$:
$R^1$-G1:
According to one embodiment, the group $R^1$ is selected from the group $R^1$-G1 as defined hereinbefore and hereinafter.
$R^1$-G2:
According to another embodiment, the group $R^1$ is selected from the group $R^1$-G2 consisting of:

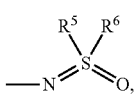

wherein $R^5$ is selected from the group consisting of:
  a) $C_{1-4}$-alkyl, which is optionally substituted with —O—($C_{1-3}$-alkyl), —O—$C_{3-7}$-cycloalkyl, $C_{3-7}$-cycloalkyl, or phenyl,
    wherein each alkyl group is optionally substituted with one or more F; and
  b) $C_{3-7}$-cycloalkyl, pyridinyl, and phenyl; and
$R^6$ is $C_{1-3}$-alkyl which is optionally substituted with one or more F;
or wherein $R^5$ and $R^6$ together with the sulfur atom to which they are attached form a 3- to 7-membered saturated or partly unsaturated heterocycle that further to the sulfur atom may contain one additional heteroatom selected from the group consisting of O, S and $NR^N$,
  wherein $R^N$ is H, $C_{1-3}$-alkyl, —C(=O)—($C_{1-3}$-alkyl), —C(=O)—O—($C_{1-4}$-alkyl), —C(=O)—($C_{1-3}$-alkyl)-O—($C_{1-4}$-alkyl), —C(=O)—$NH_2$, —C(=O)—NH($C_{1-3}$-alkyl), —C(=O)—N($C_{1-3}$-alkyl)$_2$ or —$SO_2$($C_{1-4}$-alkyl);
and wherein $R^5$, $R^6$ and the heterocycles formed by $R^5$ and $R^6$ together with the sulfur atom to which they are attached may each be independently substituted with F, Cl, Br, CN, OH, $NH_2$, —NH($C_{1-4}$-alkyl), —N($C_{1-4}$-alkyl)$_2$, —NH—C(=O)—($C_{1-4}$-alkyl), —NH—C(=O)—O—($C_{1-4}$-alkyl), —NH—C(=O)—$NH_2$, —NH—C(=O)—NH—($C_{1-4}$-alkyl), —NH—C(=O)—N($C_{1-4}$-alkyl)$_2$, —N($C_{1-4}$-alkyl)-C(=O)—($C_{1-4}$-alkyl), —N($C_{1-4}$-alkyl)-C(=O)—O—($C_{1-4}$-alkyl), —N($C_{1-4}$-alkyl)-C(=O)—$NH_2$, —N($C_{1-4}$-alkyl)-C(=O)—NH—($C_{1-4}$-alkyl), —N($C_{1-4}$-alkyl)-C(=O)—N($C_{1-4}$-alkyl)$_2$, —O—($C_{1-4}$-alkyl), $C_{1-6}$-alkyl, $C_{3-7}$-cycloalkyl, piperidinyl, piperazinyl, morpholinyl, pyrrolyl, furanyl, thienyl, pyridinyl, pyrimidinyl, pyrazinyl, pyridazinyl, —C(=O)—$NH_2$, —C(=O)—NH($C_{1-4}$-alkyl), —C(=O)—N($C_{1-4}$-alkyl)$_2$, —COOH, —C(=O)—O—(C$_{1-4}$-alkyl), —(C$_{1-4}$-alkyl)-NH—C(=O)—(C$_{1-4}$-alkyl); —SO—(C$_{1-4}$-alkyl) or —SO$_2$—(C$_{1-4}$-alkyl).

Preferably, R$^1$ is selected from the group consisting of:

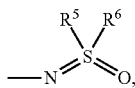

wherein R$^5$ is selected from the group consisting of:
a) C$_{1-3}$-alkyl, which is optionally substituted with —O—(C$_{1-3}$-alkyl), cycloalkyl, C$_{3-7}$-cycloalkyl, or phenyl,
   wherein each alkyl group is optionally substituted with one or more F; and
b) C$_{3-7}$-cycloalkyl, tetrahydropyranyl, pyridinyl, and phenyl; and R$^6$ is C$_{1-3}$-alkyl which is optionally substituted with one or more F;

or wherein R$^5$ and R$^6$ together with the sulfur atom to which they are attached form a 4- to 7-membered saturated or partly unsaturated heterocycle that further to the sulfur atom may contain one additional heteroatom selected from the group consisting of O, S and NR$^N$,
   wherein R$^N$ is H, C$_{1-3}$-alkyl, —C(=O)—(C$_{1-3}$-alkyl), —C(=O)—O—(C$_{1-4}$-alkyl), —C(=O)—(C$_{1-3}$-alkyl)-O—(C$_{1-4}$-alkyl), —C(=O)—NH$_2$, —C(=O)—NH(C$_{1-3}$-alkyl), —C(=O)—N(C$_{1-3}$-alkyl)$_2$ or —SO$_2$(C$_{1-4}$-alkyl).

R$^1$-G3:

According to another embodiment, the group R$^1$ is selected from the group R$^1$-G3 consisting of:

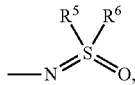

wherein R$^5$ is selected from the group consisting of C$_{1-4}$-alkyl, tetrahydropyranyl, pyridinyl and phenyl,
   wherein the alkyl group is optionally substituted with —O—CH$_3$ or phenyl; and R$^6$ is C$_{1-3}$-alkyl;

or wherein R$^5$ and R$^6$ together with the sulfur atom to which they are attached form a 5- or 6-membered saturated heterocycle that further to the sulfur atom may contain one additional heteroatom selected from the group consisting of O, S and NR$^N$,
   wherein R$^N$ is H, CH$_3$, —C(=O)—CH$_3$, —C(=O)—OCH$_3$, —C(=O)—CH$_2$—OCH$_3$ or —C(=O)—NH—CH$_2$CH$_3$.

R$^1$-G3a:

According to another embodiment, the group R$^1$ is selected from the group R$^1$-G3a consisting of:

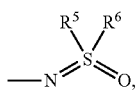

wherein R$^5$ is methyl or ethyl; and
R$^6$ is methyl or ethyl.

R$^1$-G3b:

According to another embodiment, the group R$^1$ is selected from the group R$^1$-G3b consisting of:

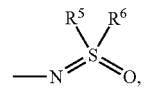

wherein R$^5$ and R$^6$ together with the sulfur atom to which they are attached form a 5- or 6-membered saturated heterocycle that further to the sulfur atom may contain one additional heteroatom selected from the group consisting of O and NR$^N$,
   wherein R$^N$ is H, CH$_3$, —C(=O)—CH$_3$, —C(=O)—OCH$_3$, —C(=O)—CH$_2$—OCH$_3$ or —C(=O)—NH—CH$_2$CH$_3$.

R$^1$-G4:

According to another embodiment, the group R$^1$ is selected from the group R$^1$-G4 consisting of:

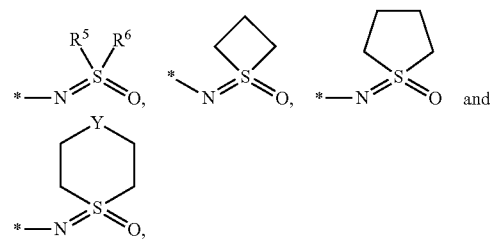

wherein R$^5$ is C$_{1-4}$-alkyl, which is optionally substituted with one or more F;
R$^6$ is CH$_3$ which is optionally substituted with one to three F; and
Y is CH$_2$, O, NH or N(C$_{1-3}$-alkyl).

R$^1$-G5:

According to another embodiment, the group R$^1$ is selected from the group R$^1$-G5 consisting of:

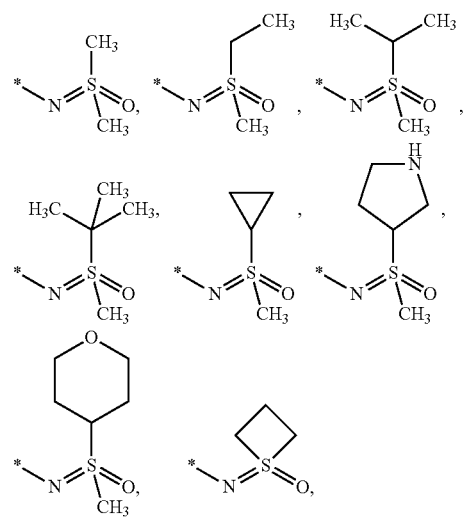

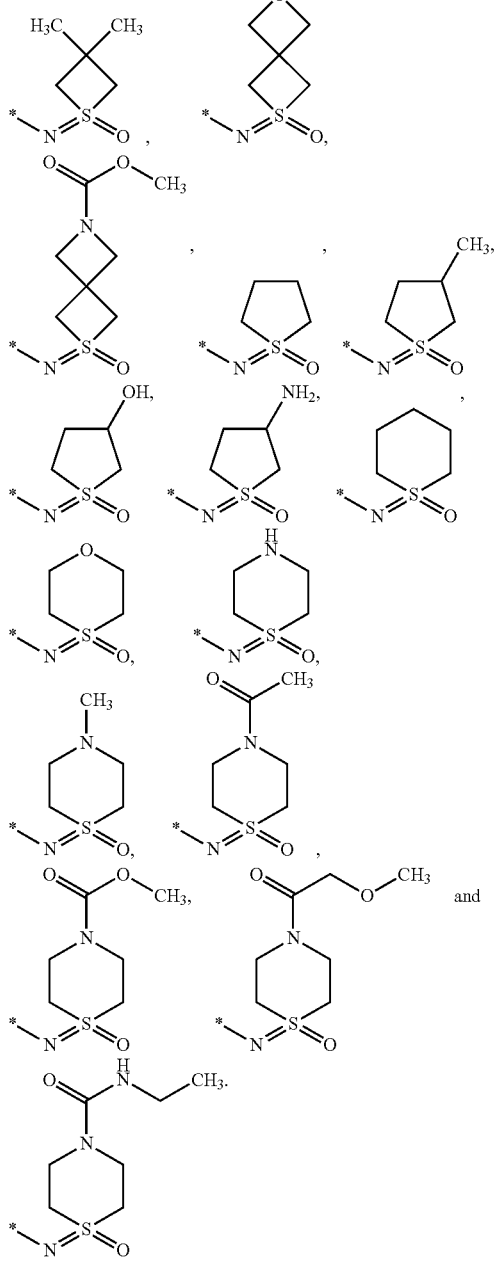

R$^1$-G5a:

According to another embodiment, the group R$^1$ is selected from the group R$^1$-G5a consisting of:

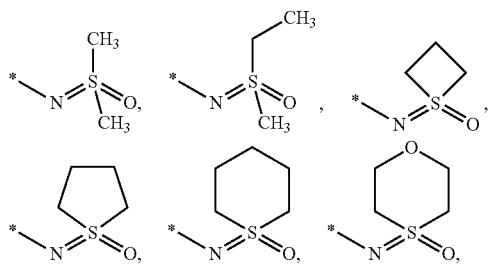

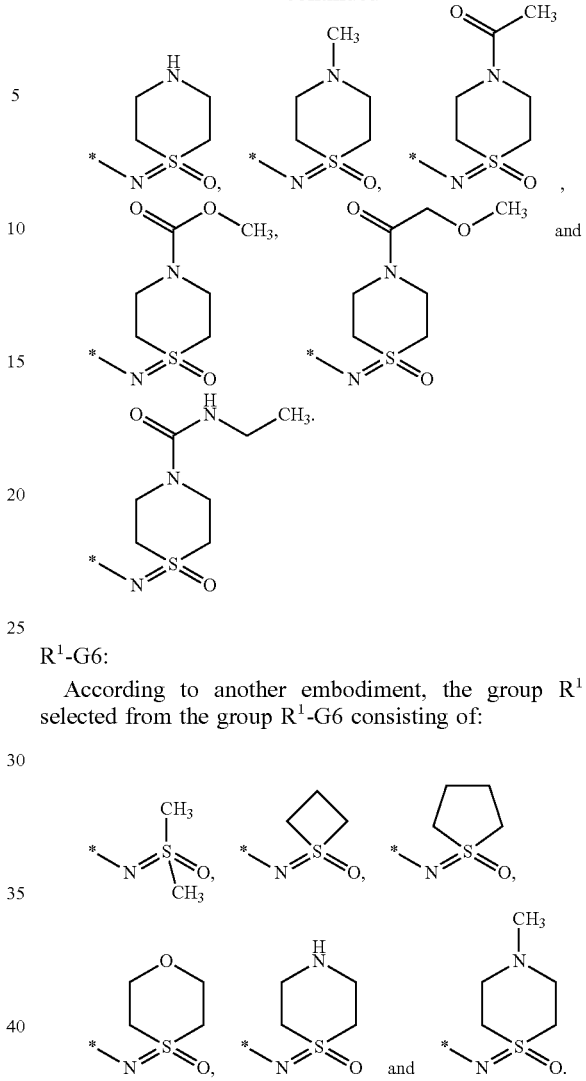

R$^1$-G6:

According to another embodiment, the group R$^1$ is selected from the group R$^1$-G6 consisting of:

R$^1$-G7:

According to another embodiment, the group R$^1$ is selected from the group R$^1$-G7 consisting of:

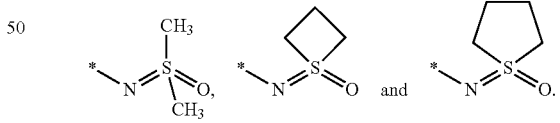

R$^2$:

R$^2$-G1:

According to one embodiment, the group R$^2$ is selected from the group R$^2$-G1 as defined hereinbefore and hereinafter.

R$^2$-G2:

According to another embodiment, the group R$^2$ is selected from the group R$^2$-G2 consisting of F, Cl, Br, CN, $C_{1-3}$-alkyl, $C_{3-5}$-cycloalkyl and —O—$C_{1-3}$-alkyl, wherein each alkyl group is optionally substituted with one to three F.

R²-G3:

According to another embodiment, the group R² is selected from the group R²-G3 consisting of F, Cl, Br, CH₃, CF₃, cyclopropyl and —O—CH₃.

R²-G4:

According to another embodiment, the group R² is selected from the group R²-G4 consisting of of F, Cl, CH₃, CF₃ and —O—CH₃.

R²-G5:

According to another embodiment, the group R² is selected from the group R²-G5 consisting of of F, Cl, CH₃ and CF₃.

R²-G6:

According to another embodiment, the group R² is selected from the group R²-G6 consisting of CH₃.

The following preferred embodiments of compounds of the formula I are described using generic formulae I.1 to I.5, wherein any tautomers and stereoisomers, solvates, hydrates and salts thereof, in particular the pharmaceutically acceptable salts thereof, are encompassed.

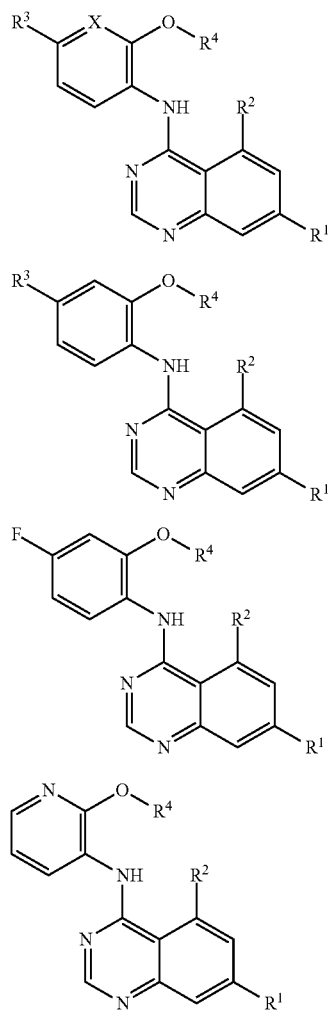

wherein the variables $R^1$, $R^2$, $R^3$, $R^4$ and X are defined as hereinbefore and hereinafter.

Examples of preferred subgeneric embodiments according to the present invention are set forth in the following table, wherein each substituent group of each embodiment is defined according to the definitions set forth hereinbefore and wherein all other substituents of the formula I are defined according to the definitions set forth hereinbefore:

| Embodiment | Ar | R⁴ | R¹ | R² |
|---|---|---|---|---|
| E-1 | Ar-G1 | R⁴-G1 | R¹-G1 | R²-G1 |
| E-2 | Ar-G1 | R⁴-G2 | R¹-G2 | R²-G2 |
| E-3 | Ar-G1 | R⁴-G2a | R¹-G2 | R²-G2 |
| E-4 | Ar-G2 | R⁴-G3 | R¹-G3 | R²-G3 |
| E-5 | Ar-G2 | R⁴-G3 | R¹-G3 | R²-G4 |
| E-6 | Ar-G2 | R⁴-G3 | R¹-G3 | R²-G6 |
| E-7 | Ar-G2 | R⁴-G4 | R¹-G3 | R²-G3 |
| E-8 | Ar-G2 | R⁴-G4 | R¹-G4 | R²-G4 |
| E-9 | Ar-G2 | R⁴-G4 | R¹-G5 | R²-G6 |
| E-10 | Ar-G2 | R⁴-G4 | R¹-G6 | R²-G6 |
| E-11 | Ar-G2 | R⁴-G5 | R¹-G3 | R²-G3 |
| E-12 | Ar-G2 | R⁴-G5 | R¹-G4 | R²-G4 |
| E-13 | Ar-G2 | R⁴-G5 | R¹-G5 | R²-G6 |
| E-14 | Ar-G2 | R⁴-G5 | R¹-G6 | R²-G6 |
| E-15 | Ar-G2 | R⁴-G6 | R¹-G3 | R²-G3 |
| E-16 | Ar-G2 | R⁴-G6 | R¹-G4 | R²-G4 |
| E-17 | Ar-G2 | R⁴-G6 | R¹-G5 | R²-G6 |
| E-18 | Ar-G2 | R⁴-G6 | R¹-G6 | R²-G6 |
| E-19 | Ar-G3 | R⁴-G3 | R¹-G3 | R²-G3 |
| E-20 | Ar-G3 | R⁴-G3 | R¹-G3 | R²-G4 |
| E-21 | Ar-G3 | R⁴-G3 | R¹-G3 | R²-G6 |
| E-22 | Ar-G3 | R⁴-G4 | R¹-G3 | R²-G3 |
| E-23 | Ar-G3 | R⁴-G4 | R¹-G4 | R²-G4 |
| E-24 | Ar-G3 | R⁴-G4 | R¹-G5 | R²-G6 |
| E-25 | Ar-G3 | R⁴-G4 | R¹-G6 | R²-G6 |
| E-26 | Ar-G3 | R⁴-G5 | R¹-G3 | R²-G3 |
| E-27 | Ar-G3 | R⁴-G5 | R¹-G4 | R²-G4 |
| E-28 | Ar-G3 | R⁴-G5 | R¹-G5 | R²-G6 |
| E-29 | Ar-G3 | R⁴-G5 | R¹-G6 | R²-G6 |
| E-30 | Ar-G3 | R⁴-G6 | R¹-G3 | R²-G3 |
| E-31 | Ar-G3 | R⁴-G6 | R¹-G4 | R²-G4 |
| E-32 | Ar-G3 | R⁴-G6 | R¹-G5 | R²-G6 |
| E-33 | Ar-G3 | R⁴-G6 | R¹-G6 | R²-G6 |
| E-34 | Ar-G4 | R⁴-G3 | R¹-G3 | R²-G3 |
| E-35 | Ar-G4 | R⁴-G3 | R¹-G3 | R²-G4 |
| E-36 | Ar-G4 | R⁴-G3 | R¹-G3 | R²-G6 |
| E-37 | Ar-G4 | R⁴-G4 | R¹-G3 | R²-G3 |
| E-38 | Ar-G4 | R⁴-G4 | R¹-G4 | R²-G4 |
| E-39 | Ar-G5 | R⁴-G4 | R¹-G5 | R²-G6 |
| E-40 | Ar-G5 | R⁴-G4 | R¹-G6 | R²-G6 |
| E-41 | Ar-G4 | R⁴-G5 | R¹-G3 | R²-G3 |
| E-42 | Ar-G4 | R⁴-G5 | R¹-G4 | R²-G4 |
| E-43 | Ar-G5 | R⁴-G5 | R¹-G5 | R²-G6 |
| E-44 | Ar-G5 | R⁴-G5 | R¹-G6 | R²-G6 |
| E-45 | Ar-G4 | R⁴-G6 | R¹-G3 | R²-G3 |
| E-46 | Ar-G4 | R⁴-G6 | R¹-G4 | R²-G4 |
| E-47 | Ar-G5 | R⁴-G6 | R¹-G5 | R²-G6 |
| E-48 | Ar-G6 | R⁴-G3 | R¹-G3 | R²-G3 |
| E-49 | Ar-G6 | R⁴-G3 | R¹-G3 | R²-G4 |
| E-50 | Ar-G6 | R⁴-G3 | R¹-G3 | R²-G6 |
| E-51 | Ar-G6 | R⁴-G4 | R¹-G3 | R²-G3 |
| E-52 | Ar-G6 | R⁴-G4 | R¹-G4 | R²-G4 |
| E-53 | Ar-G6 | R⁴-G4 | R¹-G5 | R²-G6 |
| E-54 | Ar-G6 | R⁴-G4 | R¹-G6 | R²-G6 |
| E-55 | Ar-G6 | R⁴-G5 | R¹-G3 | R²-G3 |
| E-56 | Ar-G6 | R⁴-G5 | R¹-G4 | R²-G4 |
| E-57 | Ar-G6 | R⁴-G5 | R¹-G5 | R²-G6 |
| E-58 | Ar-G6 | R⁴-G5 | R¹-G6 | R²-G6 |
| E-59 | Ar-G6 | R⁴-G6 | R¹-G3 | R²-G3 |
| E-60 | Ar-G6 | R⁴-G6 | R¹-G4 | R²-G4 |
| E-61 | Ar-G6 | R⁴-G6 | R¹-G5 | R²-G6 |
| E-62 | Ar-G6 | R⁴-G6 | R¹-G6 | R²-G6 |
| E-63 | Ar-G6 | R⁴-G6 | R¹-G6 | R²-G6 |

One embodiment of the invention concerns those compounds of formula I, wherein Ar is selected from the group Ar-G2 consisting of:

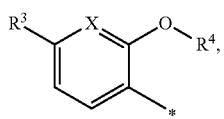

wherein X is CH or N;
$R^3$ is H, F, Cl, Br, CN or —C(=O)—NH$_2$; and
$R^4$ is selected from the group $R^4$-G2a consisting of:

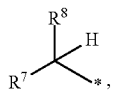

wherein $R^7$ is selected from a group consisting of CN, $C_{1-6}$-alkyl, $C_{3-7}$-cycloalkyl heterocyclyl, phenyl, 5- or 6-membered heteroaryl, —(C=O)—N=S(=O)($C_{1-3}$-alkyl)$_2$ and —(C=O)—NR$^{N1}$R$^{N2}$;
wherein $R^{N1}$ is H or $C_{1-3}$-alkyl; and
$R^{N2}$ is selected from a group consisting of H, $C_{1-6}$-alkyl, $C_{2-5}$-alkynyl, $C_{3-7}$-cycloalkyl, heterocyclyl, —($C_{1-3}$-alkyl)-heterocyclyl and —($C_{1-3}$-alkyl)-phenyl;
or $R^{N1}$ and $R^{N2}$ together with the N-atom to which they are attached form a azetidinyl, pyrrolidinyl, piperidinyl, 4-oxo-piperidinyl, piperazinyl, morpholinyl, thiomorpholinyl or 1-oxo-thiomorpholinyl ring, which may be substituted with one OH, $C_{1-3}$-alkyl or —O—$C_{1-3}$-alkyl; and
wherein in the definition of $R^4$, each heterocyclyl is selected from a group consisting of 2-oxo-pyrrolidinyl, 2-oxo-piperidinyl, 2-oxo-oxazolidinyl, oxetanyl, tetrahydrofuranyl, tetrahydropyranyl and [1,4]-dioxanyl and is optionally substituted with $C_{1-3}$-alkyl;
wherein in the definition of $R^4$, each heteroaryl is selected from a group consisting of pyrazolyl, imidazolyl, oxazolyl, isoxazolyl, oxadiazolyl, thiazolyl, thiadiazolyl, pyridinyl, pyrimidinyl, pyrazinyl and pyridazinyl and is optionally substituted with $C_{1-3}$-alkyl;
wherein in the definition of $R^4$, each alkyl is optionally substituted with 1-3 F or with one or two substituents independently selected from the group consisting of CN, OH, —O—($C_{1-3}$-alkyl), —O-tetrahydrofuranyl, NH$_2$, —NH—(C=O)—($C_{1-3}$-alkyl), —NH—(C=O)—NH—($C_{1-3}$-alkyl) or —NH—SO$_2$—($C_{1-3}$-alkyl); and
wherein in the definition of $R^4$, each cycloalkyl is optionally substituted with 1-3 F or one CN, OH, OF$_3$ or =O; and
$R^8$ is selected from the group consisting of H, CH$_3$, CH$_2$F, OF$_3$ or CH$_2$CH$_3$;
$R^1$ is selected from the group consisting of:

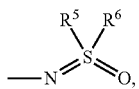

wherein $R^5$ is methyl or ethyl; and
$R^6$ is methyl or ethyl;
or wherein $R^5$ and $R^6$ together with the sulfur atom to which they are attached form a 5- or 6-membered saturated heterocycle that further to the sulfur atom may contain one additional heteroatom selected from the group consisting of O and NR$^N$,
wherein $R^N$ is H, CH$_3$, —C(=O)—OH$_3$, —C(=O)—OCH$_3$, —C(=O)—CH$_2$—OCH$_3$ or —C(=O)—NH—CH$_2$CH$_3$; and
$R^2$ is selected from the group $R^2$-G3 consisting of F, Cl, Br, CH$_3$, CF$_3$, cyclopropyl and —O—CH$_3$;
and the pharmaceutically acceptable salts thereof.

Another embodiment of the invention concerns those compounds of formula I, wherein Ar is selected from the group Ar-G5 consisting of:

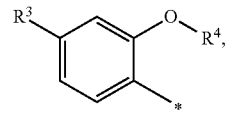

wherein $R^3$ is F, and
$R^4$ is selected from the group $R^4$-G5 consisting of:

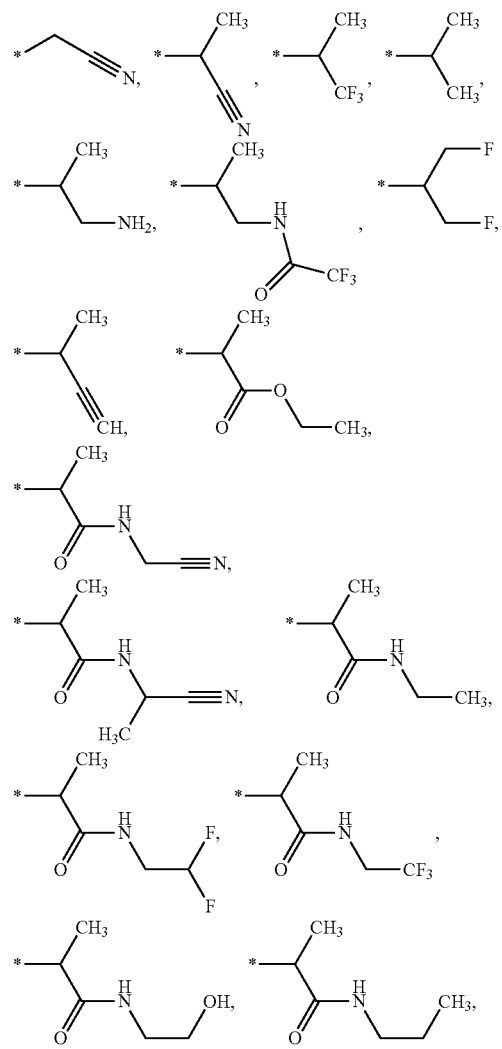

-continued
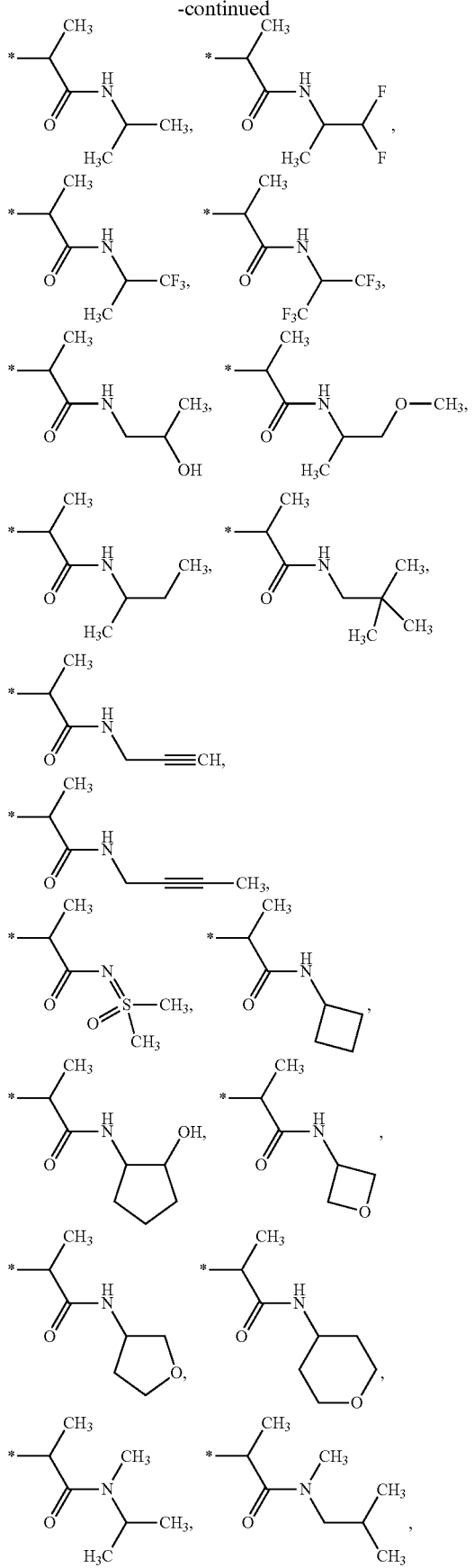
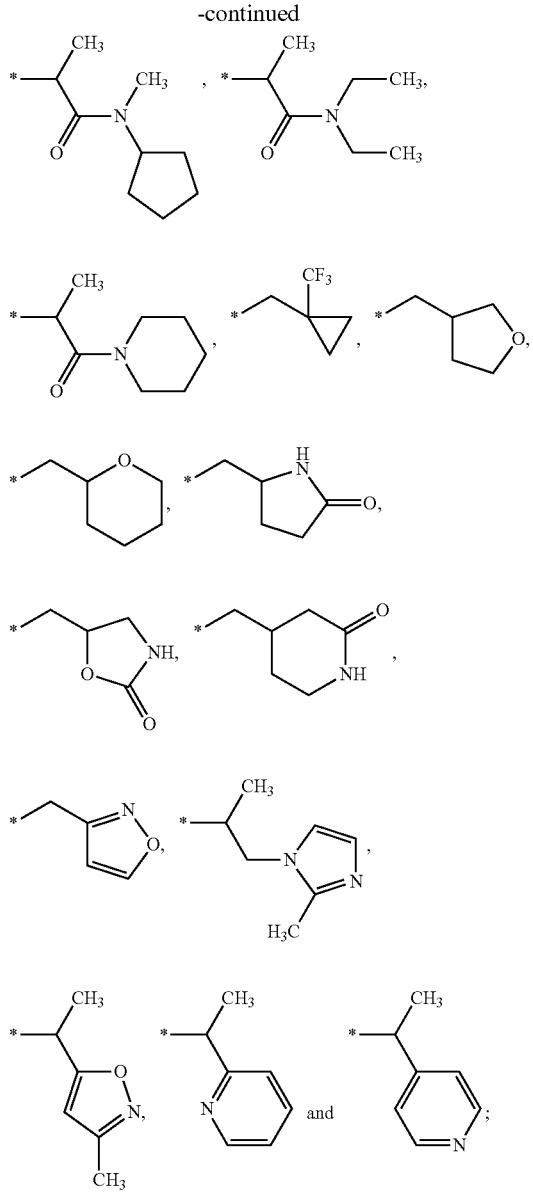
$R^1$ is selected from the group $R^1$-G6 consisting of:
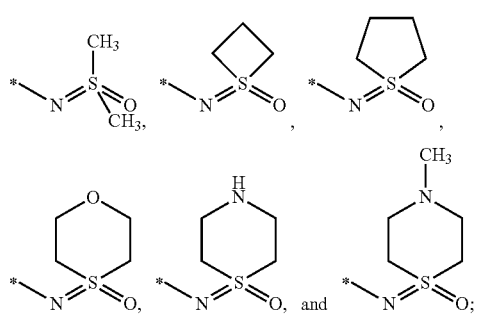
and
$R^2$ is selected from the group $R^2$-G6 consisting of $CH_3$; and the pharmaceutically acceptable salts thereof.

Preferred examples for compounds of formula I are:
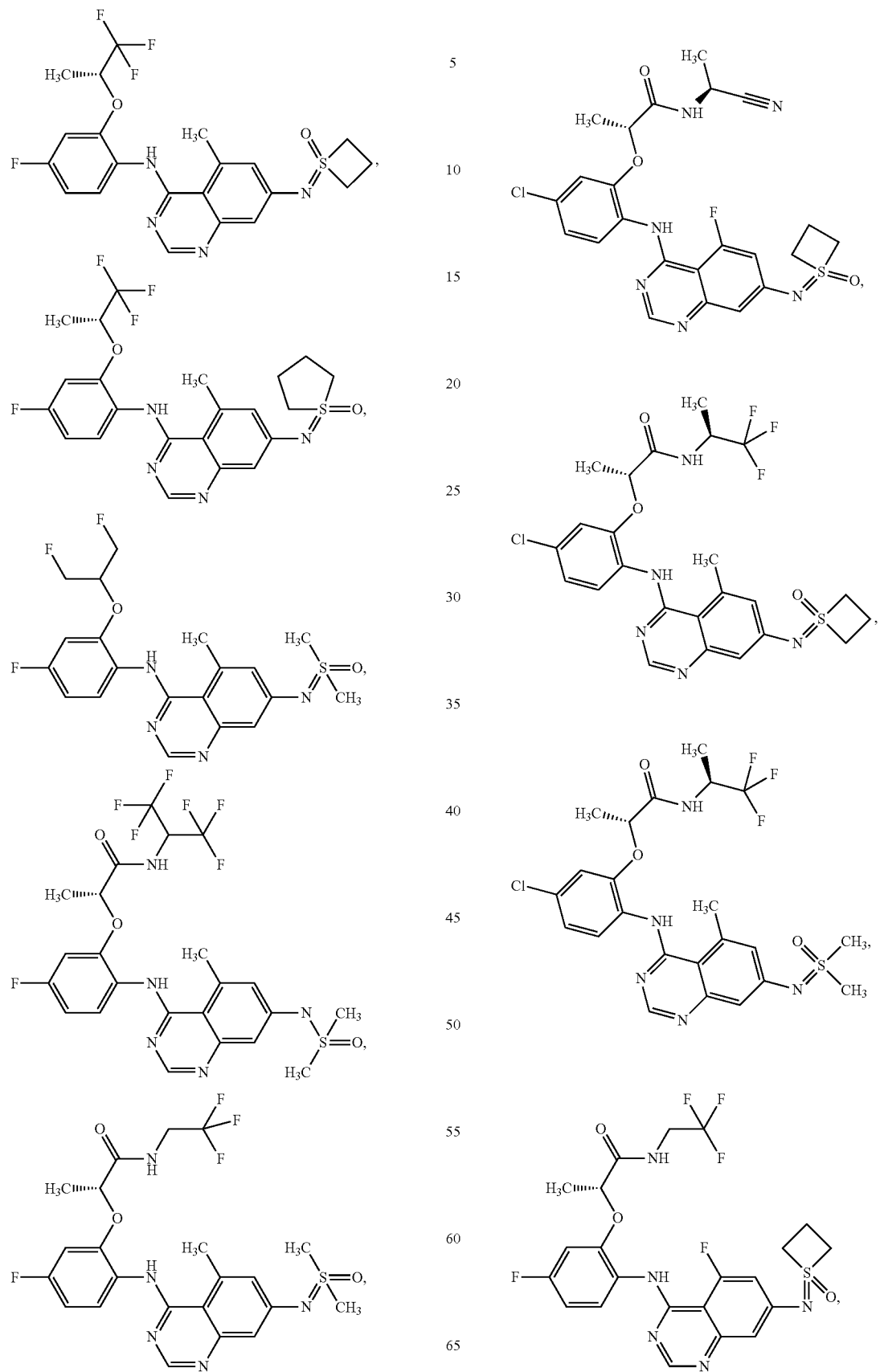

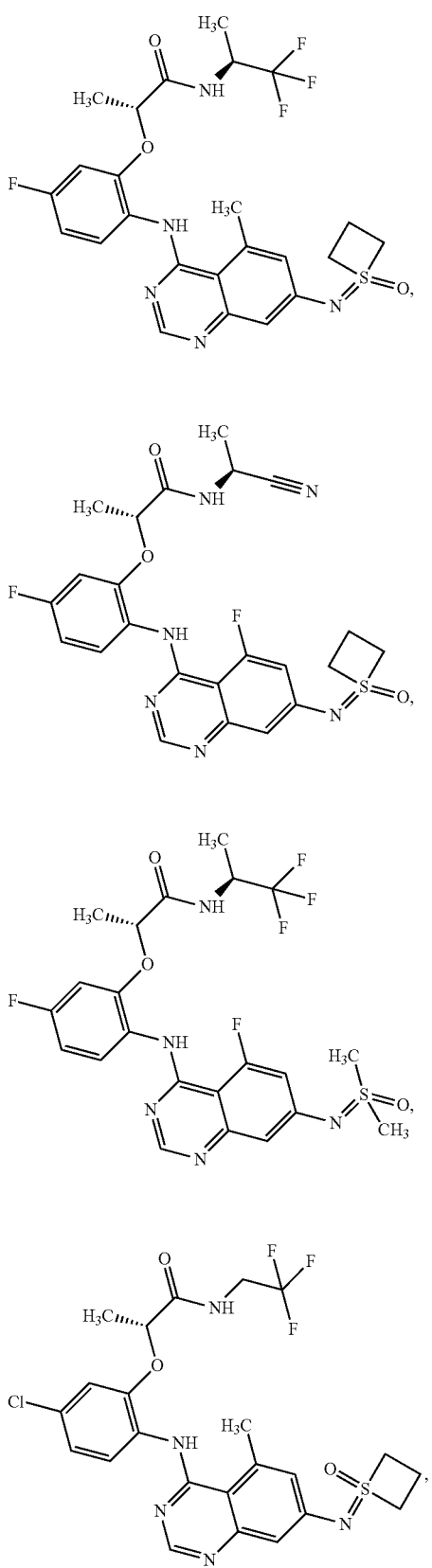
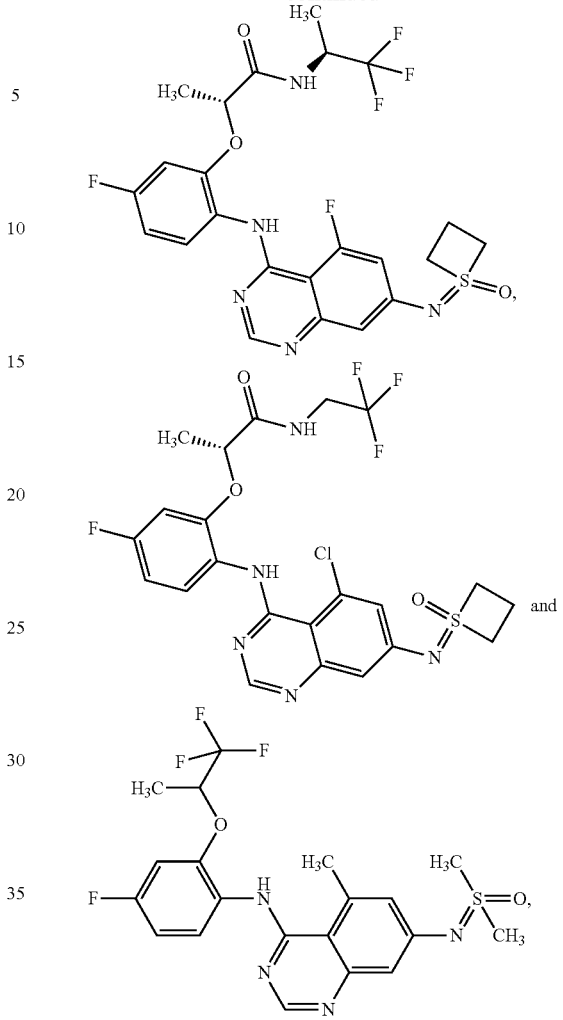

and the pharmaceutically acceptable salts thereof.

Particularly preferred compounds, including their tautomers and stereoisomers, the salts thereof, or any solvates or hydrates thereof, are described in the experimental section hereinafter.

The compounds according to the invention and their intermediates may be obtained using methods of synthesis which are known to the one skilled in the art and described in the literature of organic synthesis. Preferably the compounds are obtained analogously to the methods of preparation explained more fully hereinafter, in particular as described in the experimental section. In some cases the sequence adopted in carrying out the reaction schemes may be varied. Variants of these reactions that are known to one skilled in the art but are not described in detail here may also be used. The general processes for preparing the compounds according to the invention will become apparent to a person skilled in the art on studying the schemes that follow. Starting compounds are commercially available or may be prepared by methods that are described in the literature or herein, or may be prepared in an analogous or similar manner. Before the reaction is carried out any corresponding functional groups in the compounds may be protected using conventional protecting groups. These protecting groups may be cleaved again at a suitable stage within the reaction sequence using methods familiar to a person skilled in the art.

Typical methods of preparing the compounds of the invention are described in the experimental section.

The potent inhibitory effect of the compounds of the invention can be determined by in vitro enzyme assays as described in the experimental section.

The compounds of the present invention may also be made by methods known in the art including those described below and including variations within the skill of the art.

Scheme 1:

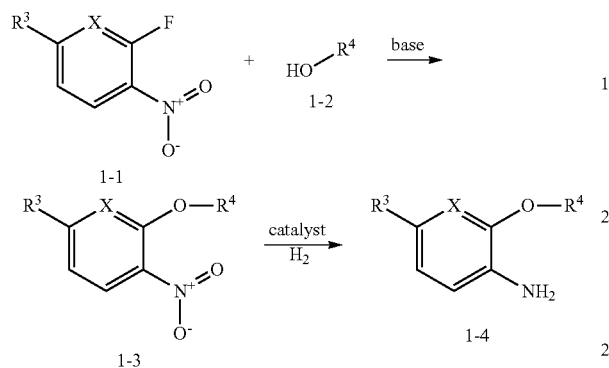

Compounds of the general formula 1-3, wherein X, $R^3$ and $R^4$ are as previously defined, can be prepared via the process outlined in Scheme 1 using a compound of the general formula 1-1, wherein X and $R^3$ are as previously defined, with an alcohol of the general formula 1-2, wherein $R^4$ is as previously defined, in presence of a base in appropriate solvents such as THF or DMF at a temperature between 0° C. and 150° C. As base sodium hydride or lithium hexamethyldisilazane may be used. Hydrogenation of a compound of the general formula 1-3, wherein X, $R^3$ and $R^4$ are as previously defined, in order to obtain a compound of the general formula 1-4, wherein X, $R^3$ and $R^4$ are as previously defined, may be achieved in the presence of hydrogen and a catalyst such as palladium or Raney nickel in an appropriate solvent. Hydrogen can be introduced as a gas or stem from a hydrogen source such as ammonium formate.

Scheme 2:

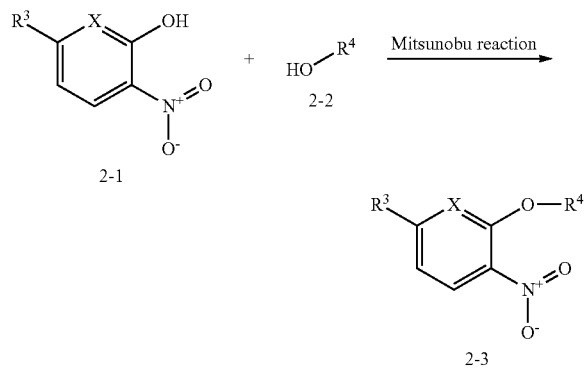

In Scheme 2 compounds of the general formula 2-3, wherein X, $R^3$ and $R^4$ are as previously defined, may be obtained by Mitsunobu reaction of a compound with the general formula 2-1, wherein X, $R^3$ are as previously defined, with an alcohol of the general formula 2-2, wherein $R^4$ is as previously defined, in the presence of triphenylphosphine and an dialkylazodicarboxylate such as diethylazodicarboxylate, diisopropylazodicarboxylate or di-tert.butylazodiacarboxylate in a solvent such as THF at temperatures between −10° C. and 80° C., preferably between 0° C. and 30° C.

Scheme 3:

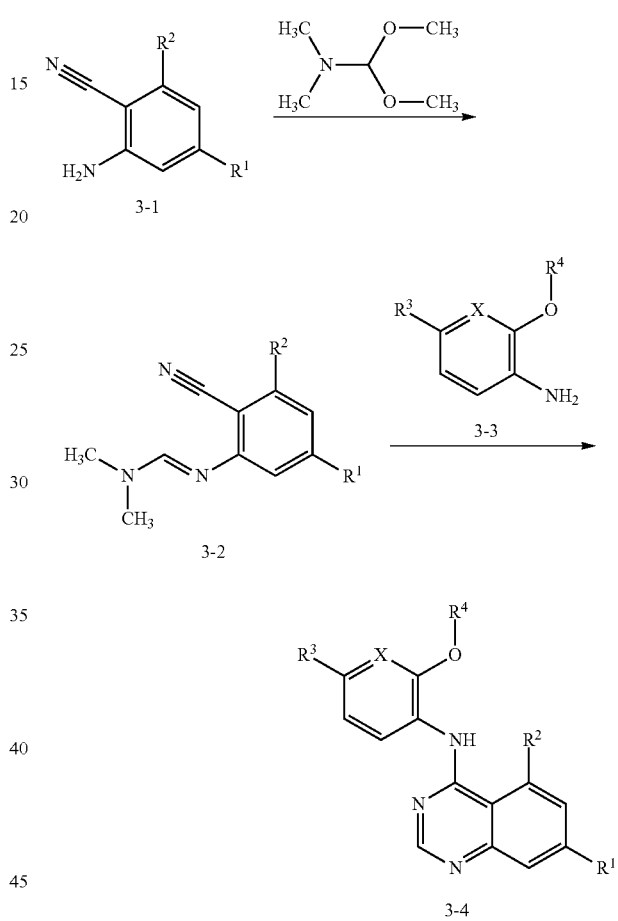

4,5,7-substituted quinazolines of the general formula 3-4, wherein X, $R^1$, $R^2$, $R^3$ and $R^4$ are as previously defined, may be prepared as shown in scheme 3. Substituted antranilonitriles of the general formula 3-1, wherein $R^1$ and $R^2$ are as previously defined, may react with N,N-dimethylformamide dimethyl acetal under reflux. The resulting formamidines of the general formula 3-2, wherein $R^1$ and $R^2$ are as previously defined, may be condensed with primary aromatic amines of the general formula 3-3, wherein X, $R^3$ and $R^4$ are as previously defined, in acetic acid (J. Med. Chem., 2010, 53 (7), 2892-2901). Dioxane can be used as cosolvent in this reaction.

The sulphoximine-substituent of the general formula 4-3, wherein $R^5$ and $R^6$ are as previously defined, may be introduced as shown in Scheme 4 by Pd or Cu-catalyzed coupling reactions from the corresponding boronic acid derivatives of the general formula 4-2, wherein $R^2$ is as previously defined.

Scheme 4:

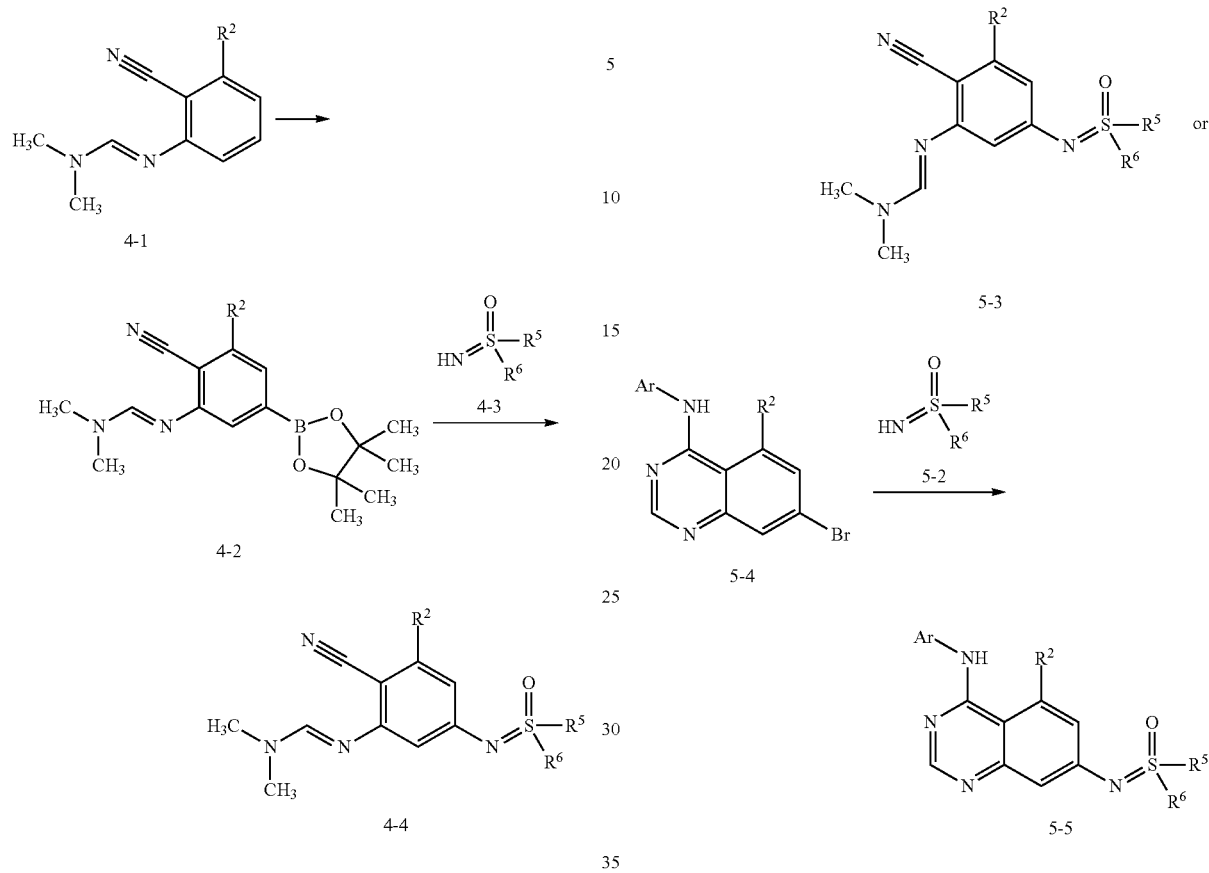

The boronic esters of the general formula 4-2, wherein $R^2$ is as previously defined, may be prepared using a Ir-catalyzed boronylation reaction (*Chem. Rev.,* 2010, 110 (2), 890-931) and coupled with the sulphoximine of the general formula 4-3, wherein $R^5$ and $R^6$ are as previously defined, under Cu-catalysis in a suitable solvent like MeOH (*Org. Lett.,* 2005, 7(13), 2667-2669).

The sulphoximine-substituent of the general formula 5-2, wherein $R^5$ and $R^6$ are as previously defined, may be introduced as shown in Scheme 5 by Pd or Cu-catalyzed coupling reactions from the corresponding bromo derivatives of the general formula 5-1 or 5-4, wherein Ar and $R^2$ are as previously defined.

For the palladium catalyzed coupling one of the following reaction conditions may be used Pd(OAc)$_2$, BINAP, Cs$_2$CO$_3$ in toluene as solvent (*J. Org. Chem.,* 2000, 65 (1), 169-175), or Pd$_2$dba$_3$, 2-(di-t-butylphosphino) biphenyl, NaO$^t$Bu in dioxane or DMF as solvent (cf. WO 2008/141843 A1).

In case the $R^2$-substituent of compounds of the general formula 6-2 or 6-4 in Scheme 6, wherein Ar, $R^2$, $R^5$ and $R^6$ are as previously defined, is linked via a nitrogen, oxygen or sulphur atom to the ring system, the corresponding substituent $R^2$ may be introduced by nucleophilic aromatic substitution from the aryl flouride of the general formula 6-1 or 6-3, wherein Ar, $R^5$ and $R^6$ are as previously defined, using a suitable base in an inert solvent like Cs$_2$CO$_3$ in dioxane or NaH, LiHMDS or DIPEA in NMP.

Scheme 5:

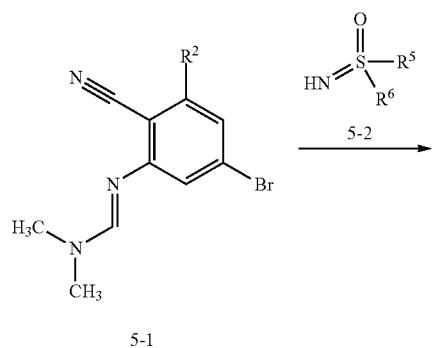

Scheme 6:

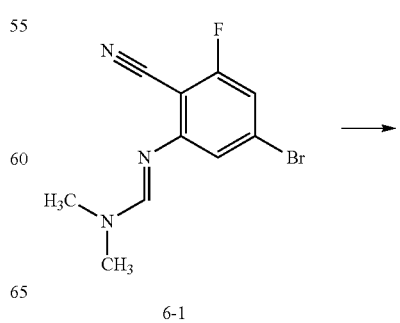

-continued

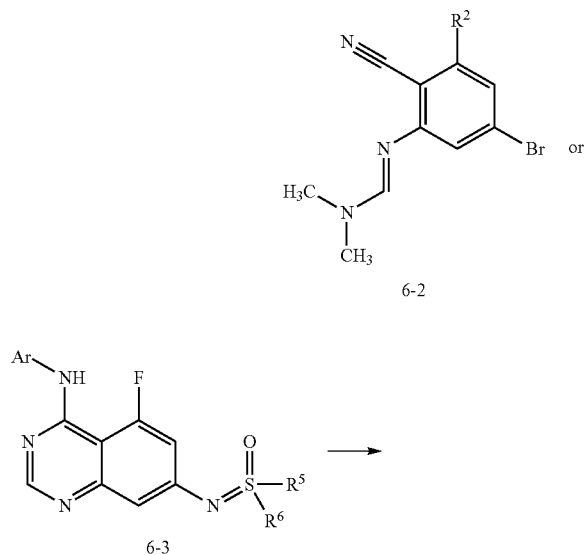

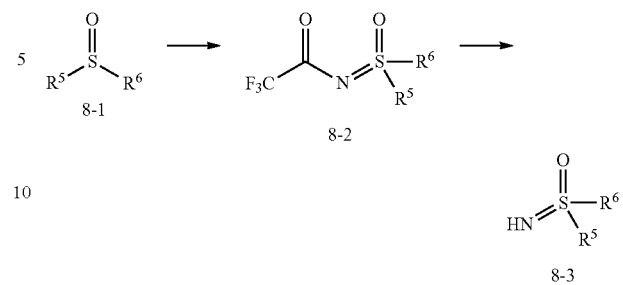

Sulfoximines of the general formula 8-3, wherein $R^5$ and $R^6$ are as previously defined, may be prepared by samponification of compounds of the general formula 8-2, wherein $R^5$ and $R^6$ are as previously defined (Org. Lett., 2004, 6 (8), 1305-1307). Alternatively, other suitable protecting groups and Iron as catalyst can be utilized (Org. Lett., 2006, 8 (11), 2349-2352).

In scheme 9 a general synthesis of sulfoximines of the general formula 9-5, wherein $R^5$ and $R^6$ are as previously defined, is described.

Scheme 9:

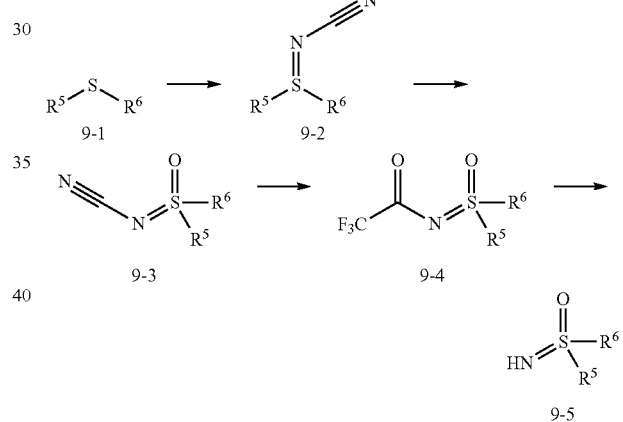

As shown in Scheme 7 the sulphoximines of the general formula 7-2, wherein $R^5$ and $R^6$ are as previously defined, may be prepared from the corresponding sulphoxides of the general formula 7-1, wherein $R^5$ and $R^6$ are as previously defined, by reaction with sodium azide and sulfuric acid ($H_2SO_4$). A suitable solvent like dichloromethane maybe used.

Scheme 7:

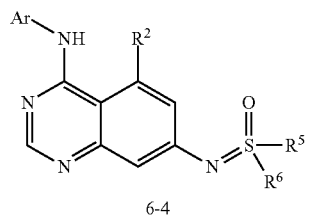

Alternatively, sulfoximines of the general formula 7-2, wherein $R^5$ and $R^6$ are as previously defined, may be prepared from the corresponding sulphoxides of the general formula 7-1, wherein $R^5$ and $R^6$ are as previously defined, by reaction with o-mesitylenesulphonylhydroxylamine (MSH) in presence of a suitable solvent like dichlormethane.

As shown in scheme 8 sulphoxides of the general formula 8-1, wherein $R^5$ and $R^6$ are as previously defined, may be react with trifluoracetamide in presence of $PhI(OAc)_2$, $Rh_2(OAc)_4$, and MgO in a suitable solvent like dichlormethane to form compounds of the general formula 8-2, wherein $R^5$ and $R^6$ are as previously defined.

Starting from the thioethers of the general formula 9-1, wherein $R^5$ and $R^6$ are as previously defined, the corresponding N-cyano sulfilimines of the general formula 9-2, wherein $R^5$ and $R^6$ are as previously defined, maybe be prepared by reaction with cyanamide in the presence of a base like NaO$^t$Bu or KO$^t$Bu and NBS or $I_2$ in a suitable solvent like methanol. The sulfilimines of the general formula 9-2, wherein $R^5$ and $R^6$ are as previously defined, are oxidized to the N-cyanosulfoximines of the general formula 9-3, wherein $R^5$ and $R^6$ are as previously defined. After removal of the N-cyano group the N-trifluoroacetylsulfoximines of the general formula 9-4, wherein $R^5$ and $R^6$ are as previously defined, may be obtained. After removal of the trifluoroacetyl moiety the NH-free sulfoximines of the general formula 9-5, wherein $R^5$ and $R^6$ are as previously defined, can be obtained (Org. Lett., 2007, 9 (19), 3809-3811).

TERMS AND DEFINITIONS

Terms not specifically defined herein should be given the meanings that would be given to them by one skilled in the art in light of the disclosure and the context. As used in the specification, however, unless specified to the contrary, the following terms have the meaning indicated and the following conventions are adhered to.

The terms "compound(s) according to this invention", "compound(s) of formula I", "compound(s) of the invention" and the like denote the compounds of the formula I according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "mediated" or "mediating" or "mediate", as used herein, unless otherwise indicated, refers to the (i) treatment, including prevention of the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk may be used in sub-formulas to indicate the bond which is connected to the core molecule as defined.

The numeration of the atoms of a substituent starts with the atom which is closest to the core or the group to which the substituent is attached.

For example, the term "3-carboxypropyl-group" represents the following substituent:

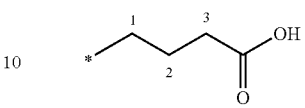

wherein the carboxy group is attached to the third carbon atom of the propyl group. The terms "1-methylpropyl-", "2,2-dimethylpropyl-" or "cyclopropylmethyl-" group represent the following groups:

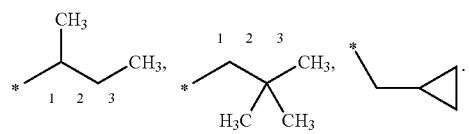

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$" or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

Unless specifically indicated, throughout the specification and the appended claims, a given chemical formula or name shall encompass tautomers and all stereo-, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making pharmaceutically acceptable acid or base salts thereof.

Salts of acids which are useful, for example, for purifying or isolating the compounds of the present invention are also part of the invention.

The term halogen generally denotes fluorine, chlorine, bromine and iodine.

The term "$C_{1-n}$-alkyl", wherein n is an integer from 2 to n, either alone or in combination with another radical denotes an acyclic, saturated, branched or linear hydrocarbon radical with 1 to n C atoms. For example, the term $C_{1-5}$-alkyl embraces the radicals H$_3$C—, H$_3$C—CH$_2$—, H$_3$C—CH$_2$—CH$_2$—, H$_3$C—CH(CH$_3$)—, H$_3$C—CH$_2$—CH$_2$—CH$_2$—, H$_3$C—CH$_2$—CH(CH$_3$)—, H$_3$C—CH(CH$_3$)—CH$_2$—, H$_3$C—C(CH$_3$)$_2$—, H$_3$C—CH$_2$—CH$_2$—CH$_2$—CH$_2$—, H$_3$C—CH$_2$—CH$_2$—CH(CH$_3$)—, H$_3$C—CH$_2$—CH(CH$_3$)—CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "$C_{1-n}$-alkylene" wherein n is an integer from 2 to n, either alone or in combination with another radical, denotes an acyclic, straight-chain or branched divalent alkyl radical containing from 1 to n carbon atoms. For example, the term $C_{1-4}$-alkylene includes —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_3$))—, —(CHCH(CH$_3$)$_2$)— and —C(CH$_3$)(CH$_2$CH$_3$)—.

The term "$C_{2-n}$-alkenyl", is used for a group as defined in the definition for "$C_{1-n}$-alkyl" with at least two carbon atoms, if at least two of those carbon atoms of said group are bonded to each other by a double bond. For example the term $C_{2-3}$-alkenyl includes —CH=CH$_2$, —CH=CH—CH$_3$, —CH$_2$—CH=CH$_2$.

The term "$C_{2-n}$-alkenylene" is used for a group as defined in the definition for "$C_{1-n}$-alkylene" with at least two carbon atoms, if at least two of those carbon atoms of said group are bonded to each other by a double bond. For example the term $C_{2-3}$-alkenylene includes —CH=CH—, —CH=CH—CH$_2$—, —CH$_2$—CH=CH—.

The term "$C_{2-n}$-alkynyl", is used for a group as defined in the definition for "$C_{1-n}$-alkyl" with at least two carbon atoms, if at least two of those carbon atoms of said group are bonded to each other by a triple bond. For example the term $C_{2-3}$-alkynyl includes —C≡CH, —C≡C—CH$_3$, —CH$_2$—C≡CH.

The term "$C_{2-n}$-alkynylene" is used for a group as defined in the definition for "$C_{1-n}$-alkylene" with at least two carbon atoms, if at least two of those carbon atoms of said group are bonded to each other by a triple bond. For example the term $C_{2-3}$-alkynylene includes —C≡C—, —C≡C—CH$_2$—, —CH$_2$—C≡C—.

The term "$C_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term $C_{3-10}$-carbocyclyl includes $C_{3-10}$-cycloalkyl, $C_{3-10}$-cycloalkenyl, octahydropentalenyl, octahydroindenyl, decahydronaphthyl, indanyl, tetrahydronaphthyl. Most preferably the term $C_{3-n}$-carbocyclyl denotes $C_{3-n}$-cycloalkyl, in particular $C_{3-7}$-cycloalkyl.

The term "$C_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclo-pentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term bicyclic includes spirocyclic.

The term "$C_{3-n}$-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term $C_{3-7}$-cycloalkenyl includes cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

The term "heterocyclyl" means a saturated or unsaturated mono-, bi-, tri- or spirocarbocyclic, preferably mono-, bi- or spirocyclic-ring system containing one or more heteroatoms selected from N, O or S(O)$_r$ with r=0, 1 or 2, which in addition may have a carbonyl group. More preferably the term "heterocyclyl" as used herein, either alone or in combination with another radical, means a saturated or unsaturated, even more preferably a saturated mono-, bi- or spirocyclic-ring system containing 1, 2, 3 or 4 heteroatoms selected from N, O or S(O)$_r$ with r=0, 1 or 2 which in addition may have a carbonyl group. The term "heterocyclyl" is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl and morpholinonyl.

Thus, the term "heterocyclyl" includes the following exemplary structures which are not depicted as radicals as each form may be attached through a covalent bond to any atom so long as appropriate valences are maintained:

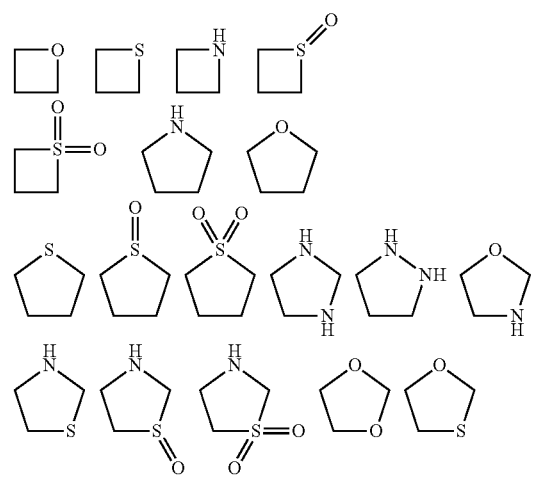

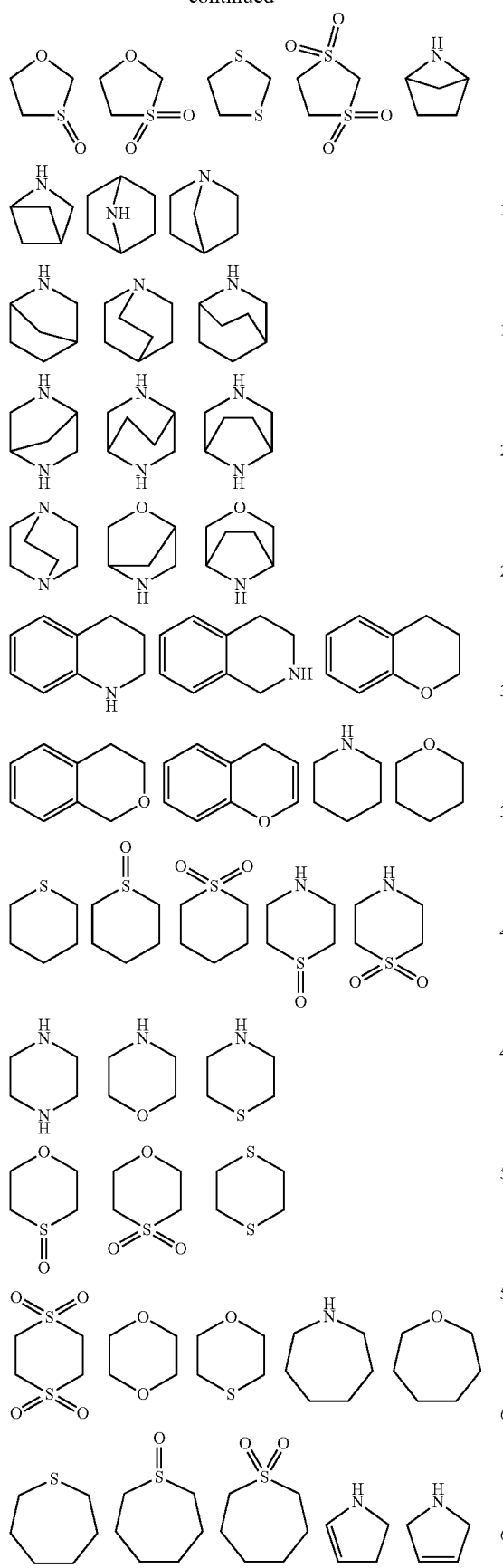
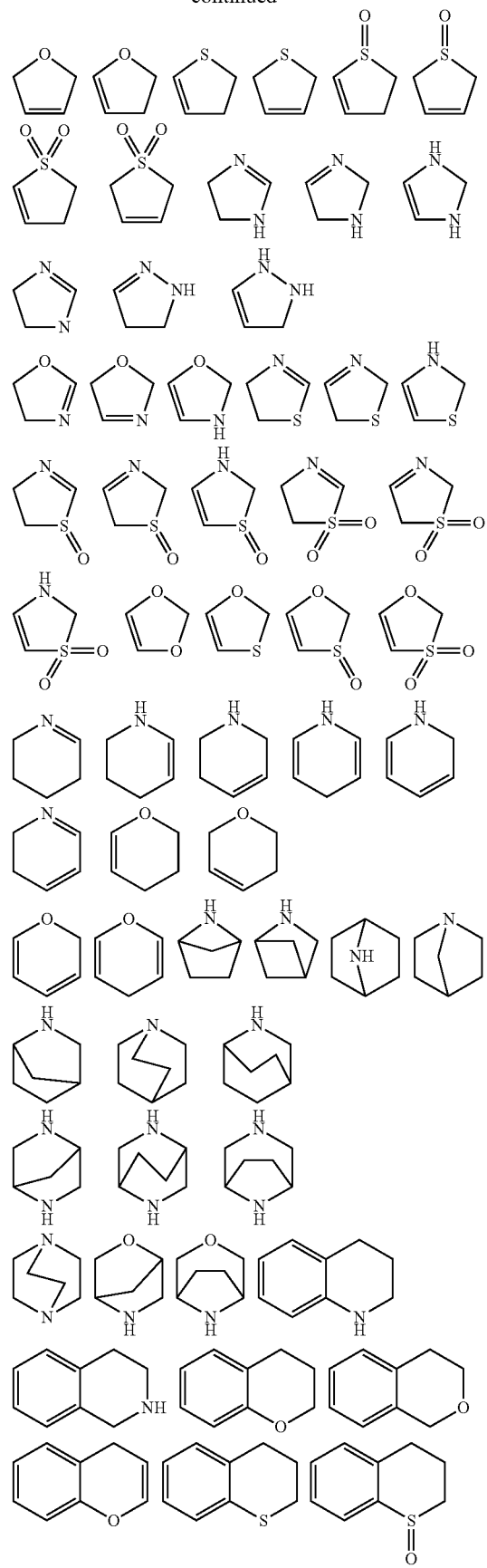

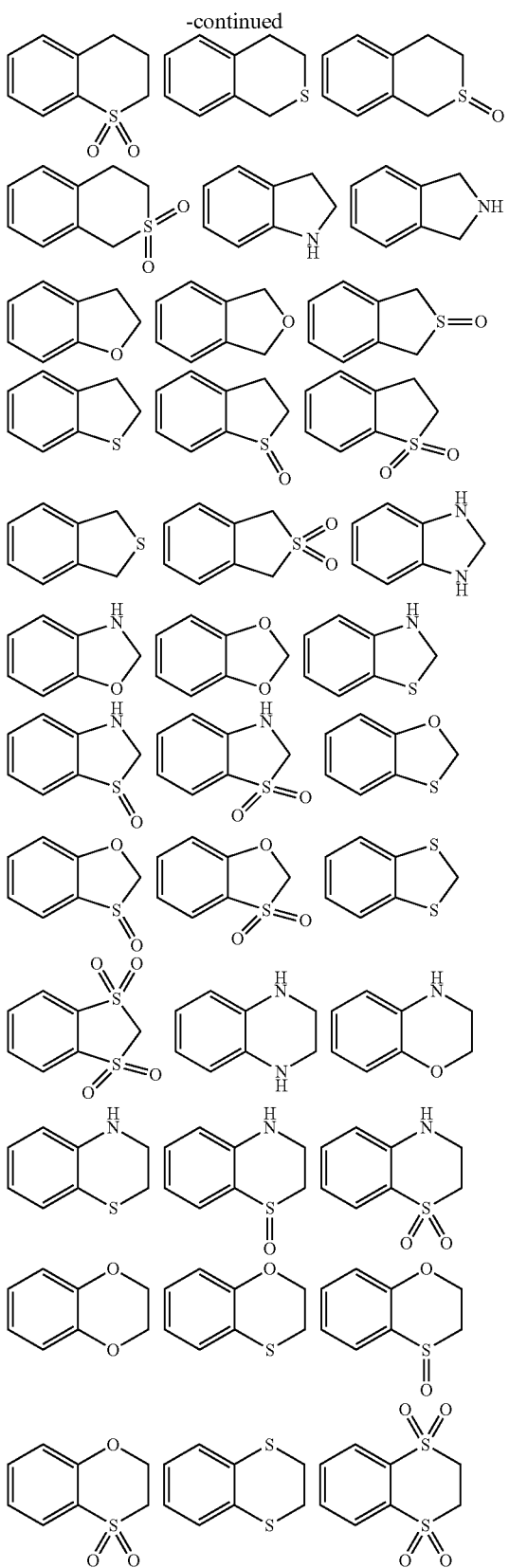

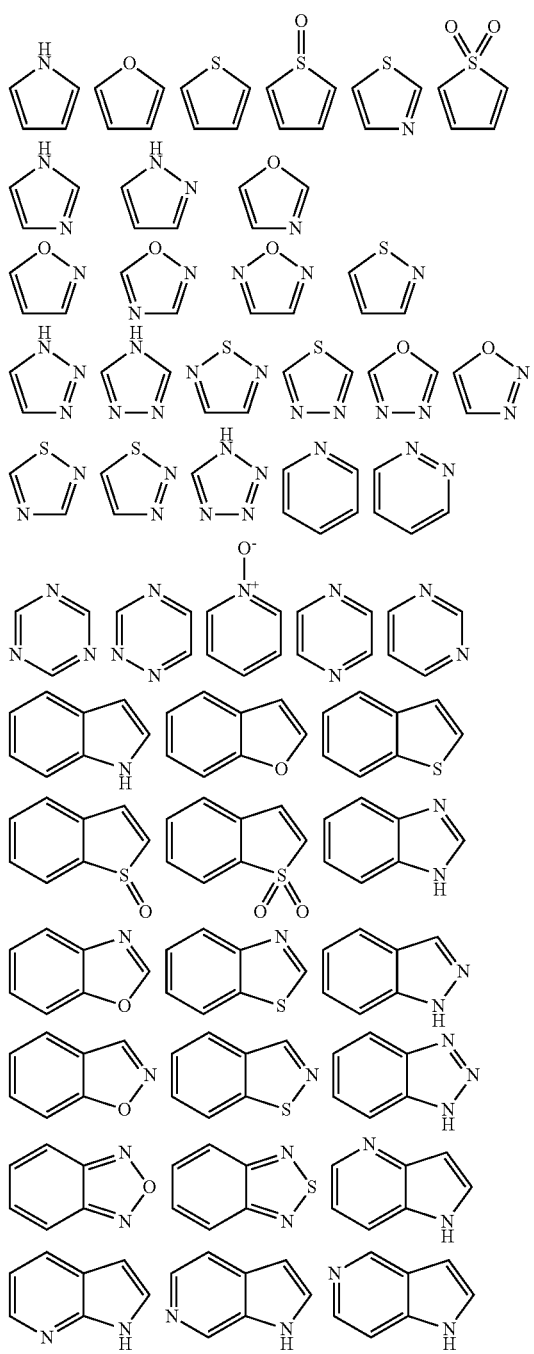

The term "heteroaryl" means a mono- or polycyclic, preferably mono- or bicyclic ring system containing one or more heteroatoms selected from N, O or S(O)$_r$ with r=0, 1 or 2 wherein at least one of the heteroatoms is part of an aromatic ring, and wherein said ring system may have a carbonyl group. More preferably the term "heteroaryl" as used herein, either alone or in combination with another radical, means a mono- or bicyclic ring system containing 1, 2, 3 or 4 heteroatoms selected from N, O or S(O)$_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

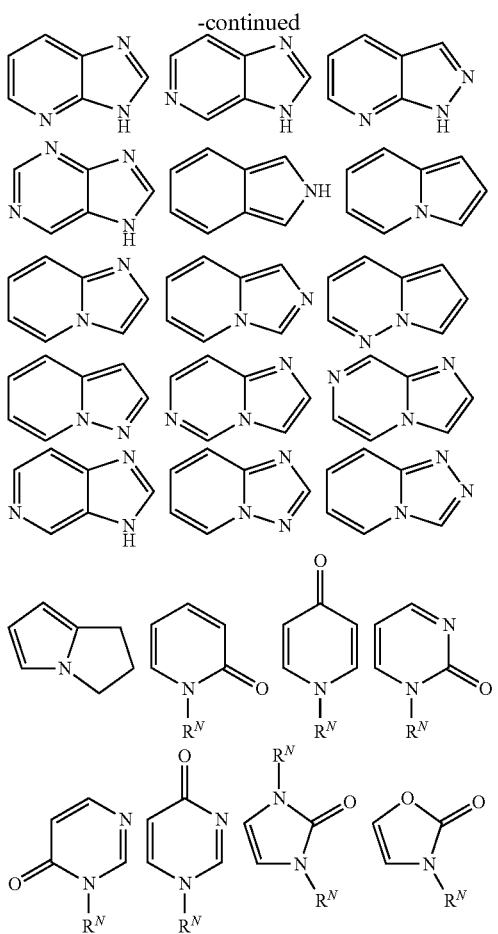

$R^N$=H or residue attached via a C atom

Many of the terms given above may be used repeatedly in the definition of a formula or group and in each case have one of the meanings given above, independently of one another.

Pharmacological Activity

The biological activity of compounds was determined by the following methods:

A. MNK2a In Vitro Kinase Assay (Assay 1)

The MNK2a in vitro kinase assay is described in detail in WO 2011/104340.

ASSAY SETUP: The inhibition of kinase activity of MNK2a was assessed using pre-activated GST-MNK2a. The kinase reaction contains 24 µM substrate peptide (NH$_2$-TATKSGSTTKNR-CONH$_2$ (SEQ ID NO: 1), differing from Seq. ID No. 5 of WO 2011/104340 by the C-terminal-CONH$_2$ group), 20 µM ATP, 14 nM ligand and 2 nM pre-activated MNK2a. The reaction buffer conditions are 16 mM HEPES/KOH pH 7.4, 8 mM MgCl$_2$, 0.4 mM DTT, 0.08% (w/v) bovine serum albumin (BSA, Sigma, Germany, cat. no. A3059), 0.008% (w/v) Pluronic F127 (Sigma, Germany, cat. no. P2443), 3% (v/v) DMSO (Applichem, Germany, cat. no. A3006). The kinase reaction is at room temperature for 60 min. The kinase reaction is terminated by addition of 0.67 reaction volumes of 1 µM antibody in 20 mM HEPES/KOH pH 7.4, 50 mM ethylenediaminetetraacetic acid, disodium salt (EDTA, Sigma, Germany, cat. no. E5134), 0.5 mM DTT, 0.05% (w/v) polyoxyethylenesorbitan monolaureate (Tween 20, Sigma, Germany, cat. no. P7949). After 1 h equilibration time at room temperature, samples are subjected to fluorescence polarization measurement. The fluorescence polarization readout was generated on an Envision multimode reader (PerkinElmer) equipped with a FP Dual Emission filter and mirror set (PerkinElmer 2100-4260). Excitation filter 620 nm, S and P polarized emission filters 688 nM.

B. MNK2a In Vitro Kinase Assay (Assay 2) ASSAY SETUP: The inhibition of kinase activity of MNK2a was assessed using pre-activated GST-MNK2a. The white, 384-well OptiPlate F plates were purchased from PerkinElmer. The ADP-Glo Kinase Assay (including ultra pure ATP) was purchased from Promega (V9103). Activated MNK2a was obtained as described in WO2011/104340. The unlabeled eIF4E peptide (NH$_2$-TATKSGSTTKNR-CONH$_2$ (SEQ ID NO: 1)), differing from Seq. ID No. 5 of WO 2011/104340 by the C-terminal CONH$_2$ group, was purchased from Thermo Fisher Scientific. All other materials were of highest grade commercially available. Compounds are tested in either serial dilutions or single dose concentrations. The compound stock solutions are 10 mM in 100% DMSO The serial compound dilutions are prepared in 100% DMSO followed by 1:27.3 intermediate dilution in assay buffer. The final DMSO concentration in assay will be <3%.

In the 384-well plates 3 µl of test compound from the intermediate dilution is mixed with 4 µl of the activated MNK2 enzyme (final concentration of 10 nM) and 4 µl of the peptide (final concentration of 25 µM)/ultra pure ATP (final concentration of 20 µM), all dissolved in assay buffer. This step is followed by an incubation time of 90 min, then 10 µl of ADP Glo reagent are added, followed by 40 min of incubation. Then 20 µl of kinase detection reagent are admixed. The plates are sealed and after an incubation period of 30 min, the luminescence signal is measured in an Envision reader to determine the amount of produced ADP. All incubation steps are performed at room temperature. The assay buffer consists of 20 mM HEPES, 2 mM DTT, 0.01% BSA, 20 mM MgCl$_2$ and 0.1% Pluronic F-127.

Each assay microtiter plate contains wells with vehicle controls instead of compound (1% DMSO in water) as reference for the high signal (100% CTL, high signal), and wells containing a potent MNK2 inhibitor (final 20 µM, 1% DMSO) as reference for low signal (0% CTL, low signal).

The luminescent signal generated is proportional to the ADP concentration produced and is correlated with activated MNK2 activity. The analysis of the data is performed by the calculation of the percentage of ATP consumption of activated MNK2 in the presence of the test compound compared to the consumption of ATP in the presence of activated MNK2 without compound.

(RLU(sample)−RLU(low control))*100/(RLU(high value)−RLU(low control))[RLU=relative luminescence units]

An inhibitor of the MNK2 enzyme will give values between 100% CTL (no inhibition) and 0% CTL (complete inhibition). Values of more than 100% CTL are normally related to compound/sample specific physico-chemical properties (e.g. solubility, light absorbance, fluorescence).

IC50 values based on dose response curves are calculated with the AssayExplorer software.

C. MNK1 In Vitro Kinase Assay (Assay 3)

MNK1 Data can be obtained from the MNK1 Z'-LYTE® assay. The MNK1 Z'-LYTE® screening protocol and assay conditions are also described on www.invitrogen.com.

The assay is described as follows:

The Z'-LYTE® biochemical assay employs a fluorescence-based, coupled-enzyme format and is based on the differential sensitivity of phosphorylated and non-phosphorylated peptides to proteolytic cleavage. The peptide substrate is labeled with two fluorophores—one at each end—that make up a FRET pair.

In the primary reaction, the kinase transfers the gamma-phosphate of ATP to a single tyrosine, serine or threonine residue in a synthetic FRET-peptide. In the secondary reaction, a site-specific protease recognizes and cleaves non-phosphorylated FRET-peptides. Phosphorylation of FRET-peptides suppresses cleavage by the Development Reagent. Cleavage disrupts FRET between the donor (i.e., coumarin) and acceptor (i.e., fluorescein) fluorophores on the FRET-peptide, whereas uncleaved, phosphorylated FRET-peptides maintain FRET. A ratiometric method, which calculates the ratio (the Emission Ratio) of donor emission to acceptor emission after excitation of the donor fluorophore at 400 nm, is used to quantitate reaction progress, as shown in the equation below.

$$\text{Emission Ratio} = \text{Coumarin Emission (445 nm)} / \text{Fluorescein Emission (520 nm)}$$

ASSAY SETUP: The inhibition of kinase activity of MNK1a was assessed using pre-activated GST-MNK1a. The 2×MKNK1 (MNK1) mixture is prepared in 50 mM HEPES pH 7.5, 0.01% BRIJ-35, 10 mM $MgCl_2$, 4 mM $MnCl_2$, 1 mM EGTA, 2 mM DTT. The final 10 µL Kinase Reaction consists of 13.5-54 ng MKNK1 (MNK1) and 2 µM Ser/Thr 07 in 50 mM HEPES pH 7.5, 0.01% BRIJ-35, 10 mM $MgCl_2$, 2 mM $MnCl_2$, 1 mM EGTA, 1 mM DTT. After the 1 hour Kinase Reaction incubation, 5 µL of a 1:32768 dilution of Development Reagent A is added.

Assay Conditions
Test Compounds:
The Test Compounds are screened in 1% DMSO (final) in the well.
Peptide/Kinase Mixtures:
All Peptide/Kinase Mixtures are diluted to a 2× working concentration in the MNK1 Kinase Buffer.
ATP Solution:
All ATP Solutions are diluted to a 4× working concentration in Kinase Buffer (50 mM HEPES pH 7.5, 0.01% BRIJ-35, 10 mM $MgCl_2$, 1 mM EGTA).
Development Reagent Solution:
The Development Reagent is diluted in Development Buffer
Assay Protocol:
Bar-coded Corning, low volume NBS, 384-well plate (Corning Cat. #3676)
1. 2.5 µL—4× Test Compound
2. 5 µL—2× Peptide/Kinase Mixture
3. 2.5 µL—4×ATP Solution
4. 30-second plate shake
5. 60-minute Kinase Reaction incubation at room temperature
6. 5 µL—Development Reagent Solution
7. 30-second plate shake
8. 60-minute Development Reaction incubation at room temperature
9. Read on fluorescence plate reader and analyze the data
Data Analysis
The following equations are used for each set of data points:
Correction for Background Fluorescence: $FI_{Sample} - FI_{TCFl\ Ctl}$
Emission Ratio (using values corrected for background fluorescence):Coumarin
Emission (445 nm)/Fluorescein Emission (520 nm)

% Phosphorylation (% Phos):

$$1 - ((\text{Emission Ratio} \times F_{100\%}) - C_{100\%}) / ((C_{0\%} - C_{100\%}) + [\text{Emission Ratio} \times (F_{100\%} - F_{0\%})]) * 100\%$$

% Inhibition:

$$1 - (\%\ \text{Phos}_{Sample} / \%\ \text{Phos}_{0\%\ Inhibition\ Ctl}) * 100$$

FI=Fluorescence Intensity
$C_{100\%}$=Average Coumarin emission signal of the 100% Phos. Control
$C_{0\%}$=Average Coumarin emission signal of the 0% Phos. Control
$F_{100\%}$=Average Fluorescein emission signal of the 100% Phos. Control
$F_{0\%}$=Average Fluorescein emission signal of the 0% Phos. Control
Graphing Software
SelectScreen® Kinase Profiling Service uses XLfit from IDBS. The dose response curve is curve fit to model number 205 (sigmoidal dose-response model). If the bottom of the curve does not fit between −20% & 20% inhibition, it is set to 0% inhibition. If the top of the curve does not fit between 70% and 130% inhibition, it is set to 100% inhibition.

The activity of MNK proteins can be assayed also by other in vitro kinase assay formats. For example, suitable kinase assays have been described in the literature in Knauf et al., Mol Cell Biol. 2001 August; 21(16):5500-11 or in Scheper et al., Mol Cell Biol. 2001 February; 21(3):743-54. In general, MNK kinase assays can be performed such that a MNK substrate such as a protein or a peptide, which may or may not include modifications as further described below, or others are phosphorylated by MNK proteins having enzymatic activity in vitro. The activity of a candidate agent can then be determined via its ability to decrease the enzymatic activity of the MNK protein. The kinase activity may be detected by change of the chemical, physical or immunological properties of the substrate due to phosphorylation.

In one example, the kinase substrate may have features, designed or endogenous, to facilitate its binding or detection in order to generate a signal that is suitable for the analysis of the substrates phosphorylation status. These features may be, but are not limited to, a biotin molecule or derivative thereof, a glutathione-S-transferase moiety, a moiety of six or more consecutive histidine residues (SEQ ID NO: 2), an amino acid sequence or hapten to function as an epitope tag, a fluorochrome, an enzyme or enzyme fragment. The kinase substrate may be linked to these or other features with a molecular spacer arm to avoid steric hindrance.

In another example the kinase substrate may be labelled with a fluorophore. The binding of the reagent to the labelled substrate in solution may be followed by the technique of fluorescence polarization as it is described in the literature. In a variation of this example, a fluorescent tracer molecule may compete with the substrate for the analyte to detect kinase activity by a technique which is know to those skilled in the art as indirect fluorescence polarization.

In yet another example, radioactive gamma-ATP is used in the kinase reaction, and the effect of the test agent on the incorporation of radioactive phosphate in the test substrate is determined relative to control conditions.

It has been shown that the compounds of the invention exhibit low $IC_{50}$ values in in vitro biological screening assays for inhibition of MNK 1 and/or MNK 2 kinase activity. The following table contains the test results for exemplary compounds.

E. Biological Data

TABLE 1

Biological data of the compounds of the present invention as obtained in assay 2.

| Example | MNK2 IC50 [nM] |
|---|---|
| 1.001 | 17 nM |
| 1.002 | 6 nM |
| 1.003 | 1 nM |
| 1.004 | 3 nM |
| 1.005 | 2 nM |
| 1.006 | 5 nM |
| 1.007 | 8 nM |
| 1.008 | 8 nM |
| 1.009 | 26 nM |
| 1.010 | 17 nM |
| 1.011 | 2 nM |
| 1.012 | 6 nM |
| 1.013 | 2 nM |
| 1.014 | 5 nM |
| 1.015 | 54 nM |
| 1.016 | 1 nM |
| 1.017 | 12 nM |
| 1.018 | 6 nM |
| 1.019 | 1 nM |
| 1.020 | 7 nM |
| 1.021 | 1 nM |
| 1.022 | 3 nM |
| 1.023 | 8 nM |
| 2.001 | 5 nM |
| 2.002 | 6 nM |
| 2.003 | 13 nM |
| 2.004 | 6 nM |
| 2.005 | 1 nM |
| 2.006 | 2 nM |
| 2.007 | 3 nM |
| 2.008 | 1 nM |
| 2.009 | 1 nM |
| 2.010 | 11 nM |
| 2.011 | 2 nM |
| 2.012 | 28 nM |
| 2.013 | 2 nM |
| 2.014 | 2 nM |
| 2.015 | 190 nM |
| 2.016 | 1 nM |
| 2.017 | 2 nM |
| 2.018 | 1 nM |
| 2.019 | 1 nM |
| 2.020 | 3 nM |
| 2.021 | 2 nM |
| 2.022 | 2 nM |
| 2.023 | 2 nM |
| 2.024 | 3 nM |
| 2.025 | 7 nM |
| 2.026 | 1 nM |
| 2.028 | 3 nM |
| 2.029 | 4 nM |
| 2.030 | 4 nM |
| 2.031 | 10 nM |
| 2.032 | 1 nM |
| 2.033 | 4 nM |
| 2.034 | 1 nM |
| 2.035 | 2 nM |
| 2.036 | 4 nM |
| 2.037 | 2 nM |
| 2.038 | 3 nM |
| 2.039 | 3 nM |
| 2.040 | 18 nM |
| 2.041 | 1 nM |
| 2.042 | 5 nM |
| 2.043 | 2 nM |
| 2.044 | 1 nM |
| 2.045 | 1 nM |
| 2.046 | 3 nM |
| 2.047 | 3 nM |
| 2.048 | 2 nM |
| 3.001 | 2 nM |
| 3.002 | 8 nM |
| 3.003 | 2 nM |
| 3.004 | 17 nM |
| 3.005 | 1 nM |
| 3.006 | 1 nM |
| 3.007 | 9 nM |
| 3.008 | 5 nM |
| 3.009 | 7 nM |
| 3.010 | 23 nM |
| 3.011 | 2 nM |
| 3.012 | 23 nM |
| 3.013 | 8 nM |
| 3.014 | 8 nM |
| 3.015 | 3 nM |
| 3.016 | 2 nM |
| 3.017 | 138 |
| 3.018 | 1 nM |
| 3.019 | 24 nM |
| 3.020 | n.D. |
| 3.021 | 2 nM |
| 3.022 | 2 nM |
| 3.023 | 42 nM |
| 3.024 | 16 nM |
| 3.025 | n.D. |
| 3.026 | 4 nM |
| 3.027 | 2 nM |
| 3.028 | 6 nM |
| 3.029 | 17 nM |
| 3.030 | 8 nM |
| 3.031 | 5 nM |
| 3.032 | 16 nM |
| 3.033 | 2 nM |
| 3.034 | 58 nM |
| 3.035 | 37 nM |
| 3.036 | 9 nM |
| 3.037 | 3 nM |
| 3.038 | 2 nM |
| 3.039 | 1 nM |
| 3.040 | 6 nM |
| 3.041 | 33 nM |
| 3.042 | 15 nM |
| 3.043 | 5 nM |
| 3.044 | 63 nM |
| 3.045 | 10 nM |
| 3.046 | 2 nM |
| 3.047 | 1 nM |
| 3.048 | 11 nM |
| 3.049 | 2 nM |
| 3.050 | 32 nM |
| 3.051 | 3 nM |
| 3.052 | 3 nM |
| 3.053 | 2 nM |
| 3.054 | 1 nM |
| 3.055 | 3 nM |
| 4.001 | 5 nM |
| 4.002 | 5 nM |
| 4.003 | 2 nM |
| 4.004 | 6 nM |
| 4.005 | 28 nM |
| 4.006 | 5 nM |
| 4.007 | 2 nM |
| 4.008 | 2 nM |
| 4.009 | 2 nM |
| 4.010 | 4 nM |
| 4.011 | 24 nM |
| 4.012 | 34 nM |
| 4.013 | 5 nM |
| 4.014 | 3 nM |
| 4.015 | 2 nM |
| 4.016 | 20 nM |
| 4.017 | 9 nM |
| 4.018 | 4 nM |

TABLE 1-continued

Biological data of the compounds of the present invention as obtained in assay 2.

| Example | MNK2 IC50 [nM] |
|---|---|
| 4.019 | 6 nM |
| 4.020 | 4 nM |
| 4.021 | 12 nM |
| 4.022 | 10 nM |
| 4.023 | 5 nM |
| 4.024 | 3 nM |
| 4.025 | 3 nM |
| 4.026 | 3 nM |
| 4.027 | 1 nM |
| 4.028 | 4 nM |
| 4.029 | 3 nM |
| 4.030 | 11 nM |
| 4.031 | 8 nM |
| 4.032 | 56 nM |
| 4.033 | 2 nM |
| 4.034 | 3 nM |
| 4.035 | 66 nM |
| 4.036 | 1 nM |
| 4.037 | 28 nM |
| 4.038 | 27 nM |
| 4.039 | 1 nM |
| 4.040 | 2 nM |
| 4.041 | 7 nM |
| 4.042 | 1 nM |
| 4.043 | 2 nM |
| 4.044 | 3 nM |
| 4.045 | 3 nM |
| 4.046 | 15 nM |
| 4.047 | 5 nM |
| 4.048 | 2 nM |
| 4.049 | 19 nM |
| 4.050 | 1 nM |
| 4.051 | 5 nM |
| 4.052 | 3 nM |
| 4.053 | 16 nM |
| 4.054 | 9 nM |
| 4.055 | 14 nM |
| 4.056 | 25 nM |
| 4.057 | 2 nM |
| 4.058 | 3 nM |
| 4.059 | 4 nM |
| 4.060 | 2 nM |
| 4.061 | 13 nM |
| 4.062 | 13 nM |
| 4.063 | 10 nM |
| 4.064 | 8 nM |
| 4.065 | 9 nM |
| 4.066 | 9 nM |
| 4.067 | 3 nM |
| 4.068 | 4 nM |
| 4.069 | 6 nM |
| 4.070 | 7 nM |
| 4.071 | 1 nM |
| 4.072 | 3 nM |
| 4.073 | 13 nM |
| 4.074 | 1 nM |
| 4.075 | 9 nM |
| 4.076 | 4 nM |
| 4.077 | 2 nM |
| 4.078 | 2 nM |
| 4.079 | 1 nM |
| 4.080 | 2 nM |
| 4.081 | 2 nM |
| 4.082 | 2 nM |
| 4.083 | 8 nM |
| 4.084 | 2 nM |
| 4.085 | 2 nM |
| 4.086 | 2 nM |
| 4.087 | 2 nM |
| 4.088 | 2 nM |
| 4.089 | 1 nM |
| 4.090 | 1 nM |
| 4.091 | 1 nM |
| 4.092 | 2 nM |
| 4.093 | 1 nM |
| 4.094 | 1 nM |
| 4.095 | 2 nM |
| 4.096 | 1 nM |
| 4.097 | 1 nM |
| 4.098 | 4 nM |
| 4.099 | 2 nM |
| 4.100 | 2 nM |
| 4.101 | 3 nM |
| 4.102 | 2 nM |
| 4.103 | 1 nM |
| 4.104 | 1 nM |
| 4.105 | 2 nM |
| 4.106 | 2 nM |
| 4.107 | 2 nM |
| 4.108 | 2 nM |
| 4.109 | 2 nM |
| 4.110 | 2 nM |
| 4.111 | 1 nM |
| 4.112 | 2 nM |
| 4.113 | 1 nM |
| 4.114 | 5 nM |
| 4.115 | 2 nM |
| 4.116 | 2 nM |
| 4.117 | 3 nM |
| 4.118 | 3 nM |
| 4.119 | 2 nM |
| 4.120 | 2 nM |
| 4.121 | 5 nM |
| 4.122 | 1 nM |
| 4.123 | 3 nM |
| 4.124 | 1 nM |
| 4.125 | 1 nM |
| 4.126 | 2 nM |
| 4.127 | 2 nM |
| 4.128 | 2 nM |
| 4.129 | 2 nM |
| 4.130 | 3 nM |
| 4.131 | 1 nM |
| 4.132 | 1 nM |
| 4.133 | 4 nM |
| 4.134 | 3 nM |
| 4.135 | 2 nM |
| 4.136 | 1 nM |
| 4.137 | 1 nM |
| 4.138 | 1 nM |
| 4.139 | 1 nM |
| 4.140 | 1 nM |
| 4.141 | 1 nM |
| 4.142 | 2 nM |
| 4.143 | 2 nM |
| 4.144 | 2 nM |
| 4.145 | 2 nM |
| 4.146 | 4 nM |
| 4.147 | 3 nM |
| 5.001 | 1 nM |
| 5.002 | 7 nM |
| 5.003 | 83 nM |
| 5.004 | 2 nM |
| 5.005 | 2 nM |
| 5.006 | 29 nM |
| 5.007 | 4 nM |
| 5.008 | 2 nM |
| 5.009 | 35 nM |
| 5.010 | 28 nM |
| 5.011 | 99 nM |
| 5.012 | 56 nM |
| 5.013 | 2 nM |
| 6.001 | 5 nM |
| 6.002 | 2 nM |
| 6.003 | 4 nM |
| 6.004 | 3 nM |

TABLE 1-continued

Biological data of the compounds of the present invention as obtained in assay 2.

| Example | MNK2 IC50 [nM] |
|---|---|
| 7.001 | 1 nM |
| 7.002 | 6 nM |
| 7.003 | 2 nM |
| 7.004 | 67 nM |
| 7.005 | 3 nM |
| 7.006 | 3 nM |
| 7.007 | 10 nM |
| 7.008 | 3 nM |
| 7.009 | 3 nM |
| 7.010 | 2 nM |
| 7.011 | 3 nM |
| 7.012 | 46 nM |
| 7.013 | 4 nM |

TABLE 2

Biological data of selected compounds of the present invention as obtained in assay 3.

| # | MNK1 IC50 [nM] |
|---|---|
| 1.011 | 34 nM |
| 1.016 | 53 nM |
| 1.019 | 54 nM |
| 2.001 | 228 nM |
| 2.006 | 71 nM |
| 2.008 | 25 nM |
| 2.009 | 49 nM |
| 2.018 | 34 nM |
| 2.048 | 40 nM |
| 3.001 | 60 nM |
| 3.031 | 75 nM |
| 3.039 | 77 nM |
| 3.049 | 68 nM |
| 3.054 | 51 nM |
| 4.034 | 51 nM |
| 4.058 | 75 nM |
| 4.071 | 55 nM |
| 4.074 | 38 nM |
| 4.088 | 36 nM |
| 4.100 | 14 nM |
| 4.118 | 21 nM |
| 4.136 | 29 nM |
| 4.138 | 27 nM |
| 5.004 | 66 nM |
| 5.008 | 39 nM |
| 7.006 | 164 nM |
| 7.009 | 50 nM |
| 7.010 | 40 nM |

TABLE 3

% Inhibition of MNK1 at a compound concentration of 1 μM as obtained in assay 3

| # | MNK1 % INH |
|---|---|
| 1.002 | 59 |
| 1.003 | 95 |
| 1.004 | 79 |
| 1.005 | 98 |
| 1.006 | 96 |
| 1.008 | 63 |
| 1.009 | 64 |
| 1.012 | 96 |
| 1.014 | 97 |
| 1.015 | 100 |
| 1.018 | 93 |
| 1.020 | 80 |
| 1.021 | 52 |
| 1.022 | 79 |
| 1.023 | 65 |
| 2.002 | 94 |
| 2.003 | 76 |
| 2.004 | 75 |
| 2.005 | 96 |
| 2.010 | 76 |
| 2.011 | 94 |
| 2.012 | 102 |
| 2.014 | 99 |
| 2.017 | 90 |
| 3.002 | 80 |
| 3.003 | 73 |
| 3.006 | 70 |
| 3.007 | 96 |
| 3.008 | 89 |
| 3.009 | 95 |
| 3.012 | 100 |
| 3.013 | 88 |
| 3.014 | 78 |
| 3.015 | 45 |
| 3.016 | 90 |
| 3.018 | 92 |
| 3.019 | 48 |
| 3.021 | 86 |
| 3.022 | 98 |
| 3.026 | 53 |
| 3.027 | 98 |
| 3.028 | 92 |
| 3.029 | 72 |
| 3.030 | 91 |
| 3.032 | 26 |
| 3.033 | 56 |
| 3.035 | 89 |
| 3.038 | 86 |
| 3.042 | 78 |
| 3.043 | 82 |
| 3.044 | 49 |
| 3.045 | 78 |
| 3.046 | 97 |
| 3.047 | 96 |
| 3.048 | 88 |
| 3.050 | 87 |
| 3.054 | 58 |
| 4.001 | 97 |
| 4.002 | 54 |
| 4.003 | 96 |
| 4.005 | 74 |
| 4.008 | 97 |
| 4.009 | 99 |
| 4.010 | 89 |
| 4.011 | 86 |
| 4.012 | 56 |
| 4.013 | 88 |
| 4.014 | 96 |
| 4.015 | 102 |
| 4.017 | 73 |
| 4.018 | 99 |
| 4.019 | 92 |
| 4.020 | 98 |
| 4.021 | 92 |
| 4.022 | 85 |
| 4.023 | 99 |
| 4.024 | 98 |
| 4.027 | 99 |
| 4.028 | 86 |
| 4.029 | 99 |
| 4.031 | 78 |
| 4.032 | 94 |

TABLE 3-continued

% Inhibition of MNK1 at a compound concentration of 1 μM as obtained in assay 3

| # | MNK1 % INH |
|---|---|
| 4.035 | 87 |
| 4.037 | 45 |
| 4.038 | 78 |
| 4.040 | 97 |
| 4.041 | 82 |
| 4.042 | 97 |
| 4.044 | 96 |
| 4.045 | 99 |
| 4.047 | 86 |
| 4.048 | 98 |
| 4.050 | 100 |
| 4.051 | 82 |
| 4.052 | 94 |
| 4.053 | 80 |
| 4.054 | 95 |
| 4.055 | 62 |
| 4.056 | 74 |
| 4.057 | 102 |
| 4.059 | 90 |
| 4.060 | 99 |
| 4.061 | 70 |
| 4.062 | 88 |
| 4.063 | 56 |
| 4.064 | 82 |
| 4.065 | 93 |
| 4.067 | 97 |
| 4.068 | 86 |
| 4.069 | 93 |
| 4.072 | 98 |
| 4.073 | 70 |
| 4.075 | 90 |
| 4.088 | 99 |
| 4.100 | 97 |
| 4.104 | 100 |
| 4.118 | 99 |
| 4.136 | 93 |
| 4.138 | 64 |
| 5.001 | 97 |
| 5.002 | 88 |
| 5.003 | 38 |
| 5.005 | 95 |
| 5.006 | 78 |
| 5.007 | 97 |
| 5.009 | 74 |
| 5.010 | 62 |
| 5.011 | 27 |
| 5.012 | 61 |
| 7.001 | 98 |
| 7.002 | 73 |
| 7.003 | 102 |
| 7.004 | 51 |
| 7.005 | 93 |
| 7.006 | 84 |
| 7.007 | 67 |
| 7.008 | 99 |

Method of Treatment

In view of their ability to inhibit the activity of the MNK1 (MNK1a or MNK1b) and/or MNK2 (MNK2a or MNK2b) kinase, the compounds of general formula I according to the invention, including the corresponding salts thereof, are theoretically suitable for the treatment of all those diseases or conditions which may be affected or which are mediated by the inhibition of the the MNK1 (MNK1a or MNK1b) and/or MNK2 (MNK2a or MNK2b) kinase.

Accordingly, the present invention relates to a compound of general formula I as a medicament.

Furthermore, the present invention relates to the use of a compound of general formula I or a pharmaceutical composition according to this invention for the treatment and/or prevention of diseases or conditions which are mediated by the the inhibition of the the MNK1 (MNK1a or MNK1b) and/or MNK2 (MNK2a or MNK2b) kinase in a patient, preferably in a human.

In yet another aspect the present invention relates to a method for treating a disease or condition mediated by the the inhibition of the the MNK1 (MNK1a or MNK1b) and/or MNK2 (MNK2a or MNK2b) kinase in a mammal that includes the step of administering to a patient, preferably a human, in need of such treatment a therapeutically effective amount of a compound or a pharmaceutical composition of the present invention.

Diseases and conditions mediated by inhibitors of the the inhibition of the the MNK1 (MNK1a or MNK1b) and/or MNK2 (MNK2a or MNK2b) kinase embrace metabolic diseases or conditions.

The present invention is directed to compounds which are useful in the treatment and/or prevention of a disease, disorder and/or condition wherein the inhibition of the activity of the MNK1 (MNK1a or MNK1b) and/or MNK2 (MNK2a or MNK2b) kinase is of therapeutic benefit, including but not limited to the treatment of metabolic diseases, such as obesity, eating disorders, cachexia, diabetes mellitus, metabolic syndrome, hypertension, coronary heart diseases, hypercholesterolemia, dyslipidemia, osteoarthritis, biliary stones and/or sleep apnea and diseases related to reactive oxygen compounds (ROS defense) such as diabetes mellitus, neurodegenerative diseases and cancer.

The pharmaceutical compositions of the invention are particularly useful for prophylaxis and treatment of obesity, diabetes mellitus and other metabolic diseases of the carbohydrate and lipid metabolism as stated above, in particular diabetes mellitus and obesity.

Thus, in a more preferred embodiment of this invention the use of a compound of the invention for the production of a pharmaceutical composition for the prophylaxis or therapy of metabolic diseases is provided.

In yet a further aspect of the invention the use of a compound of the invention for the production of a pharmaceutical composition for treating or preventing a cytokine mediated disorder such as an inflammatory disease is provided.

The pharmaceutical compositions of the invention are thus useful for the prophylaxis or therapy of inflammatory diseases, in particular chronic or acute inflammation, chronic inflammatory arthritis, rheumatoid arthritis, psoriatic arthritis, osteoarthritis, juvenile rheumatoid arthritis, gouty arthritis; psoriasis, erythrodermic psoriasis, pustular psoriasis, inflammatory bowel disease, Crohn's disease and related conditions, ulcerative colitis, colitis, diverticulitis, nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, chronic obstructive disease (COPD), inflammatory lung disease, allergic rhinitis, endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjubctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis, oesophagitis, gastritis, peritonitis, hepatitis, cholelithiasis, cholecystitis, glomerulonephritis, goodpasture's disease, crescentic glomerulonephritis, pancreatitis, dermatitis, endomyometritis, myometritis, metritis, cervicitis, endocervicitis, exocervicitis, parametritis, tuberculosis, vaginitis, vulvitis, silicosis, sarcoidosis, pneumoconiosis, inflammatory polyarthropathies, psoriatric arthropathies, intestinal fibrosis, bronchiectasis and enteropathic arthropathies.

As already stated above, the compositions of the present invention are particularly useful for treating or preventing a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

Thus, in a more preferred embodiment of this invention the use of a compound according to the invention for the production of a pharmaceutical composition for the prophylaxis or therapy of inflammatory diseases selected from chronic or acute inflammation, chronic inflammatory arthritis, rheumatoid arthritis, psoriasis, COPD, inflammatory bowel disease, septic shock Crohn's disease, ulcerative colitis, multiple sclerosis and asthma is provided.

In yet a further aspect of the invention the use of a compound of the invention for the production of a pharmaceutical composition for treating or preventing cancer, viral diseases or neurodegenerative diseases is provided.

In a further aspect of the invention the use of a compound of the present invention for the production of a pharmaceutical composition for inhibiting the activity of the kinase activity of MNK1 (MNK1a or MNK1b) and/or MNK2 (MNK2a, MNK2b) or further variants thereof is provided, in particular for the prophylaxis or therapy of metabolic diseases, hematopoietic disorders, cancer and their consecutive complications and disorders. Whereby the prophylaxis and therapy of metabolic diseases of the carbohydrate and/or lipid metabolism is preferred.

For the purpose of the present invention, a therapeutically effective dosage will generally be from about 1 to 2000 mg/day, preferably from about 10 to about 1000 mg/day, and most preferably from about 10 to about 500 mg/day, which may be administered in one or multiple doses.

It will be appreciated, however, that specific dose level of the compounds of the invention for any particular patient will depend on a variety of factors such as age, sex, body weight, general health condition, diet, individual response of the patient to be treated time of administration, severity of the disease to be treated, the activity of particular compound applied, dosage form, mode of application and concomitant medication. The therapeutically effective amount for a given situation will readily be determined by routine experimentation and is within the skills and judgment of the ordinary clinician or physician. In any case the compound or composition will be administered at dosages and in a manner which allows a therapeutically effective amount to be delivered based upon patient's unique condition.

It will be appreciated by the person of ordinary skill in the art that the compounds of the invention and the additional therapeutic agent may be formulated in one single dosage form, or may be present in separate dosage forms and may be either administered concomitantly (i.e. at the same time) or sequentially.

The pharmaceutical compositions of the present invention may be in any form suitable for the intended method of administration.

The compounds, compositions, including any combinations with one or more additional therapeutic agents, according to the invention may be administered by oral, transdermal, inhalative, parenteral or sublingual route. Of the possible methods of administration, oral or intravenous administration is preferred.

Pharmaceutical Compositions

Suitable preparations for administering the compounds of formula I, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula I with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to a person skilled in the art on the basis of his specialist knowledge. The preferred ones are those that are suitable for the particular formulation and method of administration that are desired. The preparations or formulations according to the invention may be prepared using methods known per se that are familiar to one skilled in the art, such as for example by mixing or combining at least one compound of formula I according to the invention, or a pharmaceutically acceptable salt of such a compound and one or more excipients, carriers and/or diluents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia. Additional therapeutic agents which are suitable for such combinations include in particular those which for example potentiate the therapeutic effect of one or more active substances with respect to one of the indications mentioned and/or which allow the dosage of one or more active substances to be reduced.

Other active substances which are suitable for such combinations include, for example, antidiabetics like insulin, long and short acting insulin analogues, sulfonylureas, biguanides, DPP-IV inhibitors, SGLT2 inhibitors, 11β-HSD inhibitors, glucokinase activators, AMPK activators, Glp-1 receptor agonists, GlP receptor agonists, DGAT inhibitors, PPARgamma agonists, PPARdelta agonists, and other antidiabetics derived from thiazolidinediones, lipid lowering agents such as statines, fibrates, ion exchange resins nicotinic acid derivatives, or HMG-CoA reductase inhibitors, cardiovascular therapeutics such as nitrates, antihypertensiva such as β-blockers, ACE inhibitors, Ca-channel blockers, angiotensin II receptor antagonists, diuretics, thrombocyte aggregation inhibitors, or antineoplastic agents such as alkaloids, alkylating agents, antibiotics, or antimetabolites, or anti-obesity agents. Further preferred compositions are compositions wherein the additional therapeutic agent is selected from a histamine antagonist, a bradikinin antagonist, serotonin antagonist, leukotriene, an anti-asthmatic, an NSAID, an antipyretic, a corticosteroid, an antibiotic, an analgetic, a uricosuric agent, chemotherapeutic agent, an anti gout agent, a bronchodilator, a cyclooxygenase-2 inhibitor, a steroid, a 5-lipoxygenase inhibitor, an immunosuppressive agent, a leukotriene antagonist, a cytostatic agent, an antineoplastic agent, a mTor inhibitor, a Tyrosine kinase inhibitor, antibodies or fragments thereof against cytokines and soluble parts (fragments) of cytokine receptors.

More particularly preferred are compounds such as human NPH insulin, human lente or ultralente insulin, insulin Lispro, insulin Aspart, insulin Glulisine, insulin detemir or insulin Glargine, metformin, phenformin, acarbose, miglitol, voglibose, pioglitazone, rosiglizatone, rivoglitazone, aleglitazar, alogliptin, saxagliptin, sitagliptin, vildagliptin, exenatide, liraglutide, albiglutide, pramlintide, carbutamide, chlorpropamide, glibenclamide (glyburide), gliclazide, glimepiride, glipizide, gliquidone, tolazamide, tolbutamide, atenolol, bisoprolol, metoprolol, esmolol, celiprolol, talinolol, oxprenolol, pindolol, propanolol, bupropanolol, penbutolol, mepindolol, sotalol, certeolol, nadolol, carvedilol, nifedipin, nitrendipin, amlodipin, nicardipin, nisoldipin, diltiazem, enalapril, verapamil, gallopamil, quinapril, captopril, lisinopril, benazepril, ramipril, peridopril, fosinopril, trandolapril, irbesatan, losartan, valsartan, telmisartan, eprosartan, olmesartan, hydrochlorothiazide, piretanid, chlorotalidone, mefruside, furosemide, bendroflumethiazid, triamterene, dehydralazine, acetylsalicylic acid, tirofiban-HCl, dipyramidol, triclopidin, iloprost-trometanol, eptifibatide, clopidogrel, piratecam, abciximab, trapidil, simvastatine, bezafibrate, fenofibrate, gemfibrozil, etofyllin, clofibrate, etofibrate, fluvastatine, lovastatine, pravastatin, colestyramide, colestipol-HCl, xantinol nicotinat, inositol nicotinat, acipimox, nebivolol, glycerolnitrate, isosorbide mononitrate, isosorbide dinitrate, pentaerythrityl tetranitrate, indapamide, cilazepril, urapidil, eprosartan, nilvadipin, metoprolol, doxazosin, molsidormin, moxaverin, acebutolol, prazosine, trapidil, clonidine, vinca alkaloids and analogues such as vinblastin, vincristin, vindesin, vinorelbin, podophyllotoxine derivatives, etoposid, teniposid, alkylating agents, nitroso ureas, N-lost analogues, cycloplonphamid, estamustin, melphalan, ifosfamid, mitoxantron, idarubicin, doxorubicin, bleomycin, mitomycin, dactinomycin, daptomycin, docetaxel, paclitaxel, carboplatin, cisplatin, oxaliplatin, BBR3464, satraplatin, busulfan, treosulfan, procarbazine, dacarbazine, temozolomide, chlorambucil, chlormethine, cyclophosphamide, ifosfamide, melphalan, bendamustine, uramustine, ThioTEPA, camptothecin, topotecan, irinotecan, rubitecan, etoposide, teniposide, cetuximab, panitumumab, trastuzumab, rituximab, tositumomab, alemtuzumab, bevacizumab, gemtuzumab, aminolevulinic acid, methyl aminolevulinate, porfimer sodium, verteporfin, axitinib, bosutinib, cediranib, dasatinib, erlotinib, gefitinib, imatinib, lapatinib, lestaurtinib, nilotinib, semaxanib, sorafenib, sunitinib, vandetanib, retinoids (alitretinoin, tretinoin), altretamine, amsacrine, anagrelide, arsenic trioxide, asparaginase (pegaspargase), bexarotene, bortezomib, denileukin diftitox, estramustine, ixabepilone, masoprocol, mitotane, testolactone, tipifarnib, abetimus, deforolimus, everolimus, gusperimus, pimecrolimus, sirolimus, tacrolimus, temsirolimus, antimetabolites such as cytarabin, fluorouracil, fluoroarabin, gemcitabin, tioguanin, capecitabin, combinations such as adriamycin/daunorubicin, cytosine arabinosid/cytarabine, 4-HC, or other phosphamides.

Other particularly preferred compounds are compounds such as clemastine, diphenhydramine, dimenhydrinate, promethazine, cetirizine, astemizole, levocabastine, loratidine, terfenadine, acetylsalicylic acid, sodoum salicylate, salsalate, diflunisal, salicylsalicylic acid, mesalazine, sulfasalazine, osalazine, acetaminophen, indomethacin, sulindac, etodolac, tolmetin, ketorolac, bethamethason, budesonide, chromoglycinic acid, dimeticone, simeticone, domperidone, metoclopramid, acemetacine, oxaceprol, ibuprofen, naproxen, ketoprofen, flubriprofen, fenoprofen, oxaprozin, mefenamic acid, meclofenamic acid, pheylbutazone, oxyphenbutazone, azapropazone, nimesulide, metamizole, leflunamide, eforicoxib, lonazolac, misoprostol, paracetamol, aceclofenac, valdecoxib, parecoxib, celecoxib, propyphenazon, codein, oxapozin, dapson, prednisone, prednisolon, triamcinolone, dexibuprofen, dexamethasone, flunisolide, albuterol, salmeterol, terbutalin, theophylline, caffeine, naproxen, glucosamine sulfate, etanercept, ketoprofen, adalimumab, hyaluronic acid, indometacine, proglumetacine dimaleate, hydroxychloroquine, chloroquine, infliximab, etofenamate, auranofin, gold, [$^{224}$Ra]radium chloride, tiaprofenic acid, dexketoprofen(trometamol), cloprednol, sodium aurothiomalate aurothioglucose, colchicine, allopurinol, probenecid, sulfinpyrazone, benzbromarone, carbamazepine, lornoxicam, fluorcortolon, diclofenac, efalizumab, idarubicin, doxorubicin, bleomycin, mitomycin, dactinomycin, daptomycin, cytarabin, fluorouracil, fluoroarabin, gemcitabin, tioguanin, capecitabin, adriamydin/daunorubicin, cytosine arabinosid/cytarabine, 4-HC, or other phosphamides, penicillamine, a hyaluronic acid preparation, arteparon, glucosamine, MTX, soluble fragments of the TNF-receptor (such as etanercept (Enbrel)) and antibodies against TNF (such as infliximab (Remicade), natalizumab (Tysabri) and adalimumab (Humira)).

EXAMPLES

Preliminary Remarks:

The hereinafter described compounds have been characterized through their characteristic mass after ionisation in a mass-spectrometer and their retention time on an analytical HPLC.

LIST OF ABBREVIATIONS

ACN Acetonitrile
AcOH acetic acid
aq. Aqueous
BOC tert-butoxy-carbonyl-
° C. degree celsius
DCM Dichloromethane
DEA Diethylamine
DIPEA N,N-Diisopropylethylamine
DMF N,N-dimethylformamide
DMSO Dimethyl sulfoxide
ESI-MS electrospray ionisation mass spectrometry
EtOAc ethyl acetate
EtOH Ethanol
h Hour
HATU 1-[Bis(dimethylamino)methylene]-1H-1,2,3-triazolo[4,5-b]pyridinium 3-oxid hexafluorophosphate
HPLC high performance liquid chromatography
L Liter
MeOH Methanol
min Minute
mL Milliliter
MS mass spectrum
μW Reaction was performed in a microwave
n.d. not determined NH4OH solution of NH$_3$ in water
Pd$_2$dba$_3$ Tris(dibenzylideneacetone)dipalladium(0)
psi pound per square inch
RT room temperature (about 20° C.)
R$_t$ retention time
TBTU O-(Benzotriazol-1-yl)-N,N,N',N'-tetramethyluronium tetrafluoroborate
TEA Triethylamine
TF/TFA trifluoroacetic acid
THF Tetrahydrofuran
Xantphos 4,5-Bis(diphenylphosphino)-9,9-dimethylxanthene HPLC Methods HPLC-A:
Agilent 1200 with DA- and MS-detector, XBridge C18_3.0×30 mm, 2.5 μm (Waters), 60° C.

| Time [min] | % Sol [H2O 0.1% TFA] | % Sol [Acetonitrile] | Flow [ml/min] |
|---|---|---|---|
| 0.0 | 97.0 | 3.0 | 2.2 |
| 0.2 | 97.0 | 3.0 | 2.2 |
| 1.2 | 0.0 | 100.0 | 2.2 |
| 1.25 | 0.0 | 100.0 | 3.0 |
| 1.4 | 0.0 | 100.0 | 3.0 |

HPLC-B:
Agilent 1200 with DA- and MS-Detector, Sunfire C18_3.0×30 mm, 2.5 μm (Waters), 60° C.

| Time [min] | % Sol [H2O 0.1% TFA] | % Sol [Acetonitrile] | Flow [ml/min] |
|---|---|---|---|
| 0.0 | 97.0 | 3.0 | 2.2 |
| 0.2 | 97.0 | 3.0 | 2.2 |
| 1.2 | 0.0 | 100.0 | 2.2 |
| 1.25 | 0.0 | 100.0 | 3.0 |
| 1.4 | 0.0 | 100.0 | 3.0 |

HPLC-C:
Waters Acquity with DA- and MS-detector and CTC Autosampler, BEH C18_2.1×30 mm, 1.7 μm (Waters), 60° C.

| Time [min] | % Sol [H2O 0.1% NH4OH] | % Sol [Acetonitrile] | Flow [ml/min] |
|---|---|---|---|
| 0.0 | 98.0 | 2.0 | 1.5 |
| 1.2 | 0.0 | 100.0 | 1.5 |
| 1.4 | 0.0 | 100.0 | 1.5 |
| 1.45 | 98.0 | 2.0 | 1.5 |

HPLC-D:
Waters 1525 with DA- and MS-detector, Sunfire C18_4.6×30 mm, 2.5 μm (Waters), 60° C.

| Time [min] | % Sol [H2O 0.1% TFA] | % Sol [Acetonitrile] | Flow [ml/min] |
|---|---|---|---|
| 0.0 | 97.0 | 3.0 | 4.0 |
| 0.15 | 97.0 | 3.0 | 3.0 |
| 2.15 | 0.0 | 100.0 | 3.0 |
| 2.2 | 0.0 | 100.0 | 4.5 |
| 2.4 | 0.0 | 100.0 | 4.5 |

HPLC-E:
Agilent 1200 with DA- and MS-detector, StableBond C18_3.0×30 mm, 1.8 μm (Agilent), 60° C.

| Time [min] | % Sol [H2O 0.1% TFA] | % Sol [Acetonitrile] | Flow [ml/min] |
|---|---|---|---|
| 0.0 | 97.0 | 3.0 | 2.2 |
| 0.2 | 97.0 | 3.0 | 2.2 |
| 1.2 | 0.0 | 100.0 | 2.2 |
| 1.25 | 0.0 | 100.0 | 3.0 |
| 1.4 | 0.0 | 100.0 | 3.0 |

HPLC-F:
Waters 1525 with DA- and MS-detector, XBridge C18_4.6×30 mm, 2.5 μm (Waters), 60° C.

| Time [min] | % Sol [H2O 0.1% TFA] | % Sol [Acetonitrile] | Flow [ml/min] |
|---|---|---|---|
| 0.0 | 60.0 | 40.0 | 4.0 |
| 0.15 | 60.0 | 40.0 | 3.0 |
| 2.15 | 0.0 | 100.0 | 3.0 |
| 2.2 | 0.0 | 100.0 | 4.5 |
| 2.4 | 0.0 | 100.0 | 4.5 |

HPLC-G:
Waters Acquity with DA- and MS-Detector, XBridge BEH C18_2.1×30 mm, 1.7 μm (Waters), 60° C.

| Time [min] | % Sol [H2O 0.1% TFA] | % Sol [Acetonitrile] | Flow [ml/min] |
|---|---|---|---|
| 0.0 | 99.0 | 1.0 | 1.6 |
| 0.02 | 99.0 | 1.0 | 1.6 |
| 1.0 | 0.0 | 100.0 | 1.6 |
| 1.1 | 0.0 | 100.0 | 1.6 |

HPLC-H:
Agilent 1200 with DA- and MS-detector, XBridge C18_3×30 mm, 2.5 μm (Waters), 60° C.

| Time [min] | % Sol [H2O 0.1% TFA] | % Sol [Methanol] | Flow [ml/min] |
|---|---|---|---|
| 0.0 | 95.0 | 5.0 | 2.2 |
| 0.3 | 95.0 | 5.0 | 2.2 |
| 1.5 | 0.0 | 100.0 | 2.2 |
| 1.55 | 0.0 | 100.0 | 2.9 |
| 1.65 | 0.0 | 100.0 | 2.9 |

HPLC-I:
Agilent 1100 with DAD, Waters autosampler and MS-detector, SunFire C18_4.6×30 mm, 3.5 μm (Waters), 60° C.

| Time [min] | % Sol [H2O 0.1% TFA] | % Sol [Acetonitrile] | Flow [ml/min] |
|---|---|---|---|
| 0.0 | 98.0 | 2.0 | 2.5 |
| 1.5 | 0.0 | 100.0 | 2.5 |
| 1.8 | 0.0 | 100.0 | 2.5 |

HPLC-J:
Agilent 1200 with DA- and MS-Detector, SunFire C18_3.0×30 mm, 2.5 μm (Waters), 60° C.

| Time [min] | % Sol [H2O 0.1% TFA] | % Sol [Methanol] | Flow [ml/min] |
|---|---|---|---|
| 0.0 | 95.0 | 5.0 | 1.8 |
| 0.25 | 95.0 | 5.0 | 1.8 |

-continued

| Time [min] | % Sol [H2O 0.1% TFA] | % Sol [Methanol] | Flow [ml/min] |
|---|---|---|---|
| 1.7 | 0.0 | 100.0 | 1.8 |
| 1.75 | 0.0 | 100.0 | 2.5 |
| 1.9 | 0.0 | 100.0 | 2.5 |

HPLC-K:

Waters Acquity with 3100 MS, XBridge BEH C18_3.0×30 mm, 1.7 μm (Waters), 60° C.

| Time [min] | % Sol [H2O 0.1% NH4OH] | % Sol [Acetonitrile] | Flow [ml/min] |
|---|---|---|---|
| 0.0 | 95.0 | 5.0 | 1.5 |
| 0.7 | 0.1 | 99.9 | 1.5 |
| 0.8 | 0.1 | 99.9 | 1.5 |
| 0.81 | 95.0 | 5.0 | 1.5 |
| 1.1 | 95.0 | 5.0 | 1.5 |

HPLC-L:

Waters Acquity with DA- and MS-detector, BEH C18_2.1×30 mm, 1.7 μm (Waters), 60° C.

| Time [min] | % Sol [H2O 0.1% NH4OH] | % Sol [Acetonitrile] | Flow [ml/min] |
|---|---|---|---|
| 0.0 | 95.0 | 5.0 | 1.5 |
| 0.8 | 0.1 | 99.9 | 1.5 |
| 0.9 | 0.1 | 99.9 | 1.5 |

HPLC-M:

Agilent 1200 with DA- and MS-detector, XBridge C18_3.0×30 mm, 2.5 μm (Waters), 60° C.

| Time [min] | % Sol [H2O 0.1% NH4OH] | % Sol [Acetonitrile] | Flow [ml/min] |
|---|---|---|---|
| 0.0 | 97.0 | 3.0 | 2.2 |
| 0.2 | 97.0 | 3.0 | 2.2 |
| 1.2 | 0.0 | 100.0 | 2.2 |
| 1.25 | 0.0 | 100.0 | 3.0 |
| 1.4 | 0.0 | 100.0 | 3.0 |

Waters Acquity with DA- and MS-detector and CTC autosampler, XBridge C18_3.0×30 mm, 2.5 μm (Waters), 60° C.

| Time [min] | % Sol [H2O 0.1% NH4OH] | % Sol [Acetonitrile] | Flow [ml/min] |
|---|---|---|---|
| 0.0 | 98.0 | 2.0 | 2.0 |
| 1.2 | 0.0 | 100.0 | 2.0 |
| 1.4 | 0.0 | 100.0 | 2.0 |

HPLC-O:

Waters 1525 with DA- and MS-Detector, Sunfire C18_4.6×30 mm, 2.5 μm (Waters), 60° C.

| Time [min] | % Sol [H2O 0.1% TFA] | % Sol [Acetonitrile] | Flow [ml/min] |
|---|---|---|---|
| 0.0 | 60.0 | 40.0 | 4.0 |
| 0.15 | 60.0 | 40.0 | 3.0 |
| 2.15 | 0.0 | 100.0 | 3.0 |
| 2.2 | 0.0 | 100.0 | 4.5 |
| 2.4 | 0.0 | 100.0 | 4.5 |

HPLC-P:

Agilent 1100 with DAD, CTC autosampler and Waters MS-detector, XBridge C18_4.6×30 mm, 3.5 μm (Waters), 60° C.

| Gradient/Solvent Time [min] | % Sol [H2O 0.1% NH4OH] | % Sol [Acetonitrile] | Flow [ml/min] |
|---|---|---|---|
| 0.0 | 98.0 | 2.0 | 2.5 |
| 1.5 | 0.0 | 100.0 | 2.5 |
| 1.8 | 0.0 | 100.0 | 2.5 |

HPLC-Q:

Waters Acquity with 3100 MS, Sunfire C18_2.1×50 mm, 2.5 μm (Waters), 60° C.

| Time [min] | % Sol [H2O 0.1% TFA] | % Sol [Acetonitrile 0.08% TFA] | Flow [ml/min] |
|---|---|---|---|
| 0.0 | 95.0 | 5.0 | 1.5 |
| 0.75 | 0.0 | 100.0 | 1.5 |
| 0.85 | 0.0 | 100.0 | 1.5 |

HPLC-R:

Waters 1525 with DA- and MS-detector, XBridge C18_4.6×30 mm, 2.5 μm (Waters), 60° C.

| Time [min] | % Sol [H2O 0.1% TFA] | % Sol [Methanol] | Flow [ml/min] |
|---|---|---|---|
| 0.0 | 95.0 | 5.0 | 4.0 |
| 0.05 | 95.0 | 5.0 | 3.0 |
| 2.05 | 0.0 | 100.0 | 3.0 |
| 2.1 | 0.0 | 100.0 | 4.5 |
| 2.4 | 0.0 | 100.0 | 4.5 |

HPLC-S:

Waters 1525 with DA- and MS-detector, XBridge C18_4.6×30 mm, 2.5 μm (Waters), 60° C.

| Gradient/Solvent Time [min] | % Sol [H2O 0.1% TFA] | % Sol [Acetonitrile] | Flow [ml/min] |
|---|---|---|---|
| 0.0 | 97.0 | 3.0 | 4.0 |
| 0.15 | 97.0 | 3.0 | 3.0 |
| 2.15 | 0.0 | 100.0 | 3.0 |
| 2.2 | 0.0 | 100.0 | 4.5 |
| 2.4 | 0.0 | 100.0 | 4.5 |

HPLC-T:

Agilent 1100 with DA-detector, XBridge C18_3.0×30 mm, 2.5 μm (Waters), 60° C.

| Time [min] | % Sol [$H_2O$ 0.1% $NH_4OH$] | % Sol [Acetonitrile] | Flow [ml/min] |
|---|---|---|---|
| 0.0 | 98.0 | 2.0 | 2.0 |
| 1.2 | 0.0 | 100.0 | 2.0 |
| 1.4 | 0.0 | 100.0 | 2.0 |

HPLC-U:

Agilent 1100 with DA- and MS-detector, XBridge C18_4.6×30 mm, 3.5 μm (Waters), 60° C.

| Time [min] | % Sol [H₂O 0.1% NH₄OH] | % Sol [Acetonitrile] | Flow [ml/min] |
|---|---|---|---|
| 0.0 | 95.0 | 5.0 | 4.0 |
| 0.15 | 95.0 | 5.0 | 4.0 |
| 1.5 | 0.0 | 100.0 | 4.0 |
| 1.85 | 0.0 | 100.0 | 4.0 |

HPLC-V:

Sunfire C18_3.0×30 mm, 2.5 μm (Waters), 60° C.

| Time [min] | % Sol [H₂O 0.1% TFA] | % Sol [Acetonitrile] | Flow [ml/min] |
|---|---|---|---|
| 0.0 | 98.0 | 2.0 | 2.0 |
| 1.2 | 0.0 | 100.0 | 2.0 |
| 1.4 | 0.0 | 100.0 | 2.0 |

HPLC-W:

Sunfire C18_3.0×30 mm, 2.5 μm (Waters), 60° C.

| Time [min] | % Sol [H₂O 0.1% TFA] | % Sol [Acetonitrile] | Flow [ml/min] |
|---|---|---|---|
| 0.0 | 99.0 | 1.0 | 2.0 |
| 0.9 | 0.0 | 100.0 | 2.0 |
| 1.1 | 0.0 | 100.0 | 2.0 |

HPLC-X:

Waters Acquity with DA- and MS-detector and CTC autosampler, Sunfire C18_2.1×30 mm, 2.5 μm (Waters), 60° C.

| Time [min] | % Sol [H₂O 0.1% TFA] | % Sol [Acetonitrile] | Flow [ml/min] |
|---|---|---|---|
| 0.0 | 99.0 | 1.0 | 1.5 |
| 0.02 | 99.0 | 1.0 | 1.5 |
| 1.0 | 0.0 | 100.0 | 1.5 |
| 1.1 | 0.0 | 100.0 | 1.5 |

HPLC-Y:

Waters Acquity with 3100 MS, Sunfire C18_3.0×30 mm, 2.5 μm (Waters), 60° C.

| Time [min] | % Sol [H2O 0.1% TFA] | % Sol [Acetonitrile 0.08% TFA] | Flow [ml/min] |
|---|---|---|---|
| 0.0 | 95.0 | 5.0 | 1.5 |
| 1.3 | 0.0 | 100.0 | 1.5 |
| 1.5 | 0.0 | 100.0 | 1.5 |
| 1.6 | 95.0 | 5.0 | 1.5 |

Preparation of Intermediates:

Intermediate I.1:
2-amino-4-bromo-6-fluoro-benzonitrile

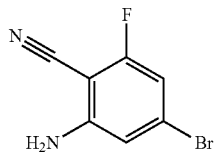 [SMILES: N#Cc1c(N)cc(Br)cc1F]

5.0 g (22.9 mmol) 4-bromo-2,6-difluorobenzonitrile are dissolved in 200 ml of a solution of $NH_3$ in ethanol and heated in a pressure vessel to 90° C. for 20 h. After cooling to RT the solvent is evaporated and the residual taken in up in water/DCM. The organic phase is separated, dried and evaporated.

Yield: 4.9 g (99%), ESI-MS: m/z=213/215 (M–H)⁻, $R_t$(HPLC): 1.72 min (HPLC-R)

Intermediate II.1: N'-(5-bromo-2-cyano-3-fluoro-phenyl)-N,N-dimethyl-formamidine

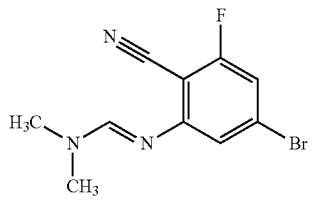

A mixture of 17.0 g (79.1 mmol) 2-amino-4-bromo-6-fluoro-benzonitrile and 140 ml of N,N-dimethylformamide dimethyl acetal is heated to 120° C. for 2 h. After cooling RT the solvent is evaporated and the residual taken up in diethyl ether, filtered and dried. Yield: 20.5 g (96%), ESI-MS: m/z=270/272 (M+H)⁺, $R_t$(HPLC): 0.83 min (HPLC-H)

The following Intermediates are prepared in a similar manner to intermediate II.1 from the corresponding anilines which are commercially available or can be obtained according to (a) U.S. Pat. No. 3,987,192 A1 and (b) *J. Med. Chem.* 1981, 24 (6), 742.

| Int# | Structure | Starting Material | ESI-MS m/z M + H+ | $R_t$(HPLC) |
|---|---|---|---|---|
| II.2 | ![structure] | 2-amino-4-bromo-6-methyl-benzonitrile[a] | 266/268 | 0.57 min (HPLC-A) |

| Int# | Structure | Starting Material | ESI-MS m/z M + H+ | $R_f$(HPLC) |
|---|---|---|---|---|
| II.3 | 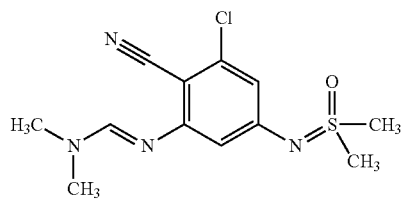 | 2-amino-6-chloro-benzonitrile[b] | 208 | 0.47 min (HPLC-A) |
| II.4 | 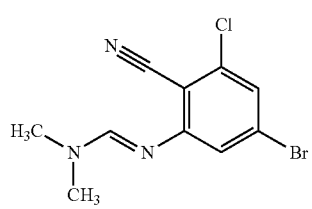 | 2-amino-6-bromo-benzonitrile[b] | 252/254 | 0.53 min (HPLC-A) |

Intermediate II.5: N'-[3-bromo-2-cyano-5-[[dimethyl(oxo)-$\lambda^6$-sulfanylidene]amino]phenyl]-N,N-dimethyl-formamidine A mixture of 0.2 g (0.96 mmol) intermediate II.3, 0.2 g (0.67 mmol) Bis(pinacolato)diborane, 26 mg (0.01 mmol) 4,4'-Di-tert-butyl-[2,2]bipyridinyl and 40 mg (0.06 mmol) chloro(1,5-cyclooctadiene)iridium(I) dimer is heated in heptane at reflux for 2 days. After cooling to RT the solvent is evaporated and the residual taken in up in water/EtOAc. The organic phase is separated, dried and evaporated yielding the crude corresponding boronic acid derivative which is dissolved in MeOH. 0.1 g (0.75 mmol) dimethylsulfoximine and 14 mg (0.08 mmol) Copper(II) acetate are added and the reaction mixture stirred at RT over night. After addition of MeOH and concentrated NH$_3$ solution, the solvent is evaporated and the residual purified by FC.

Yield: 0.1 g (58%), ESI-MS: m/z=299 (M+H)$^+$, $R_f$(HPLC): 0.68 min (HPLC-M)

Intermediate II.6: N'-[3-bromo-2-cyano-5-[[dimethyl(oxo)-$\lambda^6$-sulfanylidene]amino]phenyl]-N,N-dimethyl-formamidine A mixture of 2.0 g (9.63 mmol) intermediate II.3, 1.7 g (6.72 mmol) Bis(pinacolato)diborane, 21 mg (0.08 mmol) 4,4'-Di-tert-butyl-[2,2]bipyridinyl and 16 mg (0.02 mmol) chloro(1,5-cyclooctadiene)iridium(I) dimer and THF is heated in a pressure vessel to 80° C. for 21 h. Additional 0.2 g (0.79 mmol) Bis(pinacolato)diborane, 4'-Di-tert-butyl-[2,2]bipyridinyl and chloro(1,5-cyclooctadiene)iridium(I) dimer are added and heating is continued over night. After cooling to RT the solvent is evaporated and the residual is treated with cyclohexane, filtered and washed with cyclohexane giving rise to 2.3 g of the crude boronic acid derivative.

To 2.3 g (4.8 mmol) of the crude boronic acid derivative, 3.0 g (13.4 mmol) CuBr$_2$ methanol and water are added and the mixture is heated in a pressure vessel to 80° C. for 4 h. The reaction mixture is concentrated and DCM added. The organic phase is separated, washed with brine, dried and evaporated and the residual purified by FC giving rise to 0.9 g 2-Amino-4-bromo-6-chloro-benzonitrile which was converted to the formamidine derivative in similar manner as intermediate II.1.

ESI-MS: m/z=286 (M+H)$^+$, $R_f$(HPLC): 0.85 min (HPLC-A)

Intermediate II.7: N'-[3-bromo-2-cyano-5-[[dimethyl(oxo)-$\lambda^6$-sulfanylidene]amino]phenyl]-N,N-dimethyl-formamidine

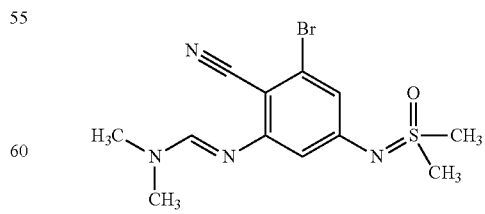

Was prepared in a similar manner as intermediate II.5 from intermediate II.4. ESI-MS: m/z=343/345 (M+H)$^+$, $R_f$(HPLC): 0.66 min (HPLC-E)

Intermediate II.8: N'-(5-bromo-2-cyano-3-methoxy-phenyl)-N,N-dimethyl-formamidine

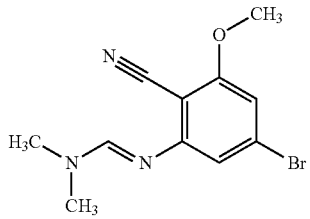

A mixture of 3.0 g (11.1 mmol) intermediate II.1, 17.4 g MeOH (555.4 mmol), 4.3 g (13.3 mmol) $Cs_2CO_3$ and 50 ml dioxane was heated in a pressure vessel for 5 h to reflux. After cooling to RT the solvent was evaporated and the residual purified by FC (DCM). Yield: 2.4 g (75%), ESI-MS: m/z=282/284 (M+H)$^+$, $R_t$(HPLC): 0.97 min (HPLC-D)

Intermediate II.9: N'-[2-cyano-5-[[dimethyl(oxo)-$\lambda^6$-sulfanylidene]amino]-3-methyl-phenyl]-N,N-dimethyl-formamidine

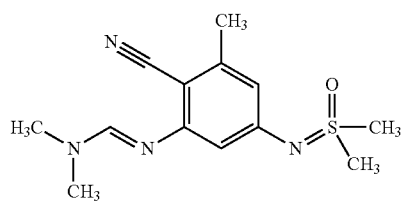

To a solution of 0.5 g (1.9 mmol) intermediate II.2 in 20 ml dioxane 0.2 g (2.3 mmol) dimethylsulphoximine, 0.1 g (0.4 mmol) 2-(di-t-butylphosphino) biphenyl, 0.1 g (0.14 mmol) $Pd_2dba_3$ and 0.3 g (2.7 mmol) sodium tert-butoxide were added and the mixture heated to 80° C. for 1 h. The reaction mixture was diluted with water and acidified with citric acid and extracted with EtOAc, then basified and extracted with DCM. The organic phases were pooled dried and evaporated.

Yield: 0.4 g (83%), ESI-MS: m/z=279 (M+H)$^+$, $R_t$(HPLC): 0.59 min (HPLC-F)

Intermediate II.10: N'-[2-cyano-3-cyclopropyl-5-[[dimethyl(oxo)-$\lambda^6$-sulfanylidene]amino]phenyl]-N,N-dimethyl-formamidine

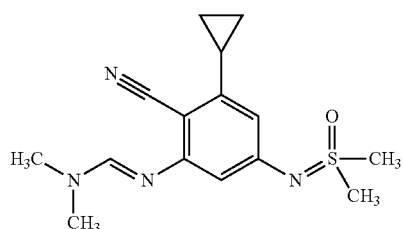

To a solution of 100 mg (0.29 mmol) intermediate II.7 in 20 ml dioxane 25 mg (0.29 mmol) cyclopropylboronic acid, 0.1 g (0.4 mmol) 1,1'-bis(diphenylphosphino)ferrocene-dichloropalladium(II), 121 mg (2.7 mmol) potassium carbonate were added and the mixture heated to 80° C. over night. The reaction mixture was cooled to RT and diluted with MeOH and evaporated. The residual was purified by HPLC.

Yield: 70 mg (79%), ESI-MS: m/z=305 (M+H)$^+$, $R_t$(HPLC): 0.68 min (HPLC-A)

Intermediate II.11: N'-[2-cyano-5-[[dimethyl(oxo)-$\lambda^6$-sulfanylidene]amino]-3-(trifluoromethyl)phenyl]-N,N-dimethyl-formamidine

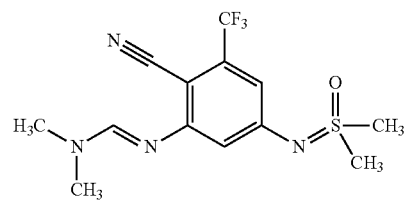

Was prepared in a similar manner as intermediate II.5 via 11.3 from 2-amino-6-(trifluoromethyl)benzonitrile.

ESI-MS: m/z=242 (M+H)$^+$, $R_t$(HPLC): 0.71 min (HPLC-E)

Intermediate II.12: N'-[2-cyano-5-[(1-oxothiolan-1-ylidene)amino]-3-(trifluoromethyl)phenyl]-N,N-dimethyl-formamidine

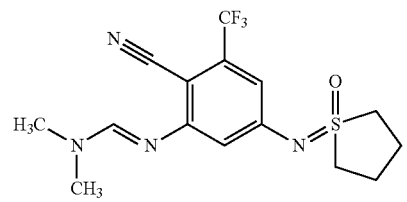

Was prepared in a similar manner as intermediate II.5 via 11.3 from 2-amino-6-(trifluoromethyl)benzonitrile.

ESI-MS: m/z=359 (M+H)$^+$, $R_t$(HPLC): 0.77 min (HPLC-E)

Intermediate II.13: N'-[2-cyano-3-methyl-5-[(4-oxo-1,4-oxathian-4-ylidene)amino]phenyl]-N,N-dimethyl-formamidine

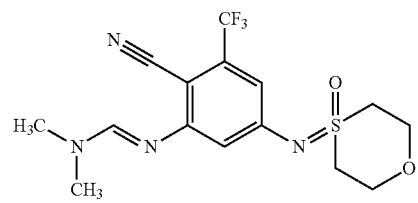 [SMILES: CN(C)/C=N/c1cc(N=S2(=O)CCOCC2)cc(C(F)(F)F)c1C#N]

Was prepared in a similar manner as intermediate II.5 via 11.3 from 2-amino-6-(trifluoromethyl)benzonitrile.

ESI-MS: m/z=375 (M+H)$^+$, $R_t$(HPLC): 0.75 min (HPLC-E)

Intermediate II.14: tert-butyl 1-[4-cyano-3-[dimethylaminomethyleneamino]-5-methyl-phenyl]imino-1-oxo-1,4-thiazinane-4-carboxylate

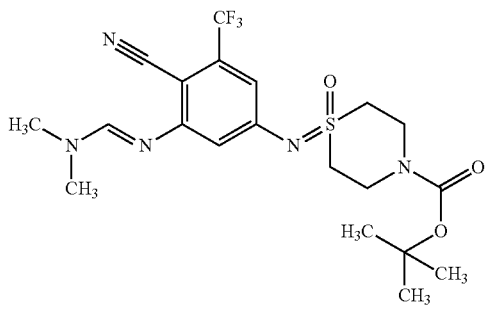 [SMILES: CN(C)/C=N/c1cc(N=S2(=O)CCN(C(=O)OC(C)(C)C)CC2)cc(C(F)(F)F)c1C#N]

Was prepared in a similar manner as intermediate II.5 via 11.3 from 2-amino-6-(trifluoromethyl)benzonitrile.

ESI-MS: m/z=474 (M+H)$^+$, R$_t$(HPLC): 0.91 min (HPLC-E)

Intermediate II.15: N'-[3-flouro-2-cyano-5-[[dimethyl(oxo)-λ$^6$-sulfanylidene]amino]phenyl]-N,N-dimethyl-formamidine

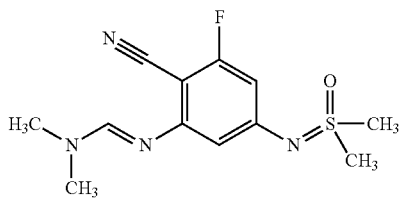

Was prepared in a similar manner as intermediate II.9 from intermediate II.1.

ESI-MS: m/z=283 (M+H)$^+$, R$_t$(HPLC): 0.58 min (HPLC-B)

Intermediate II.16: N'-[3-chloro-2-cyano-5-[(ethyl-methyl-oxo λ$^6$-sulfanylidene)amino]phenyl]-N,N-dimethyl-formamidine

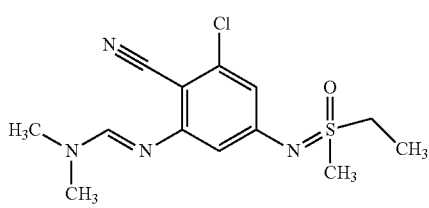 [SMILES: CCS(C)(=O)=Nc1cc(Cl)c(C#N)c(/N=C/N(C)C)c1]

Was prepared in a similar manner as intermediate II.5 from intermediate II.3.

ESI-MS: m/z=313 (M+H)$^+$, R$_t$(HPLC): 0.35 min (HPLC-G)

Intermediate II.17: N'-[3-flouro-2-cyano-5-[[dimethyl(oxo)-λ$^6$-sulfanylidene]amino]phenyl]-N,N-dimethyl-formamidine

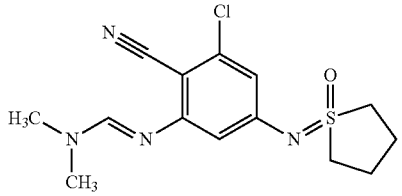 [SMILES: CN(C)/C=N/c1cc(N=S2(=O)CCCC2)cc(Cl)c1C#N]

Was prepared in a similar manner as intermediate II.9 from intermediate II.2.

ESI-MS: m/z=305 (M+H)$^+$, R$_t$(HPLC): 0.63 min (HPLC-B)

Intermediate II.18 N'-(3-chloro-2-cyano-5-iodo-phenyl)-N,N-dimethyl-formamidine

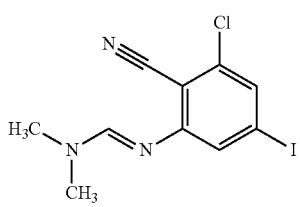

A mixture of 4.0 g (19.3 mmol) intermediate II.3, 5.4 g (21.2 mmol) bis(pinacolato)diborane, 60 mg (0.22 mmol) 4,4'-di-tert-butyl-[2,2]bipyridinyl and 50 mg (0.08 mmol) methoxy(1,5-cyclooctadiene)iridium(I) dimer and heptane is heated in a pressure vessel to 110° C. over night. After cooling to RT the precipitate is filtered off and dried giving rise to 5.5 g of the crude boronic acid derivative.

To 1.6 g (4.8 mmol) of the crude boronic acid derivative, 0.1 g (0.6 mmol) CuI, 1.2 g (7.2 mmol) KI, methanol and water are added and the mixture is heated in a pressure vessel to 90° C. over night. The reaction mixture is cooled to RT and EtOAc is added. The organic phase is separated, dried and evaporated and the residual purified by FC.

ESI-MS: m/z=334 (M+H)$^+$, R$_t$(HPLC): 0.80 min (HPLC-A)

Intermediate III.1: 4-Fluoro-2-(2-fluoro-1-methyl-ethoxy)-phenylamine

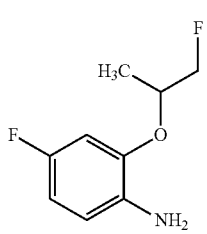

0.29 g (3.77 mmol) 1-fluoro-propan-2-ol in 20 mL THF is cooled down to 0° C. 4.90 mL (1M in THF; 4.90 mmol) LiHMDS is added drop wise. After 60 minutes of stirring at 0° C. 0.60 g (3.77 mmol) 2,4-difluoro-1-nitro-benzene is added. The mixture is stirred for 2 h. The mixture is diluted with water and EtOAc. The organic layer is washed with brine, separated, dried and evaporated giving rise to the crude 4-fluoro-2-(2-fluoro-1-methyl-ethoxy)-1-nitro-benzene. 80.0 mg palladium on charcoal (10%) and MeOH are added hydrogenated in a Parr apparatus (RT; 50 psi; 5 h). The catalyst is filtered off and the solvent is evaporated.

Yield: 0.60 g (87%), ESI-MS: m/z=188 (M+H)$^+$, R$_f$(HPLC): 0.60 min (HPLC-E)

Intermediate III.2: 2-(1-ethoxy-2,2,2-trifluoro-ethoxy)-4-fluoro-aniline

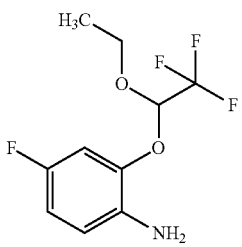

Was prepared in a similar manner as intermediate III.1 from 2,4-difluoro-1-nitro-benzene and 1-ethoxy-2,2,2-trifluoro-ethanol.

ESI-MS: m/z=254 (M+H)$^+$, R$_f$(HPLC): 0.93 min (HPLC-E)

Intermediate III.3:
2-(1-ethoxy-2,2,2-trifluoro-ethoxy)pyridin-3-amine

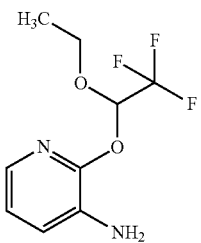 [SMILES: CCOC(Oc1ncccc1N)C(F)(F)F]

Was prepared in a similar manner as intermediate III.1 from 2-chloropyridin-3-amine and 1-ethoxy-2,2,2-trifluoro-ethanol.

ESI-MS: m/z=237 (M+H)$^+$, R$_f$(HPLC): 0.98 min (HPLC-E)

Intermediate III.4: 4-Fluoro-2-[1-(3-methyl-isoxazol-5-yl)ethoxy]-phenylamine

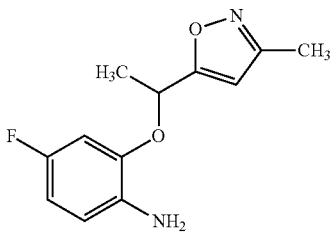 [SMILES: Cc1cc(C(C)Oc2cc(F)ccc2N)on1]

To a solution of 4.15 g (32.64 mmol) 1-(3-Methylisoxazol-5-yl)ethanol in THF 32.64 mL (1M in THF; 32.64 mmol) LiHMDS is added drop wise. After 30 minutes of stirring 5.19 g (32.64 mmol) 2,4-difluoro-1-nitro-benzene is added. The mixture is stirred over night. The mixture is diluted with water and EtOAc. The organic layer is separated, washed with water, dried and evaporated. The residue is purified by FC giving rise to 5-[1-(5-fluoro-2-nitro-phenoxy)ethyl]-3-methyl-isoxazole.

6.61 g (24.84 mmol) 5-[1-(5-fluoro-2-nitro-phenoxy)ethyl]-3-methyl-isoxazole and 24.66 g (109.30 mmol) tin (II)chloride dihydrate in EtOAc are stirred for 1 h at reflux. The mixture is diluted with 180 mL EtOAc and 180 mL aq. NaOH (4M). The organic layer is separated and the aqueous layer is extracted with EtOAc. The combined organic layers are washed with water and brine, separated, dried and evaporated. The residue is purified by FC.

Yield: 4.90 g (84%), ESI-MS: m/z=237 (M+H)$^+$

Intermediate III.5: 4-fluoro-2-[(1R)-1-(3-methyl-isoxazol-5-yl)ethoxy]aniline

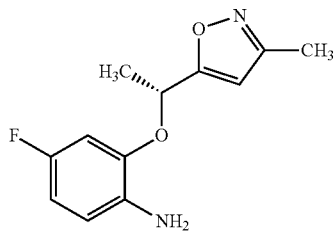 [SMILES: Cc1cc([C@@H](C)Oc2cc(F)ccc2N)on1]

To a mixture of 1.0 g (16.9 mmol) acetaldehyde oxime, 1.19 g (16.9 mmol) (R)-(+)-3-butyl-2-ol, 0.18 g (1.72 mmol) triethylamine and DCM are added dropwise 21.4 ml (28.78 mmol) of 10% sodium hypochlorite in water. The reaction mixture is stirred for 1 h and the evaporated and purified by FC (DCM/MeOH 9:1) giving rise to (1R)-1-(3-methylisoxazol-5-yl)ethanol.

Yield: 0.7 g (33%), ESI-MS: m/z=128 (M+H)$^+$, R$_f$(HPLC): 0.28 min (HPLC-G) III.5 was prepared in a similar manner as the racemate intermediate III.4 from 2,4-difluoro-1-nitro-benzene and (1R)-1-(3-methylisoxazol-5-yl)ethanol.

ESI-MS: m/z=237 (M+H)$^+$

Intermediate III.6: 2-[(1R)-1-(3-methylisoxazol-5-yl)ethoxyl]pyridin-3-amine

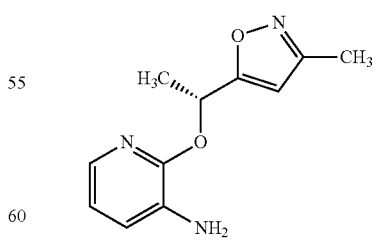

To a solution of 0.3 g (2.44 mmol) 1(1R)-1-(3-methyl-isoxazol-5-yl)ethanol in THF 2.45 mL (1M in THF; 2.45 mmol) LiHMDS is added drop wise. After 30 minutes of stirring 0.3 g (2.04 mmol) 2-fluoro-3-nitro-pyridine is added. The mixture is stirred over night. The mixture is diluted with 1 N HCl and water and neutralized with NH₃. EtOAc is added and the organic layer is separated, washed with brine, dried and evaporated to furnish 3-methyl-5-[(1R)-1-[(3-nitro-2-pyridyl)oxy]ethyl]isoxazole.

A mixture of 0.5 g (2.09 mmol) 3-methyl-5-[(1R)-1-[(3-nitro-2-pyridyl)oxy]ethyl]isoxazole and acetone are cooled to 5° C. and 87 ml (17.4 mmol) of titanium(III)chloride 20% in water and 24 ml (96 mmol) of a 4M solution of NH₄Cl in water are added. The mixture is warmed to RT and stirred over night diluted with EtOAc and water. The organic layer is separated and the aqueous layer is extracted with EtOAc. The combined organic layers are washed with brine, dried and evaporated. The residue is purified by FC (DCM/MeOH 95:5).

Yield: 0.3 g (72%), ESI-MS: m/z=220 (M+H)⁺, R$_t$(H-PLC): 0.41 min (HPLC-G)

Intermediate III.7: (2R)-2-[(3-amino-2-pyridyl)oxy]-N-(2,2,2-trifluoroethyl)propanamide

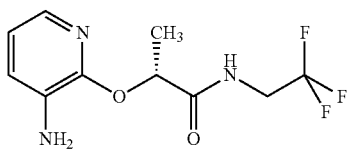

To a solution of 5.3 g (50.5 mmol) (R)-2-Hydroxy-propionic acid methyl ester in THF 50.5 mL (1M in THF; 50.5 mmol) LiHMDS is added drop wise. After 10 minutes of stirring 4.0 g (25.2 mmol) 2-choro-3-nitro-pyridine is added. The mixture is stirred at 60° C. over night. The solvent is evaporated and the residue take up EtOAc washed with water, dried and evaporated to give rise to methyl (2R)-2-[(3-nitro-2-pyridyl)oxy]propanoate A mixture of 3.0 g (13.3 mmol) of methyl (2R)-2-[(3-nitro-2-pyridyl)oxy]propanoate and 5.0 ml 4 mol/l aq. NaOH solution in methanol are stirred at RT for 30 min. 5.0 ml 4 mol/l aq. HCl are added and the reaction mixture concentrated. The precipitate is filtered off, dissolved in DCM, dried and evaporated yielding (2R)-2-[(3-nitro-2-pyridyl)oxy]propanoic acid.

A mixture of 500 mg (2.4 mmol) (2R)-2-[(3-nitro-2-pyridyl)oxy]propanoic acid 320 mg (2.4 mmol) 2,2,2-Trifluoro-ethylamine hydrochloride, 896 mg (2.4 mmol) HATU and 1210 μl (7.0 mmol) N,N-Diisopropylethylamine in DMF stirred at RT over night. The solvent is evaporated. The residual is dissolved in DCM, dried, evaporated and purified by FC yielding (2R)-2-[(3-nitro-2-pyridyl)oxy]-N-(2,2,2-trifluoroethyl)propanamide.

To 500 mg (1.7 mmol) (2R)-2-[(3-nitro-2-pyridyl)oxy]-N-(2,2,2-trifluoroethyl)propanamide 100 mg Raney-Nickel and MeOH are added and the mixture is hydrogenated in a Parr apparatus (RT; 3 bar; over night). The catalyst is filtered off and the solvent is evaporated.

Yield: 440 mg (98%), ESI-MS: m/z=264 (M+H)⁺

Intermediate III.8: 4-fluoro-2-[2,2,2-trifluoro-1-(3-methylisoxazol-5-yl)ethoxy]aniline

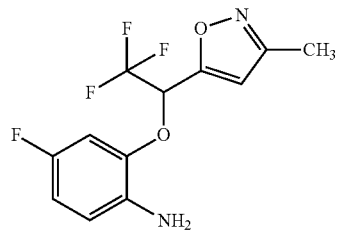 [SMILES: Cc1cc(C(Oc2cc(F)ccc2N)C(F)(F)F)on1]

A mixture of 0.1 g (0.9 mmol) 3-Methyl-isoxazole-5-carbaldehyde and 14 mg (0.09 mmol) CsF and THF is cooled to −5° C. 540 μl (1.1 mmol) trimethyl(trifluormethyl)-silane 2 M in THF is added dropwise and after 30 min the mixture is allowed to reach RT. After cooling with ice and addition of 5 ml 1 N aq. HCl, the mixture is stirred at RT over night, diluted with water and extracted with DCM. The combined organic layers are dried and evaporated giving rise to 2,2,2-trifluoro-1-(3-methylisoxazol-5-yl)ethanol. Intermediate III.8 is prepared in a similar manner as intermediate III.4 from 2,4-difluoro-1-nitro-benzene and 2,2,2-trifluoro-1-(3-methylisoxazol-5-yl)ethanol.

ESI-MS: m/z=291 (M+H)⁺, R$_t$(HPLC): 0.90 min (HPLC-E)

Intermediate III.9: 3-(2-amino-5-fluoro-phenoxy)-2-methyl-butan-2-ol

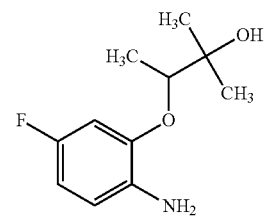

Is prepared in a similar manner as intermediate III.1 from 2,4-difluoro-1-nitro-benzene and 2-methylbutane-2,3-diol.
ESI-MS: m/z=254 (M+H)⁺

Intermediate III.10: 3-(2-amino-5-fluoro-phenoxy)-2,2-dimethyl-butanenitrile

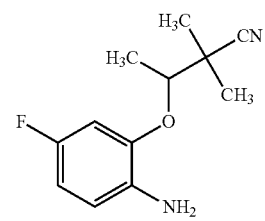 [SMILES: CC(Oc1cc(F)ccc1N)C(C)(C)C#N]

Is prepared in a similar manner as intermediate III.1 from 2,4-difluoro-1-nitro-benzene and 3-hydroxy-2,2-dimethyl-butanenitrile.
ESI-MS: m/z=223 (M+H)⁺

Intermediate III.11: 4-fluoro-2-[(1R)-2,2,2-trifluoro-1-methyl-ethoxy]aniline

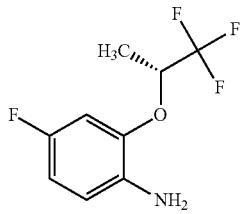

Is prepared in a similar manner as intermediate III.1 from 2,4-difluoro-1-nitro-benzene and (2R)-1,1,1-trifluoropropan-2-ol.

ESI-MS: m/z=224 (M+H)$^+$, R$_t$(HPLC): 0.77 min (HPLC-B)

Intermediate III.12: 4-amino-3-(2,2,2-trifluoro-1-methyl-ethoxy)benzonitrile

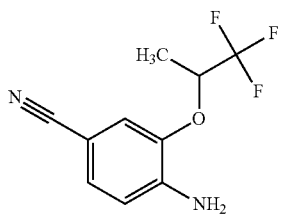 [SMILES: CC(Oc1cc(C#N)ccc1N)C(F)(F)F]

Is prepared in a similar manner as intermediate III.4 from 3-fluoro-4-nitro-benzonitrile and 1,1,1-trifluoro-propan-2-ol.

ESI-MS: m/z=231 (M+H)$^+$, R$_t$(HPLC): 0.95 min (HPLC-E)

Intermediate III.13: 4-amino-3-[1-(3-methylisoxazol-5-yl)ethoxy]benzamide

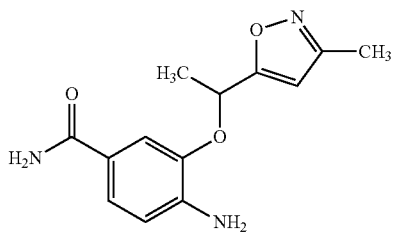 [SMILES: Cc1cc(C(C)Oc2cc(C(N)=O)ccc2N)on1]

Is prepared in a similar manner as intermediate III.4 from 3-fluoro-4-nitro-benzamide and 1-(3-methylisoxazol-5-yl)ethanol.

ESI-MS: m/z=262 (M+H)$^+$, R$_t$(HPLC): 0.35 min (HPLC-G)

Intermediate III.14: (2R)-2-(2-amino-5-fluoro-phenoxy)-3-fluoro-propan-1-ol

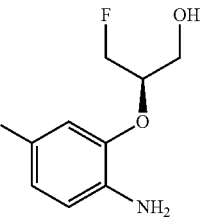

Is prepared in a similar manner as intermediate III.1 from 2,4-difluoro-1-nitro-benzene and (2R)-1-benzyloxy-3-fluoro-propan-2-ol.

ESI-MS: m/z=204 (M+H)$^+$

Intermediate III.15: (2R)-2-(2-amino-5-fluoro-phenoxy)-3,3,3-trifluoro-propan-1-ol

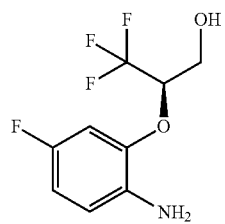 [SMILES: Nc1ccc(F)cc1O[C@H](CO)C(F)(F)F]

Is prepared in a similar manner as intermediate III.1 from 2,4-difluoro-1-nitro-benzene and (2R)-3-benzyloxy-1,1,1-trifluoro-propan-2-ol.

ESI-MS: m/z=240 (M+H)$^+$

Intermediate III.16: (2R)-2-(2-amino-5-fluoro-phenoxy)-N-(2,2,2-trifluoroethyl)propanamide

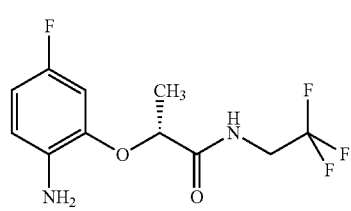 [SMILES: C[C@@H](Oc1cc(F)ccc1N)C(=O)NCC(F)(F)F]

Is prepared in a similar manner as intermediate III.7 from 2,4-difluoro-1-nitro-benzene.

ESI-MS: m/z=281 (M+H)$^+$, R$_t$(HPLC): 0.67 min (HPLC-A)

Intermediate III.17: (2R)-2-[(3-amino-2-pyridyl)oxy]-N-(2,2-difluoroethyl)propanamide

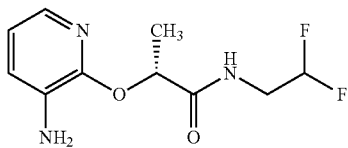 [SMILES: C[C@@H](Oc1ncccc1N)C(=O)NCC(F)F]

Is prepared in a similar manner as intermediate III.7 from 2-choro-3-nitro-pyridine and 2,2-difluoroethanamine.
ESI-MS: m/z=246 (M+H)$^+$

Intermediate III.18: (2R)-2-(2-amino-5-fluoro-phenoxy)-N-[2,2,2-trifluoro-1-(trifluoromethyl)ethyl]propanamide

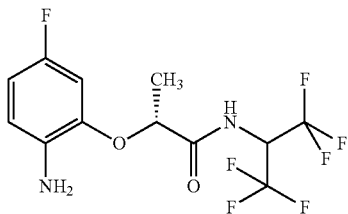 [SMILES: C[C@@H](Oc1cc(F)ccc1N)C(=O)NC(C(F)(F)F)C(F)(F)F]

Is prepared in a similar manner as intermediate III.7 from 2,4-difluoro-1-nitro-benzene and 1,1,1,3,3,3-hexafluoropropan-2-amine.
ESI-MS: m/z=349 (M+H)$^+$, R$_t$(HPLC): 0.97 min (HPLC-B)

The following Intermediates are prepared according to the given references, if no reference is given the intermediate is commercially available:

| Name | Structure | Reference |
|---|---|---|
| III.50 | ![structure] | WO2011/104338 |
| III.51 | ![structure] | |
| III.52 | ![structure] | WO2011/212103 |
| III.53 | ![structure] | WO2010/23181 |
| III.54 | ![structure] | U.S. Pat. No. 5,750,471 |
| III.55 | ![structure] | |
| III.56 | ![structure] | |

The following Intermediates are prepared according to the given references:

| Name | Structure | Reference |
|---|---|---|
| IV.1 | ![structure] | WO 2008/141843 |
| IV.2 | ![structure] | WO 2008/141843 |

-continued

| Name | Structure | Reference |
|---|---|---|
| IV.3 | 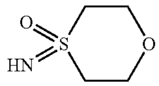 | WO2008/141843 |
| IV.4 | 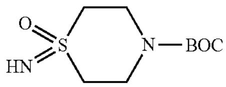 [SMILES: CC(C)(C)OC(=O)N1CCS(=N)(=O)CC1] | Adaptation of WO2011/29537 |
| IV.5 | 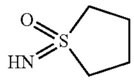 | WO 2008/141843 |
| IV.6 | 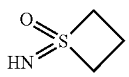 | Adaptation of WO 2008/141843 |
| V.7 | 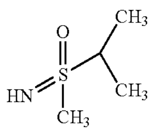 | Adaptation of Org. Lett., 2004, 6(8), 1305-1307 |
| V.8 | 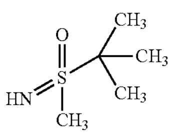 | Org. Lett., 2004, 6(8), 1305-1307 |
| V.9 | 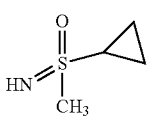 | Adaptation of Org. Lett., 2004, 6(8), 1305-1307 |
| V.10 | 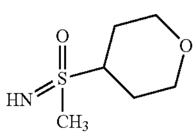 | Adaptation of Org. Lett., 2004, 6(8), 1305-1307 |
| V.11 | 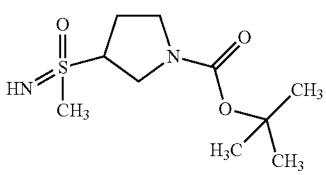 [SMILES: CC(C)(C)OC(=O)N1CCC(S(C)(=N)=O)C1] | Adaptation of Org. Lett., 2004, 6(8), 1305-1307 |
| V.12 | 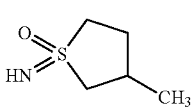 | Adaptation of Org. Lett., 2004, 6(8), 1305-1307 |
| V.13 | 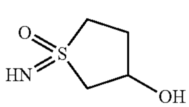 | Adaptation of Org. Lett., 2004, 6(8), 1305-1307 |
| V.14 | 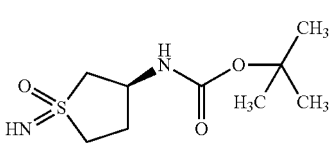 | Adaptation of Org. Lett., 2004, 6(8), 1305-1307. Isomer 1: $R_t$: 0.64 min (HPLC-B) |

-continued

| Name | Structure | Reference |
|---|---|---|
| V.15 | 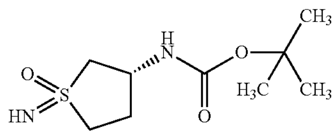 | Adaptation of Org. Lett., 2004, 6(8), 1305-1307. Isomer 2: $R_t$: 0.58 min (HPLC-Y) |
| V.16 | 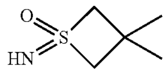 | Adaptation of Org. Lett., 2004, 6(8), 1305-1307. EI-MS: m/z = 134 (M + H)$^+$, mp: 48-50° C. |
| V.17 | 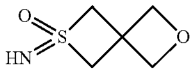 | Adaptation of Org. Lett., 2004, 6(8), 1305-1307. EI-MS: m/z = 148 (M + H)$^+$, mp: 135-139° C. |
| V.18 | 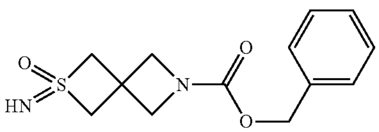 [SMILES: N=S1(=O)CC2(CN(C(=O)OCc3ccccc3)C2)C1] | Adaptation of Org. Lett., 2004, 6(8), 1305-1307. EI-MS: m/z = 281 (M + H)$^+$, $R_t$: 0.74 min (HPLC-A) |
| V.19 | 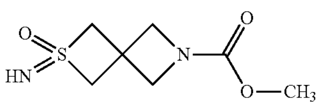 | Side product in the last step of the sythesis of V.18. EI-MS: m/z = 205 (M + H)$^+$ |

Intermediate V.1: 2-[[7-[[dimethyl(oxo)-λ$^6$-sulfanylidene]amino]-5-methyl-quinazolin-4-yl]amino]-5-fluoro-phenol

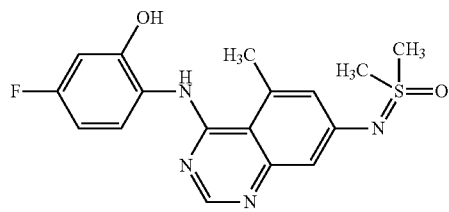 [SMILES: Cc1cc(N=S(C)(C)=O)cc2ncnc(Nc3ccc(F)cc3O)c12]

6.7 g (25 mmol) of II.2 and 5.7 g (26 mmol) of IV.60 is dissolved in acetic acid and heated to 100° C. for 1 h. After cooling to RT the reaction mixture is diluted with water and the precipitate is filtered off and washed with water. The crude product is treated with 80 ml ethanol, filtered and dried yielding N-(2-benzyloxy-4-fluoro-phenyl)-7-bromo-5-methyl-quinazolin-4-amine.

Yield: 7.1 g (65%), ESI-MS: m/z=438 (M+H)$^+$, $R_t$(HPLC): 1.12 min (HPLC-M) 3.1 g (7 mmol) of N-(2-benzyloxy-4-fluoro-phenyl)-7-bromo-5-methyl-quinazolin-4-amine, 0.8 g (8.8 mmol) dimethylsulphoximine (IV.1), 0.4 g (1.4 mmol) 2-(di-t-butylphosphino) biphenyl, 0.5 g (0.5 mmol) Pd$_2$dba$_3$ and 1.0 g (10.2 mmol) sodium tert-butoxide in dioxane are heated to 80° C. for 4.5 h. After cooling to RT the reaction mixture is filtered, diluted with water and extracted with EtOAc. The organic layers are pooled, dried and evaporated. The residue is purified by FC giving rise to N-(2-benzyloxy-4-fluoro-phenyl)-7-[[dimethyl(oxo)-λ$^6$-sulfanylidene]amino]-5-methyl-quinazolin-4-amine.

Yield: 2.8 g (88%), ESI-MS: m/z=451 (M+H)+

To 0.5 g (1.1 mmol) of N-(2-benzyloxy-4-fluoro-phenyl)-7-[[dimethyl(oxo)-λ$^6$-sulfanylidene]amino]-5-methyl-quinazolin-4-amine are added 50 mg palladium on charcoal (10%) and MeOH and THF and mixture is hydrogenated in a Parr apparatus (RT; 3 bar; 3 h). DMF and Ethanol are added and mixture heated to 70° C., the catalyst is filtered off and the solvent is evaporated.

Yield: 0.33 g (83%), ESI-MS: m/z=361 (M+H)$^+$, $R_t$(HPLC): 0.75 in (HPLC-E)

Intermediate V.2: 5-fluoro-2-[[5-methyl-7-[(1-oxo-thiolan-1-ylidene)amino]quinazolin-4-yl]amino]phenol

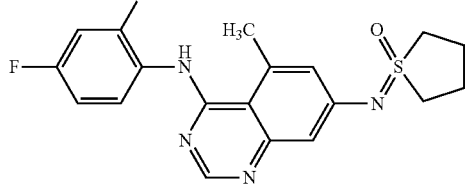

Is prepared in a similar manner as intermediate V.1 using II.2, III.54 and IV.5.

ESI-MS: m/z=387 (M+H)$^+$, $R_t$(HPLC): 0.56 min (HPLC-M)

Intermediate V.3: 2-[[7-[[dimethyl(oxo)-λ$^6$-sulfanylidene]amino]-5-fluoro-quinazolin-4-yl]amino]-5-fluoro-phenol

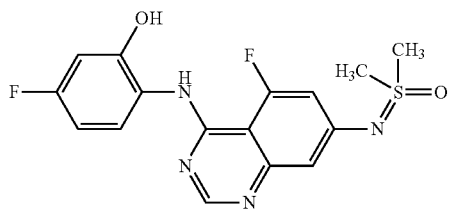 [SMILES: CS(C)(=O)=Nc1cc(F)c2c(Nc3ccc(F)cc3O)ncnc2c1]

Is prepared in a similar manner as intermediate V.1 using II.1, III.54 and IV.1.

ESI-MS: m/z=365 (M+H)$^+$, $R_t$(HPLC): 1.13 min (HPLC-F)

Intermediate V.4: 5-fluoro-2-[[5-fluoro-7-[(1-oxothi-olan-1-ylidene)amino]quinazolin-4-yl]amino]phenol

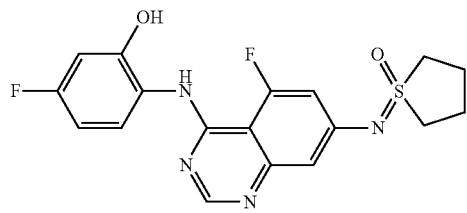 [SMILES: O=S1(=Nc2cc(F)c3c(Nc4ccc(F)cc4O)ncnc3c2)CCCC1]

Is prepared in a similar manner as intermediate V.1 using II.1, III.54 and IV.5.
ESI-MS: m/z=391 (M+H)$^+$, R$_t$(HPLC): 1.11 min (HPLC-F)

Intermediate V.5: 2-[[7-[[dimethyl(oxo)-$\lambda^6$-sulfa-nylidene]amino]-5-methoxy-quinazolin-4-yl]amino]-5-fluoro-phenol

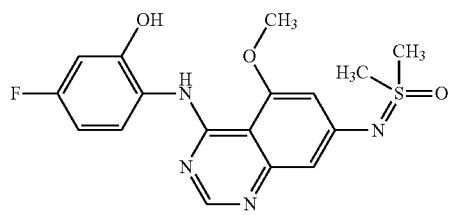 [SMILES: COc1cc(N=S(C)(C)=O)cc2ncnc(Nc3ccc(F)cc3O)c12]

Is prepared in a similar manner as intermediate V.1 using II.8, III.54 and IV.1.
ESI-MS: m/z=377 (M+H)$^+$, R$_t$(HPLC): 1.13 min (HPLC-F)

Intermediate V.6: 5-fluoro-2-[[5-methoxy-7-[(1-oxothiolan-1-ylidene)amino]quinazolin-4-yl]amino] phenol

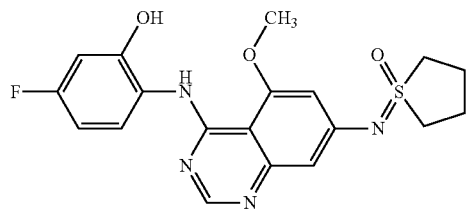 [SMILES: COc1cc(N=S2(=O)CCCC2)cc2ncnc(Nc3ccc(F)cc3O)c12]

Is prepared in a similar manner as intermediate V.1 using II.8, III.54 and IV.5.
ESI-MS: m/z=403 (M+H)$^+$, R$_t$(HPLC): 1.12 min (HPLC-F)

Intermediate V.9: 5-fluoro-2-[[5-methyl-7-[(1-oxothietan-1-ylidene)amino]quinazolin-4-yl]amino] phenol

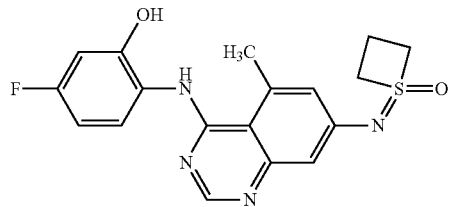 [SMILES: Cc1cc(N=S2(=O)CCC2)cc2ncnc(Nc3ccc(F)cc3O)c12]

A mixture of 10 g (22.8 mmol) of N-(2-benzyloxy-4-fluoro-phenyl)-7-bromo-5-methyl-quinazolin-4-amine (Intermediate V.1 step 1) and DCM is cooled to 0° C. and 34.2 ml (34.2 mmol) 1M BBr$_3$ in DCM are added dropwise. After 6 h water is added carefully and the precipitate is filtered off, suspended in water and neutralized with 32% aq. ammonia solution. After 2 h the precipitate is filtered off and dried furnishing 2-[(7-bromo-5-methyl-quinazolin-4-yl)amino]-5-fluoro-phenol. 1.5 g (4.3 mmol) 2-[(7-bromo-5-methyl-quinazolin-4-yl)amino]-5-fluoro-phenol, 0.45 g (4.3 mmol) 1-iminothietane 1-oxide (IV.6), 0.26 g (0.86 mmol) 2-(di-t-butylphosphino) biphenyl, 0.3 g (0.33 mmol) Pd$_2$dba$_3$ and 0.61 g (6.4 mmol) sodium tert-butoxide in dioxane are heated to 80° C. for 3 h. After cooling to RT the reaction mixture is filtered and evaporated. The residue is purified by FC.
ESI-MS: m/z=373 (M+H)$^+$, R$_t$(HPLC): 0.79 min (HPLC-A)

Intermediate VI.1: (2R)-2-[2-[[7-[[dimethyl(oxo)-$\lambda^6$-sulfanylidene]amino]-5-methyl-quinazolin-4-yl]amino]-5-fluoro-phenoxy]propanoic acid

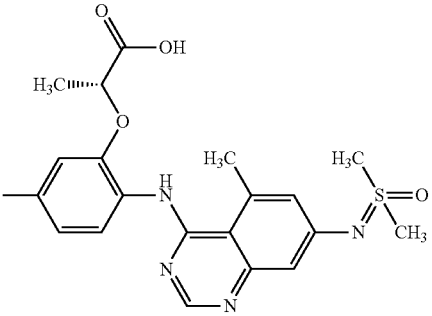

A mixture of 0.4 g (0.9 mmol) of example 3.022 and 2.6 ml 1 mol/l aq. NaOH solution in ethanol:THF 1:1 are stirred over night. 2.6 ml 1 mol/l aq. HCl are added and the precipitate is filtered off, washed with MeOH and dried.
Yield: 0.3 g (80%), ESI-MS: m/z=433 (M+H)$^+$, R$_t$(HPLC): 0.64 min (HPLC-B)

Intermediate VI.2: (2R)-2-[5-fluoro-2-[[5-methyl-7-[(1-oxothiolan-1-ylidene)amino]quinazolin-4-yl] amino]phenoxy]propanoic acid

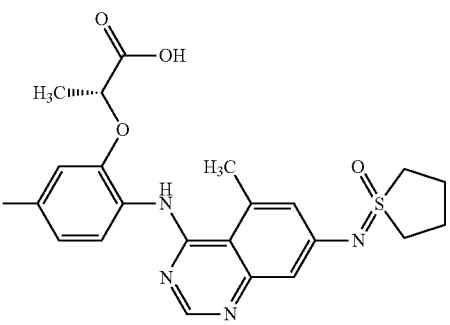

Is prepared in a similar manner as Intermediate from example 3.012
ESI-MS: m/z=459 (M+H)$^+$, R$_t$(HPLC): 0.65 min (HPLC-B)

The following Intermediates are prepared in a similar manner to intermediate VI.1 from the corresponding starting materials

| Name | Structure | ESI-MS m/z M + H⁺ | HPLC R_t Method |
|---|---|---|---|
| VI.3 | 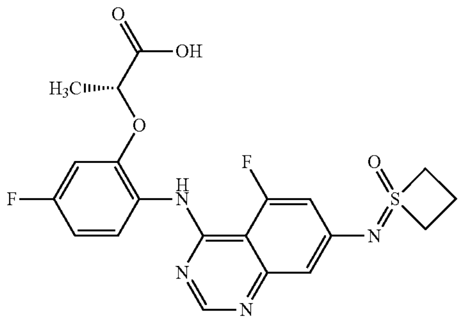 [SMILES: C[C@@H](Oc1cc(F)ccc1Nc1ncnc2cc(N=S3(=O)CCC3)cc(F)c12)C(=O)O] | 449 | 0.63 HPLC-M |
| VI.4 | 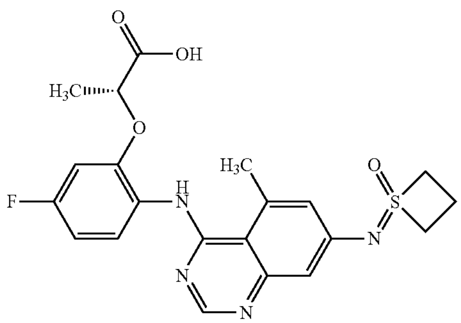 | 445 | 0.64 HPLC-M |
| VI.5 | 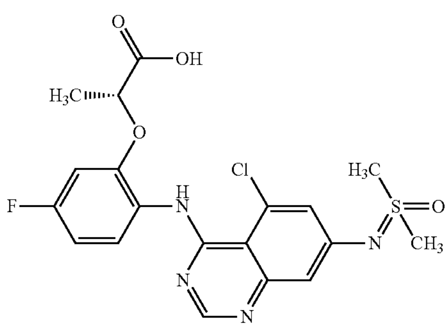 [SMILES: C[C@@H](Oc1cc(F)ccc1Nc1ncnc2cc(N=S(C)(C)=O)cc(Cl)c12)C(=O)O] | 453 | 0.66 HPLC-B |
| VI.6 | 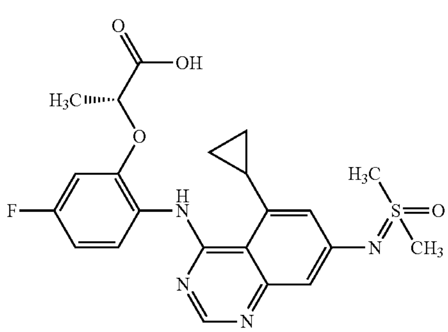 [SMILES: C[C@@H](Oc1cc(F)ccc1Nc1ncnc2cc(N=S(C)(C)=O)cc(C3CC3)c12)C(=O)O] | 459 | 0.82 HPLC-E |

-continued

| Name | Structure | ESI-MS m/z M + H⁺ | HPLC R_t Method |
|---|---|---|---|
| VI.7 | 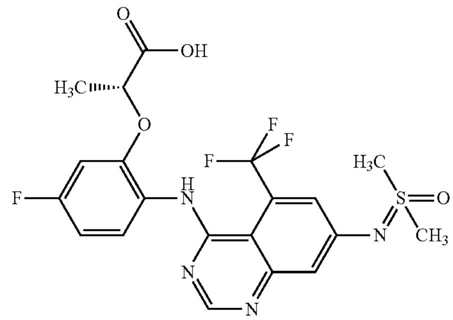 [SMILES: C[C@@H](Oc1cc(F)ccc1Nc1ncnc2cc(N=S(C)(C)=O)cc(C(F)(F)F)c12)C(=O)O] | 487 | 0.85 HPLC-E |
| VI.8 | 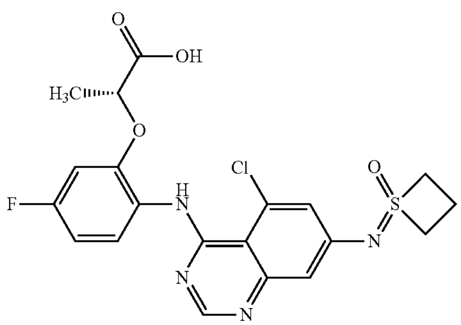 [SMILES: C[C@@H](Oc1cc(F)ccc1Nc1ncnc2cc(N=S3(=O)CCC3)cc(Cl)c12)C(=O)O] | 465 | 0.67 HPLC-M |
| VI.9 | 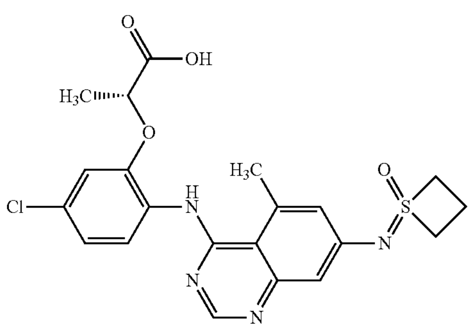 [SMILES: Cc1cc(N=S2(=O)CCC2)cc2ncnc(Nc3ccc(Cl)cc3O[C@H](C)C(=O)O)c12] | 461 | 0.66 HPLC-M |
| VI.10 | 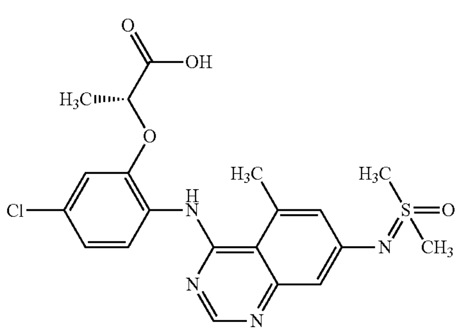 [SMILES: Cc1cc(N=S(C)(C)=O)cc2ncnc(Nc3ccc(Cl)cc3O[C@H](C)C(=O)O)c12] | 449 | 0.69 HPLC-M |

-continued

| Name | Structure | ESI-MS m/z M + H⁺ | HPLC R_t Method |
|---|---|---|---|
| VI.11 | 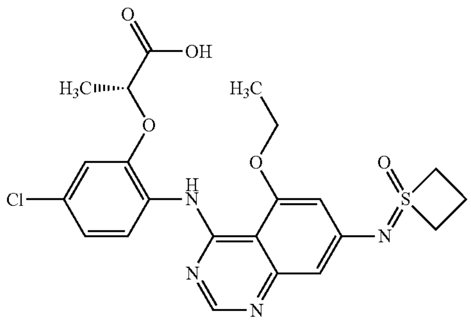 [SMILES: CCOc1cc(N=S2(=O)CCC2)cc2ncnc(Nc3ccc(Cl)cc3O[C@H](C)C(=O)O)c12] | 491 | 0.68 HPLC-M |
| VI.12 | 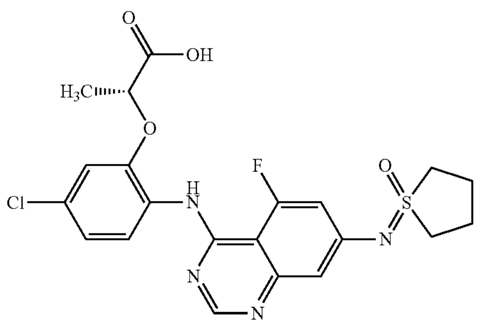 [SMILES: C[C@@H](Oc1cc(Cl)ccc1Nc1ncnc2cc(N=S3(=O)CCCC3)cc(F)c12)C(=O)O] | 491 | 0.67 HPLC-M |
| VI.13 | 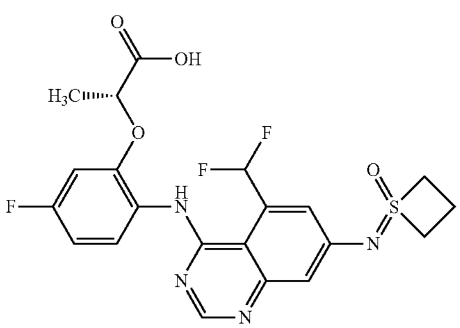 [SMILES: C[C@@H](Oc1cc(F)ccc1Nc1ncnc2cc(N=S3(=O)CCC3)cc(C(F)F)c12)C(=O)O] | 481 | 0.69 HPLC-M |
| VI.14 | 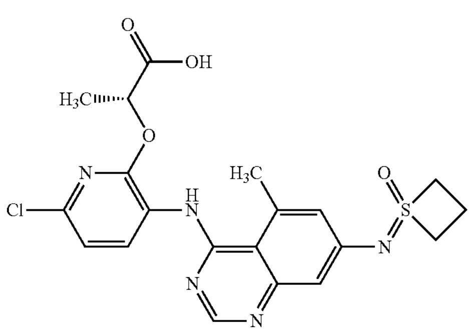 | 460 | 0.82 HPLC-E |

| Name | Structure | ESI-MS m/z M + H⁺ | HPLC R$_t$ Method |
|---|---|---|---|
| VI.15 | 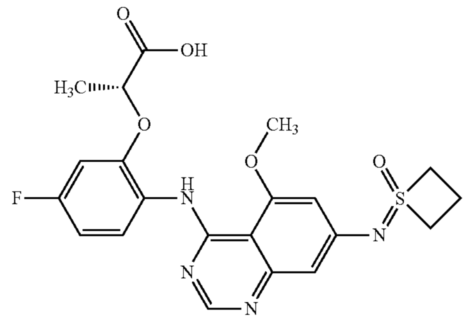 [SMILES: COc1cc(N=S2(=O)CCC2)cc2ncnc(Nc3ccc(F)cc3O[C@H](C)C(=O)O)c12] | 461 | |
| VI.16 | 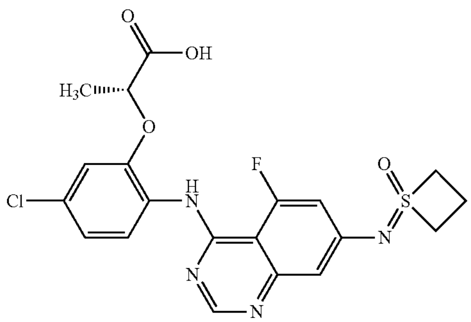 | 465 | 0.66 HPLC-M |
| VI.17 | 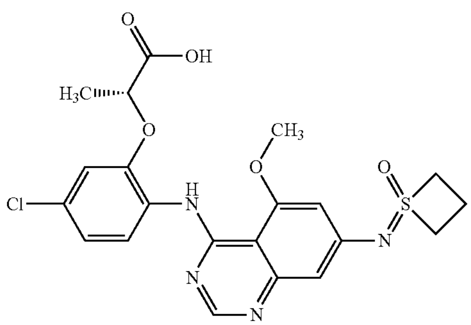 [SMILES: COc1cc(N=S2(=O)CCC2)cc2ncnc(Nc3ccc(Cl)cc3O[C@H](C)C(=O)O)c12] | 477 | 0.67 HPLC-M |

Intermediate VII.1: (2R)-2-[2-[(7-bromo-5-fluoro-quinazolin-4-yl)amino]-5-fluoro-phenoxy]-N-(2,2,2-trifluoroethyl)propanamide

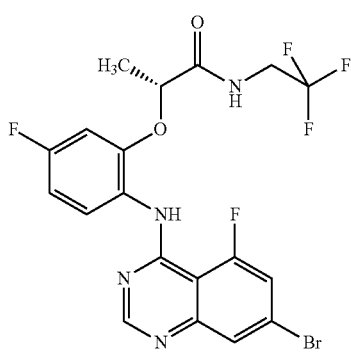 [SMILES: C[C@@H](Oc1cc(F)ccc1Nc1ncnc2cc(Br)cc(F)c12)C(=O)NCC(F)(F)F]

30 g (111 mmol) of 11.1 and 24.1 g (111 mmol) of IV.60 is dissolved in acetic acid and heated to 80° C. for 1 h. After cooling to RT the reaction mixture is diluted with water and the precipitate is filtered off and washed with water and dried yielding N-(2-benzyloxy-4-fluoro-phenyl)-7-bromo-5-fluoro-quinazolin-4-amine.

Yield: 47 g (96%), ESI-MS: m/z=442 (M+H)⁺, R$_t$(HPLC): 1.15 min (HPLC-E)

A mixture of 47 g (106 mmol) of N-(2-benzyloxy-4-fluoro-phenyl)-7-bromo-5-fluoro-quinazolin-4-amine and DCM is cooled to 0° C. and 159.4 ml (159.4 mmol) 1M BBr3 in DCM are added dropwise. After 3 h aq NaHCO₃ solution is added carefully and the precipitate is filtered off, suspended in water and neutralized with 32% aq. ammonia solution. The precipitate is filtered off and dried furnishing 2-[(7-bromo-5-fluoro-quinazolin-4-yl)amino]-5-fluoro-phenol.

Yield: 38 g, ESI-MS: m/z=352 (M+H)⁺, R$_t$(HPLC): 0.85 min (HPLC-E)

To a mixture of 28 g (79.5 mmol) 2-[(7-bromo-5-fluoro-quinazolin-4-yl)amino]-5-fluoro-phenol, 9.4 g (79.5 mmol) (S)-2-Hydroxy-propionic acid ethyl ester, 25.1 g (95.6 mmol) PPh₃ and THF 22 g (95.4 mmol) di-tert-butyl azodicarboxylate are added and the mixture stirred over night. The solvent is evaporated and isopropanol is added, the precipitate is filtered off and dried furnishing ethyl (2R)-2-[2-[(7-bromo-5-fluoro-quinazolin-4-yl)amino]-5-fluoro-phenoxy]propanoate.

Yield: 34 g (95%), ESI-MS: m/z=452 (M+H)⁺, R$_f$(HPLC): 1.09 min (HPLC-E)

A mixture of 34 g (75 mmol) of ethyl (2R)-2-[2-[(7-bromo-5-fluoro-quinazolin-4-yl)amino]-5-fluoro-phenoxy]propanoate and 225.5 ml 1 mol/l aq. NaOH solution in THF are stirred for 2 h at RT. The solvent is evaporated and water is added. The mixture is neutralized with 1 mol/l aq. HCl and the precipitate is filtered off and dried yielding (2R)-2-[2-[(7-bromo-5-fluoro-quinazolin-4-yl)amino]-5-fluoro-phenoxy]propanoic acid.

Yield: 28.3 g (89%), ESI-MS: m/z=424 (M+H)⁺, R$_f$(HPLC): 0.90 min (HPLC-E)

To a mixture of 300 mg (0.78 mmol) (2R)-2-[2-[(7-bromo-5-fluoro-quinazolin-4-yl)amino]-5-fluoro-phenoxy]propanoic acid and DMF, 0.3 ml (1.8 mmol) DIPEA, 105 mg (0.89 mmol) 2,2,2-trifluoro-ethylamine and 344 mg (0.9 mmol) HATU are added. The mixture is stirred at RT for 3 h, water is added and the precipitate is filtered and dried.

Yield: 350 mg (98%), ESI-MS: m/z=505 (M+H)⁺, R$_f$(HPLC): 0.97 min (HPLC-E)

Intermediate VII.3: (2R)-2-[2-[(7-bromo-5-methoxy-quinazolin-4-yl)amino]-5-fluoro-phenoxy]-N-(2,2,2-trifluoroethyl)propanamide

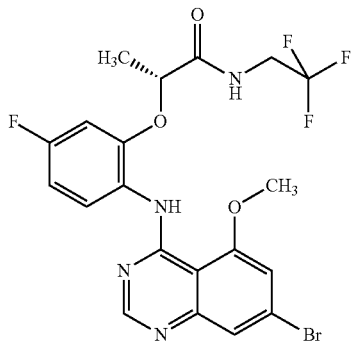 [SMILES: COc1cc(Br)cc2ncnc(Nc3ccc(F)cc3O[C@H](C)C(=O)NCC(F)(F)F)c12]

A mixture of 1.2 g (2.4 mmol) intermediate VII.1 1.2 g (3.7 mmol) Cs₂CO₃ and THF:MeOH 1:1 is heated to 70° C. for 4 h and over night at 50° C. The reaction mixture was evaporated and the residual washed with methanol and water and dried.

Yield: 1.3 g, ESI-MS: m/z=519 (M+H)⁺, R$_f$(HPLC): 0.76 min (HPLC-B)

Intermediate VII.7: (2R)-2-[2-[(5-chloro-7-iodo-quinazolin-4-yl)amino]-5-fluoro-phenoxy]-N-(2,2,2-trifluoroethyl)propanamide

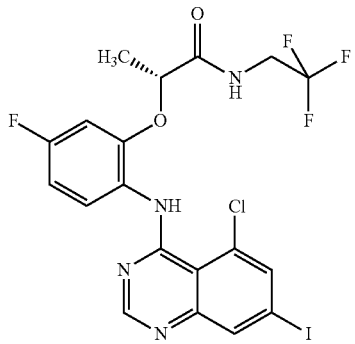 [SMILES: C[C@@H](Oc1cc(F)ccc1Nc1ncnc2cc(I)cc(Cl)c12)C(=O)NCC(F)(F)F]

A mixture of 0.5 g (1.5 mmol) intermediate II.18 and formic acid is heated to 130° C. in a sealed tube, 1 ml 37% aq. HCl is added and the mixture is heated to 130° C. for 24 h. After cooling to RT, water is added and the precipitate is filtered off, washed with 5% aq. NaHCO₃ solution and dried giving rise to 5-chloro-7-iodo-3H-quinazolin-4-one.

Yield: 0.4 g, ESI-MS: m/z=307 (M+H)⁺, R$_f$(HPLC): 0.71 min (HPLC-M) To a mixture of 0.4 g (1.27 mmol) 5-chloro-7-iodo-3H-quinazolin-4-one, 0.5 ml (3.18 mmol) DIPEA and toluene, 0.3 ml (2.8 mmol) POCl₃ is added dropwise and stirred at RT for 1 h, the heated to 90° C. for 1.5 h. After cooling to RT the solvent is evaporated giving rise to crude 4,5-dichloro-7-iodo-quinazoline.

To a mixture of the crude 4,5-dichloro-7-iodo-quinazoline and dioxane, 0.4 g (1.27 mmol) intermediate III.16 is added and the mixture is stirred at RT for 2 h. The reaction mixture is diluted with water and neutralized with saturated aq. NaHCO₃ solution. The precipitate is filtered off and dried.

Yield: 0.5 g, ESI-MS: m/z=569 (M+H)⁺, R$_f$(HPLC): 0.98 min (HPLC-A)

Intermediate VII.9: (2R)-2-[[3-[(7-bromo-5-methyl-quinazolin-4-yl)amino]-2-pyridyl]oxy]-N-(2,2-difluoroethyl)propanamide

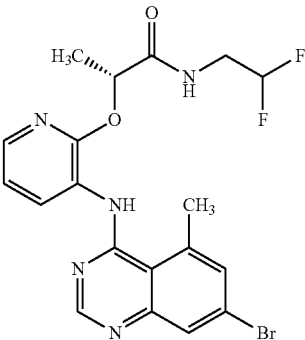 [SMILES: Cc1cc(Br)cc2ncnc(Nc3cccnc3O[C@H](C)C(=O)NCC(F)F)c12]

673 mg (2.5 mmol) of 11.2 and 620 mg (2.5 mmol) of III.17 are dissolved in acetic acid and heated to 80° C. for 1 h. After cooling to RT the reaction mixture is stirred over night and evaporated. The crude product is purified via HPLC.

Yield: 400 mg (34%), ESI-MS: m/z=466 (M+H)⁺

The following Intermediates are prepared in a similar manner to intermediate VII.1, VII.7 or VII.9 from the corresponding starting materials

| Name | Structure | ESI-MS m/z M + H⁺ | HPLC R$_f$ Method |
|---|---|---|---|
| VII.2 | 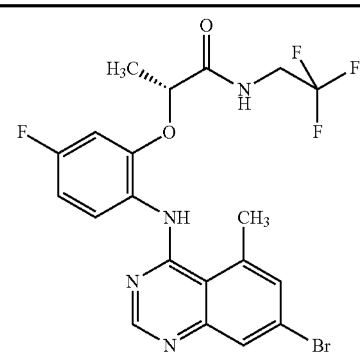 | 501 | |

-continued

| Name | Structure | ESI-MS m/z M + H+ | HPLC Rt Method |
|---|---|---|---|
| VII.4 | 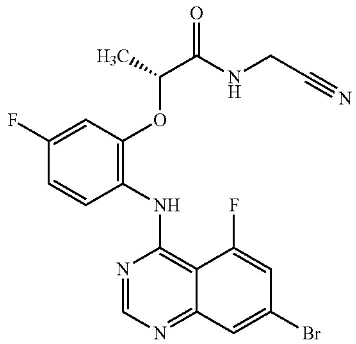 [SMILES: C[C@@H](Oc1cc(F)ccc1Nc1ncnc2cc(Br)cc(F)c12)C(=O)NCC#N] | 462 | 0.77 HPLC-B |
| VII.5 | 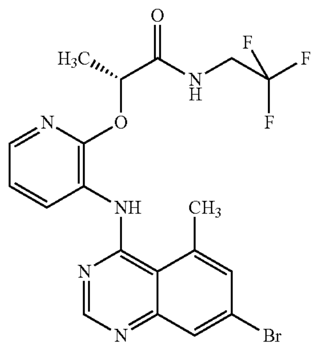 | 484 | 0.77 HPLC-X |
| VII.6 | 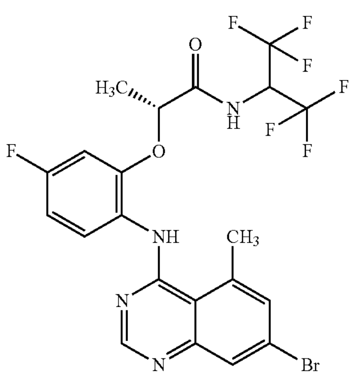 [SMILES: Cc1cc(Br)cc2ncnc(Nc3ccc(F)cc3O[C@H](C)C(=O)NC(C(F)(F)F)C(F)(F)F)c12] | 569 | 1.17 HPLC-M |

-continued

| Name | Structure | ESI-MS m/z M + H+ | HPLC Rt Method |
|---|---|---|---|
| VII.8 | 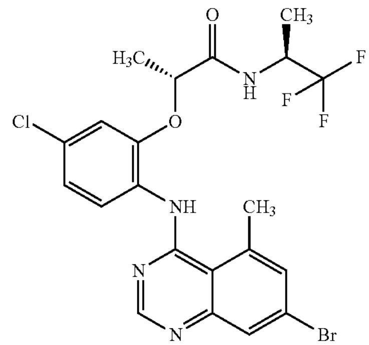 [SMILES: Cc1cc(Br)cc2ncnc(Nc3ccc(Cl)cc3O[C@H](C)C(=O)N[C@@H](C)C(F)(F)F)c12] | 533 | 0.94 HPLC-B |

Methods of Preparation of Final Compounds

General Procedure 1 (P1) for Examples Shown in Table 1 and Table 2:

Equimolar amounts of the respective intermediates II and III are dissolved in AcOH and heated to the given temperature for the given time. The reaction mixture is evaporated and the residue is purified by HPLC.

The following examples in table 1 (example number given in column #) are prepared according to P1, details are given in the column synthesis comment, the retention-time and mass (ESI-MS m/z M+H+) determined by HPLC-MS are given in the columns MS and RT.

TABLE 1

| # | Structure | SM | MS | RT | Synthesis Comment |
|---|---|---|---|---|---|
| 1.001 | 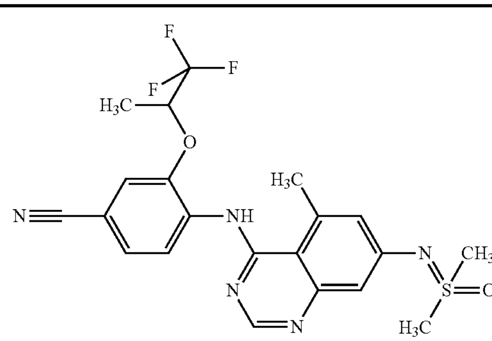 | II.9 III.12 | 464 | 0.7 min (HPLC-N) | 75° C. 48 h |

TABLE 1-continued

| # | Structure | SM | MS | RT | Synthesis Comment |
|---|---|---|---|---|---|
| 1.002 | 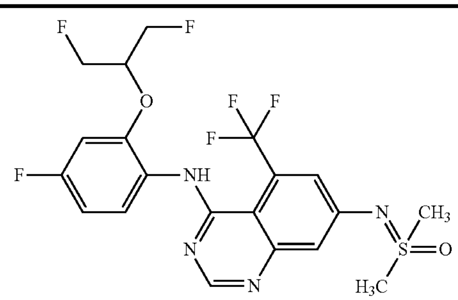 | II.11<br>III.50 | 493 | 0.83 min<br>(HPLC-I) | 65° C. 4 h |
| 1.003 | 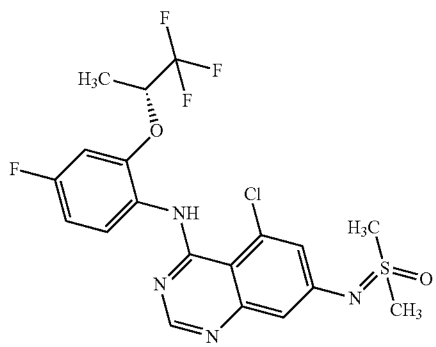 [SMILES: C[C@@H](Oc1cc(F)ccc1Nc1ncnc2cc(N=S(C)(C)=O)cc(Cl)c12)C(F)(F)F] | II.5<br>III.11 | 477 | 0.93 min<br>(HPLC-M) | 65° C. 2 h |
| 1.004 | 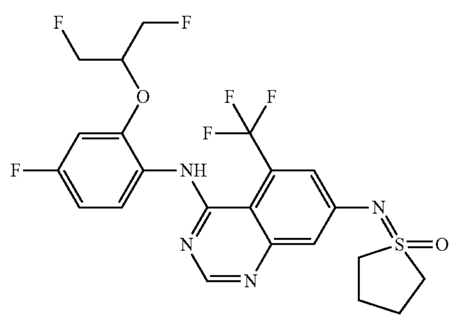 [SMILES: O=S1(=Nc2cc(C(F)(F)F)c3c(Nc4ccc(F)cc4OC(CF)CF)ncnc3c2)CCCC1] | II.12<br>III.50 | 519 | 1.13 min<br>(HPLC-P) | 75° C.<br>over night |
| 1.005 | 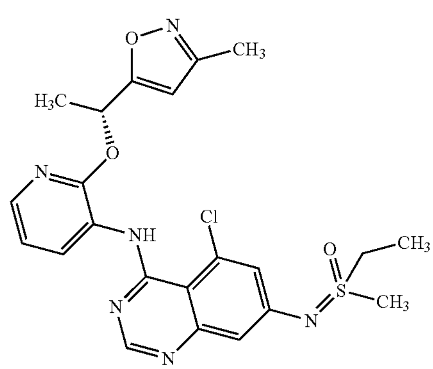 [SMILES: CCS(C)(=O)=Nc1cc(Cl)c2c(Nc3cccnc3O[C@H](C)c3cc(C)no3)ncnc2c1] | II.16<br>III.6 | 487 | 0.78 min<br>(HPLC-N) | 95° C. 5 h |

TABLE 1-continued

| # | Structure | SM | MS | RT | Synthesis Comment |
|---|---|---|---|---|---|
| 1.006 | 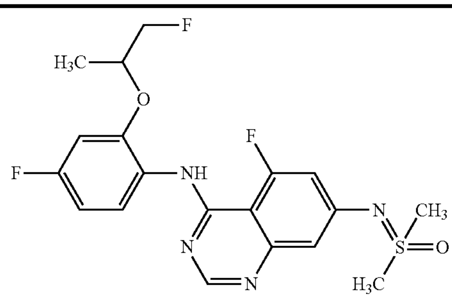 | II.15<br>III.1 | 425 | 0.72 min<br>(HPLC-B) | 75° C. 4 h |
| 1.007 | 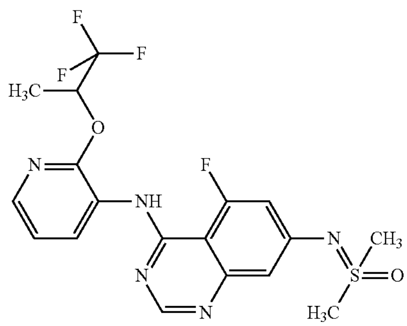 [SMILES: CC(Oc1ncccc1Nc1ncnc2cc(N=S(C)(C)=O)cc(F)c12)C(F)(F)F] | II.15<br>III.52 | 444 | 0.9 min<br>(HPLC-E) | 75° C.<br>over night |
| 1.008 | 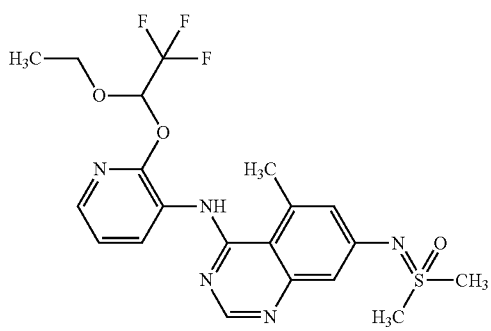 [SMILES: CCOC(Oc1ncccc1Nc1ncnc2cc(N=S(C)(C)=O)cc(C)c12)C(F)(F)F] | II.9<br>III.3 | 470 | 0.92 min<br>(HPLC-E) | 80° C. 4 h |
| 1.009 | 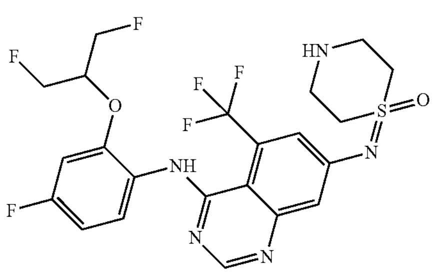 [SMILES: O=S1(=Nc2cc(C(F)(F)F)c3c(Nc4ccc(F)cc4OC(CF)CF)ncnc3c2)CCNCC1] | II.14<br>III.50 | 534 | 0.7 min<br>(HPLC-I) | 65° C. 4 h |
| 1.010 | 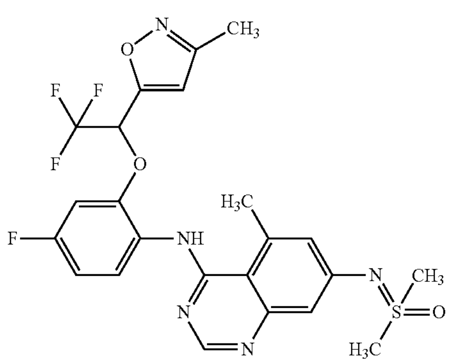 [SMILES: Cc1cc(C(Oc2cc(F)ccc2Nc2ncnc3cc(N=S(C)(C)=O)cc(C)c23)C(F)(F)F)on1] | II.9<br>III.8 | 524 | 0.81 min<br>(HPLC-I) | 65° C.<br>over night |

TABLE 1-continued

| # | Structure | SM | MS | RT | Synthesis Comment |
|---|---|---|---|---|---|
| 1.011 | 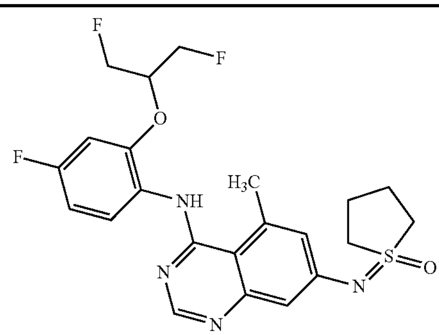 | II.17 III.50 | 465 | 0.82 min (HPLC-B) | 65° C. over night |
| 1.012 | 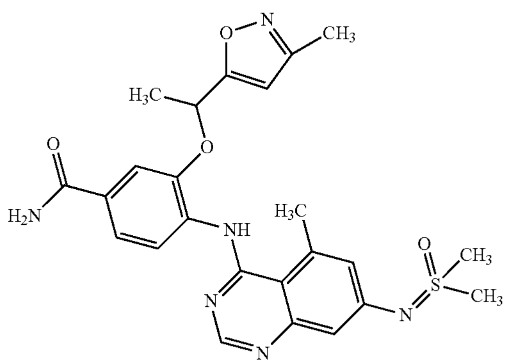 [SMILES: Cc1cc(C(C)Oc2cc(C(N)=O)ccc2Nc2ncnc3cc(N=S(C)(C)=O)cc(C)c23)on1] | II.9 III.13 | 495 | 0.4 min (HPLC-G) | 80° C. 24 h |
| 1.013 | 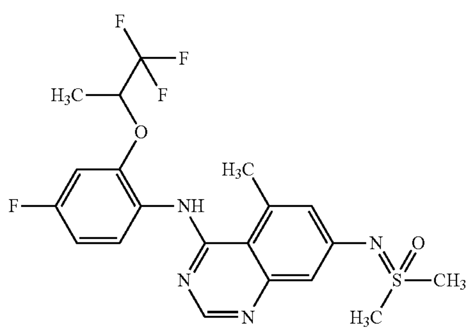 [SMILES: Cc1cc(N=S(C)(C)=O)cc2ncnc(Nc3ccc(F)cc3OC(C)C(F)(F)F)c12] | II.9 III.51 | 457 | 1.06 min (HPLC-P) | 80° C. 2 h; racemate |
| 1.014 | 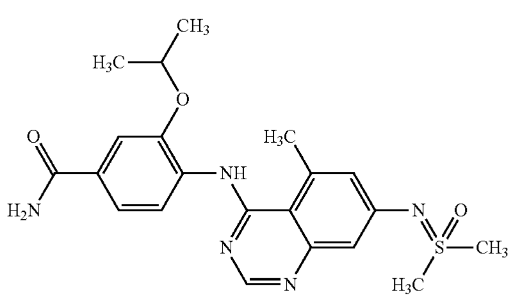 [SMILES: Cc1cc(N=S(C)(C)=O)cc2ncnc(Nc3ccc(C(N)=O)cc3OC(C)C)c12] | II.9 III.56 | 428 | 0.4 min (HPLC-G) | 80° C. 24 h |
| 1.015 | 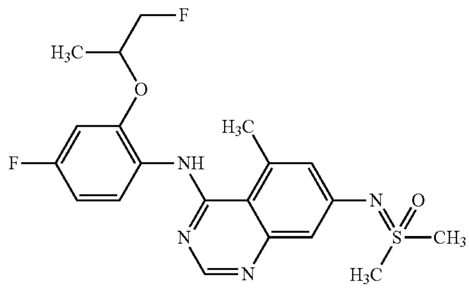 [SMILES: Cc1cc(N=S(C)(C)=O)cc2ncnc(Nc3ccc(F)cc3OC(C)CF)c12] | II.9 III.1 | 421 | 0.72 min (HPLC-I) | 80° C. 2 h |

TABLE 1-continued

| # | Structure | SM | MS | RT | Synthesis Comment |
|---|---|---|---|---|---|
| 1.016 | 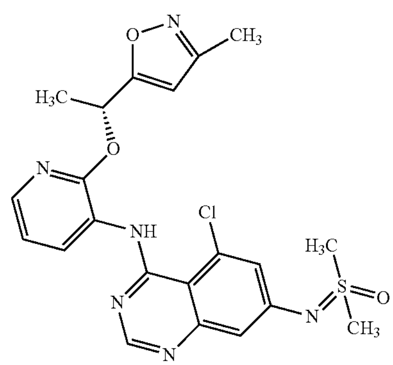 [SMILES: Cc1cc([C@@H](C)Oc2ncccc2Nc2ncnc3cc(N=S(C)(C)=O)cc(Cl)c23)on1] | II.5<br>III.6 | 473 | 0.88 min<br>(HPLC-M) | 65° C. 3 h |
| 1.017 | 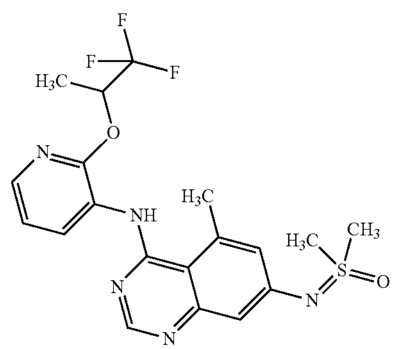 [SMILES: Cc1cc(N=S(C)(C)=O)cc2ncnc(Nc3cccnc3OC(C)C(F)(F)F)c12] | II.9<br>III.52 | 440 | 0.89 min<br>(HPLC-E) | 80° C.<br>over night |
| 1.018 | 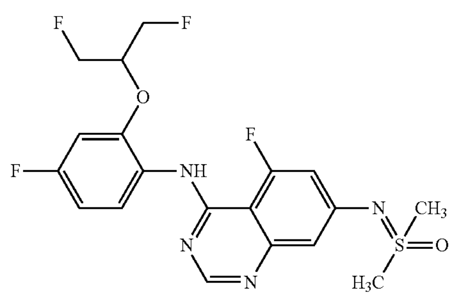 [SMILES: CS(C)(=O)=Nc1cc(F)c2c(Nc3ccc(F)cc3OC(CF)CF)ncnc2c1] | II.15<br>III.50 | 443 | 0.79 min<br>(HPLC-B) | 75° C. 4 h |
| 1.019 | 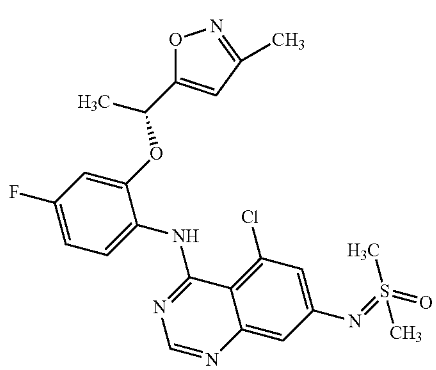 [SMILES: Cc1cc([C@@H](C)Oc2cc(F)ccc2Nc2ncnc3cc(N=S(C)(C)=O)cc(Cl)c23)on1] | II.5<br>III.5 | 490 | 0.42 min<br>(HPLC-Q) | 80° C. 3 h |

TABLE 1-continued

| # | Structure | SM | MS | RT | Synthesis Comment |
|---|---|---|---|---|---|
| 1.020 | 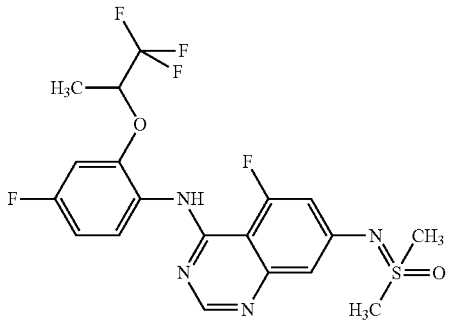 [SMILES: CC(Oc1cc(F)ccc1Nc1ncnc2cc(N=S(C)(C)=O)cc(F)c12)C(F)(F)F] | II.15<br>III.51 | 461 | 0.85 min<br>(HPLC-B) | 75° C. 4 h |
| 1.021 | 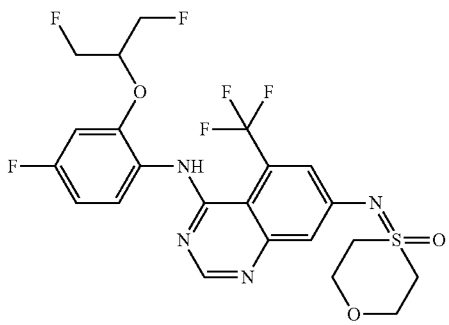 [SMILES: O=S1(=Nc2cc(C(F)(F)F)c3c(Nc4ccc(F)cc4OC(CF)CF)ncnc3c2)CCOCC1] | II.13<br>III.50 | 535 | 1.11 min<br>(HPLC-P) | 65° C. 4 h |
| 1.022 | 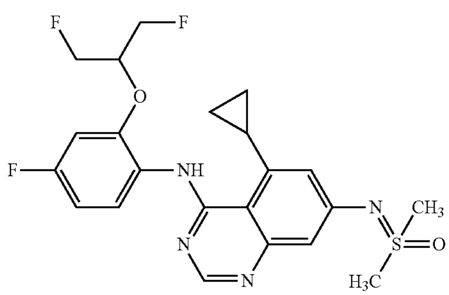 [SMILES: CS(C)(=O)=Nc1cc(C2CC2)c2c(Nc3ccc(F)cc3OC(CF)CF)ncnc2c1] | II.10<br>III.50 | 465 | 0.68 min<br>(HPLC-N) | 65° C.<br>over night |
| 1.023 | 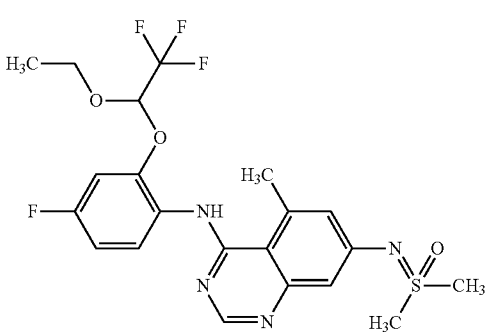 | II.9<br>III.2 | 487 | 0.91 min<br>(HPLC-E) | 80° C. 4 h |

General Procedure 2 (P2) for Examples Shown in Table 2:

1 eq of aryl bromide (if not described prepared according to P1) or aryl iodide, 1.2 eq sulphoximine, 20 mol % 2-(di-tert-butylphosphino) biphenyl, 10 mol % Pd$_2$dba$_3$ and 1.4 eq sodium tert-butoxide are mixed with dioxane and heated under an argon atmosphere to the given temperature for the given time. The reaction mixture is concentrated and the crude product purified by HPLC or FC.

The following examples in table 2 (example number given in column #) are prepared according to P2, details are given in the column synthesis comment, the retention-time and mass (ESI-MS m/z M+H$^+$) determined by HPLC-MS are given in the columns MS and RT.

TABLE 2
| # | Structure | SM | MS | RT | Synthesis Comment |
|---|---|---|---|---|---|
| 2.001 | 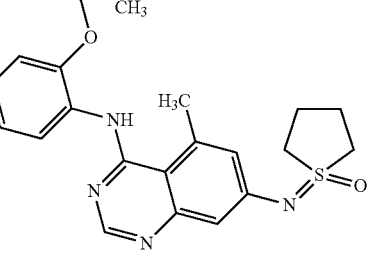 | II.2 III.9 | 473 | 1.3 min (HPLC-S) | 90° C. 2 h |
| 2.002 | 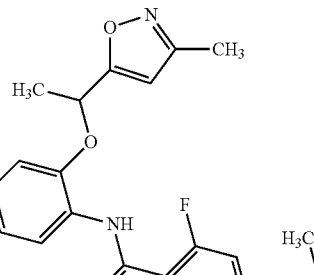 | II.1 III.4 | 474 | 1.12 min (HPLC-J) | 80° C. 2 h |
| 2.003 | 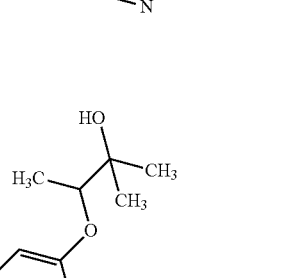 | II.2 III.9 | 447 | 1.25 min (HPLC-S) | 90° C. 2 h |
| 2.004 | 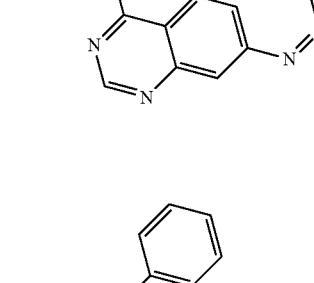 | II.2 III.53 | 477 | 0.81 min (HPLC-A) | 80° C. 4.5 h |

TABLE 2-continued

| # | Structure | SM | MS | RT | Synthesis Comment |
|---|---|---|---|---|---|
| 2.005 | 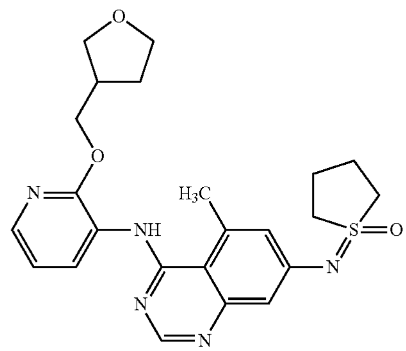 [SMILES: Cc1cc(N=S2(=O)CCCC2)cc2ncnc(Nc3cccnc3OCC3CCOC3)c12] | II.2 III.54 | 454 | 0.81 min (HPLC-E) | 80° C. 2 h; |
| 2.006 | 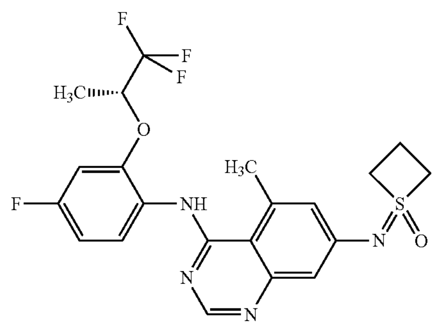 [SMILES: Cc1cc(N=S2(=O)CCC2)cc2ncnc(Nc3ccc(F)cc3O[C@H](C)C(F)(F)F)c12] | II.2 III.11 | 469 | 0.55 min (HPLC-G) | 80° C. 1 h |
| 2.007 | 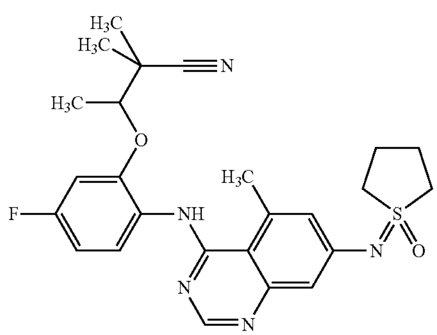 [SMILES: Cc1cc(N=S2(=O)CCCC2)cc2ncnc(Nc3ccc(F)cc3OC(C)C(C)(C)C#N)c12] | II.2 III.10 | 482 | 0.51 min (HPLC-G) | 80° C. 2 h; |
| 2.008 | 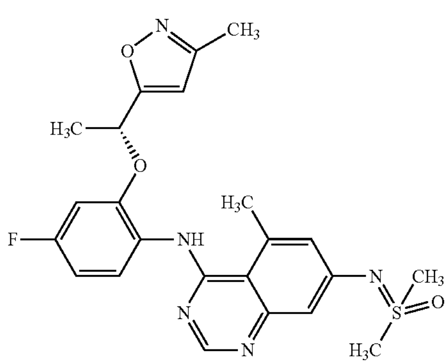 [SMILES: Cc1cc([C@@H](C)Oc2cc(F)ccc2Nc2ncnc3cc(N=S(C)(C)=O)cc(C)c23)on1] | II.2 III.5 | 470 | 1.35 min (HPLC-O) | 100° C. over night |

TABLE 2-continued

| # | Structure | SM | MS | RT | Synthesis Comment |
|---|---|---|---|---|---|
| 2.009 | 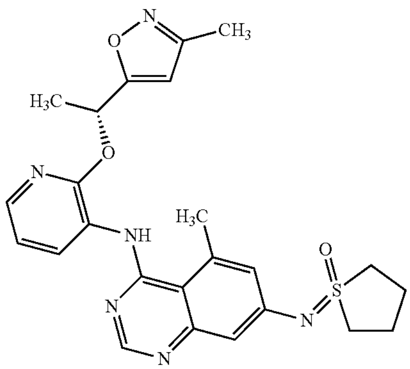 [SMILES: Cc1cc([C@@H](C)Oc2ncccc2Nc2ncnc3cc(N=S4(=O)CCCC4)cc(C)c23)on1] | II.2 III.6 | 479 | 0.55 min (HPLC-K) | 80° C. 3 h |
| 2.010 | 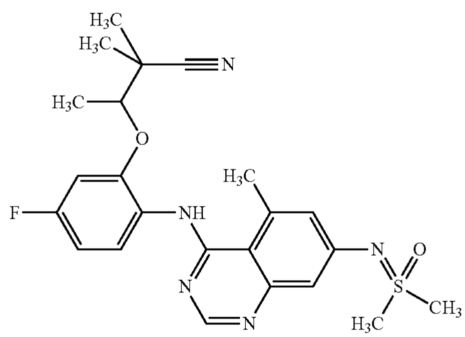 [SMILES: Cc1cc(N=S(C)(C)=O)cc2ncnc(Nc3ccc(F)cc3OC(C)C(C)(C)C#N)c12] | II.2 III.10 | 456 | 0.49 min (HPLC-G) | 80° C. 2 h; |
| 2.011 | 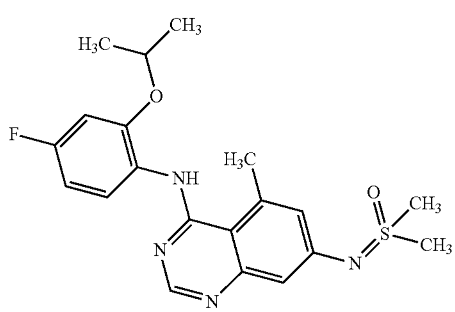 [SMILES: Cc1cc(N=S(C)(C)=O)cc2ncnc(Nc3ccc(F)cc3OC(C)C)c12] | II.2 III.55 | 403 | 0.75 min (HPLC-A) | 80° C. 2.5 h |
| 2.012 | 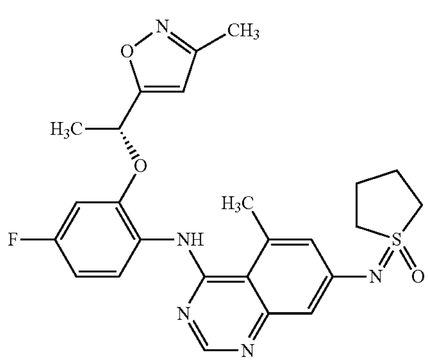 [SMILES: Cc1cc([C@@H](C)Oc2cc(F)ccc2Nc2ncnc3cc(N=S4(=O)CCCC4)cc(C)c23)on1] | II.2 III.5 | 496 | 1.37 min (HPLC-F) | 100° C. over night |

TABLE 2-continued

| # | Structure | SM | MS | RT | Synthesis Comment |
|---|---|---|---|---|---|
| 2.013 | 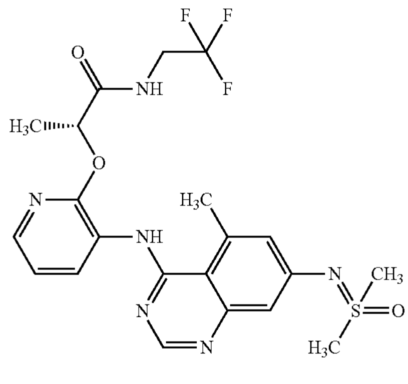 [SMILES: Cc1cc(N=S(C)(C)=O)cc2ncnc(Nc3cccnc3O[C@H](C)C(=O)NCC(F)(F)F)c12] | II.2 III.7 | 497 | 0.66 min (HPLC-B) | 80° C. 4.5 h |
| 2.014 | 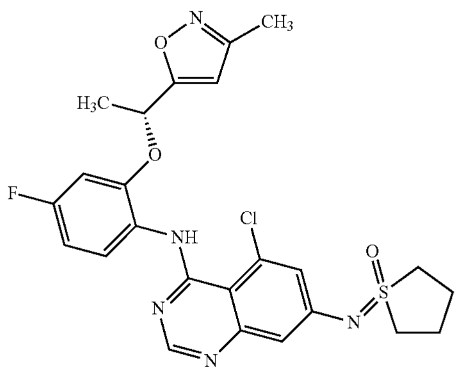 [SMILES: Cc1cc([C@@H](C)Oc2cc(F)ccc2Nc2ncnc3cc(N=S4(=O)CCCC4)cc(Cl)c23)on1] | II.6 III.5 | 516 | 0.55 min (HPLC-G) | 80° C. 2.5 h |
| 2.015 | 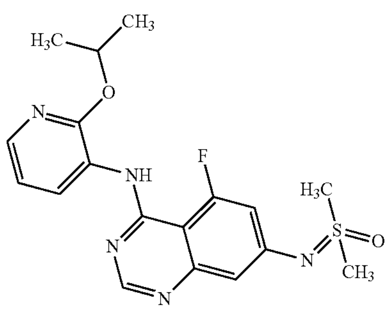 [SMILES: CC(C)Oc1ncccc1Nc1ncnc2cc(N=S(C)(C)=O)cc(F)c12] | II.1 III.53 | 390 | 0.69 min (HPLC-C) | 80° C. 2 h |
| 2.016 | 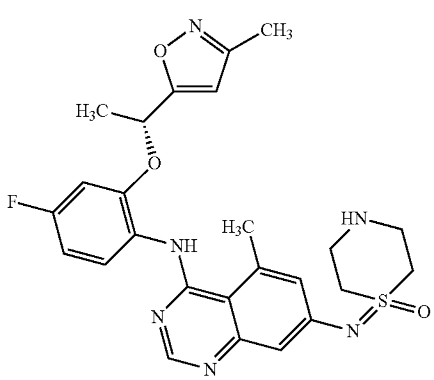 [SMILES: Cc1cc([C@@H](C)Oc2cc(F)ccc2Nc2ncnc3cc(N=S4(=O)CCNCC4)cc(C)c23)on1] | II.2 III.5 | 511 | 0.44 min (HPLC-G) | 2 h 80° C.; followed by deprotection in DCM with 11 eq TFA; over night |

TABLE 2-continued

| # | Structure | SM | MS | RT | Synthesis Comment |
|---|---|---|---|---|---|
| 2.017 | 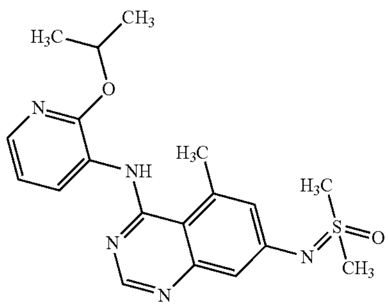 [SMILES: Cc1cc(N=S(C)(C)=O)cc2ncnc(Nc3cccnc3OC(C)C)c12] | II.2 III.53 | 386 | 0.73 min (HPLC-A) | 80° C. 2 h |
| 2.018 | 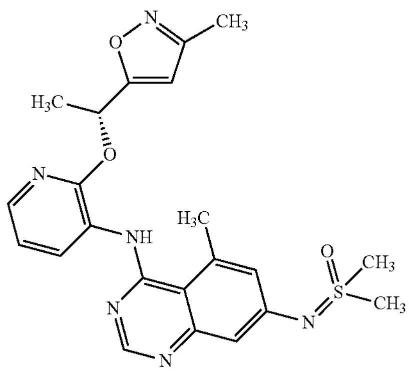 [SMILES: Cc1cc([C@@H](C)Oc2ncccc2Nc2ncnc3cc(N=S(C)(C)=O)cc(C)c23)on1] | II.2 III.6 | 453 | 0.51 min (HPLC-K) | 80° C. 3 h |
| 2.019 | 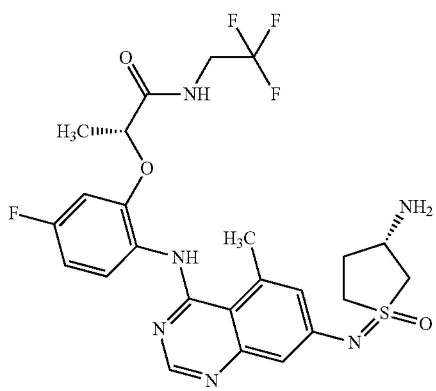 [SMILES: Cc1cc(N=S2(=O)CC[C@H](N)C2)cc2ncnc(Nc3ccc(F)cc3O[C@H](C)C(=O)NCC(F)(F)F)c12] | VII.2 | 555 | 0.35 min (HPLC-Q) | 80° C. 3 h, followed by deprotection with 10 eq TFA V.14 used absolute configuration n.D. |
| 2.020 | 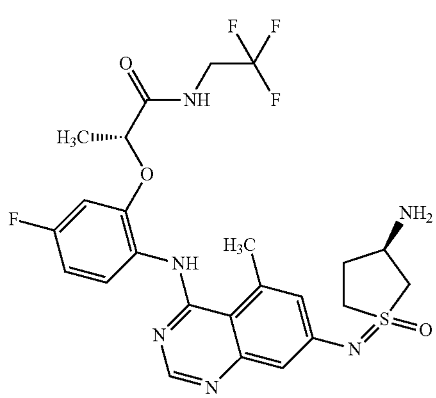 [SMILES: Cc1cc(N=S2(=O)CC[C@@H](N)C2)cc2ncnc(Nc3ccc(F)cc3O[C@H](C)C(=O)NCC(F)(F)F)c12] | VII.2 | 555 | 0.67 min (HPLC-T) | 80° C. 3 h, followed by deprotection with 10 eq TFA V.15 used absolute configuration n.D. |

TABLE 2-continued
| # | Structure | SM | MS | RT | Synthesis Comment |
|---|---|---|---|---|---|
| 2.021 | 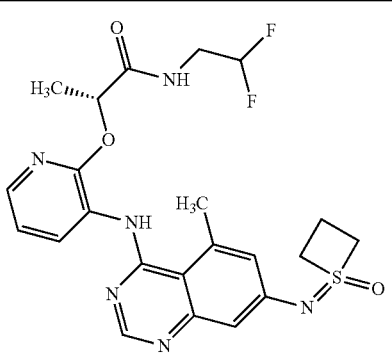 | VII.9 | 491 | 0.88 min (HPLC-M) | 80° C. 4 h |
| 2.022 | 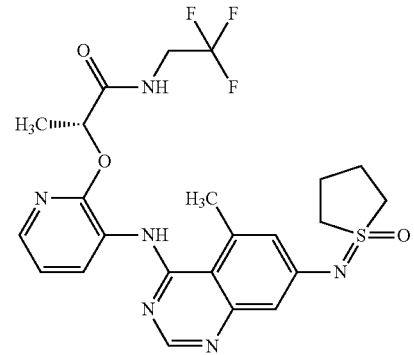 [SMILES: Cc1cc(N=S2(=O)CCCC2)cc2ncnc(Nc3cccnc3O[C@H](C)C(=O)NCC(F)(F)F)c12] | VII.5 | 523 | 0.65 min (HPLC-N) | 80° C. 6.5 h |
| 2.023 | 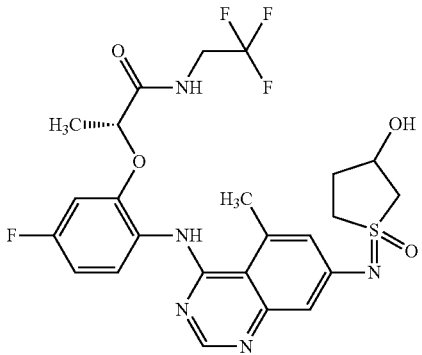 [SMILES: Cc1cc(N=S2(=O)CCC(O)C2)cc2ncnc(Nc3ccc(F)cc3O[C@H](C)C(=O)NCC(F)(F)F)c12] | VII.5 | 556 | 0.7 min (HPLC-T) | 90° C. 4 h |
| 2.024 | 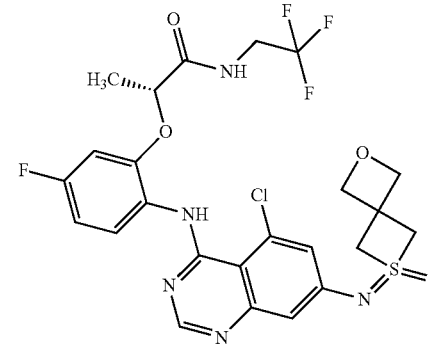 | VII.7 | 588 | 0.84 min (HPLC-A) | 80° C. 1.5 h with Xantphos and Pd(OAc)$_2$ |

TABLE 2-continued

| # | Structure | SM | MS | RT | Synthesis Comment |
|---|---|---|---|---|---|
| 2.025 | 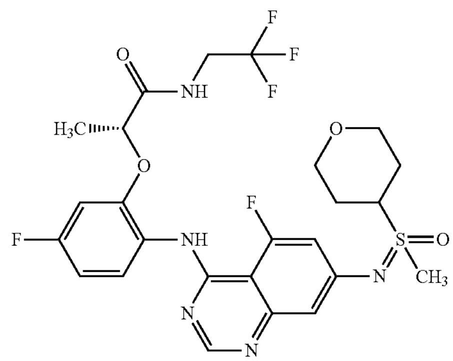 [SMILES: C[C@@H](Oc1cc(F)ccc1Nc1ncnc2cc(N=S(C)(=O)C3CCOCC3)cc(F)c12)C(=O)NCC(F)(F)F] | VII.1 | 588 | 0.77 min (HPLC-T) | 90° C. 3 h |
| 2.026 | 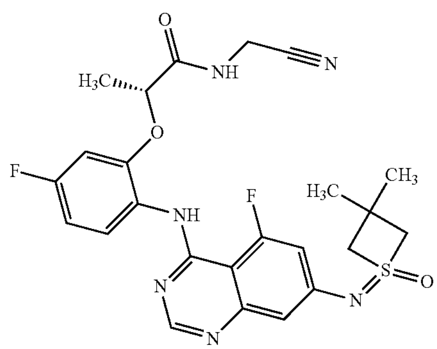 [SMILES: C[C@@H](Oc1cc(F)ccc1Nc1ncnc2cc(N=S3(=O)CC(C)(C)C3)cc(F)c12)C(=O)NCC#N] | VII.4 | 515 | 0.8 min (HPLC-A) | 80° C. 1.5 h with Xantphos and Pd(OAc)₂ |
| 2.028 | 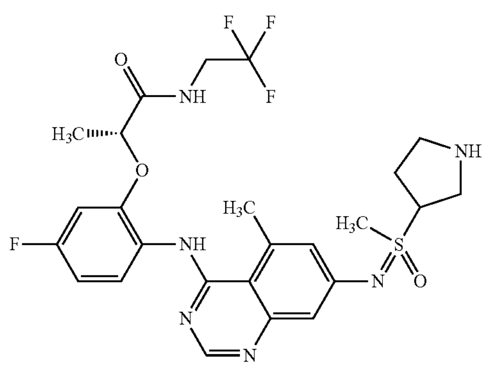 [SMILES: Cc1cc(N=S(C)(=O)C2CCNC2)cc2ncnc(Nc3ccc(F)cc3O[C@H](C)C(=O)NCC(F)(F)F)c12] | VII.2 | 569 | 0.79 min (HPLC-E) | 80° C. 3 h, followed by deprotection with 10 eq TFA |
| 2.029 | 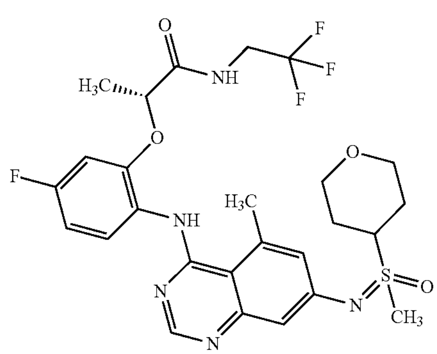 [SMILES: Cc1cc(N=S(C)(=O)C2CCOCC2)cc2ncnc(Nc3ccc(F)cc3O[C@H](C)C(=O)NCC(F)(F)F)c12] | VII.2 | 584 | 0.75 min (HPLC-T) | 90° C. 3 h |

TABLE 2-continued
| # | Structure | SM | MS | RT | Synthesis Comment |
|---|---|---|---|---|---|
| 2.030 | 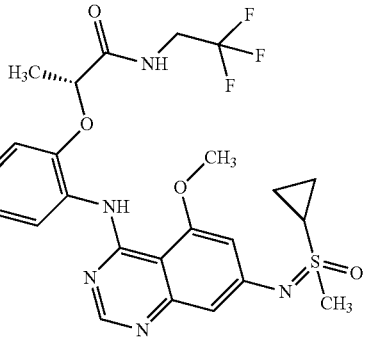 | VII.3 | 556 | 0.77 min (HPLC-T) | 90° C. 3 h |
| 2.031 | 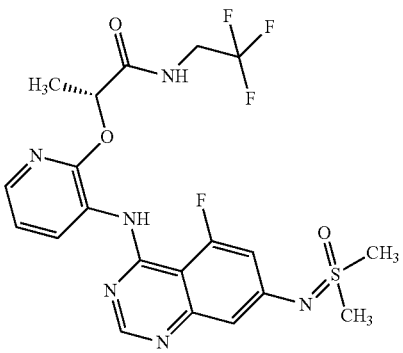 [SMILES: C[C@@H](Oc1ncccc1Nc1ncnc2cc(N=S(C)(C)=O)cc(F)c12)C(=O)NCC(F)(F)F] | VII.5 | 501 | 0.65 min (HPLC-B) | 80° C. 4.5 h |
| 2.032 | 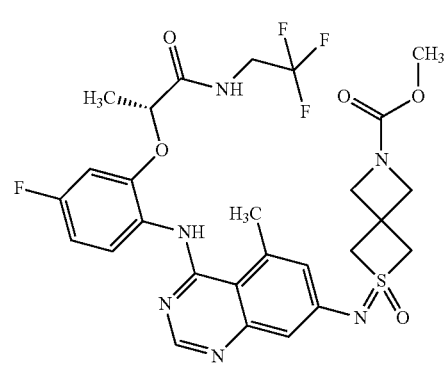 [SMILES: COC(=O)N1CC2(C1)CS(=O)(=Nc1cc(C)c3c(Nc4ccc(F)cc4O[C@H](C)C(=O)NCC(F)(F)F)ncnc3c1)C2] | VII.2 | 625 | 0.85 min (HPLC-A) | 80° C. 1.5 h with Xantphos and Pd(OAc)$_2$ |
| 2.033 | 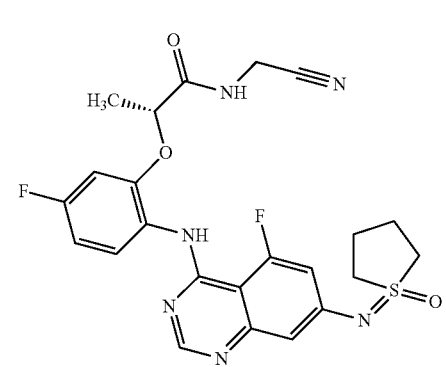 | VII.4 | 501 | 0.68 min (HPLC-T) | 90° C. 3 h |

TABLE 2-continued
| # | Structure | SM | MS | RT | Synthesis Comment |
|---|---|---|---|---|---|
| 2.034 | 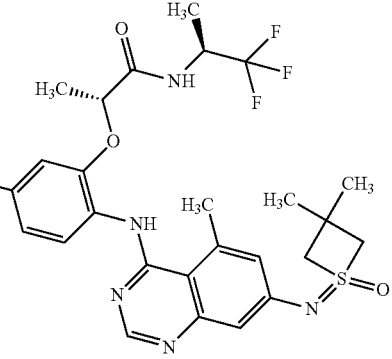 | VII.8 | 584 | 0.9 min (HPLC-T) | 90° C. 2 h |
| 2.035 | 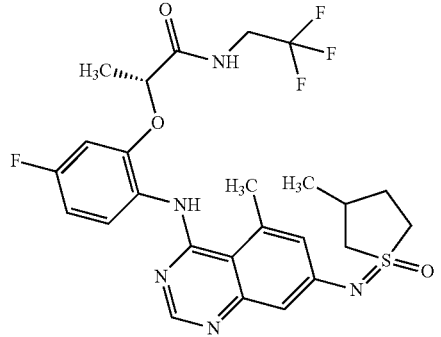 [SMILES: Cc1cc(N=S2(=O)CCC(C)C2)cc2ncnc(Nc3ccc(F)cc3O[C@H](C)C(=O)NCC(F)(F)F)c12] | VII.2 | 554 | 0.8 min (HPLC-T) | 90° C. 3 h |
| 2.036 | 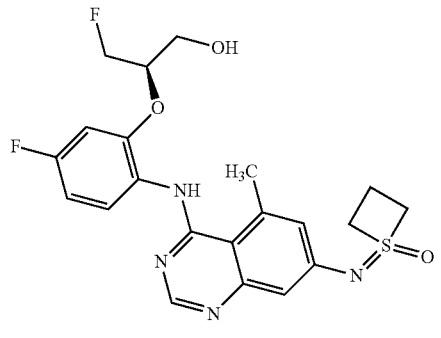 [SMILES: Cc1cc(N=S2(=O)CCC2)cc2ncnc(Nc3ccc(F)cc3O[C@H](CO)CF)c12] | II.2 III.14 | 449 | 0.5 min (HPLC-V) | 80° C. 2 h |
| 2.037 | 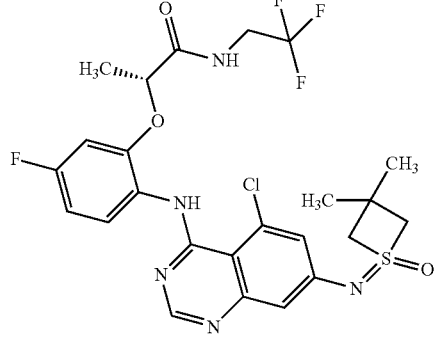 | VII.7 | 574 | 0.88 min (HPLC-T) | 80° C. 1.5 h with Xantphos and Pd(OAc)$_2$ |

TABLE 2-continued

| # | Structure | SM | MS | RT | Synthesis Comment |
|---|---|---|---|---|---|
| 2.038 | 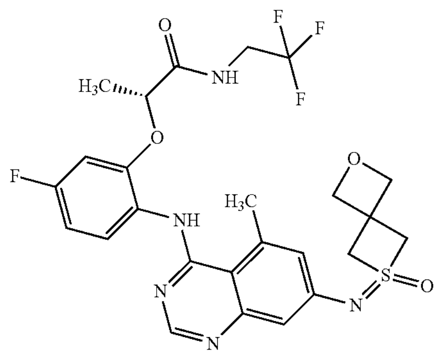 [SMILES: Cc1cc(N=S2(=O)CC3(COC3)C2)cc2ncnc(Nc3ccc(F)cc3O[C@H](C)C(=O)NCC(F)(F)F)c12] | VII.2 | 568 | 0.82 min (HPLC-A) | 80° C. 1.5 h with Xantphos and Pd(OAc)₂ |
| 2.039 | 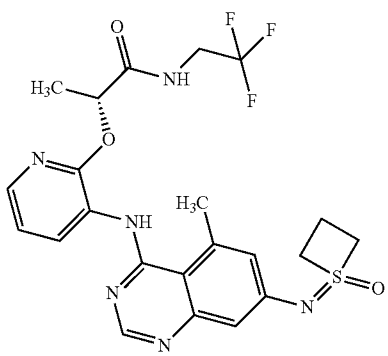 [SMILES: Cc1cc(N=S2(=O)CCC2)cc2ncnc(Nc3cccnc3O[C@H](C)C(=O)NCC(F)(F)F)c12] | VII.5 | 509 | 0.64 min (HPLC-N) | 80° C. 6.5 h |
| 2.040 | 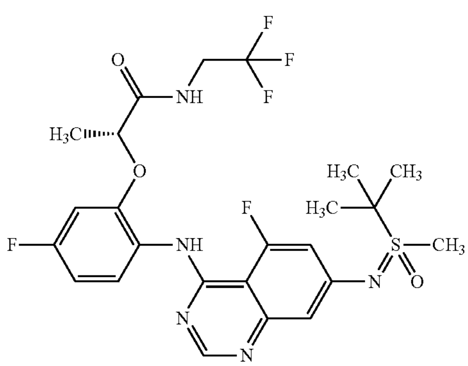 [SMILES: C[C@@H](Oc1cc(F)ccc1Nc1ncnc2cc(N=S(C)(=O)C(C)(C)C)cc(F)c12)C(=O)NCC(F)(F)F] | VII.1 | 560 | 0.85 min (HPLC-T) | 90° C. 3 h |
| 2.041 | 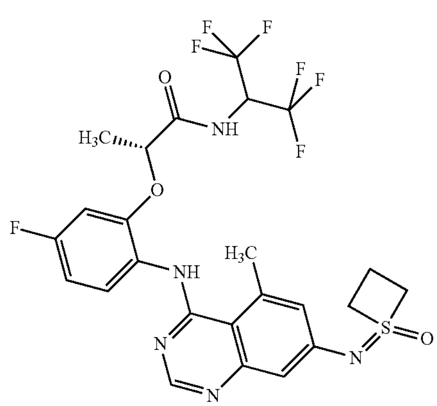 [SMILES: Cc1cc(N=S2(=O)CCC2)cc2ncnc(Nc3ccc(F)cc3O[C@H](C)C(=O)NC(C(F)(F)F)C(F)(F)F)c12] | VII.6 | 594 | 0.9 min (HPLC-B) | 80° C. 3 h |

TABLE 2-continued

| # | Structure | SM | MS | RT | Synthesis Comment |
|---|---|---|---|---|---|
| 2.042 | 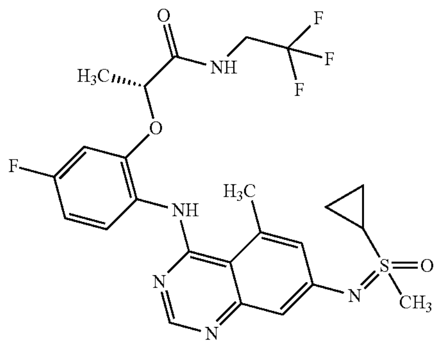 [SMILES: Cc1cc(N=S(C)(=O)C2CC2)cc2ncnc(Nc3ccc(F)cc3O[C@H](C)C(=O)NCC(F)(F)F)c12] | VII.2 | 540 | 0.76 min (HPLC-T) | 90° C. 3 h |
| 2.043 | 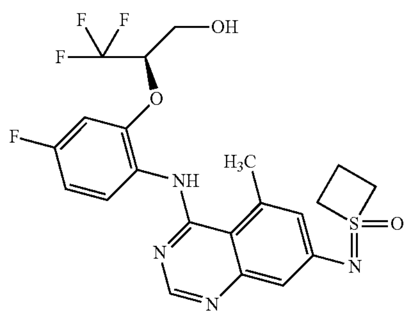 [SMILES: Cc1cc(N=S2(=O)CCC2)cc2ncnc(Nc3ccc(F)cc3O[C@H](CO)C(F)(F)F)c12] | II.2 III.15 | 485 | 0.5 min (HPLC-G) | 80° C. 2 h |
| 2.044 | 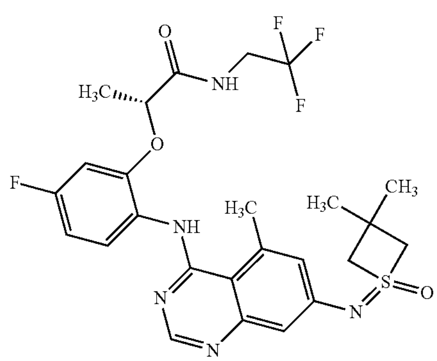 [SMILES: Cc1cc(N=S2(=O)CC(C)(C)C2)cc2ncnc(Nc3ccc(F)cc3O[C@H](C)C(=O)NCC(F)(F)F)c12] | VII.2 | 554 | 0.88 min (HPLC-A) | 80° C. 1.5 h with Xantphos and Pd(OAc)$_2$ |
| 2.045 | 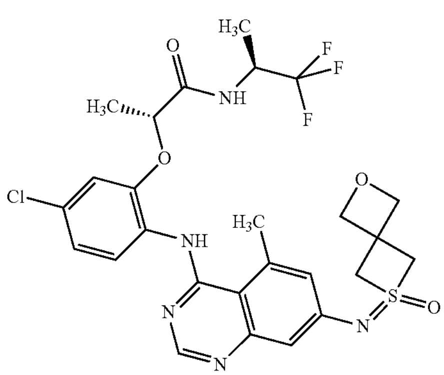 [SMILES: Cc1cc(N=S2(=O)CC3(COC3)C2)cc2ncnc(Nc3ccc(Cl)cc3O[C@H](C)C(=O)N[C@@H](C)C(F)(F)F)c12] | VII.8 | 598 | 0.81 min (HPLC-T) | 90° C. 2 h |

TABLE 2-continued

| # | Structure | SM | MS | RT | Synthesis Comment |
|---|---|---|---|---|---|
| 2.046 | 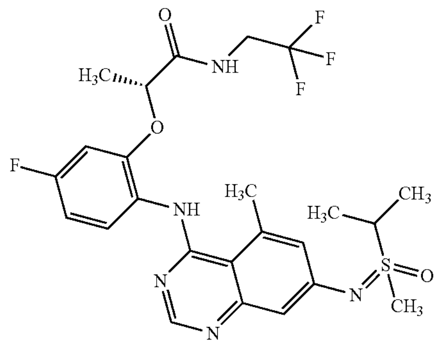 [SMILES: Cc1cc(N=S(C)(=O)C(C)C)cc2ncnc(Nc3ccc(F)cc3O[C@H](C)C(=O)NCC(F)(F)F)c12] | VII.2 | 542 | 0.78 min (HPLC-T) | 90° C. 3 h |
| 2.047 | 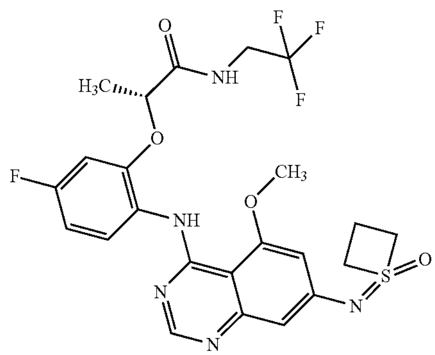 [SMILES: COc1cc(N=S2(=O)CCC2)cc2ncnc(Nc3ccc(F)cc3O[C@H](C)C(=O)NCC(F)(F)F)c12] | VII.2 | 542 | 0.73 min (HPLC-B) | 80° C. over night |
| 2.048 | 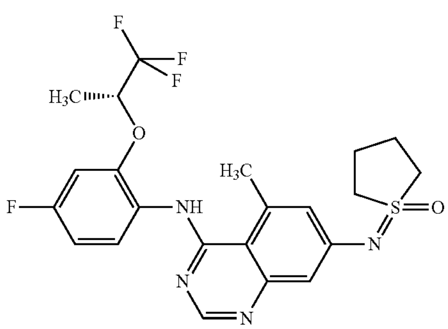 [SMILES: Cc1cc(N=S2(=O)CCCC2)cc2ncnc(Nc3ccc(F)cc3O[C@H](C)C(F)(F)F)c12] | II.2 III.11 | 483 | 0.90 min (HPLC-E) | 90° C. over night |

General Procedure 3 (P3) for Examples Shown in Table 3:

To 1 eq of the corresponding phenol intermediate V, 2 eq of the alcohol and 3 eq of triphenyl phosphine in THF 3 eq di-tert-butylazodicarboxylate are added and the reaction mixture is stirred at RT over night. The reaction mixture is concentrated and purified by HPLC or FC.

General Procedure 4 (P4) for Examples Shown in Table 3:

To 1 eq of the corresponding phenol intermediate V, 2.5 eq of the alcohol in DMSO and 3 eq triphenyl phosphine and 3 eq di-tert-butylazodicarboxylate are added. After stirring over night at RT the same equivalents of triphenyl phosphine and di-tert-butyldicarboxylate in dioxane are added. After stirring another night at RT the same equivalents of triphenyl phosphine and di-tert-butyldicarboxylate in dioxane are added again. The reaction mixture is concentrated and purified by HPLC or FC.

To obtain the following examples (example number given in column #) shown in table 3, the corresponding compounds are prepared from the intermediate V and the respective alcohol according to P3 or P4. Details are given in the column synthesis comment, the retention-time and mass (ESI-MS m/z M+H$^+$) determined by HPLC-MS are given in the columns MS and RT.

TABLE 3

| # | Structure | SM | MS | RT | Synthesis Comment |
|---|---|---|---|---|---|
| 3.001 | 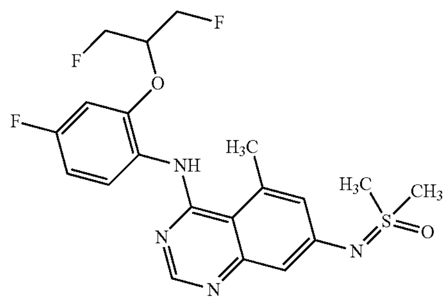 [SMILES: Cc1cc(N=S(C)(C)=O)cc2ncnc(Nc3ccc(F)cc3OC(CF)CF)c12] | V.1 | 439 | 0.68 min (HPLC-B) | P3 with 1,3-difluoropropan-2-ol |
| 3.002 | 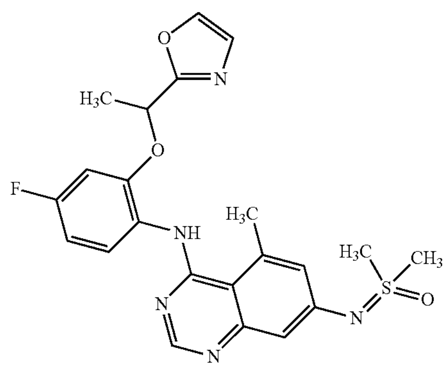 [SMILES: Cc1cc(N=S(C)(C)=O)cc2ncnc(Nc3ccc(F)cc3OC(C)c3ncco3)c12] | V.1 | 456 | 0.76 min (HPLC-K) | P3 with 1-oxazol-2-ylethanol |
| 3.003 | 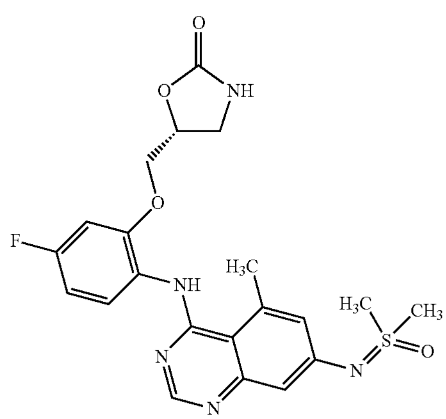 [SMILES: Cc1cc(N=S(C)(C)=O)cc2ncnc(Nc3ccc(F)cc3OC[C@H]3CNC(=O)O3)c12] | V.1 | 460 | 0.71 min (HPLC-P) | P4 with 5-(hydroxymethyl)oxazolidin-2-one |
| 3.004 | 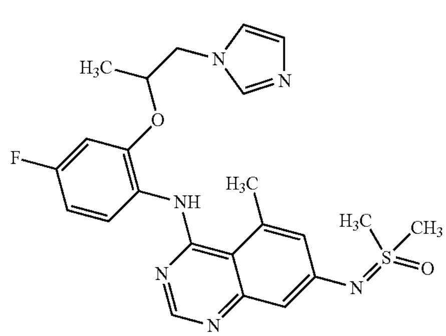 [SMILES: Cc1cc(N=S(C)(C)=O)cc2ncnc(Nc3ccc(F)cc3OC(C)Cn3ccnc3)c12] | V.1 | 469 | 0.58 min (HPLC-K) | P3 with 1-imidazol-1-ylpropan-2-ol |

TABLE 3-continued
| # | Structure | SM | MS | RT | Synthesis Comment |
|---|-----------|-----|-----|-----|-------------------|
| 3.005 | 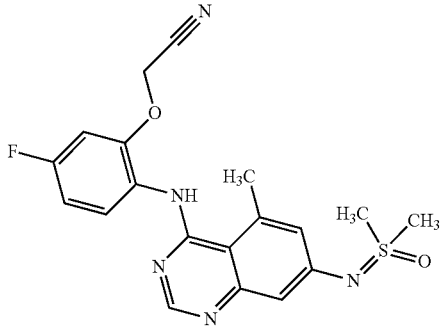 [SMILES: Cc1cc(N=S(C)(C)=O)cc2ncnc(Nc3ccc(F)cc3OCC#N)c12] | V.1 | 400 | 0.78 min (HPLC-P) | P4 with 2-hydroxyacetonitrile |
| 3.006 | 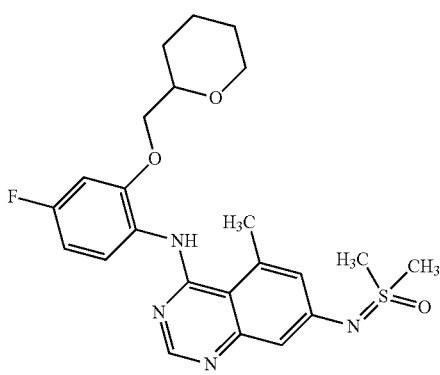 [SMILES: Cc1cc(N=S(C)(C)=O)cc2ncnc(Nc3ccc(F)cc3OCC3CCCCO3)c12] | V.1 | 459 | 0.92 min (HPLC-P) | P4 with tetrahydropyran-2-ylmethanol |
| 3.007 | 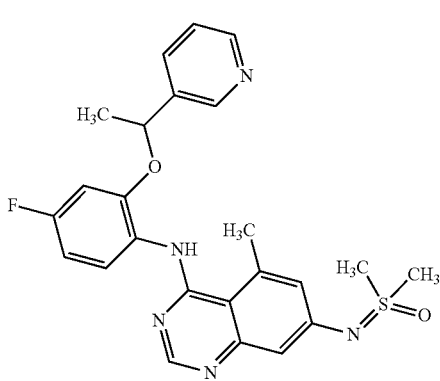 [SMILES: Cc1cc(N=S(C)(C)=O)cc2ncnc(Nc3ccc(F)cc3OC(C)c3cccnc3)c12] | V.1 | 466 | 0.6 min (HPLC-K) | P3 with 1-(3-pyridyl)ethanol |
| 3.008 | 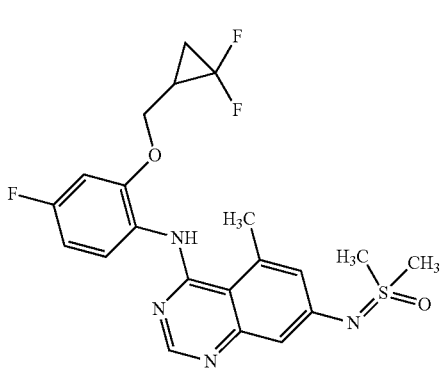 [SMILES: Cc1cc(N=S(C)(C)=O)cc2ncnc(Nc3ccc(F)cc3OCC3CC3(F)F)c12] | V.1 | 451 | 0.84 min (HPLC-K) | P3 with (2,2-difluorocyclopropyl)methanol |

TABLE 3-continued

| # | Structure | SM | MS | RT | Synthesis Comment |
|---|---|---|---|---|---|
| 3.009 | 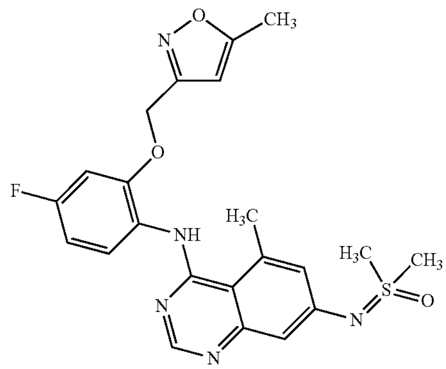 [SMILES: Cc1cc(COc2cc(F)ccc2Nc2ncnc3cc(N=S(C)(C)=O)cc(C)c23)no1] | V.1 | 456 | 0.86 min (HPLC-P) | P4 with (5-methylisoxazol-3-yl)methanol |
| 3.010 | 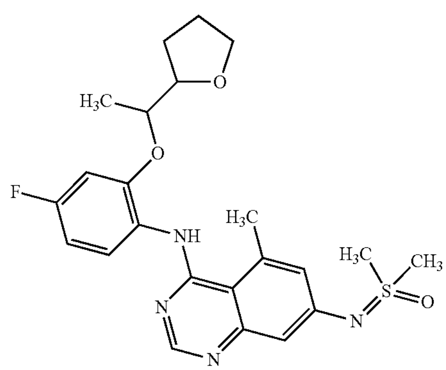 | V.1 | 459 | 0.83 min (HPLC-K) | P3 with 1-tetrahydrofuran-2-ylethanol |
| 3.011 | 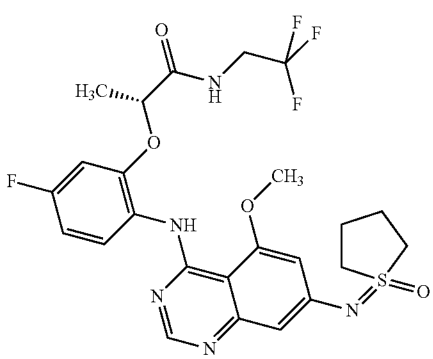 [SMILES: COc1cc(N=S2(=O)CCCC2)cc2ncnc(Nc3ccc(F)cc3O[C@H](C)C(=O)NCC(F)(F)F)c12] | V.6 | 556 | 1.26 min (HPLC-S) | P3 with 1 eq. (2R)-2-hydroxy-N-(2,2,2-trifluoroethyl)propanamide, DEAD and DCM as solvent |
| 3.012 | 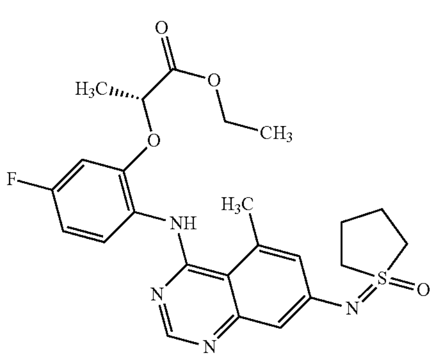 [SMILES: CCOC(=O)[C@@H](C)Oc1cc(F)ccc1Nc1ncnc2cc(N=S3(=O)CCCC3)cc(C)c12] | V.2 | 487 | 0.74 min (HPLC-B) | P3 with (S)-2-Hydroxy-propionic acid ethyl ester |

TABLE 3-continued

| # | Structure | SM | MS | RT | Synthesis Comment |
|---|---|---|---|---|---|
| 3.013 | 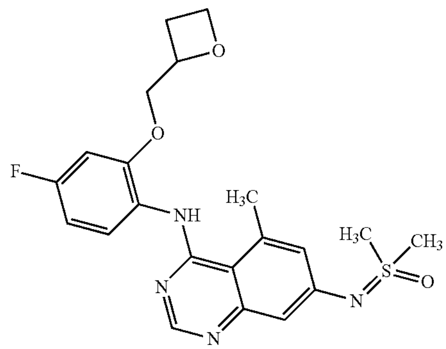 [SMILES: Cc1cc(N=S(C)(C)=O)cc2ncnc(Nc3ccc(F)cc3OCC3CCO3)c12] | V.1 | 431 | 0.79 min (HPLC-P) | P4 with 1-(oxetan-2-yl)propan-2-ol |
| 3.014 | 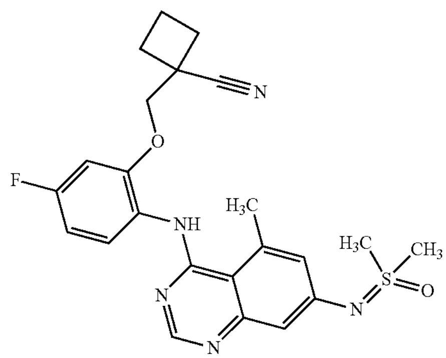 [SMILES: Cc1cc(N=S(C)(C)=O)cc2ncnc(Nc3ccc(F)cc3OCC3(C#N)CCC3)c12] | V.1 | 454 | 0.86 min (HPLC-P) | P4 with 1-(hydroxymethyl)cyclobutanecarbonitrile |
| 3.015 | 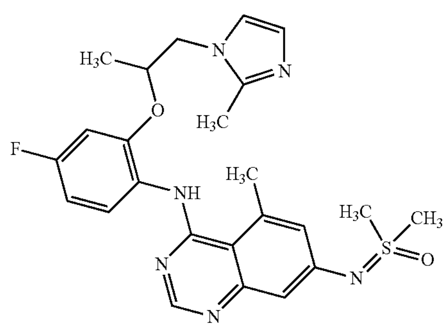 [SMILES: Cc1cc(N=S(C)(C)=O)cc2ncnc(Nc3ccc(F)cc3OC(C)Cn3ccnc3C)c12] | V.1 | 483 | 0.65 min (HPLC-P) | P4 with 1-(2-methylimidazol-1-yl)propan-2-ol |
| 3.016 | 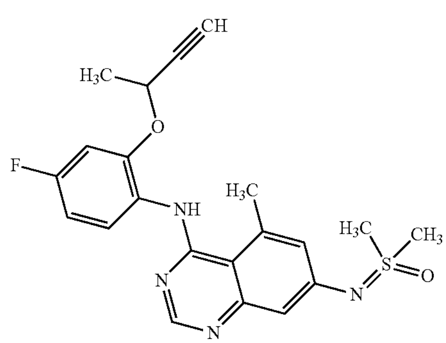 [SMILES: C#CC(C)Oc1cc(F)ccc1Nc1ncnc2cc(N=S(C)(C)=O)cc(C)c12] | V.1 | 413 | 0.89 min (HPLC-P) | P4 with but-3-yn-2-ol |

TABLE 3-continued

| # | Structure | SM | MS | RT | Synthesis Comment |
|---|---|---|---|---|---|
| 3.017 | 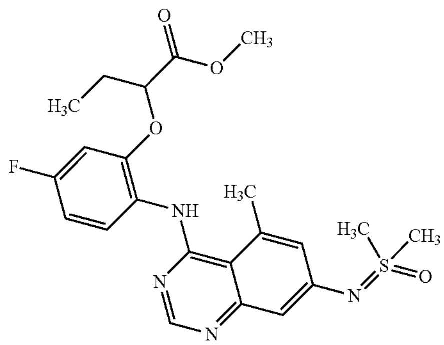 [SMILES: CCC(Oc1cc(F)ccc1Nc1ncnc2cc(N=S(C)(C)=O)cc(C)c12)C(=O)OC] | V.1 | 461 | 0.9 min (HPLC-P) | P4 with methyl 2-hydroxybutanoate |
| 3.018 | 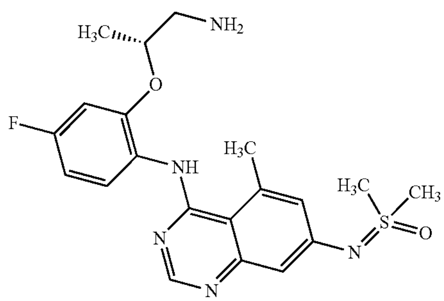 [SMILES: Cc1cc(N=S(C)(C)=O)cc2ncnc(Nc3ccc(F)cc3O[C@H](C)CN)c12] | V.1 | 418 | 0.55 min (HPLC-B) | P3 followed by deprotection with 20% TFA in DCM with ((S)-2-Hydroxy-propyl)-carbamic acid tert-butyl ester |
| 3.019 | 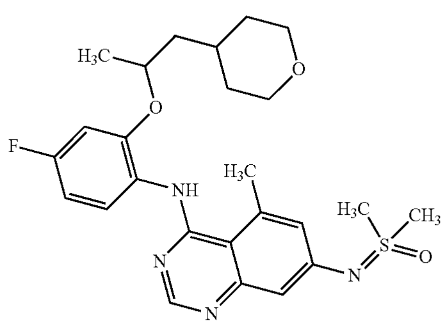 [SMILES: Cc1cc(N=S(C)(C)=O)cc2ncnc(Nc3ccc(F)cc3OC(C)CC3CCOCC3)c12] | V.1 | 487 | 0.85 min (HPLC-K) | P3 with 1-tetrahydropyran-4-ylpropan-2-ol |
| 3.020 | 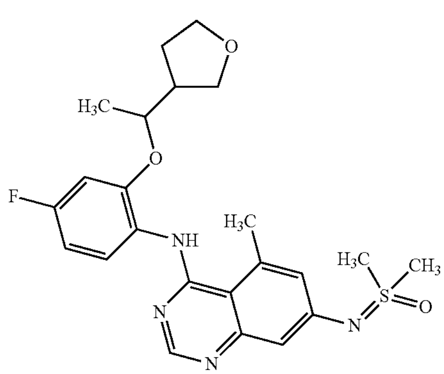 [SMILES: Cc1cc(N=S(C)(C)=O)cc2ncnc(Nc3ccc(F)cc3OC(C)C3CCOC3)c12] | V.1 | 459 | 0.79 min (HPLC-K) | P3 with 1-tetrahydrofuran-3-ylethanol |

TABLE 3-continued

| # | Structure | SM | MS | RT | Synthesis Comment |
|---|-----------|----|----|----|-------------------|
| 3.021 | 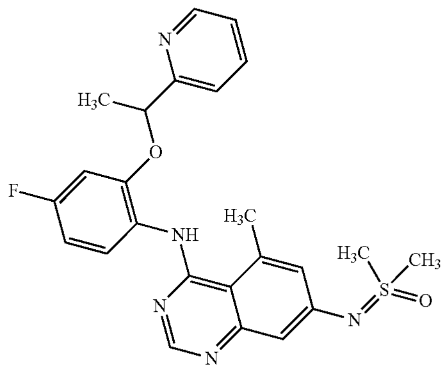 [SMILES: Cc1cc(N=S(C)(C)=O)cc2ncnc(Nc3ccc(F)cc3OC(C)c3ccccn3)c12] | V.1 | 466 | 0.77 min (HPLC-P) | P4 with 1-(2-pyridyl)ethanol |
| 3.022 | 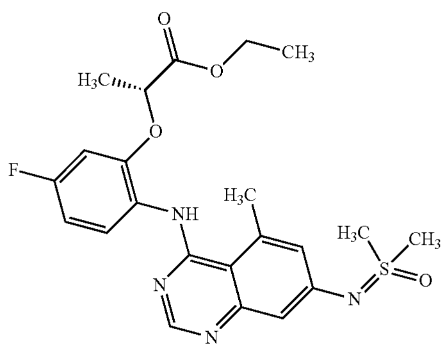 [SMILES: CCOC(=O)[C@@H](C)Oc1cc(F)ccc1Nc1ncnc2cc(N=S(C)(C)=O)cc(C)c12] | V.1 | 461 | 0.72 min (HPLC-B) | P3 with (S)-2-Hydroxy-propionic acid ethyl ester |
| 3.023 | 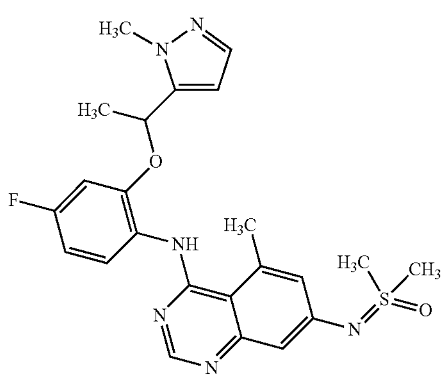 [SMILES: Cc1cc(N=S(C)(C)=O)cc2ncnc(Nc3ccc(F)cc3OC(C)c3ccnn3C)c12] | V.1 | 469 | 0.76 min (HPLC-K) | P3 with 1-(2-methylpyrazol-3-yl)ethanol |
| 3.024 | 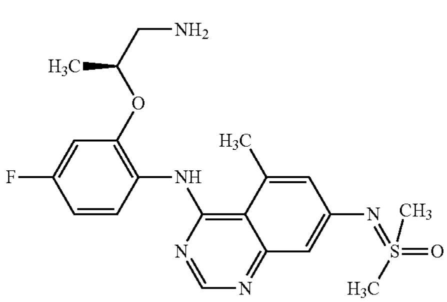 [SMILES: Cc1cc(N=S(C)(C)=O)cc2ncnc(Nc3ccc(F)cc3O[C@@H](C)CN)c12] | V.2 | 418 | 0.55 min (HPLC-B) | P3 followed by deprotection with 20% TFA in DCM with ((R)-2-Hydroxy-propyl)-carbamic acid tert-butyl ester |

TABLE 3-continued

| # | Structure | SM | MS | RT | Synthesis Comment |
|---|---|---|---|---|---|
| 3.025 | 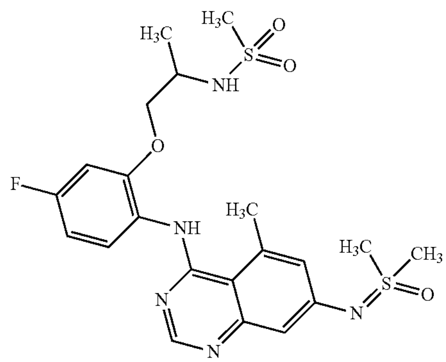 [SMILES: Cc1cc(N=S(C)(C)=O)cc2ncnc(Nc3ccc(F)cc3OCC(C)NS(C)(=O)=O)c12] | V.1 | 496 | 0.48 min (HPLC-N) | P3 with N-(2-hydroxy-1-methyl-ethyl)methanesulfonamide |
| 3.026 | 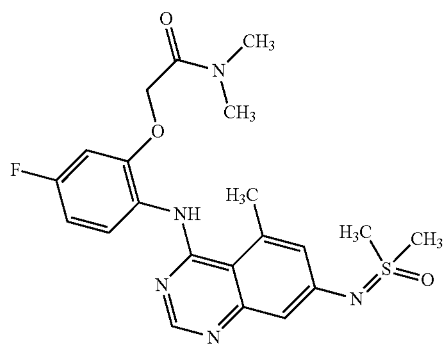 [SMILES: Cc1cc(N=S(C)(C)=O)cc2ncnc(Nc3ccc(F)cc3OCC(=O)N(C)C)c12] | V.1 | 446 | 0.77 min (HPLC-P) | P4 with 2-hydroxy-N,N-dimethyl-acetamide |
| 3.027 | 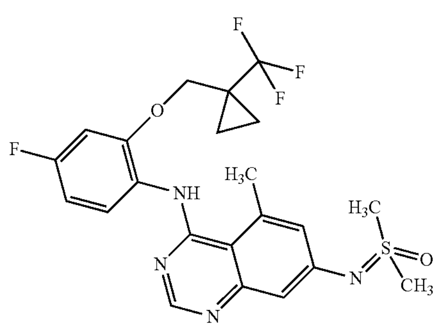 [SMILES: Cc1cc(N=S(C)(C)=O)cc2ncnc(Nc3ccc(F)cc3OCC3(C(F)(F)F)CC3)c12] | V.1 | 483 | 0.45 min (HPLC-Q) | P3 with [1-(trifluoromethyl)cyclopropyl]methanol |
| 3.028 | 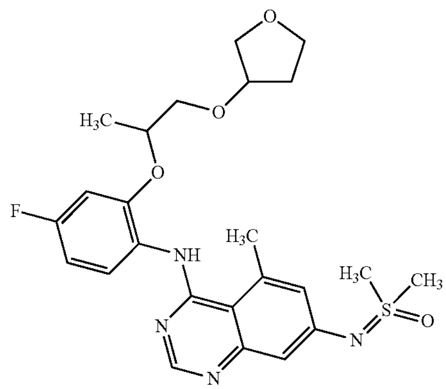 [SMILES: Cc1cc(N=S(C)(C)=O)cc2ncnc(Nc3ccc(F)cc3OC(C)COC3CCOC3)c12] | V.1 | 489 | 0.86 min (HPLC-P) | P4 with 1-tetrahydrofuran-3-yloxypropan-2-ol |

TABLE 3-continued
| # | Structure | SM | MS | RT | Synthesis Comment |
|---|---|---|---|---|---|
| 3.029 | 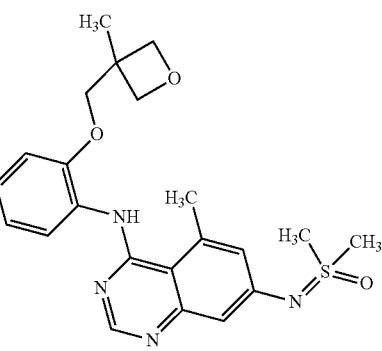 | V.1 | 445 | 0.81 min (HPLC-P) | P4 with (3-methyloxetan-3-yl)methanol |
| 3.030 | 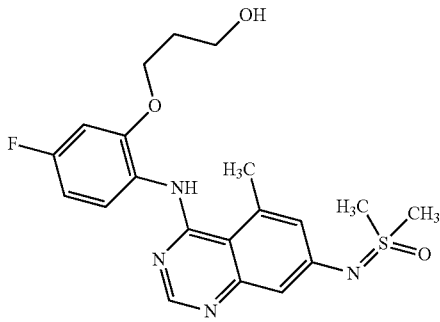 [SMILES: Cc1cc(N=S(C)(C)=O)cc2ncnc(Nc3ccc(F)cc3OCCCO)c12] | V.1 | 445 | 0.76 min (HPLC-P) | P4 with propane-1,3-diol |
| 3.031 | 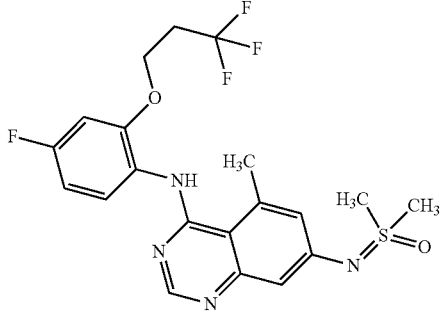 [SMILES: Cc1cc(N=S(C)(C)=O)cc2ncnc(Nc3ccc(F)cc3OCCC(F)(F)F)c12] | V.1 | 457 | 0.9 min (HPLC-P) | P4 with 3,3,3-trifluoropropan-1-ol |
| 3.032 | 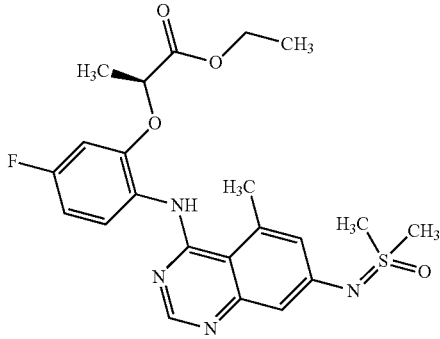 [SMILES: CCOC(=O)[C@H](C)Oc1cc(F)ccc1Nc1ncnc2cc(N=S(C)(C)=O)cc(C)c12] | V.1 | 461 | 0.84 min (HPLC-K) | P3 with ethyl (2R)-2-hydroxypropanoate |

TABLE 3-continued

| # | Structure | SM | MS | RT | Synthesis Comment |
|---|---|---|---|---|---|
| 3.033 | 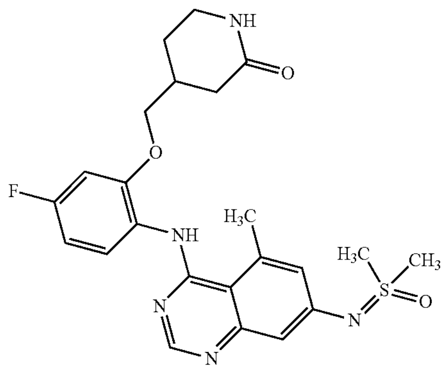 [SMILES: Cc1cc(N=S(C)(C)=O)cc2ncnc(Nc3ccc(F)cc3OCC3CCNC(=O)C3)c12] | V.1 | 472 | 0.74 min (HPLC-P) | P4 with 4-(hydroxymethyl)piperidin-2-one |
| 3.034 | 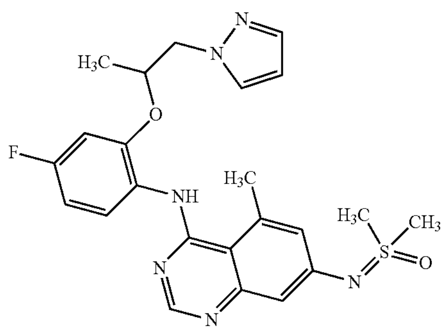 [SMILES: Cc1cc(N=S(C)(C)=O)cc2ncnc(Nc3ccc(F)cc3OC(C)Cn3cccn3)c12] | V.1 | 469 | 0.76 min (HPLC-K) | P3 with 1-pyrazol-1-ylpropan-2-ol |
| 3.035 | 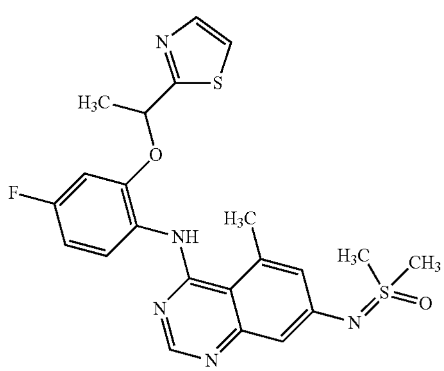 [SMILES: Cc1cc(N=S(C)(C)=O)cc2ncnc(Nc3ccc(F)cc3OC(C)c3nccs3)c12] | V.1 | 472 | 0.78 min (HPLC-K) | P3 with 1-thiazol-2-ylethanol |
| 3.036 | 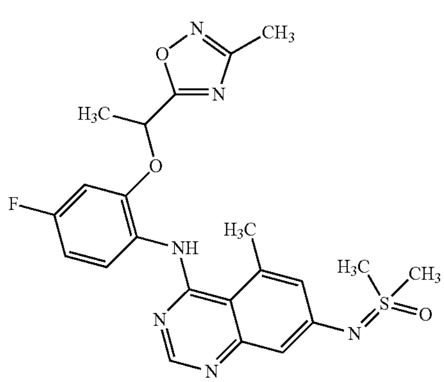 [SMILES: Cc1noc(C(C)Oc2cc(F)ccc2Nc2ncnc3cc(N=S(C)(C)=O)cc(C)c23)n1] | V.1 | 471 | 0.84 min (HPLC-P) | P4 with 1-(3-methyl-1,2,4-oxadiazol-5-yl)ethanol |

TABLE 3-continued

| # | Structure | SM | MS | RT | Synthesis Comment |
|---|---|---|---|---|---|
| 3.037 | 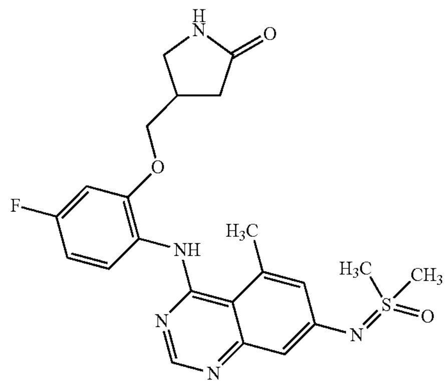 [SMILES: Cc1cc(N=S(C)(C)=O)cc2ncnc(Nc3ccc(F)cc3OCC3CNC(=O)C3)c12] | V.1 | 458 | 0.72 min (HPLC-P) | P4 with 4-(hydroxymethyl)pyrrolidin-2-one |
| 3.038 | 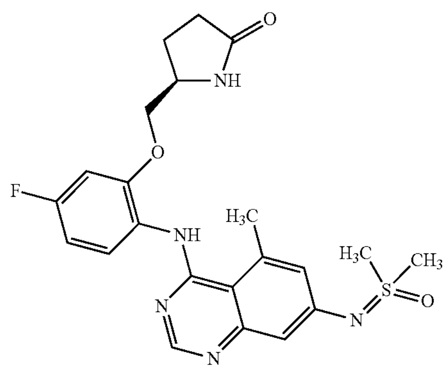 [SMILES: Cc1cc(N=S(C)(C)=O)cc2ncnc(Nc3ccc(F)cc3OC[C@H]3CCC(=O)N3)c12] | V.1 | 458 | 0.72 min (HPLC-P) | P4 with (5R)-5-(hydroxymethyl)pyrrolidin-2-one |
| 3.039 | 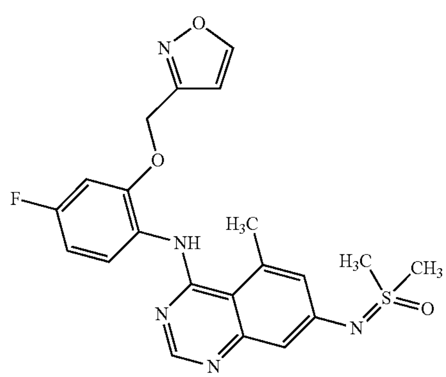 [SMILES: Cc1cc(N=S(C)(C)=O)cc2ncnc(Nc3ccc(F)cc3OCc3ccon3)c12] | V.1 | 442 | 0.83 min (HPLC-P) | P4 with isoxazol-3-ylmethanol |
| 3.040 | 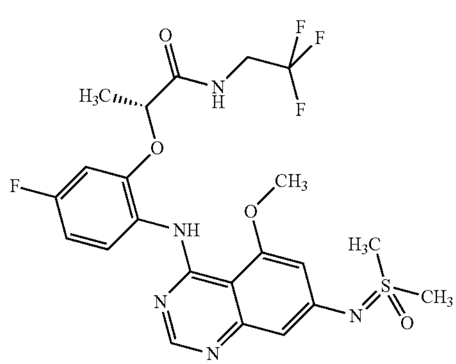 [SMILES: COc1cc(N=S(C)(C)=O)cc2ncnc(Nc3ccc(F)cc3O[C@H](C)C(=O)NCC(F)(F)F)c12] | V.5 | 530 | 1.23 min (HPLC-S) | P3 with 1 eq. (2R)-2-hydroxy-N-(2,2,2-trifluoroethyl)propanamide, DEAD and DCM as solvent |

TABLE 3-continued
| # | Structure | SM | MS | RT | Synthesis Comment |
|---|---|---|---|---|---|
| 3.041 | 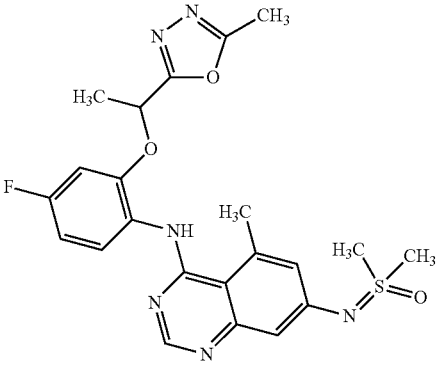 [SMILES: Cc1nnc(C(C)Oc2cc(F)ccc2Nc2ncnc3cc(N=S(C)(C)=O)cc(C)c23)o1] | V.1 | 471 | 0.78 min (HPLC-P) | P4 with 1-(5-methyl-1,3,4-oxadiazol-2-yl)ethanol |
| 3.042 | 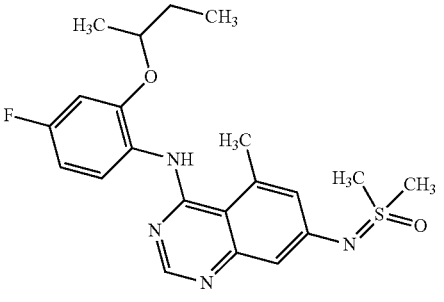 [SMILES: CCC(C)Oc1cc(F)ccc1Nc1ncnc2cc(N=S(C)(C)=O)cc(C)c12] | V.1 | 417 | 0.88 min (HPLC-K) | P3 with butan-2-ol |
| 3.043 | 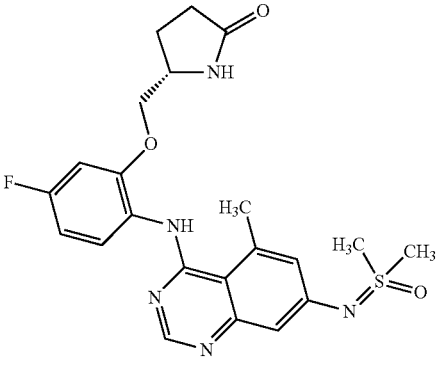 [SMILES: Cc1cc(N=S(C)(C)=O)cc2ncnc(Nc3ccc(F)cc3OC[C@@H]3CCC(=O)N3)c12] | V.1 | 458 | 0.72 min (HPLC-P) | P4 with (5S)-5-(hydroxymethyl)pyrrolidin-2-one |
| 3.044 | 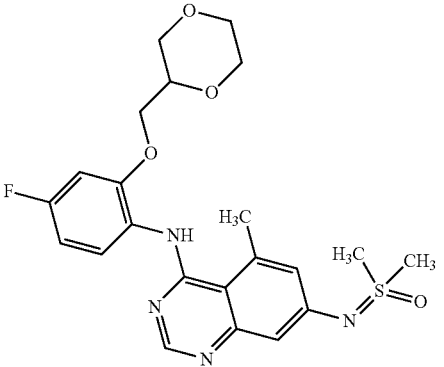 [SMILES: Cc1cc(N=S(C)(C)=O)cc2ncnc(Nc3ccc(F)cc3OCC3COCCO3)c12] | V.1 | 461 | 0.74 min (HPLC-K) | P3 with 1,4-dioxan-2-ylmethanol |

TABLE 3-continued

| # | Structure | SM | MS | RT | Synthesis Comment |
|---|---|---|---|---|---|
| 3.045 | 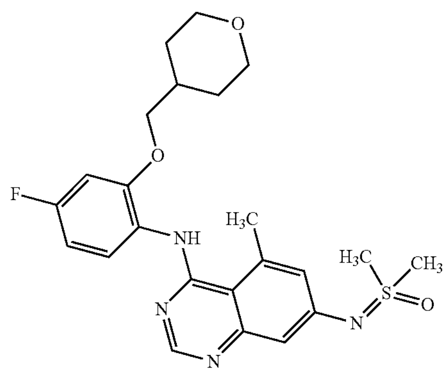 [SMILES: Cc1cc(N=S(C)(C)=O)cc2ncnc(Nc3ccc(F)cc3OCC3CCOCC3)c12] | V.1 | 459 | 0.86 min (HPLC-P) | P4 with tetrahydropyran-4-ylmethanol |
| 3.046 | 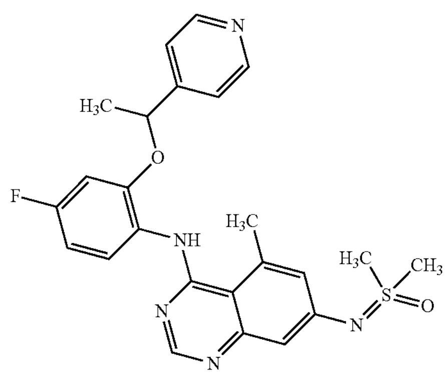 [SMILES: Cc1cc(N=S(C)(C)=O)cc2ncnc(Nc3ccc(F)cc3OC(C)c3ccncc3)c12] | V.1 | 466 | 0.65 min (HPLC-P) | P4 with 1-(4-pyridyl)ethanol |
| 3.047 | 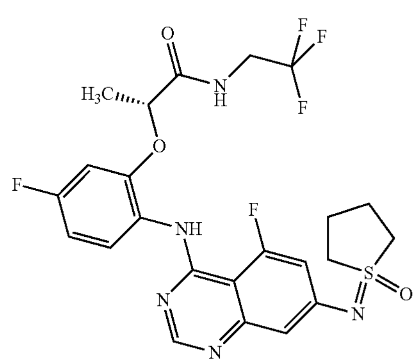 [SMILES: C[C@@H](Oc1cc(F)ccc1Nc1ncnc2cc(N=S3(=O)CCCC3)cc(F)c12)C(=O)NCC(F)(F)F] | V.4 | 544 | 1.82 min (HPLC-F) | P3 with 1 eq. (2R)-2-hydroxy-N-(2,2,2-trifluoroethyl) propanamide, DEAD and DCM as solvent |
| 3.048 | 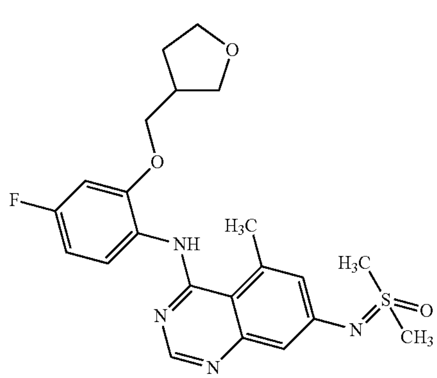 [SMILES: Cc1cc(N=S(C)(C)=O)cc2ncnc(Nc3ccc(F)cc3OCC3CCOC3)c12] | V.1 | 445 | 0.39 min (HPLC-Q) | P3 with tetrahydrofuran-3-ylmethanol and DMSO as solvent |

TABLE 3-continued
| # | Structure | SM | MS | RT | Synthesis Comment |
|---|---|---|---|---|---|
| 3.049 | 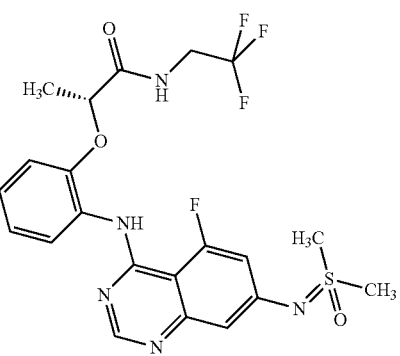 | V.3 | 518 | 1.23 min (HPLC-F) | P3 with 1 eq. (2R)-2-hydroxy-N-(2,2,2-trifluoroethyl)propanamide, DEAD and DCM as solvent |
| 3.050 | 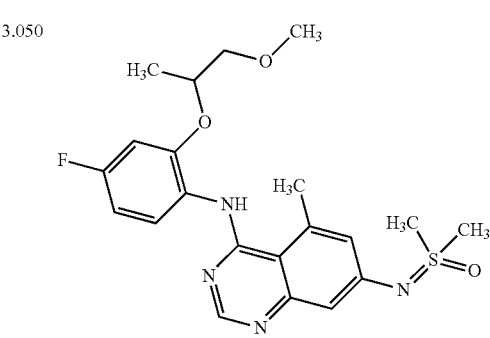 | V.1 | 433 | 0.8 min (HPLC-K) | P3 with 1-methoxypropan-2-ol |
| 3.051 | 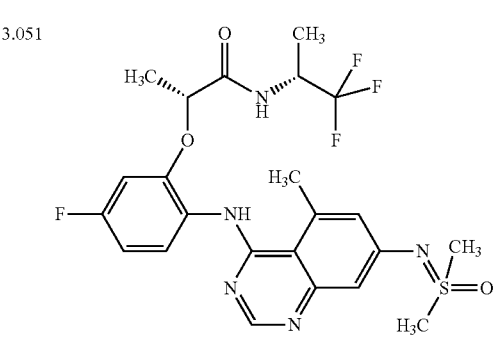 | V.1 | 528 | 0.75 min (HPLC-M) | P4 with (2S)-2-hydroxy-N-[(1R)-2,2,2-trifluoro-1-methylethyl]propanamide |
| 3.052 | 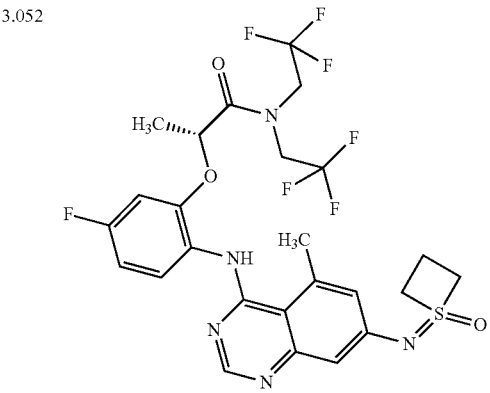 | V.9 | 608 | 1.04 min (HPLC-M) | P3 with (2S)-2-hydroxy-N,N-bis(2,2,2-trifluoroethyl)propanamide in Dioxane |

TABLE 3-continued

| # | Structure | SM | MS | RT | Synthesis Comment |
|---|---|---|---|---|---|
| 3.053 | 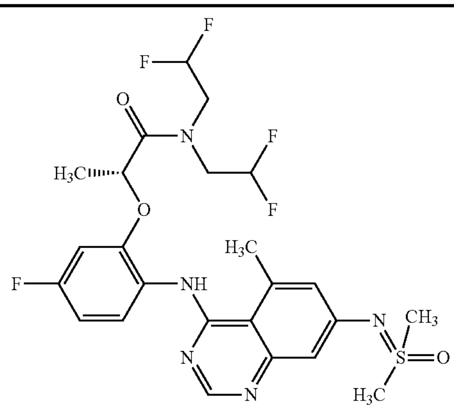 | V.1 | 560 | 0.95 min (HPLC-M) | P3 with (2S)-N,N-bis(2,2-difluoroethyl)-2-hydroxy-propanamide |
| 3.054 | 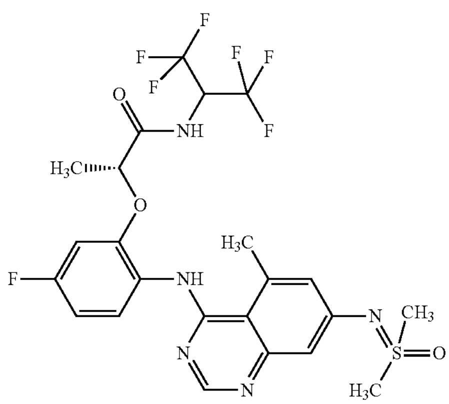 [SMILES: Cc1cc(N=S(C)(C)=O)cc2ncnc(Nc3ccc(F)cc3O[C@H](C)C(=O)NC(C(F)(F)F)C(F)(F)F)c12] | V.1 | 582 | 0.98 min (HPLC-M) | P4 with (2S)-2-hydroxy-N-[2,2,2-trifluoro-1-(trifluoromethyl)ethyl]propanamide |
| 3.055 | 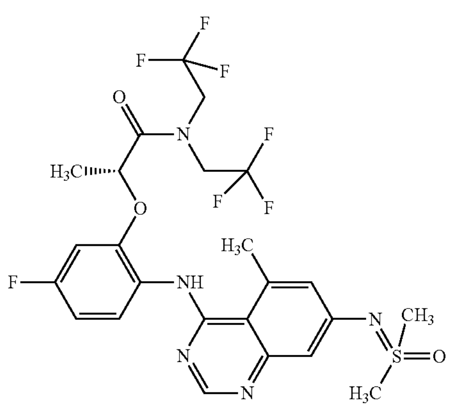 [SMILES: Cc1cc(N=S(C)(C)=O)cc2ncnc(Nc3ccc(F)cc3O[C@H](C)C(=O)N(CC(F)(F)F)CC(F)(F)F)c12] | V.1 | 596 | 0.8 min (HPLC-B) | P4 with (2S)-2-hydroxy-N,N-bis(2,2,2-trifluoroethyl)propanamide |

General Procedure 5 (P5) for Examples Shown in Table 4:

To 1 eq of the corresponding acid, 1.4 eq HATU and 2 eq TEA in DMF are added. The corresponding amine is added and the mixture is stirred at RT for 3 days. The reaction mixture is concentrated and purified by HPLC or FC.

General Procedure 6 (P6) for Examples Shown in Table 4:

To 1 eq of the corresponding acid, 1.1 eq TBTU and 2 eq TEA in DMF are added. 1.0 eq of the corresponding amine is added and the mixture is stirred at RT over night. The reaction mixture is concentrated and purified by HPLC or FC.

General Procedure 7 (P7) for Examples Shown in Table 4:

To 1 eq of the corresponding acid, 1.1 eq TBTU and 2 eq TEA in DMF are added. 1.0 eq of the corresponding amine is added and the mixture is stirred at RT over night. The reaction mixture is concentrated. Some products are taken up in DMF/MeOH (9/1) and passed through Alox followed by elution with more solvent. The filtrate is evaporated and purified by HPLC or FC.

General Procedure 8 (P8) for Examples Shown in Table 4:

To 1 eq of the corresponding acid, 7.5 eq DIPEA 5 eq of the corresponding amine in DMF are added. 1.5 eq HATU and the mixture is stirred at RT over night. The reaction mixture is concentrated and purified by HPLC or FC.

General Procedure 9 (P9) for Examples Shown in Table 4:

To a mixture of 1 eq of the corresponding acid, 2 eq DIPEA and 5 eq of the corresponding amine in DMF are cooled to −65° C. and 2 eq 1-propanephosphonic acid cyclic anhydride ca. 50% in DMF are added and the mixture is slowly warmed to RT. The reaction mixture is concentrated and purified by HPLC or FC.

To obtain the following examples (example number given in column #) shown in table 4, the corresponding compounds are prepared from the acids and the respective amine according to P5, P6, P7, P8 or P9. Details are given in the column synthesis comment, the retention-time and mass (ESI-MS m/z M+H$^+$) determined by HPLC-MS are given in the columns MS and RT.

TABLE 4

| # | Structure | SM | MS | RT | Synthesis Comment |
|---|---|---|---|---|---|
| 4.001 | 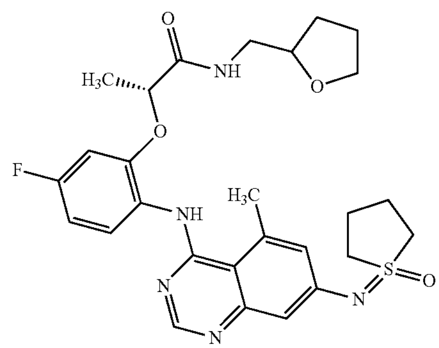 [SMILES: Cc1cc(N=S2(=O)CCCC2)cc2ncnc(Nc3ccc(F)cc3O[C@H](C)C(=O)NCC3CCCO3)c12] | VI.1 | 542 | 0.82 min (HPLC-P) | P6 with tetrahydrofuran-2-ylmethanamine |
| 4.002 | 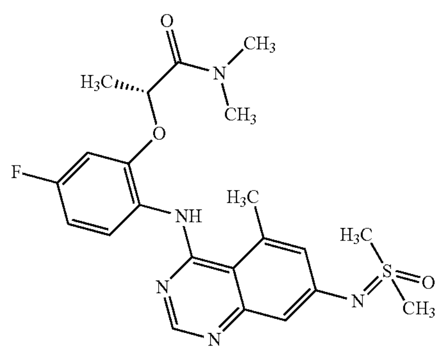 [SMILES: Cc1cc(N=S(C)(C)=O)cc2ncnc(Nc3ccc(F)cc3O[C@H](C)C(=O)N(C)C)c12] | VI.2 | 460 | 0.66 min (HPLC-B) | P5 with 24 eq. dimethyl-amine |
| 4.003 | 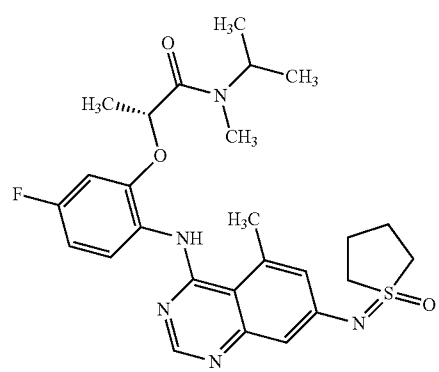 [SMILES: Cc1cc(N=S2(=O)CCCC2)cc2ncnc(Nc3ccc(F)cc3O[C@H](C)C(=O)N(C)C(C)C)c12] | VI.1 | 514 | 0.92 min (HPLC-P) | P6 with N-methylpropan-2-amine |
| 4.004 | 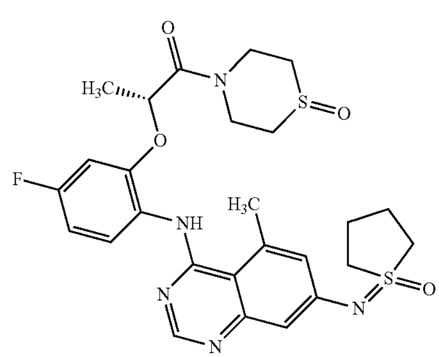 [SMILES: Cc1cc(N=S2(=O)CCCC2)cc2ncnc(Nc3ccc(F)cc3O[C@H](C)C(=O)N3CCS(=O)CC3)c12] | VI.1 | 560 | 0.75 min (HPLC-P) | P6 with 1,4-thiazinane 1-oxide |

TABLE 4-continued
| # | Structure | SM | MS | RT | Synthesis Comment |
|---|-----------|----|----|----|-------------------|
| 4.005 | 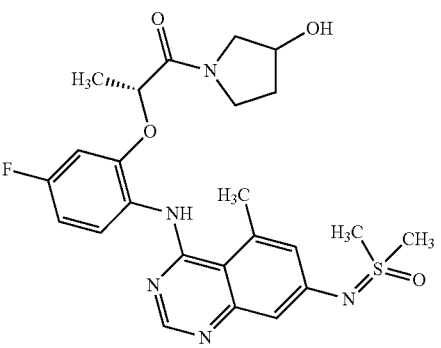 [SMILES: Cc1cc(N=S(C)(C)=O)cc2ncnc(Nc3ccc(F)cc3O[C@H](C)C(=O)N3CCC(O)C3)c12] | VI.2 | 502 | 0.62 min (HPLC-C) | P7 with pyrrolidin-3-ol |
| 4.006 | 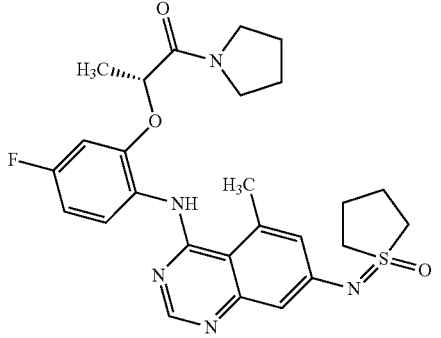 [SMILES: Cc1cc(N=S2(=O)CCCC2)cc2ncnc(Nc3ccc(F)cc3O[C@H](C)C(=O)N3CCCC3)c12] | VI.1 | 512 | 0.87 min (HPLC-P) | P6 with pyrrolidine |
| 4.007 | 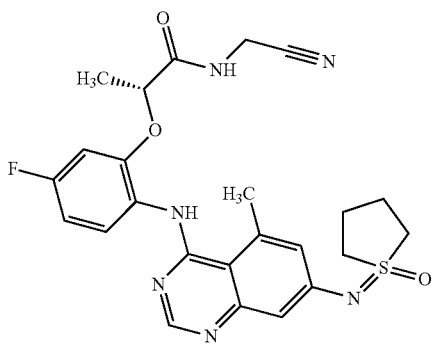 [SMILES: Cc1cc(N=S2(=O)CCCC2)cc2ncnc(Nc3ccc(F)cc3O[C@H](C)C(=O)NCC#N)c12] | VI.1 | 497 | 0.8 min (HPLC-P) | P6 with 2-aminoacetonitrile |
| 4.008 | 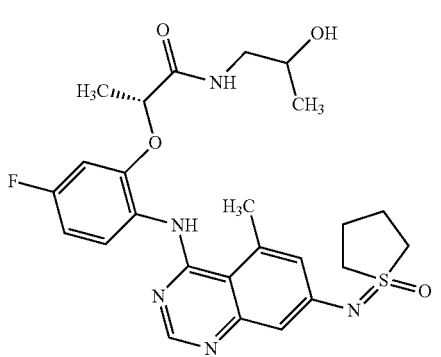 [SMILES: Cc1cc(N=S2(=O)CCCC2)cc2ncnc(Nc3ccc(F)cc3O[C@H](C)C(=O)NCC(C)O)c12] | VI.1 | 516 | 0.75 min (HPLC-P) | P6 with 1-aminopropan-2-ol |

TABLE 4-continued

| # | Structure | SM | MS | RT | Synthesis Comment |
|---|---|---|---|---|---|
| 4.009 | 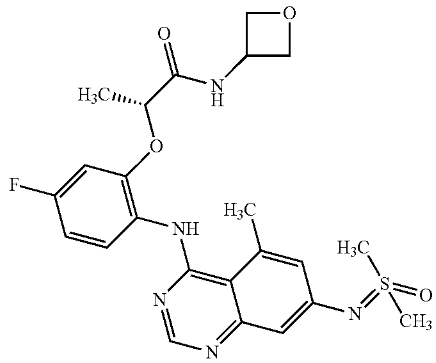 [SMILES: Cc1cc(N=S(C)(C)=O)cc2ncnc(Nc3ccc(F)cc3O[C@H](C)C(=O)NC3COC3)c12] | VI.2 | 488 | 0.33 min (HPLC-L) | P5 with 1.8 eq. oxetane-3-amine |
| 4.010 | 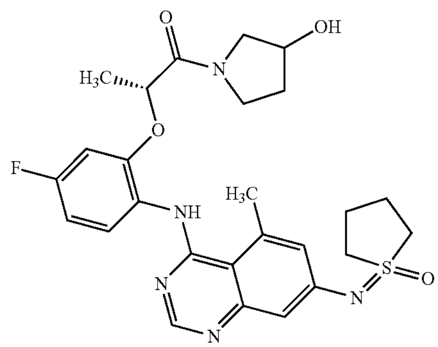 [SMILES: Cc1cc(N=S2(=O)CCCC2)cc2ncnc(Nc3ccc(F)cc3O[C@H](C)C(=O)N3CCC(O)C3)c12] | VI.1 | 528 | 0.76 min (HPLC-P) | P6 with pyrrolidin-3-ol |
| 4.011 | 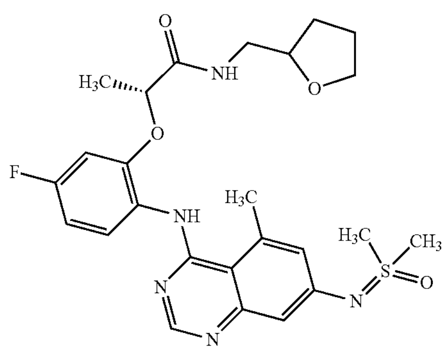 [SMILES: Cc1cc(N=S(C)(C)=O)cc2ncnc(Nc3ccc(F)cc3O[C@H](C)C(=O)NCC3CCCO3)c12] | VI.2 | 516 | 0.79 min (HPLC-P) | P6 with tetrahydrofuran-2-ylmethanamine |
| 4.012 | 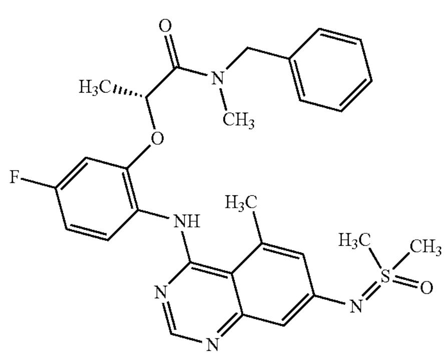 [SMILES: Cc1cc(N=S(C)(C)=O)cc2ncnc(Nc3ccc(F)cc3O[C@H](C)C(=O)N(C)Cc3ccccc3)c12] | VI.2 | 536 | 0.96 min (HPLC-P) | P6 with N-methyl-1-phenyl-methanamine |

TABLE 4-continued
| # | Structure | SM | MS | RT | Synthesis Comment |
|---|-----------|----|----|----|-------------------|
| 4.013 | 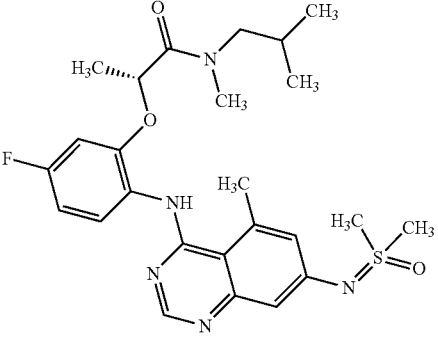 [SMILES: Cc1cc(N=S(C)(C)=O)cc2ncnc(Nc3ccc(F)cc3O[C@H](C)C(=O)N(C)CC(C)C)c12] | VI.2 | 502 | 0.94 min (HPLC-P) | P6 with N,2-dimethylpropan-1-amine |
| 4.014 | 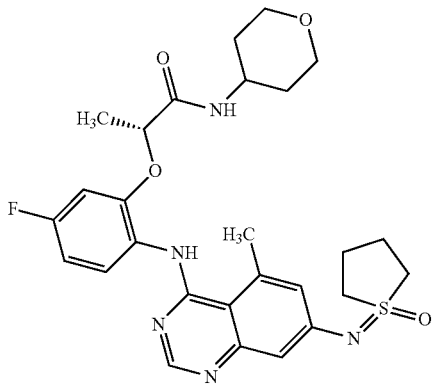 [SMILES: Cc1cc(N=S2(=O)CCCC2)cc2ncnc(Nc3ccc(F)cc3O[C@H](C)C(=O)NC3CCOCC3)c12] | VI.1 | 542 | 0.8 min (HPLC-P) | P6 with tetrahydropyran-4-amine |
| 4.015 | 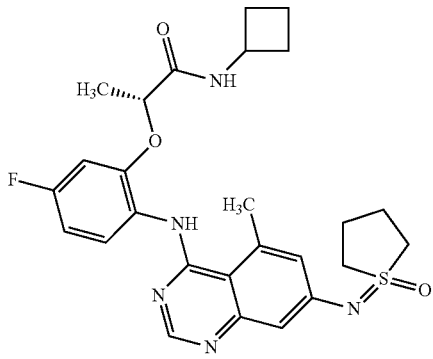 [SMILES: Cc1cc(N=S2(=O)CCCC2)cc2ncnc(Nc3ccc(F)cc3O[C@H](C)C(=O)NC3CCC3)c12] | VI.1 | 512 | 0.88 min (HPLC-P) | P6 with cyclobutanamine |
| 4.016 | 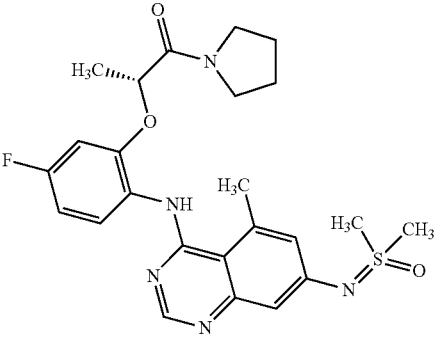 [SMILES: Cc1cc(N=S(C)(C)=O)cc2ncnc(Nc3ccc(F)cc3O[C@H](C)C(=O)N3CCCC3)c12] | VI.2 | 486 | 0.84 min (HPLC-P) | P6 with pyrrolidine |

TABLE 4-continued

| # | Structure | SM | MS | RT | Synthesis Comment |
|---|---|---|---|---|---|
| 4.017 | 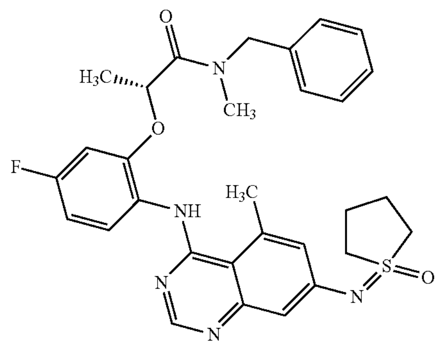 [SMILES: Cc1cc(N=S2(=O)CCCC2)cc2ncnc(Nc3ccc(F)cc3O[C@H](C)C(=O)N(C)Cc3ccccc3)c12] | VI.1 | 562 | 1.1 min (HPLC-I) | P6 with N-methyl-1-phenyl-methanamine |
| 4.018 | 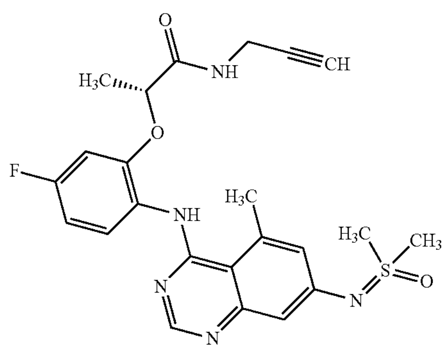 [SMILES: C#CCNC(=O)[C@@H](C)Oc1cc(F)ccc1Nc1ncnc2cc(N=S(C)(C)=O)cc(C)c12] | VI.2 | 470 | 0.79 min (HPLC-P) | P6 with prop-2-yn-1-amine |
| 4.019 | 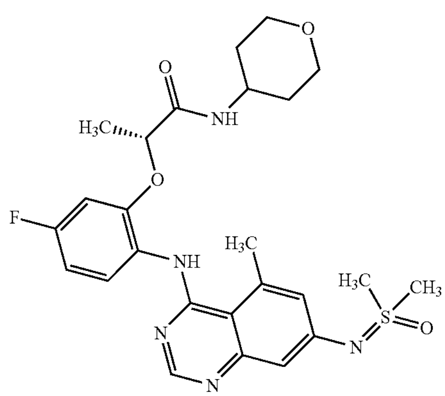 [SMILES: Cc1cc(N=S(C)(C)=O)cc2ncnc(Nc3ccc(F)cc3O[C@H](C)C(=O)NC3CCOCC3)c12] | VI.2 | 516 | 0.77 min (HPLC-P) | P6 with tetrahydropyran-4-amine |
| 4.020 | 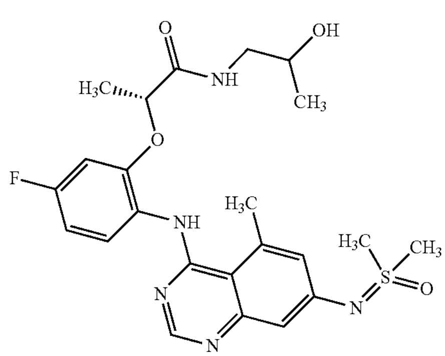 [SMILES: Cc1cc(N=S(C)(C)=O)cc2ncnc(Nc3ccc(F)cc3O[C@H](C)C(=O)NCC(C)O)c12] | VI.2 | 490 | 0.62 min (HPLC-C) | P7 with 1-aminopropan-2-ol |

TABLE 4-continued
| # | Structure | SM | MS | RT | Synthesis Comment |
|---|-----------|----|----|-----|------------------|
| 4.021 | 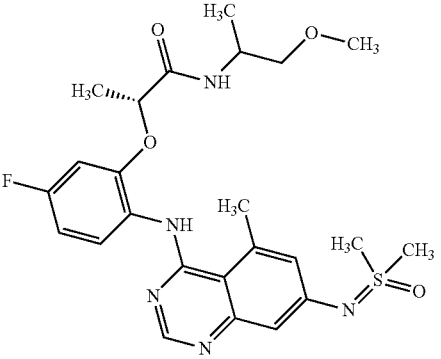 [SMILES: COCC(C)NC(=O)[C@@H](C)Oc1cc(F)ccc1Nc1ncnc2cc(N=S(C)(C)=O)cc(C)c12] | VI.2 | 504 | 0.8 min (HPLC-P) | P6 with 2-aminopropan-1-ol |
| 4.022 | 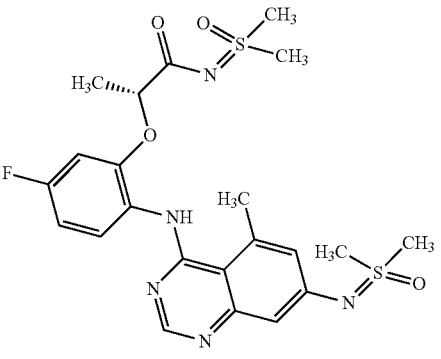 [SMILES: Cc1cc(N=S(C)(C)=O)cc2ncnc(Nc3ccc(F)cc3O[C@H](C)C(=O)N=S(C)(C)=O)c12] | VI.2 | 508 | 0.65 min (HPLC-B) | P5 with 3 eq. dimethylsulfoximine; 1.1 eq TBTU used instead of HATU |
| 4.023 | 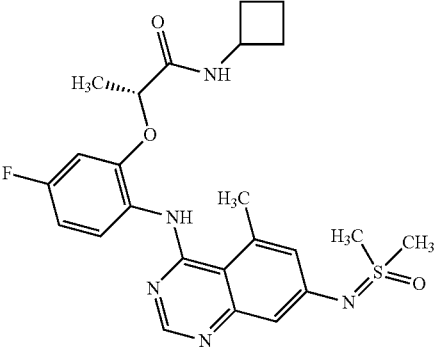 [SMILES: Cc1cc(N=S(C)(C)=O)cc2ncnc(Nc3ccc(F)cc3O[C@H](C)C(=O)NC3CCC3)c12] | VI.2 | 486 | 0.84 min (HPLC-P) | P6 with cyclobutanamine |
| 4.024 | 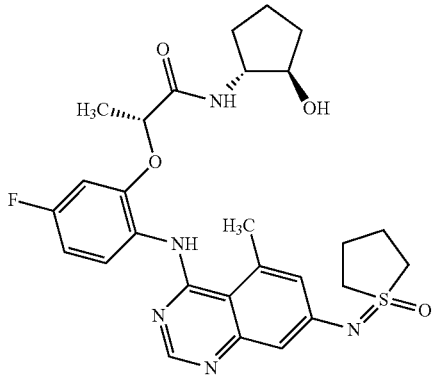 [SMILES: Cc1cc(N=S2(=O)CCCC2)cc2ncnc(Nc3ccc(F)cc3O[C@H](C)C(=O)N[C@@H]3CCC[C@H]3O)c12] | VI.1 | 543 | 0.8 min (HPLC-P) | P6 with (1R,2S)-2-aminocyclopentanol |

TABLE 4-continued
| # | Structure | SM | MS | RT | Synthesis Comment |
|---|---|---|---|---|---|
| 4.025 | 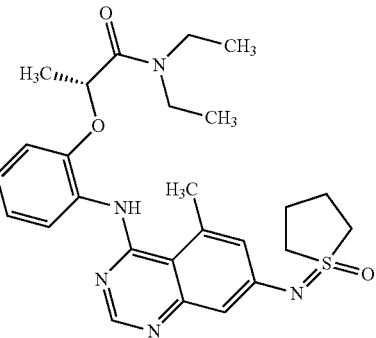 | VI.1 | 514 | 0.92 min (HPLC-P) | P6 with N-ethylethanamine |
| 4.026 | 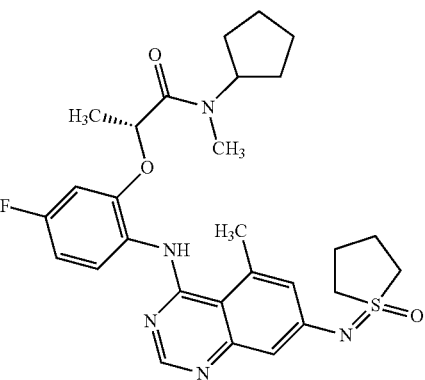 [SMILES: Cc1cc(N=S2(=O)CCCC2)cc2ncnc(Nc3ccc(F)cc3O[C@H](C)C(=O)N(C)C3CCCC3)c12] | VI.1 | 540 | 0.99 min (HPLC-P) | P6 with N-methylcyclopentanamine |
| 4.027 | 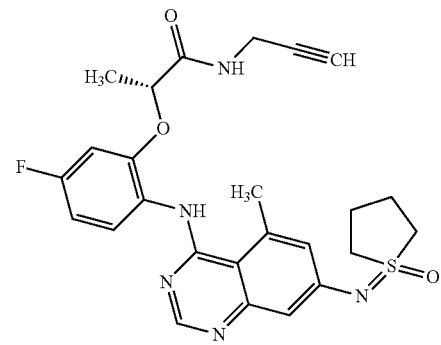 | VI.1 | 496 | 0.82 min (HPLC-P) | P6 with prop-2-yn-1-amine |
| 4.028 | 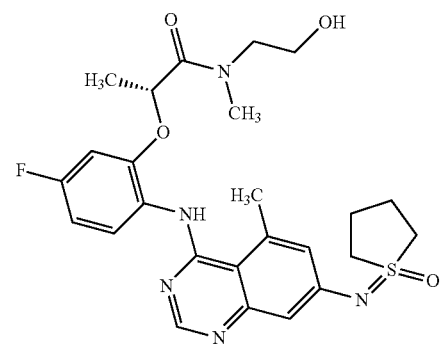 [SMILES: Cc1cc(N=S2(=O)CCCC2)cc2ncnc(Nc3ccc(F)cc3O[C@H](C)C(=O)N(C)CCO)c12] | VI.1 | 516 | 0.77 min (HPLC-P) | P6 with 2-(methylamino)ethanol |

TABLE 4-continued
| # | Structure | SM | MS | RT | Synthesis Comment |
|---|---|---|---|---|---|
| 4.029 | 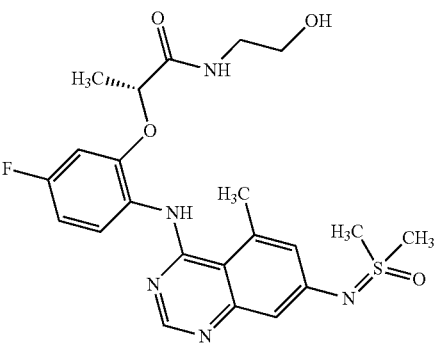 [SMILES: Cc1cc(N=S(C)(C)=O)cc2ncnc(Nc3ccc(F)cc3O[C@H](C)C(=O)NCCO)c12] | VI.2 | 476 | 0.6 min (HPLC-C) | P7 with 2-aminoethanol |
| 4.030 | 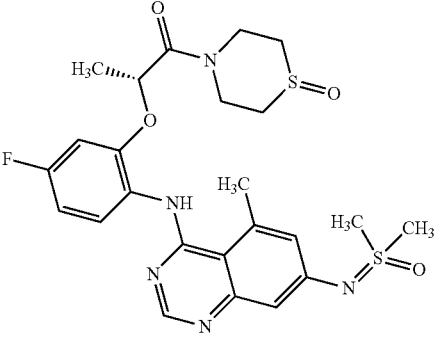 [SMILES: Cc1cc(N=S(C)(C)=O)cc2ncnc(Nc3ccc(F)cc3O[C@H](C)C(=O)N3CCS(=O)CC3)c12] | VI.2 | 534 | 0.6 min (HPLC-C) | P7 with 1,4-thiazinane 1-oxide |
| 4.031 | 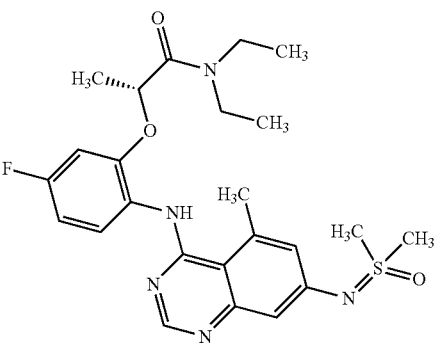 [SMILES: CCN(CC)C(=O)[C@@H](C)Oc1cc(F)ccc1Nc1ncnc2cc(N=S(C)(C)=O)cc(C)c12] | VI.2 | 488 | 0.89 min (HPLC-P) | P6 with N-ethylethanamine |
| 4.032 | 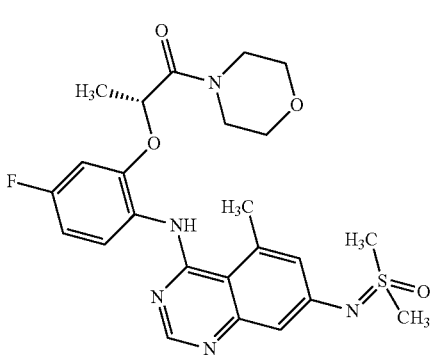 [SMILES: Cc1cc(N=S(C)(C)=O)cc2ncnc(Nc3ccc(F)cc3O[C@H](C)C(=O)N3CCOCC3)c12] | VI.2 | 502 | 0.72 min (HPLC-I) | P5 with 1.5 eq. morpholine |

TABLE 4-continued

| # | Structure | SM | MS | RT | Synthesis Comment |
|---|---|---|---|---|---|
| 4.033 | 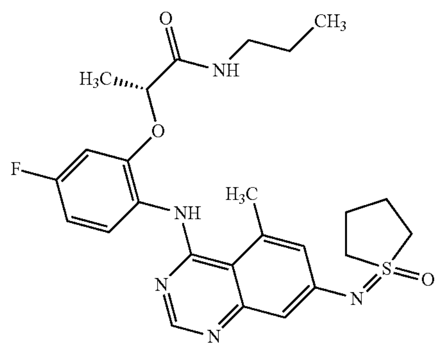 [SMILES: CCCNC(=O)[C@@H](C)Oc1cc(F)ccc1Nc1ncnc2cc(N=S3(=O)CCCC3)cc(C)c12] | VI.1 | 500 | 0.86 min (HPLC-P) | P6 with propan-1-amine |
| 4.034 | 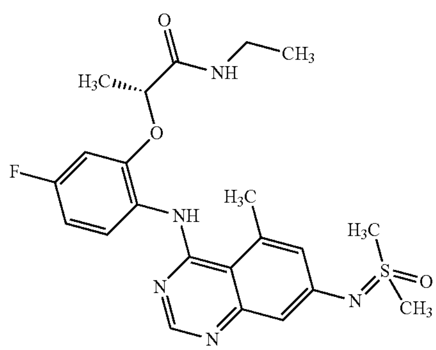 [SMILES: CCNC(=O)[C@@H](C)Oc1cc(F)ccc1Nc1ncnc2cc(N=S(C)(C)=O)cc(C)c12] | VI.2 | 460 | 0.36 min (HPLC-L) | P5 with 1.7 eq. ethylamine |
| 4.035 | 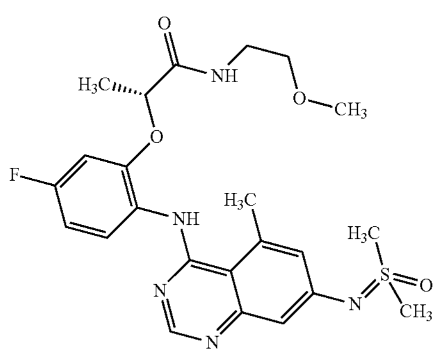 [SMILES: COCCNC(=O)[C@@H](C)Oc1cc(F)ccc1Nc1ncnc2cc(N=S(C)(C)=O)cc(C)c12] | VI.2 | 490 | 0.7 min (HPLC-I) | P5 with 1.5 eq. 2-methoxy-ethylamine |
| 4.036 | 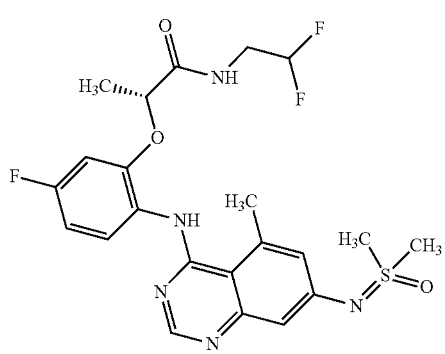 [SMILES: Cc1cc(N=S(C)(C)=O)cc2ncnc(Nc3ccc(F)cc3O[C@H](C)C(=O)NCC(F)F)c12] | VI.2 | 496 | 0.81 min (HPLC-P) | P6 with 2,2-difluoroethanamine |

TABLE 4-continued

| # | Structure | SM | MS | RT | Synthesis Comment |
|---|---|---|---|---|---|
| 4.037 | 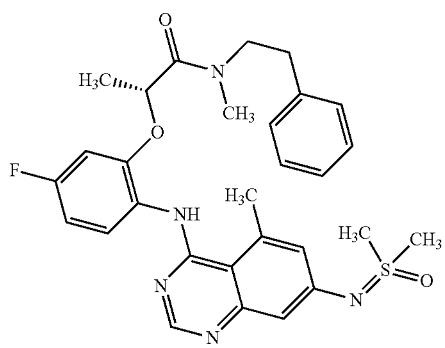 [SMILES: Cc1cc(N=S(C)(C)=O)cc2ncnc(Nc3ccc(F)cc3O[C@H](C)C(=O)N(C)CCc3ccccc3)c12] | VI.2 | 551 | 0.98 min (HPLC-P) | P6 with N-methyl-2-phenyl-ethanamine |
| 4.038 | 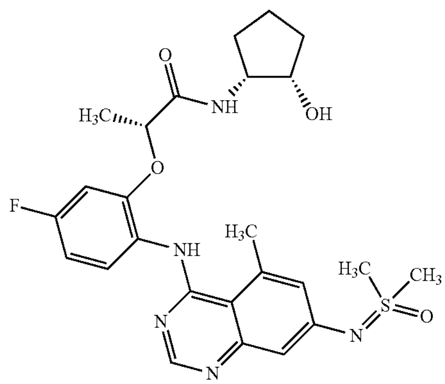 [SMILES: Cc1cc(N=S(C)(C)=O)cc2ncnc(Nc3ccc(F)cc3O[C@H](C)C(=O)N[C@@H]3CCC[C@@H]3O)c12] | VI.2 | 516 | 0.76 min (HPLC-P) | P6 with (1S,2S)-2-aminocyclopentanol |
| 4.039 | 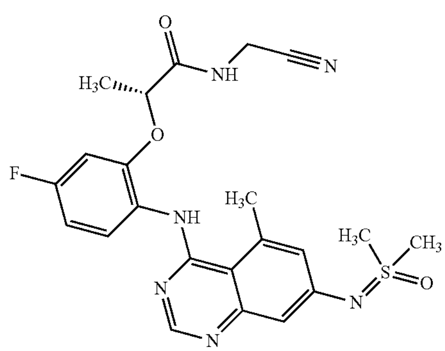 [SMILES: Cc1cc(N=S(C)(C)=O)cc2ncnc(Nc3ccc(F)cc3O[C@H](C)C(=O)NCC#N)c12] | VI.2 | 471 | 0.77 min (HPLC-P) | P6 with 2-aminoacetonitrile |
| 4.040 | 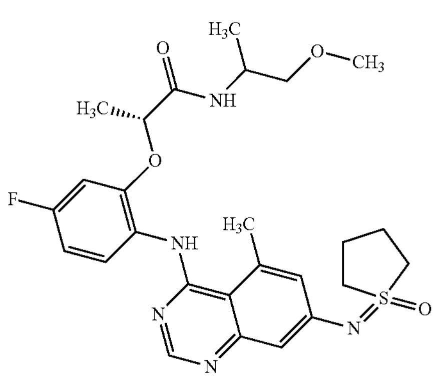 [SMILES: COCC(C)NC(=O)[C@@H](C)Oc1cc(F)ccc1Nc1ncnc2cc(N=S3(=O)CCCC3)cc(C)c12] | VI.1 | 530 | 0.83 min (HPLC-P) | P6 with 1-methoxypropan-2-amine |

TABLE 4-continued
| # | Structure | SM | MS | RT | Synthesis Comment |
|---|---|---|---|---|---|
| 4.041 | 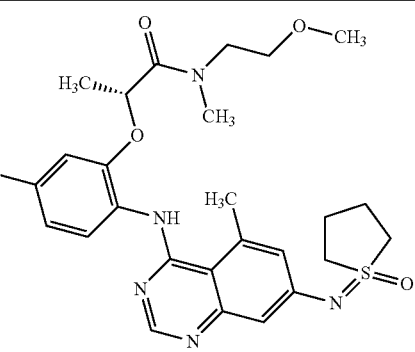 | VI.1 | 530 | 0.87 min (HPLC-P) | P6 with 2-(methylamino)ethanol |
| 4.042 | 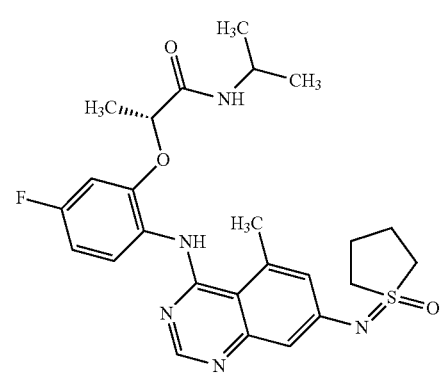 [SMILES: Cc1cc(N=S2(=O)CCCC2)cc2ncnc(Nc3ccc(F)cc3O[C@H](C)C(=O)NC(C)C)c12] | VI.1 | 500 | 0.85 min (HPLC-P) | P6 with propan-2-amine |
| 4.043 | 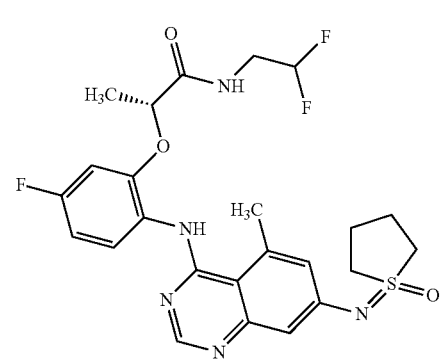 [SMILES: Cc1cc(N=S2(=O)CCCC2)cc2ncnc(Nc3ccc(F)cc3O[C@H](C)C(=O)NCC(F)F)c12] | VI.1 | 522 | 0.84 min (HPLC-P) | P6 with 2,2-difluoroethanamine |
| 4.044 | 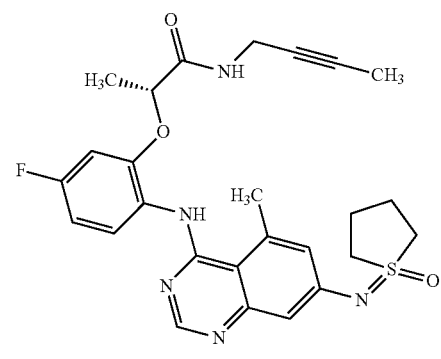 [SMILES: CC#CCNC(=O)[C@@H](C)Oc1cc(F)ccc1Nc1ncnc2cc(N=S3(=O)CCCC3)cc(C)c12] | VI.1 | 510 | 0.86 min (HPLC-P) | P6 with prop-2-yn-1-amine |

TABLE 4-continued

| # | Structure | SM | MS | RT | Synthesis Comment |
|---|---|---|---|---|---|
| 4.045 | 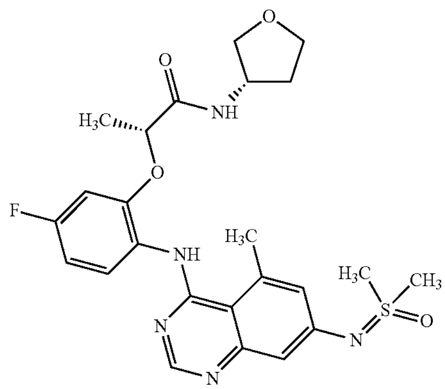 [SMILES: Cc1cc(N=S(C)(C)=O)cc2ncnc(Nc3ccc(F)cc3O[C@H](C)C(=O)N[C@H]3CCOC3)c12] | VI.2 | 502 | 0.76 min (HPLC-P) | P6 with (3S)-tetrahydrofuran-3-amine |
| 4.046 | 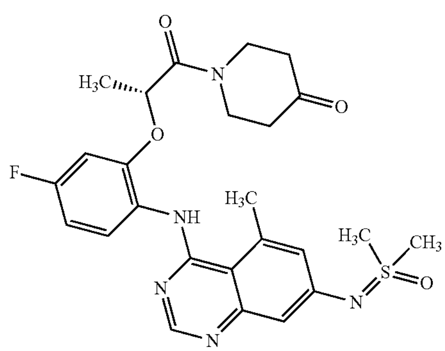 [SMILES: Cc1cc(N=S(C)(C)=O)cc2ncnc(Nc3ccc(F)cc3O[C@H](C)C(=O)N3CCC(=O)CC3)c12] | VI.2 | 514 | 0.78 min (HPLC-P) | P6 with piperidin-4-one |
| 4.047 | 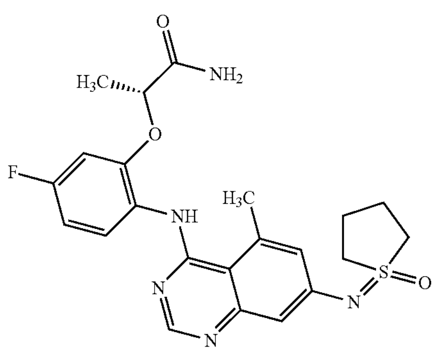 [SMILES: Cc1cc(N=S2(=O)CCCC2)cc2ncnc(Nc3ccc(F)cc3O[C@H](C)C(N)=O)c12] | VI.1 | 458 | 0.74 min (HPLC-P) | P6 with ammonia |
| 4.048 | 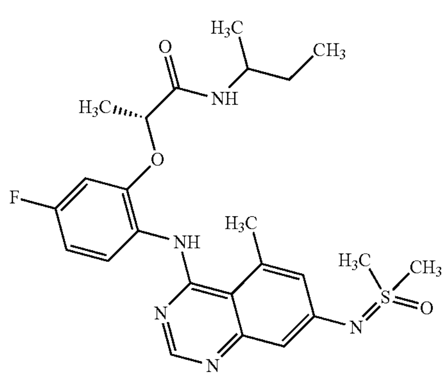 [SMILES: CCC(C)NC(=O)[C@@H](C)Oc1cc(F)ccc1Nc1ncnc2cc(N=S(C)(C)=O)cc(C)c12] | VI.2 | 488 | 0.86 min (HPLC-P) | P6 with butan-2-amine |

TABLE 4-continued
| # | Structure | SM | MS | RT | Synthesis Comment |
|---|-----------|----|----|----|-------------------|
| 4.049 | 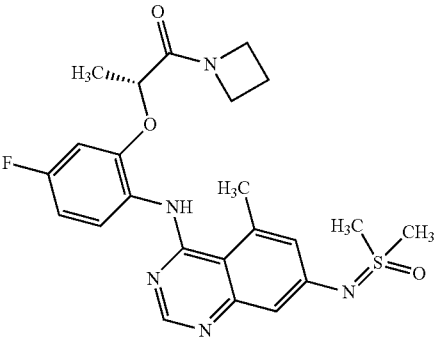 [SMILES: Cc1cc(N=S(C)(C)=O)cc2ncnc(Nc3ccc(F)cc3O[C@H](C)C(=O)N3CCC3)c12] | VI.2 | 472 | 0.78 min (HPLC-P) | P6 with azetidine |
| 4.050 | 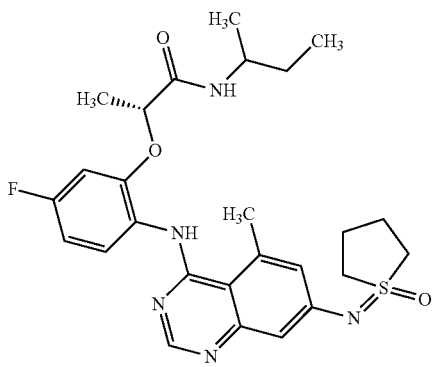 [SMILES: CCC(C)NC(=O)[C@@H](C)Oc1cc(F)ccc1Nc1ncnc2cc(N=S3(=O)CCCC3)cc(C)c12] | VI.1 | 514 | 0.89 min (HPLC-P) | P6 with butan-2-amine |
| 4.051 | 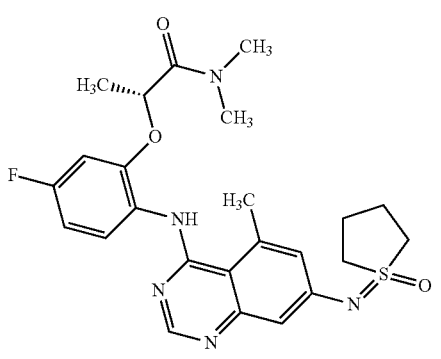 [SMILES: Cc1cc(N=S2(=O)CCCC2)cc2ncnc(Nc3ccc(F)cc3O[C@H](C)C(=O)N(C)C)c12] | VI.1 | 486 | 0.83 min (HPLC-P) | P6 with dimethyl-amine |
| 4.052 | 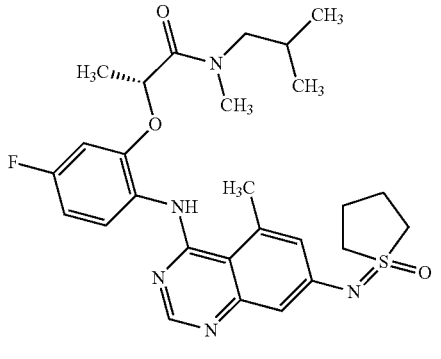 [SMILES: Cc1cc(N=S2(=O)CCCC2)cc2ncnc(Nc3ccc(F)cc3O[C@H](C)C(=O)N(C)CC(C)C)c12] | VI.1 | 528 | 0.97 min (HPLC-P) | P6 with N,2-dimethylpropan-1-amine |

TABLE 4-continued

| # | Structure | SM | MS | RT | Synthesis Comment |
|---|---|---|---|---|---|
| 4.053 | 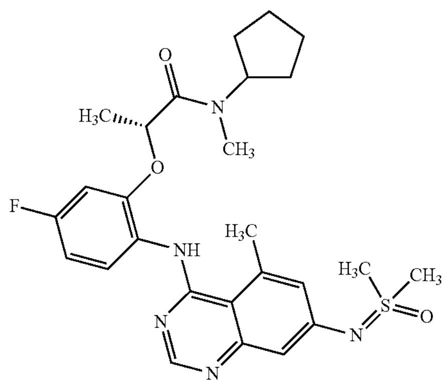 [SMILES: Cc1cc(N=S(C)(C)=O)cc2ncnc(Nc3ccc(F)cc3O[C@H](C)C(=O)N(C)C3CCCC3)c12] | VI.2 | 514 | 0.96 min (HPLC-P) | P6 with N-methylcyclopentana-mine |
| 4.054 | 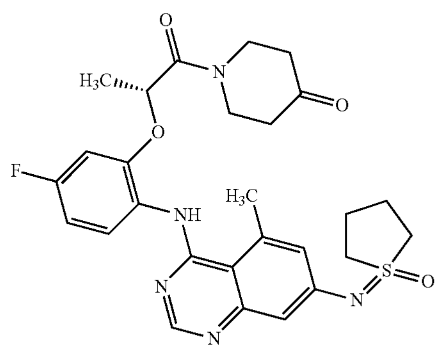 [SMILES: Cc1cc(N=S2(=O)CCCC2)cc2ncnc(Nc3ccc(F)cc3O[C@H](C)C(=O)N3CCC(=O)CC3)c12] | VI.1 | 540 | 0.81 min (HPLC-P) | P6 with piperidin-4-one |
| 4.055 | 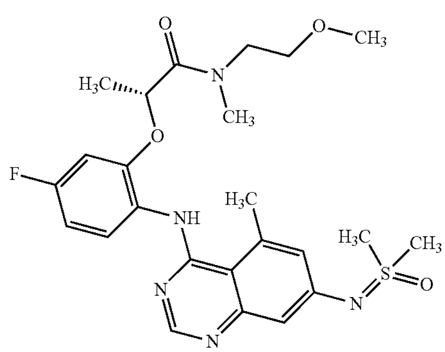 [SMILES: COCCN(C)C(=O)[C@@H](C)Oc1cc(F)ccc1Nc1ncnc2cc(N=S(C)(C)=O)cc(C)c12] | VI.2 | 504 | 0.84 min (HPLC-P) | P6 with 2-methoxy-N-methyl-ethanamine |
| 4.056 | 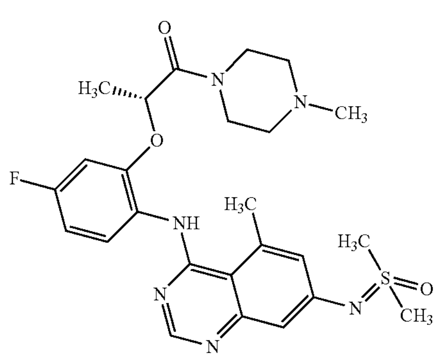 [SMILES: Cc1cc(N=S(C)(C)=O)cc2ncnc(Nc3ccc(F)cc3O[C@H](C)C(=O)N3CCN(C)CC3)c12] | VI.2 | 515 | 0.56 min (HPLC-B) | P5 with 1.5 eq 1-methylpiperazine |

TABLE 4-continued

| # | Structure | SM | MS | RT | Synthesis Comment |
|---|---|---|---|---|---|
| 4.057 | 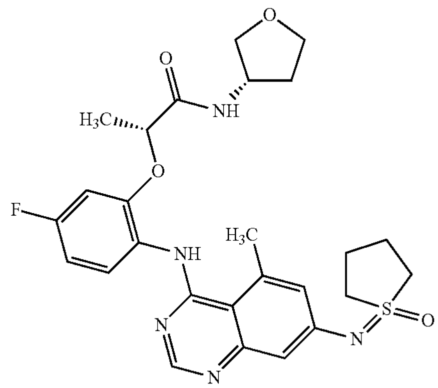 [SMILES: Cc1cc(N=S2(=O)CCCC2)cc2ncnc(Nc3ccc(F)cc3O[C@H](C)C(=O)N[C@H]3CCOC3)c12] | VI.1 | 528 | 0.79 min (HPLC-P) | P6 with (3S)-tetrahydrofuran-3-amine |
| 4.058 | 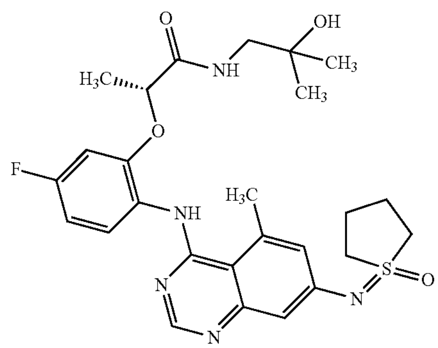 [SMILES: Cc1cc(N=S2(=O)CCCC2)cc2ncnc(Nc3ccc(F)cc3O[C@H](C)C(=O)NCC(C)(C)O)c12] | VI.1 | 530 | 0.78 min (HPLC-P) | P6 with 1-amino-2-methyl-propan-2-ol |
| 4.059 | 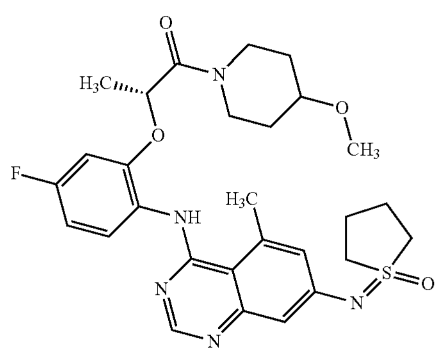 [SMILES: COC1CCN(C(=O)[C@@H](C)Oc2cc(F)ccc2Nc2ncnc3cc(N=S4(=O)CCCC4)cc(C)c23)CC1] | VI.1 | 556 | 0.87 min (HPLC-P) | P6 with 4-methoxypiperidine |
| 4.060 | 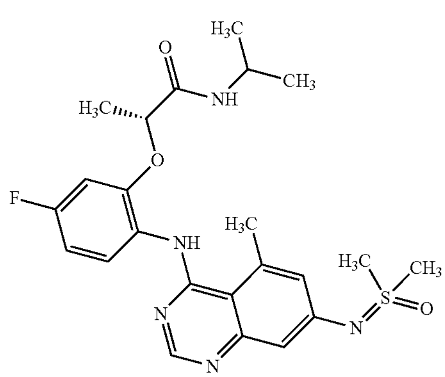 [SMILES: Cc1cc(N=S(C)(C)=O)cc2ncnc(Nc3ccc(F)cc3O[C@H](C)C(=O)NC(C)C)c12] | VI.2 | 474 | 0.82 min (HPLC-P) | P6 with propan-2-amine |

TABLE 4-continued
| # | Structure | SM | MS | RT | Synthesis Comment |
|---|-----------|----|----|----|-------------------|
| 4.061 | 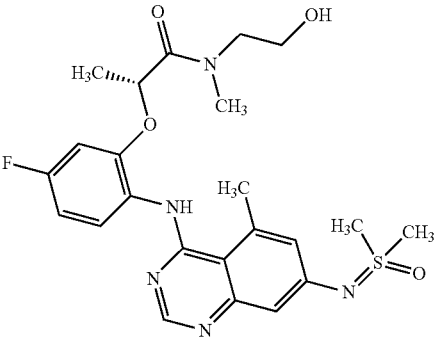 [SMILES: Cc1cc(N=S(C)(C)=O)cc2ncnc(Nc3ccc(F)cc3O[C@H](C)C(=O)N(C)CCO)c12] | VI.2 | 490 | 0.62 min (HPLC-C) | P7 with 2-(methylamino)ethanol |
| 4.062 | 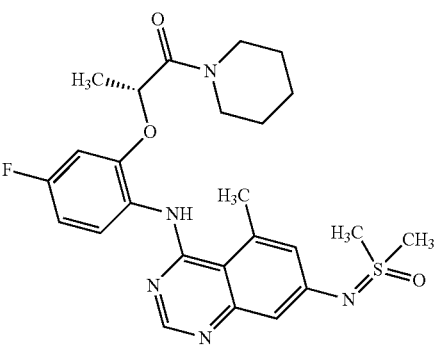 [SMILES: Cc1cc(N=S(C)(C)=O)cc2ncnc(Nc3ccc(F)cc3O[C@H](C)C(=O)N3CCCCC3)c12] | VI.2 | 500 | 0.9 min (HPLC-P) | P6 with piperidine |
| 4.063 | 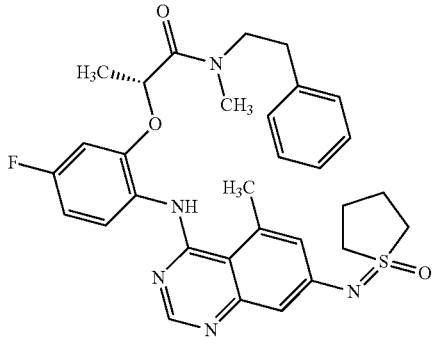 [SMILES: Cc1cc(N=S2(=O)CCCC2)cc2ncnc(Nc3ccc(F)cc3O[C@H](C)C(=O)N(C)CCc3ccccc3)c12] | VI.1 | 577 | 1.01 min (HPLC-P) | P6 with N-methyl-2-phenyl-ethanamine |
| 4.064 | 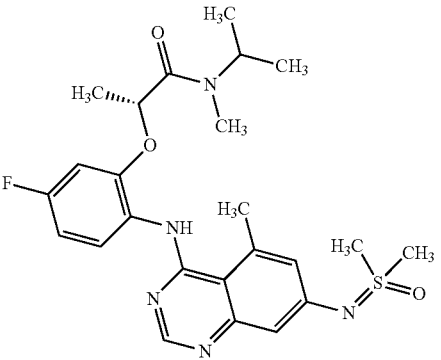 [SMILES: Cc1cc(N=S(C)(C)=O)cc2ncnc(Nc3ccc(F)cc3O[C@H](C)C(=O)N(C)C(C)C)c12] | VI.2 | 488 | 0.88 min (HPLC-P) | P6 with N-methylpropan-2-amine |

TABLE 4-continued

| # | Structure | SM | MS | RT | Synthesis Comment |
|---|-----------|----|----|----|-------------------|
| 4.065 | 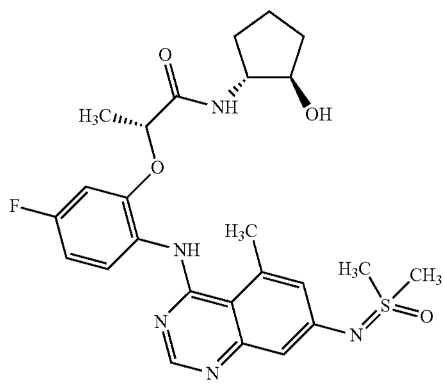 [SMILES: Cc1cc(N=S(C)(C)=O)cc2ncnc(Nc3ccc(F)cc3O[C@H](C)C(=O)N[C@@H]3CCC[C@H]3O)c12] | VI.2 | 516 | 0.78 min (HPLC-P) | P6 with (1R,2S)-2-aminocyclopentanol |
| 4.066 | 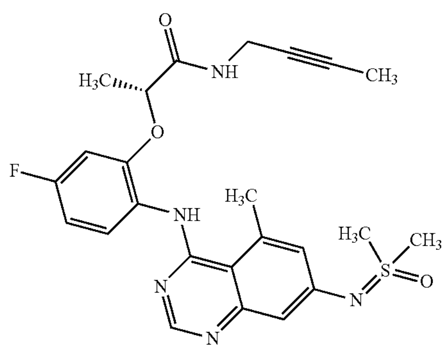 [SMILES: CC#CCNC(=O)[C@@H](C)Oc1cc(F)ccc1Nc1ncnc2cc(N=S(C)(C)=O)cc(C)c12] | VI.2 | 484 | 0.83 min (HPLC-P) | P6 with prop-2-yn-1-amine |
| 4.067 | 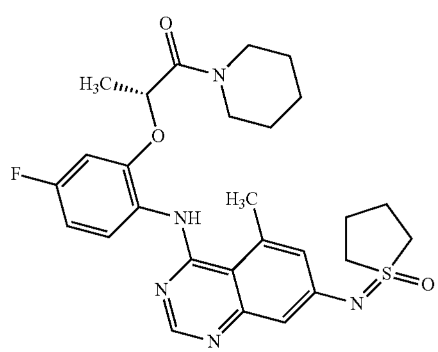 [SMILES: Cc1cc(N=S2(=O)CCCC2)cc2ncnc(Nc3ccc(F)cc3O[C@H](C)C(=O)N3CCCCC3)c12] | VI.1 | 526 | 0.93 min (HPLC-P) | P6 with piperidine |
| 4.068 | 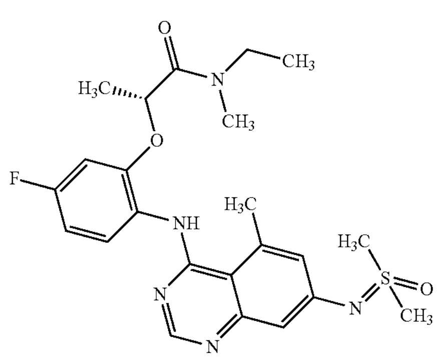 [SMILES: CCN(C)C(=O)[C@@H](C)Oc1cc(F)ccc1Nc1ncnc2cc(N=S(C)(C)=O)cc(C)c12] | VI.2 | 474 | 0.77 min (HPLC-I) | P5 with 1.5 eq. ethyl-methyl-amine |

TABLE 4-continued

| # | Structure | SM | MS | RT | Synthesis Comment |
|---|---|---|---|---|---|
| 4.069 | 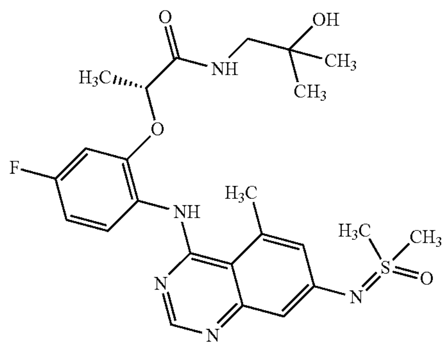 [SMILES: Cc1cc(N=S(C)(C)=O)cc2ncnc(Nc3ccc(F)cc3O[C@H](C)C(=O)NCC(C)(C)O)c12] | VI.2 | 504 | 0.75 min (HPLC-P) | P6 with 1-amino-2-methyl-propan-2-ol |
| 4.070 | 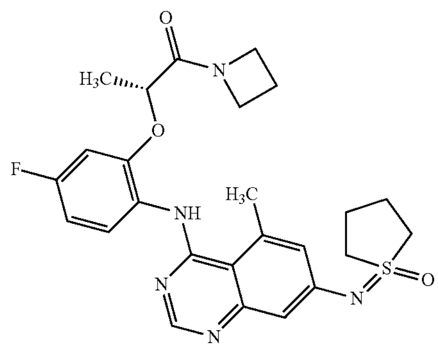 [SMILES: Cc1cc(N=S2(=O)CCCC2)cc2ncnc(Nc3ccc(F)cc3O[C@H](C)C(=O)N3CCC3)c12] | VI.1 | 498 | 0.82 min (HPLC-P) | P6 with azetidine |
| 4.071 | 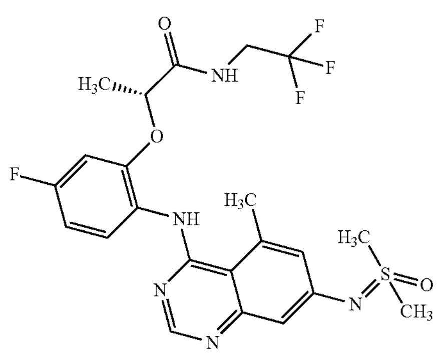 [SMILES: Cc1cc(N=S(C)(C)=O)cc2ncnc(Nc3ccc(F)cc3O[C@H](C)C(=O)NCC(F)(F)F)c12] | VI.2 | 514 | 0.69 min (HPLC-B) | P5 with 2.9 eq. 2,2,2-trifluoroethanamine |
| 4.072 | 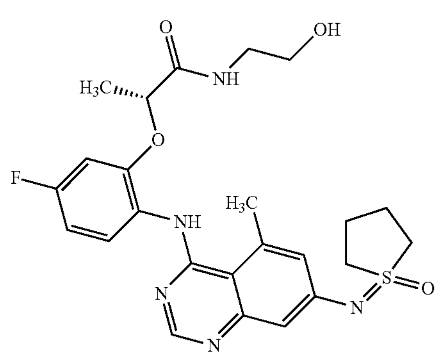 | VI.1 | 502 | 0.73 min (HPLC-P) | P6 with 2-aminoethanol |

TABLE 4-continued

| # | Structure | SM | MS | RT | Synthesis Comment |
|---|---|---|---|---|---|
| 4.073 | 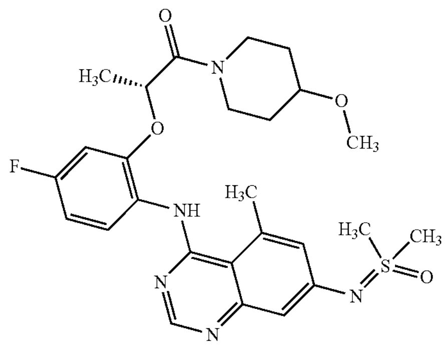 [SMILES: COC1CCN(C(=O)[C@@H](C)Oc2cc(F)ccc2Nc2ncnc3cc(N=S(C)(C)=O)cc(C)c23)CC1] | VI.2 | 531 | 0.84 min (HPLC-P) | P6 with 4-methoxypiperidine |
| 4.074 | 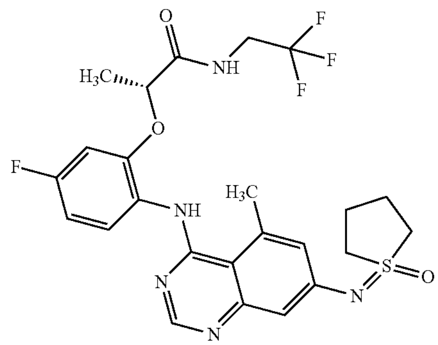 [SMILES: Cc1cc(N=S2(=O)CCCC2)cc2ncnc(Nc3ccc(F)cc3O[C@H](C)C(=O)NCC(F)(F)F)c12] | VI.1 | 540 | 0.89 min (HPLC-P) | P6 with 2,2,2-trifluoroethanamine |
| 4.075 | 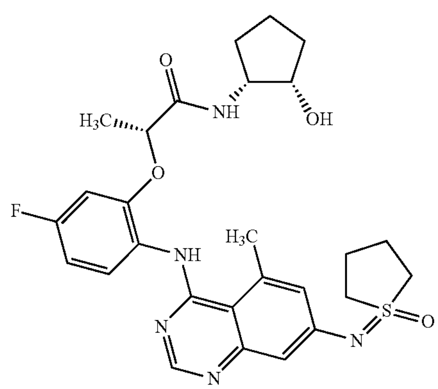 [SMILES: Cc1cc(N=S2(=O)CCCC2)cc2ncnc(Nc3ccc(F)cc3O[C@H](C)C(=O)N[C@@H]3CCC[C@@H]3O)c12] | VI.1 | 542 | 0.79 min (HPLC-P) | P6 with (1S,2S)-2-aminocyclopentanol |
| 4.076 | 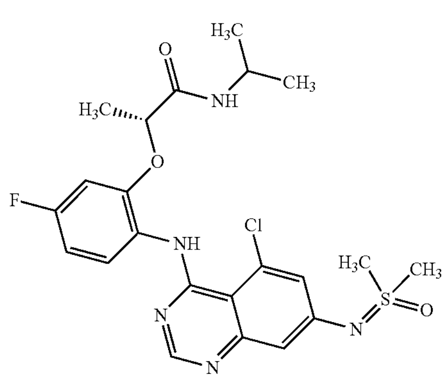 [SMILES: CC(C)NC(=O)[C@@H](C)Oc1cc(F)ccc1Nc1ncnc2cc(N=S(C)(C)=O)cc(Cl)c12] | VI.5 | 494 | 0.4 min (HPLC-Q) | P8 with propan-2-amine |

TABLE 4-continued

| # | Structure | SM | MS | RT | Synthesis Comment |
|---|---|---|---|---|---|
| 4.077 | 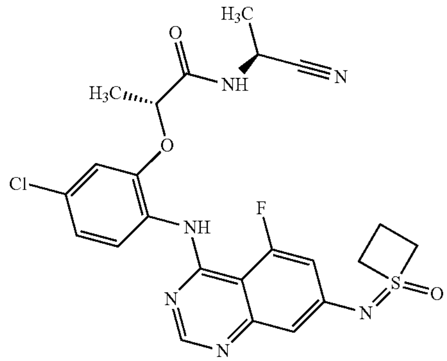 [SMILES: C[C@@H](C#N)NC(=O)[C@@H](C)Oc1cc(Cl)ccc1Nc1ncnc2cc(N=S3(=O)CCC3)cc(F)c12] | VI.16 | 517 | 0.96 min (HPLC-M) | P9 with (2S)-2-aminopropanenitrile |
| 4.078 | 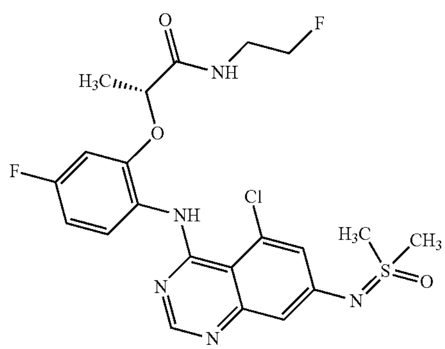 [SMILES: C[C@@H](Oc1cc(F)ccc1Nc1ncnc2cc(N=S(C)(C)=O)cc(Cl)c12)C(=O)NCCF] | VI.5 | 498 | 0.37 min (HPLC-Q) | P8 with 2-fluoroethanamine |
| 4.079 | 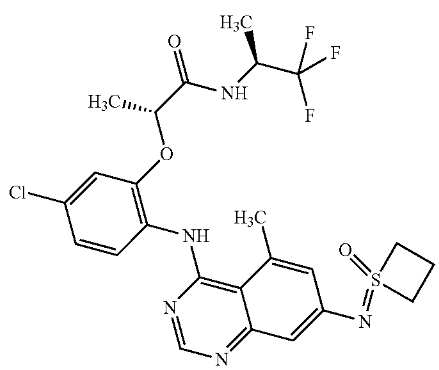 [SMILES: Cc1cc(N=S2(=O)CCC2)cc2ncnc(Nc3ccc(Cl)cc3O[C@H](C)C(=O)N[C@@H](C)C(F)(F)F)c12] | VI.9 | 556 | 1.01 min (HPLC-M) | P5 with 2 eq DIPEA and (2S)-1,1,1-trifluoropropan-2-amine |
| 4.080 | 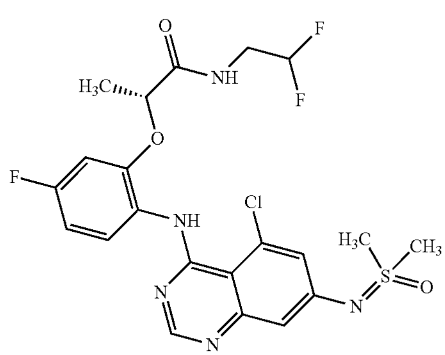 | VI.5 | 516 | 0.38 min (HPLC-Q) | P8 with 2,2-difluoroethanamine |

TABLE 4-continued

| # | Structure | SM | MS | RT | Synthesis Comment |
|---|-----------|----|----|----|-------------------|
| 4.081 | 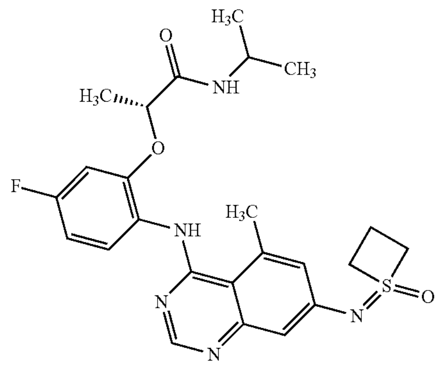 [SMILES: Cc1cc(N=S2(=O)CCC2)cc2ncnc(Nc3ccc(F)cc3O[C@H](C)C(=O)NC(C)C)c12] | VI.4 | 486 | 0.39 min (HPLC-Q) | P8 with propan-2-amine |
| 4.082 | 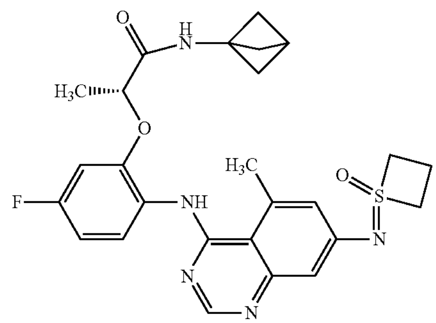 [SMILES: Cc1cc(N=S2(=O)CCC2)cc2ncnc(Nc3ccc(F)cc3O[C@H](C)C(=O)NC34CC(C3)C4)c12] | VI.4 | 510 | 0.77 min (HPLC-T) | P5 with 2.5 eq HATU, 7 eq DIPEA and bicyclo[1.1.1]pentan-3-amine |
| 4.083 | 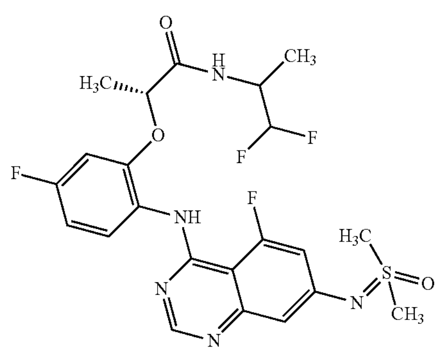 [SMILES: CC(NC(=O)[C@@H](C)Oc1cc(F)ccc1Nc1ncnc2cc(N=S(C)(C)=O)cc(F)c12)C(F)F] | VI.2 | 514 | 0.49 min (HPLC-K) | P5 with 7 eq DIPEA and 2,2,2-trifluoroethanamine |
| 4.084 | 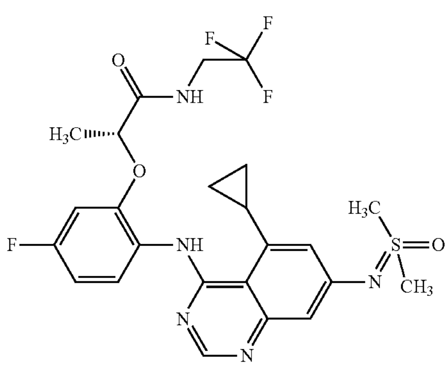 [SMILES: C[C@@H](Oc1cc(F)ccc1Nc1ncnc2cc(N=S(C)(C)=O)cc(C3CC3)c12)C(=O)NCC(F)(F)F] | VI.6 | 541 | 0.75 min (HPLC-T) | P5 with 2,2,2-trifluoroethanamine |

TABLE 4-continued
| # | Structure | SM | MS | RT | Synthesis Comment |
|---|---|---|---|---|---|
| 4.085 | 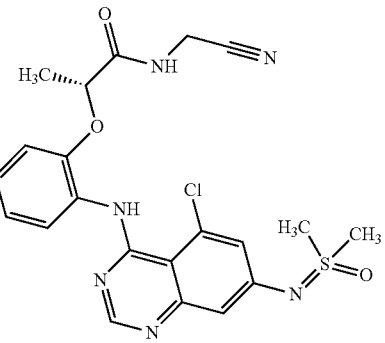 | VI.5 | 491 | 0.36 min (HPLC-Q) | P8 with 2-aminoacetonitrile |
| 4.086 | 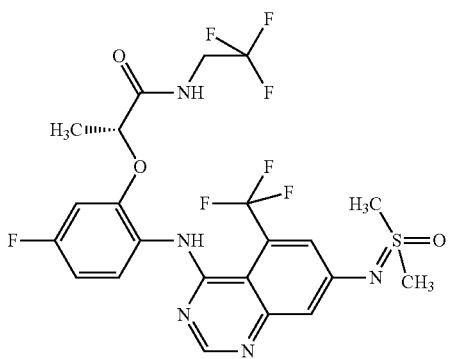 [SMILES: C[C@@H](Oc1cc(F)ccc1Nc1ncnc2cc(N=S(C)(C)=O)cc(C(F)(F)F)c12)C(=O)NCC(F)(F)F] | VI.7 | 568 | 0.43 min (HPLC-Q) | P5 with 2,2,2-trifluoroethanamine |
| 4.087 | 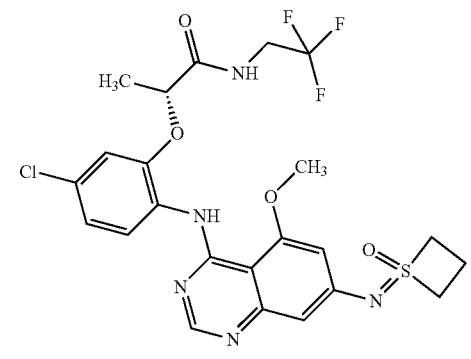 [SMILES: COc1cc(N=S2(=O)CCC2)cc2ncnc(Nc3ccc(Cl)cc3O[C@H](C)C(=O)NCC(F)(F)F)c12] | VI.17 | 558 | 0.99 min (HPLC-M) | P5 with 2,2,2-trifluoroethanamine |
| 4.088 | 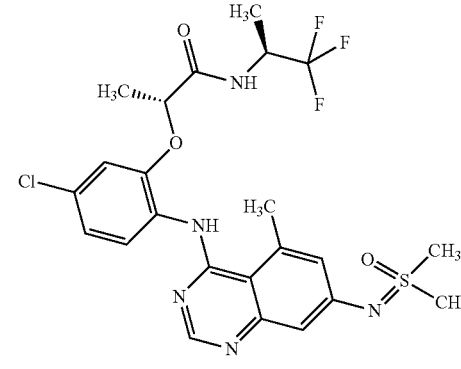 | VI.10 | 544 | 0.43 min (HPLC-Q) | P5 with 2 eq DIPEA and (2S)-1,1,1-trifluoropropan-2-amine |

TABLE 4-continued

| # | Structure | SM | MS | RT | Synthesis Comment |
|---|---|---|---|---|---|
| 4.089 | 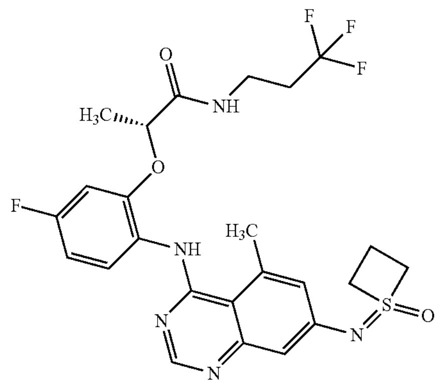 [SMILES: Cc1cc(N=S2(=O)CCC2)cc2ncnc(Nc3ccc(F)cc3O[C@H](C)C(=O)NCCC(F)(F)F)c12] | VI.4 | 540 | 0.41 min (HPLC-Q) | P8 with 3,3,3-trifluoropropan-1-amine |
| 4.090 | 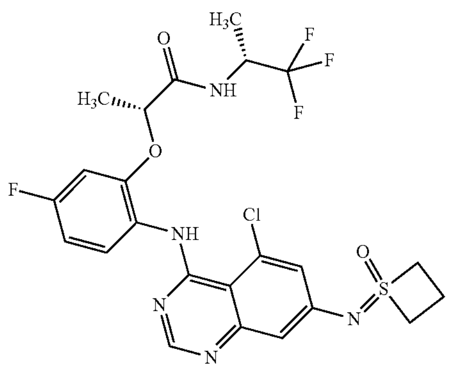 [SMILES: C[C@@H](Oc1cc(F)ccc1Nc1ncnc2cc(N=S3(=O)CCC3)cc(Cl)c12)C(=O)N[C@H](C)C(F)(F)F] | VI.8 | 560 | 0.87 min (HPLC-B) | P5 with(2R)-1,1,1-trifluoropropan-2-amine |
| 4.091 | 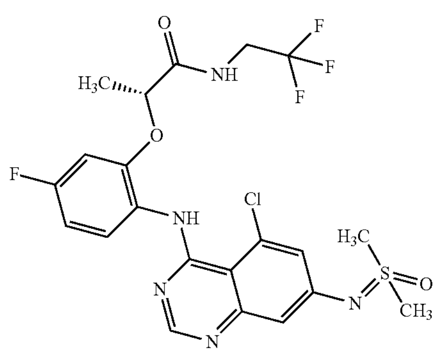 [SMILES: C[C@@H](Oc1cc(F)ccc1Nc1ncnc2cc(N=S(C)(C)=O)cc(Cl)c12)C(=O)NCC(F)(F)F] | VI.5 | 534 | 0.41 min (HPLC-Q) | P8 with 2,2,2-trifluoroethanamine |
| 4.092 | 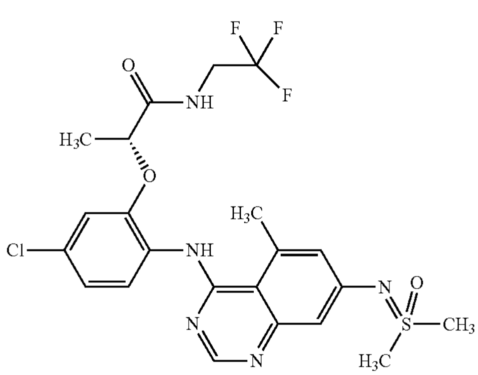 [SMILES: Cc1cc(N=S(C)(C)=O)cc2ncnc(Nc3ccc(Cl)cc3O[C@H](C)C(=O)NCC(F)(F)F)c12] | VI.10 | 530 | 0.69 min (HPLC-N) | P5 with 2,2,2-trifluoroethanamine |

TABLE 4-continued

| # | Structure | SM | MS | RT | Synthesis Comment |
|---|---|---|---|---|---|
| 4.093 | 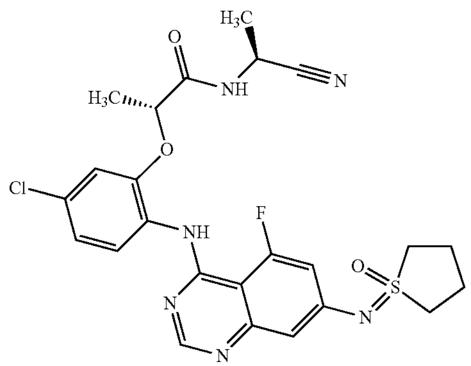 [SMILES: C[C@@H](C#N)NC(=O)[C@@H](C)Oc1cc(Cl)ccc1Nc1ncnc2cc(N=S3(=O)CCCC3)cc(F)c12] | VI.12 | 531 | 0.96 min (HPLC-M) | P5 with 7 eq DIPEA and (2S)-2-aminopropanenitrile |
| 4.094 | 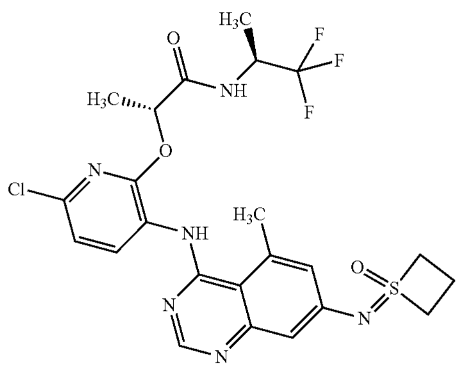 [SMILES: Cc1cc(N=S2(=O)CCC2)cc2ncnc(Nc3ccc(Cl)nc3O[C@H](C)C(=O)N[C@@H](C)C(F)(F)F)c12] | VII.14 | 557 | 0.82 min (HPLC-T) | P9 with (2S)-1,1,1-trifluoropropan-2-amine |
| 4.095 | 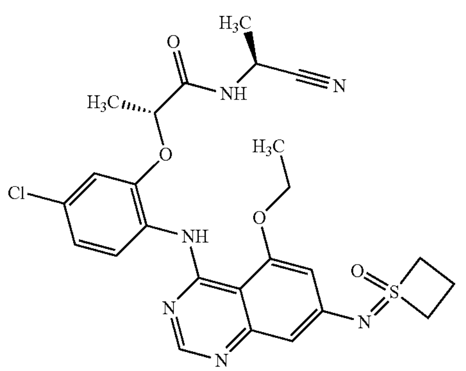 [SMILES: CCOc1cc(N=S2(=O)CCC2)cc2ncnc(Nc3ccc(Cl)cc3O[C@H](C)C(=O)N[C@@H](C)C#N)c12] | VI.11 | 543 | 0.78 min (HPLC-T) | P5 with 7 eq DIPEA and (2S)-2-aminopropanenitrile |
| 4.096 | 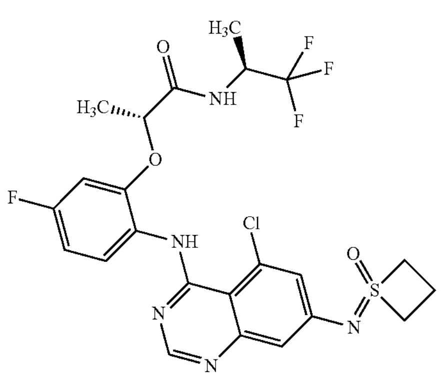 [SMILES: C[C@H](NC(=O)[C@@H](C)Oc1cc(F)ccc1Nc1ncnc2cc(N=S3(=O)CCC3)cc(Cl)c12)C(F)(F)F] | VI.8 | 560 | 0.86 min (HPLC-B) | P5 with (2S)-1,1,1-trifluoropropan-2-amine |

TABLE 4-continued

| # | Structure | SM | MS | RT | Synthesis Comment |
|---|-----------|----|----|----|-------------------|
| 4.097 | 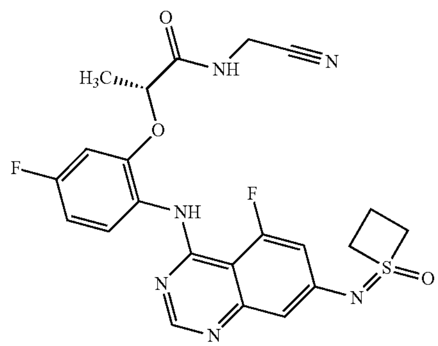 [SMILES: C[C@@H](Oc1cc(F)ccc1Nc1ncnc2cc(N=S3(=O)CCC3)cc(F)c12)C(=O)NCC#N] | VI.3 | 487 | 0.35 min (HPLC-Q) | P8 with 2-aminoacetonitrile |
| 4.098 | 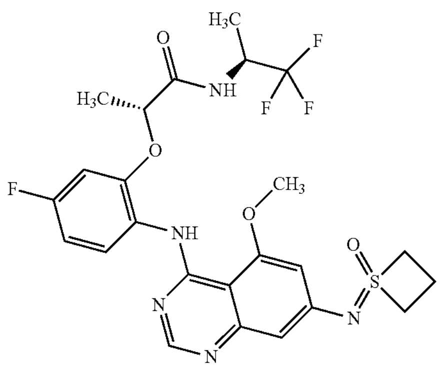 [SMILES: COc1cc(N=S2(=O)CCC2)cc2ncnc(Nc3ccc(F)cc3O[C@H](C)C(=O)N[C@@H](C)C(F)(F)F)c12] | VI.15 | 556 | 0.86 min (HPLC-B) | P5 with 1.2 eq DIPEA and (2S)-1,1,1-trifluoropropan-2-amine |
| 4.099 | 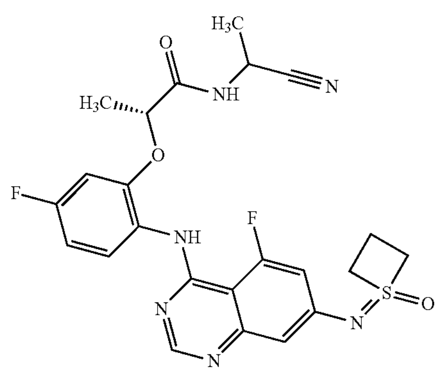 [SMILES: CC(C#N)NC(=O)[C@@H](C)Oc1cc(F)ccc1Nc1ncnc2cc(N=S3(=O)CCC3)cc(F)c12] | VI.3 | 501 | 0.37 min (HPLC-Q) | P8 with 2-aminopropanenitrile |
| 4.100 | 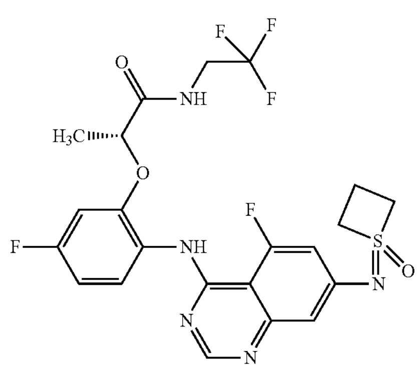 [SMILES: C[C@@H](Oc1cc(F)ccc1Nc1ncnc2cc(N=S3(=O)CCC3)cc(F)c12)C(=O)NCC(F)(F)F] | VI.3 | 530 | 0.4 min (HPLC-Q) | P8 with 2,2,2-trifluoroethanamine |

TABLE 4-continued

| # | Structure | SM | MS | RT | Synthesis Comment |
|---|---|---|---|---|---|
| 4.101 | 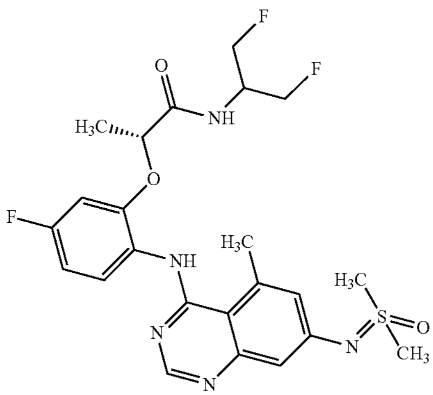 [SMILES: Cc1cc(N=S(C)(C)=O)cc2ncnc(Nc3ccc(F)cc3O[C@H](C)C(=O)NC(CF)CF)c12] | VI.2 | 510 | 0.37 min (HPLC-Q) | P5 with 7.3 eq DIPEA and 1,1-difluoropropan-2-amine |
| 4.102 | 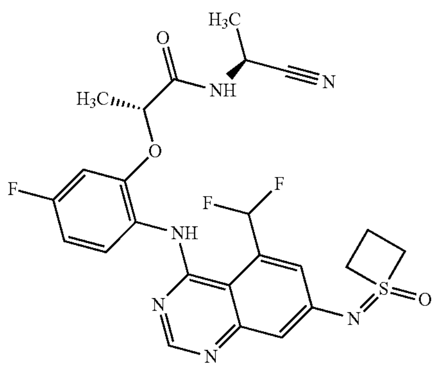 [SMILES: C[C@@H](C#N)NC(=O)[C@@H](C)Oc1cc(F)ccc1Nc1ncnc2cc(N=S3(=O)CCC3)cc(C(F)F)c12] | VI.13 | 533 | 0.94 min (HPLC-M) | P9 with (2S)-2-aminopropanenitrile |
| 4.103 | 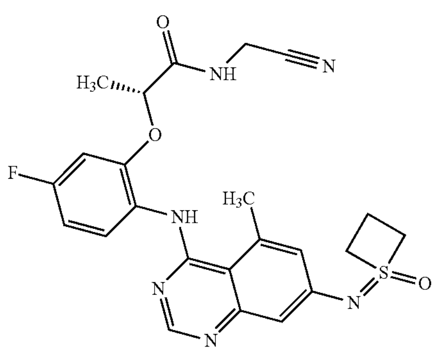 [SMILES: Cc1cc(N=S2(=O)CCC2)cc2ncnc(Nc3ccc(F)cc3O[C@H](C)C(=O)NCC#N)c12] | VI.4 | 483 | 0.75 min (HPLC-M) | P5 with 2-aminoacetonitrile |
| 4.104 | 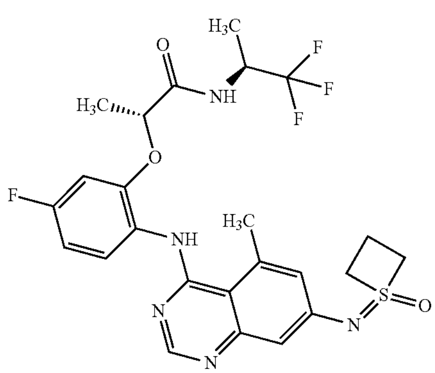 [SMILES: Cc1cc(N=S2(=O)CCC2)cc2ncnc(Nc3ccc(F)cc3O[C@H](C)C(=O)N[C@@H](C)C(F)(F)F)c12] | VI.4 | 540 | 0.84 min (HPLC-B) | P5 with 2 eq DIPEA and (2S)-1,1,1-trifluoropropan-2-amine |

TABLE 4-continued

| # | Structure | SM | MS | RT | Synthesis Comment |
|---|---|---|---|---|---|
| 4.105 | 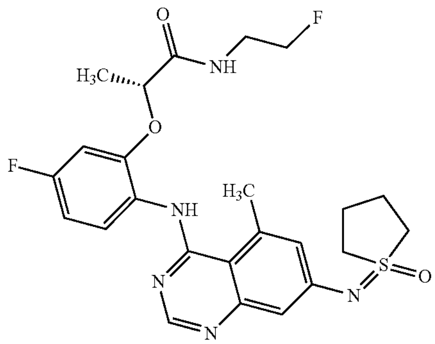 [SMILES: Cc1cc(N=S2(=O)CCCC2)cc2ncnc(Nc3ccc(F)cc3O[C@H](C)C(=O)NCCF)c12] | VI.1 | 504 | 0.5 min (HPLC-W) | P5 with 2.7 eq HATU, 11 eq DIPEA and 2-fluoroethanamine |
| 4.106 | 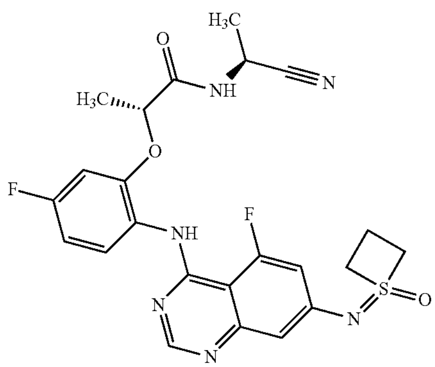 [SMILES: C[C@@H](C#N)NC(=O)[C@@H](C)Oc1cc(F)ccc1Nc1ncnc2cc(N=S3(=O)CCC3)cc(F)c12] | VI.3 | 501 | 0.78 min (HPLC-B) | P5 with 7.5 eq DIPEA and (2S)-2-aminopropanenitrile |
| 4.107 | 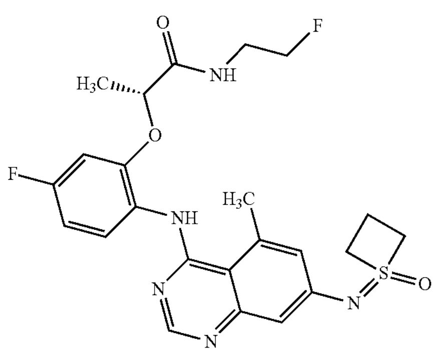 [SMILES: Cc1cc(N=S2(=O)CCC2)cc2ncnc(Nc3ccc(F)cc3O[C@H](C)C(=O)NCCF)c12] | VI.4 | 490 | 0.36 min (HPLC-Q) | P8 with 2-fluoroethanamine |
| 4.108 | 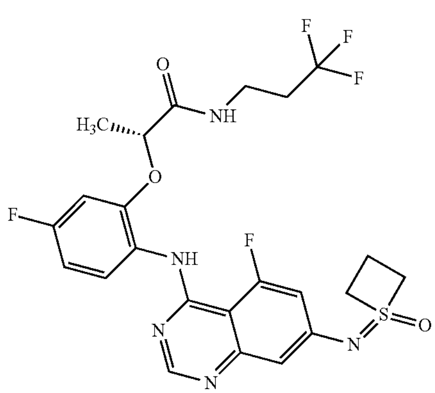 [SMILES: C[C@@H](Oc1cc(F)ccc1Nc1ncnc2cc(N=S3(=O)CCC3)cc(F)c12)C(=O)NCCC(F)(F)F] | VI.3 | 544 | 0.4 min (HPLC-Q) | P8 with 3,3,3-trifluoropropan-1-amine |

TABLE 4-continued

| # | Structure | SM | MS | RT | Synthesis Comment |
|---|---|---|---|---|---|
| 4.109 | 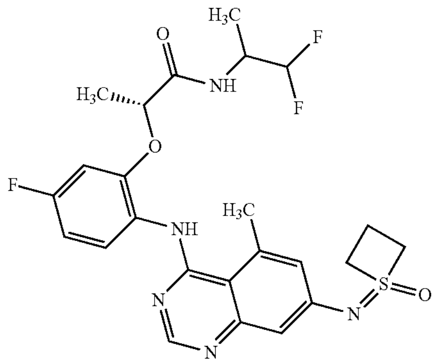 [SMILES: Cc1cc(N=S2(=O)CCC2)cc2ncnc(Nc3ccc(F)cc3O[C@H](C)C(=O)NC(C)C(F)F)c12] | VI.4 | 522 | 0.4 min (HPLC-Q) | P8 with 1,1-difluoropropan-2-amine |
| 4.110 | 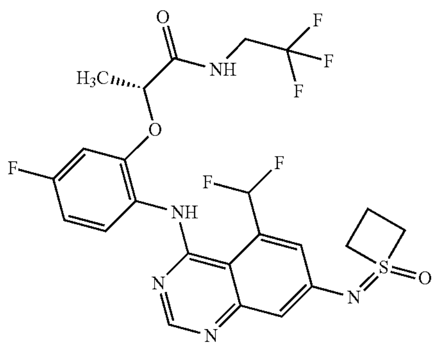 [SMILES: C[C@@H](Oc1cc(F)ccc1Nc1ncnc2cc(N=S3(=O)CCC3)cc(C(F)F)c12)C(=O)NCC(F)(F)F] | VI.13 | 562 | 0.98 min (HPLC-M) | P9 with 2,2,2-trifluoroethanamine |
| 4.111 | 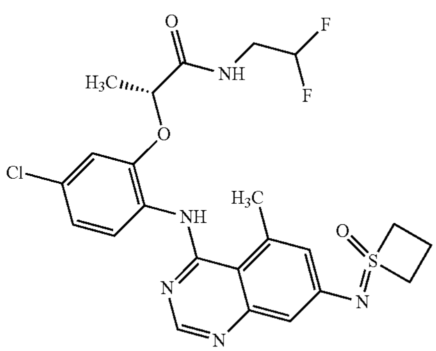 [SMILES: Cc1cc(N=S2(=O)CCC2)cc2ncnc(Nc3ccc(Cl)cc3O[C@H](C)C(=O)NCC(F)F)c12] | VI.9 | 524 | 0.96 min (HPLC-M) | P5 with 2 eq DIPEA and 2,2-difluoroethanamine |
| 4.112 | 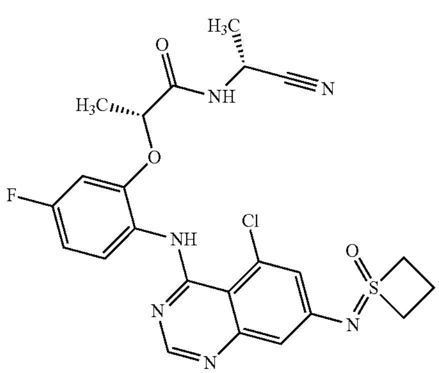 [SMILES: C[C@H](C#N)NC(=O)[C@@H](C)Oc1cc(F)ccc1Nc1ncnc2cc(N=S3(=O)CCC3)cc(Cl)c12] | VI.8 | 517 | 0.81 min (HPLC-B) | P5 with 7 eq DIPEA and (2R)-2-aminopropanenitrile |

TABLE 4-continued
| # | Structure | SM | MS | RT | Synthesis Comment |
|---|---|---|---|---|---|
| 4.113 | 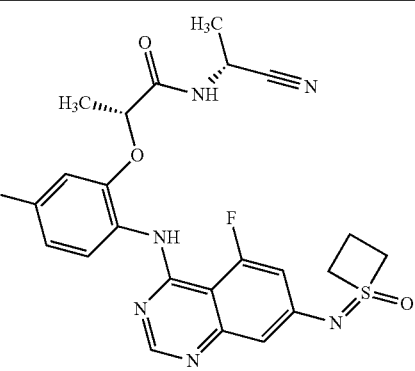 | VI.3 | 501 | 0.9 min (HPLC-M) | P5 with 1.9 eq HATU, 7.9 eq DIPEA and (2R)-2-aminopropanenitrile |
| 4.114 | 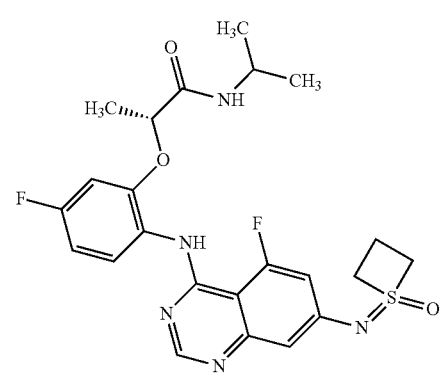 [SMILES: CC(C)NC(=O)[C@@H](C)Oc1cc(F)ccc1Nc1ncnc2cc(N=S3(=O)CCC3)cc(F)c12] | VI.3 | 490 | 0.39 min (HPLC-Q) | P8 with propan-2-amine |
| 4.115 | 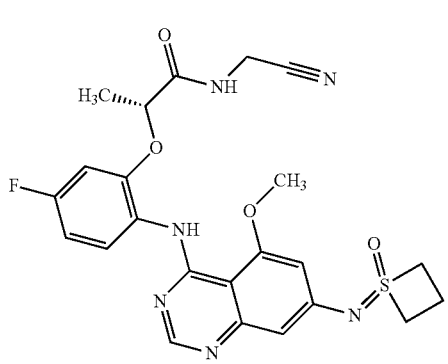 [SMILES: COc1cc(N=S2(=O)CCC2)cc2ncnc(Nc3ccc(F)cc3O[C@H](C)C(=O)NCC#N)c12] | VI.15 | 499 | 0.78 min (HPLC-B) | P5 with 1.2 eq HATU, 2.2 eq DIPEA and 2-aminoacetonitrile |
| 4.116 | 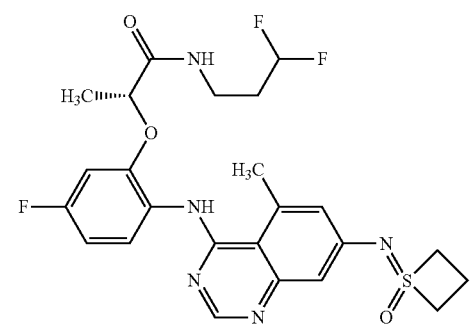 [SMILES: Cc1cc(N=S2(=O)CCC2)cc2ncnc(Nc3ccc(F)cc3O[C@H](C)C(=O)NCCC(F)F)c12] | VI.4 | 522 | 0.71 min (HPLC-T) | P5 with 2.5 eq HATU, 7 eq DIPEA and 3,3-difluoropropan-1-amine |

TABLE 4-continued

| # | Structure | SM | MS | RT | Synthesis Comment |
|---|---|---|---|---|---|
| 4.117 | 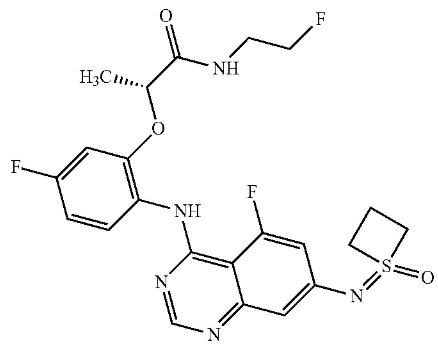 [SMILES: C[C@@H](Oc1cc(F)ccc1Nc1ncnc2cc(N=S3(=O)CCC3)cc(F)c12)C(=O)NCCF] | VI.3 | 494 | 0.36 min (HPLC-Q) | P8 with 2-fluoroethanamine |
| 4.118 | 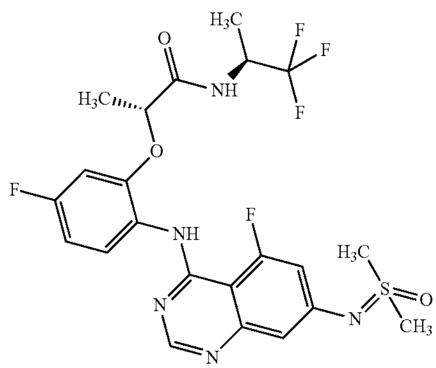 [SMILES: C[C@H](NC(=O)[C@@H](C)Oc1cc(F)ccc1Nc1ncnc2cc(N=S(C)(C)=O)cc(F)c12)C(F)(F)F] | VI.18 | 532 | 0.82 min (HPLC-B) | P5 with 2 eq DIPEA and (2S)-1,1,1-trifluoropropan-2-amine |
| 4.119 | 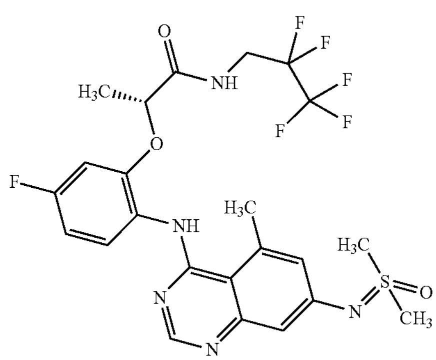 [SMILES: Cc1cc(N=S(C)(C)=O)cc2ncnc(Nc3ccc(F)cc3O[C@H](C)C(=O)NCC(F)(F)C(F)(F)F)c12] | VI.1 | 564 | 0.61 min (HPLC-V) | P5 with 2,2,3,3,3-pentafluoropropan-1-amine |
| 4.120 | 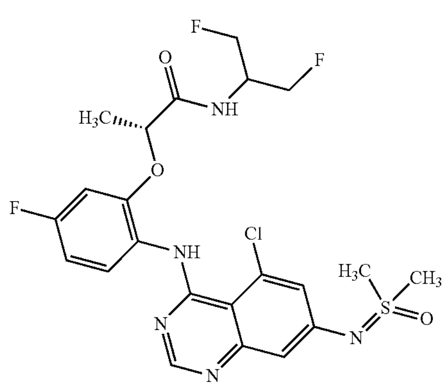 [SMILES: C[C@@H](Oc1cc(F)ccc1Nc1ncnc2cc(N=S(C)(C)=O)cc(Cl)c12)C(=O)NC(CF)CF] | VI.5 | 530 | 0.38 min (HPLC-Q) | P8 with 1,3-difluoropropan-2-amine |

TABLE 4-continued

| # | Structure | SM | MS | RT | Synthesis Comment |
|---|-----------|-----|-----|-----|-------------------|
| 4.121 | 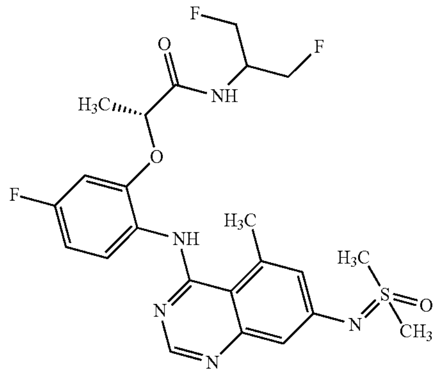 [SMILES: Cc1cc(N=S(C)(C)=O)cc2ncnc(Nc3ccc(F)cc3O[C@H](C)C(=O)NC(CF)CF)c12] | VI.18 | 514 | 0.91 min (HPLC-M) | P5 with 7.5 eq DIPEA and 1,3-difluoropropan-2-amine |
| 4.122 | 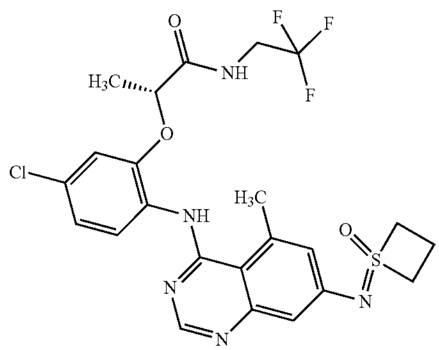 [SMILES: Cc1cc(N=S2(=O)CCC2)cc2ncnc(Nc3ccc(Cl)cc3O[C@H](C)C(=O)NCC(F)(F)F)c12] | VI.9 | 542 | 0.99 min (HPLC-M) | P5 with 2 eq DIPEA and 2,2,2-trifluoroethanamine |
| 4.123 | 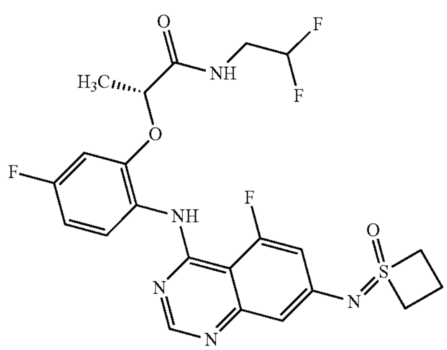 [SMILES: C[C@@H](Oc1cc(F)ccc1Nc1ncnc2cc(N=S3(=O)CCC3)cc(F)c12)C(=O)NCC(F)F] | VI.3 | 512 | 0.37 min (HPLC-Q) | P8 with 2,2-difluoroethanamine |
| 4.124 | 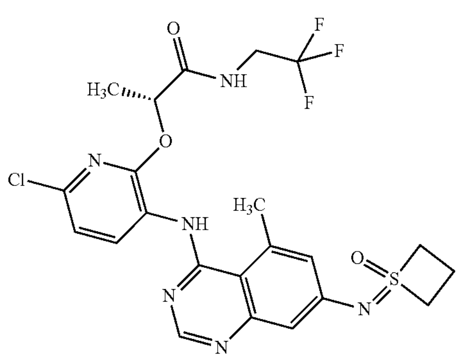 [SMILES: Cc1cc(N=S2(=O)CCC2)cc2ncnc(Nc3ccc(Cl)nc3O[C@H](C)C(=O)NCC(F)(F)F)c12] | VI.9 | 543 | 0.63 min (HPLC-U) | P9 with 2,2,2-trifluoroethanamine |

TABLE 4-continued

| # | Structure | SM | MS | RT | Synthesis Comment |
|---|---|---|---|---|---|
| 4.125 | 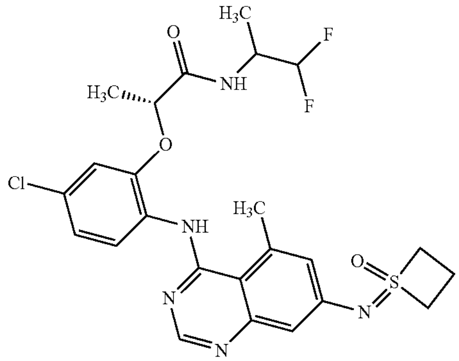 [SMILES: Cc1cc(N=S2(=O)CCC2)cc2ncnc(Nc3ccc(Cl)cc3O[C@H](C)C(=O)NC(C)C(F)F)c12] | VI.9 | 538 | 0.99 min (HPLC-M) | P9 with 2,2-difluoroethanamine |
| 4.126 | 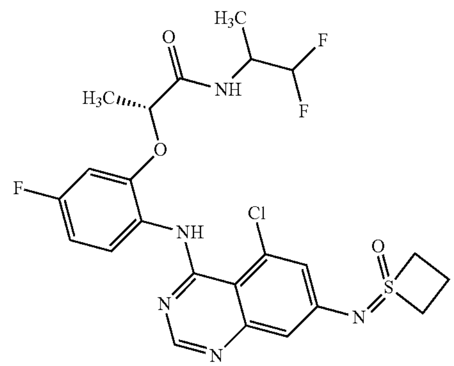 [SMILES: CC(NC(=O)[C@@H](C)Oc1cc(F)ccc1Nc1ncnc2cc(N=S3(=O)CCC3)cc(Cl)c12)C(F)F] | VI.8 | 542 | 0.83 min (HPLC-B) | P5 with 7 eq DIPEA and 1,1-difluoropropan-2-amine |
| 4.127 | 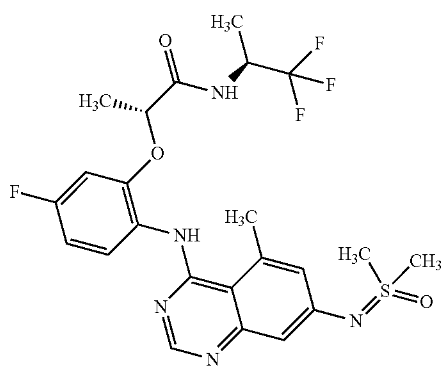 [SMILES: Cc1cc(N=S(C)(C)=O)cc2ncnc(Nc3ccc(F)cc3O[C@H](C)C(=O)N[C@@H](C)C(F)(F)F)c12] | VI.2 | 528 | 0.8 min (HPLC-I) | 3.7 eq DIPEA and (S)-2,2,2-Trifluoro-1-methyl-ethylamine |
| 4.128 | 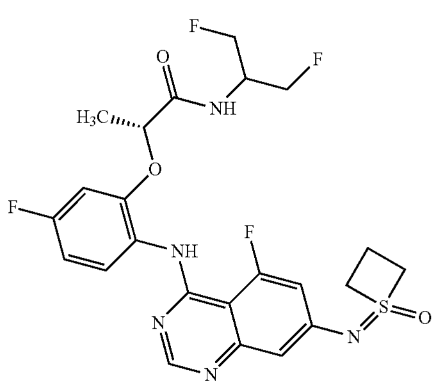 [SMILES: C[C@@H](Oc1cc(F)ccc1Nc1ncnc2cc(N=S3(=O)CCC3)cc(F)c12)C(=O)NC(CF)CF] | VI.3 | 526 | 0.38 min (HPLC-Q) | P8 with 1,3-difluoropropan-2-amine |

TABLE 4-continued

| # | Structure | SM | MS | RT | Synthesis Comment |
|---|---|---|---|---|---|
| 4.129 | 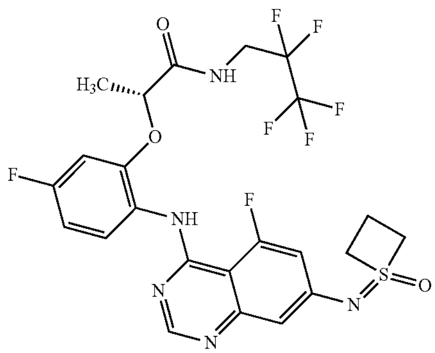 [SMILES: C[C@@H](Oc1cc(F)ccc1Nc1ncnc2cc(N=S3(=O)CCC3)cc(F)c12)C(=O)NCC(F)(F)C(F)(F)F] | VI.3 | 580 | 0.44 min (HPLC-Q) | P8 with 2,2,3,3,3-pentafluoropropan-1-amine |
| 4.130 | 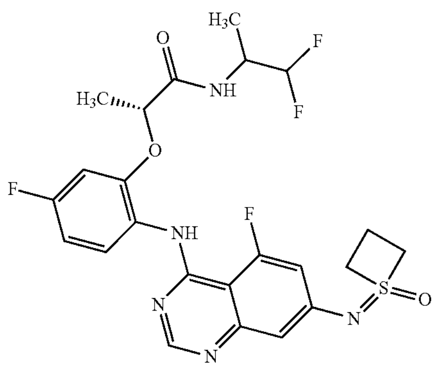 [SMILES: CC(NC(=O)[C@@H](C)Oc1cc(F)ccc1Nc1ncnc2cc(N=S3(=O)CCC3)cc(F)c12)C(F)F] | VI.3 | 526 | 0.39 min (HPLC-Q) | P8 with 1,1-difluoropropan-2-amine |
| 4.131 | 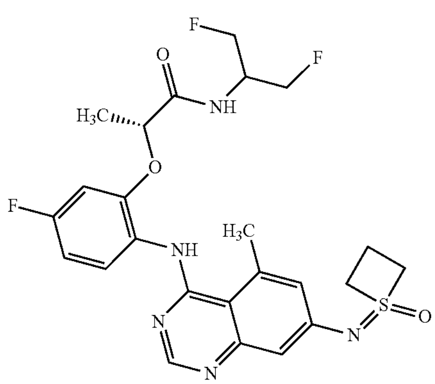 [SMILES: Cc1cc(N=S2(=O)CCC2)cc2ncnc(Nc3ccc(F)cc3O[C@H](C)C(=O)NC(CF)CF)c12] | VI.4 | 522 | 0.38 min (HPLC-Q) | P8 with 1,3-difluoropropan-2-amine |
| 4.132 | 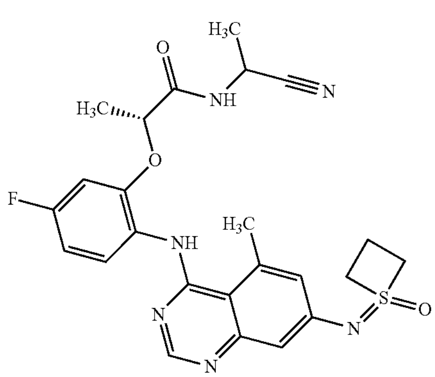 [SMILES: Cc1cc(N=S2(=O)CCC2)cc2ncnc(Nc3ccc(F)cc3O[C@H](C)C(=O)NC(C)C#N)c12] | VI.4 | 497 | 0.37 min (HPLC-Q) | P8 with 2-aminopropanenitrile |

TABLE 4-continued

| # | Structure | SM | MS | RT | Synthesis Comment |
|---|---|---|---|---|---|
| 4.133 | 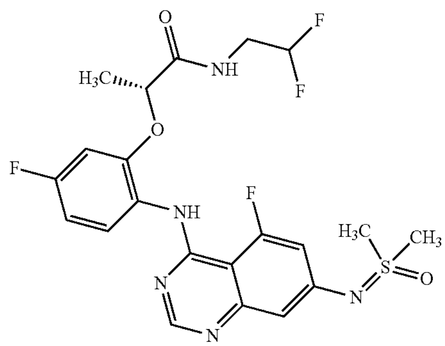 [SMILES: C[C@@H](Oc1cc(F)ccc1Nc1ncnc2cc(N=S(C)(C)=O)cc(F)c12)C(=O)NCC(F)F] | VI.18 | 500 | 0.36 min (HPLC-Q) | P5 with 10 eq TEA and 2,2-Difluoro-ethylamine |
| 4.134 | 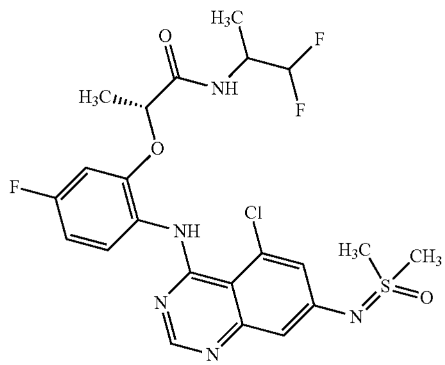 [SMILES: CC(NC(=O)[C@@H](C)Oc1cc(F)ccc1Nc1ncnc2cc(N=S(C)(C)=O)cc(Cl)c12)C(F)F] | VI.5 | 530 | 0.4 min (HPLC-Q) | P8 with 1,1-difluoropropan-2-amine |
| 4.135 | 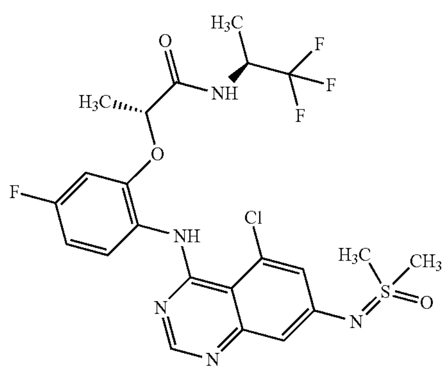 [SMILES: C[C@H](NC(=O)[C@@H](C)Oc1cc(F)ccc1Nc1ncnc2cc(N=S(C)(C)=O)cc(Cl)c12)C(F)(F)F] | VI.5 | 548 | 0.42 min (HPLC-Q) | P8 with (2S)-1,1,1-trifluoropropan-2-amine |
| 4.136 | 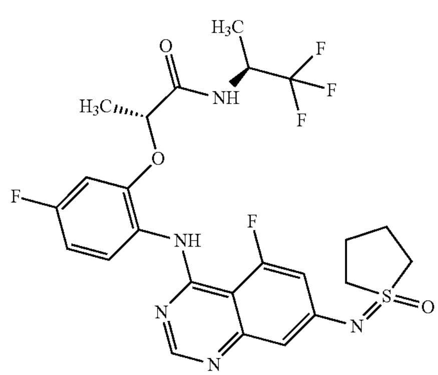 [SMILES: C[C@H](NC(=O)[C@@H](C)Oc1cc(F)ccc1Nc1ncnc2cc(N=S3(=O)CCCC3)cc(F)c12)C(F)(F)F] | VI.3 | 544 | 0.42 min (HPLC-Q) | P8 with (2S)-1,1,1-trifluoropropan-2-amine |

TABLE 4-continued

| # | Structure | SM | MS | RT | Synthesis Comment |
|---|---|---|---|---|---|
| 4.137 | 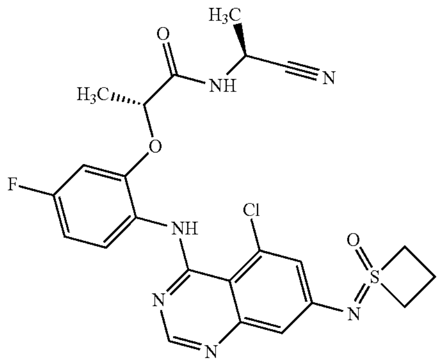 [SMILES: C[C@@H](C#N)NC(=O)[C@@H](C)Oc1cc(F)ccc1Nc1ncnc2cc(N=S3(=O)CCC3)cc(Cl)c12] | VI.8 | 517 | 0.81 min (HPLC-B) | P5 with 7 eq DIPEA and (2S)-2-aminopropanenitrile |
| 4.138 | 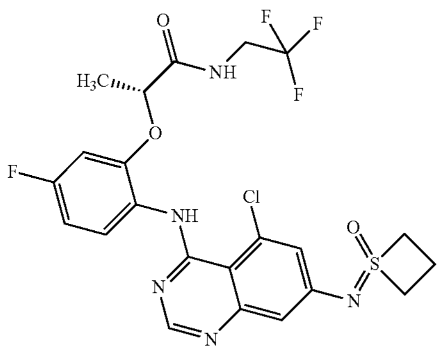 [SMILES: C[C@@H](Oc1cc(F)ccc1Nc1ncnc2cc(N=S3(=O)CCC3)cc(Cl)c12)C(=O)NCC(F)(F)F] | VI.8 | 546 | 0.84 min (HPLC-B) | P5 with 2 eq DIPEA and 2,2,2-trifluoroethanamine |
| 4.139 | 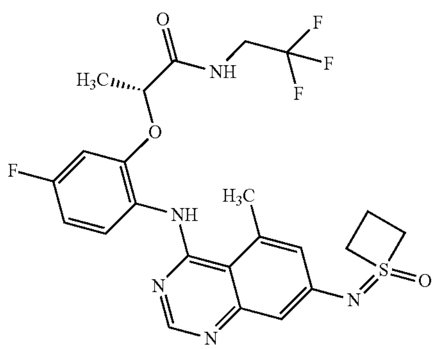 [SMILES: Cc1cc(N=S2(=O)CCC2)cc2ncnc(Nc3ccc(F)cc3O[C@H](C)C(=O)NCC(F)(F)F)c12] | VI.4 | 526 | 0.82 min (HPLC-B) | P5 with 2,2,2-trifluoroethanamine |
| 4.140 | 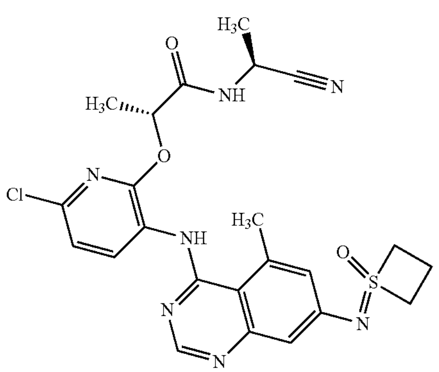 [SMILES: Cc1cc(N=S2(=O)CCC2)cc2ncnc(Nc3ccc(Cl)nc3O[C@H](C)C(=O)N[C@@H](C)C#N)c12] | VII.14 | 514 | 0.73 min (HPLC-T) | P9 with (2S)-2-aminopropanenitrile |

TABLE 4-continued

| # | Structure | SM | MS | RT | Synthesis Comment |
|---|---|---|---|---|---|
| 4.141 | 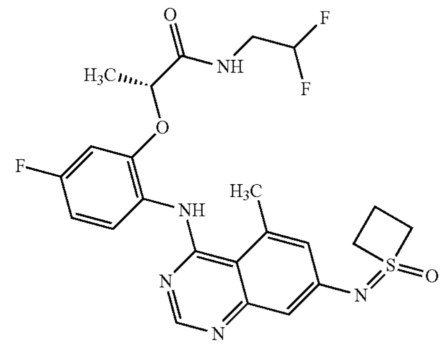 [SMILES: Cc1cc(N=S2(=O)CCC2)cc2ncnc(Nc3ccc(F)cc3O[C@H](C)C(=O)NCC(F)F)c12] | VI.4 | 508 | 0.7 min (HPLC-T) | P5 with 2,2-difluoroethanamine |
| 4.142 | 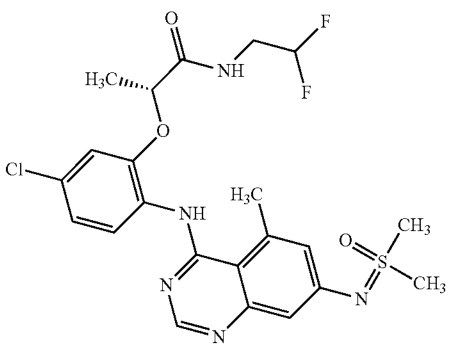 [SMILES: Cc1cc(N=S(C)(C)=O)cc2ncnc(Nc3ccc(Cl)cc3O[C@H](C)C(=O)NCC(F)F)c12] | VI.10 | 512 | 0.39 min (HPLC-Q) | P5 with 2,2-difluoroethanamine |
| 4.143 | 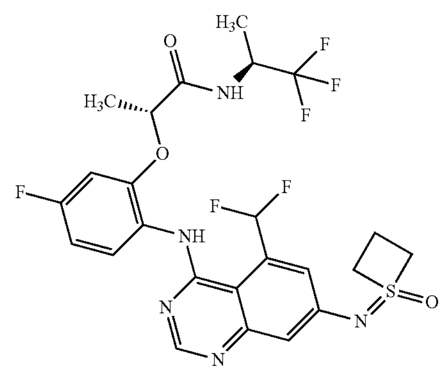 [SMILES: C[C@H](NC(=O)[C@@H](C)Oc1cc(F)ccc1Nc1ncnc2cc(N=S3(=O)CCC3)cc(C(F)F)c12)C(F)(F)F] | VI.13 | 576 | 1 min (HPLC-M) | P9 with (2S)-1,1,1-trifluoropropan-2-amine |
| 4.144 | 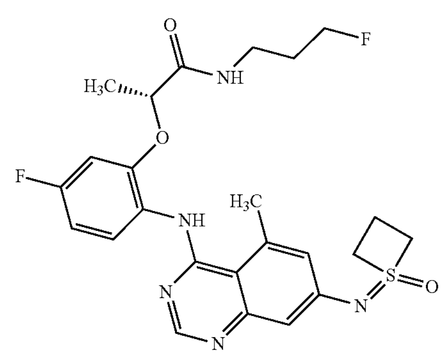 [SMILES: Cc1cc(N=S2(=O)CCC2)cc2ncnc(Nc3ccc(F)cc3O[C@H](C)C(=O)NCCCF)c12] | VI.4 | 504 | 0.37 min (HPLC-Q) | P8 with 3-fluoropropan-1-amine |

TABLE 4-continued

| # | Structure | SM | MS | RT | Synthesis Comment |
|---|---|---|---|---|---|
| 4.145 | 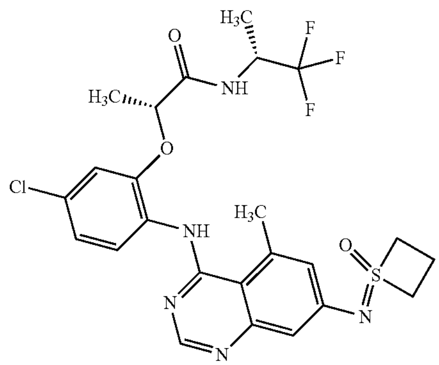 [SMILES: Cc1cc(N=S2(=O)CCC2)cc2ncnc(Nc3ccc(Cl)cc3O[C@H](C)C(=O)N[C@H](C)C(F)(F)F)c12] | VI.9 | 556 | 1.02 min (HPLC-M) | P5 with (2R)-1,1,1-trifluoropropan-2-amine |
| 4.146 | 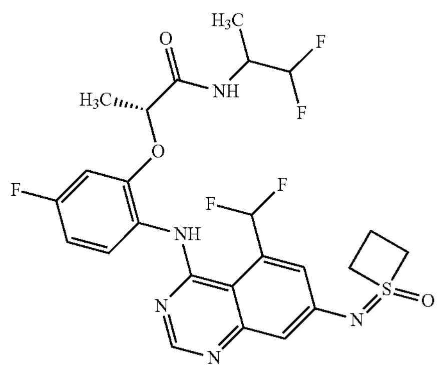 [SMILES: CC(NC(=O)[C@@H](C)Oc1cc(F)ccc1Nc1ncnc2cc(N=S3(=O)CCC3)cc(C(F)F)c12)C(F)F] | VI.13 | 558 | 0.98 min (HPLC-M) | P9 with 1,1-difluoropropan-2-amine |
| 4.147 | 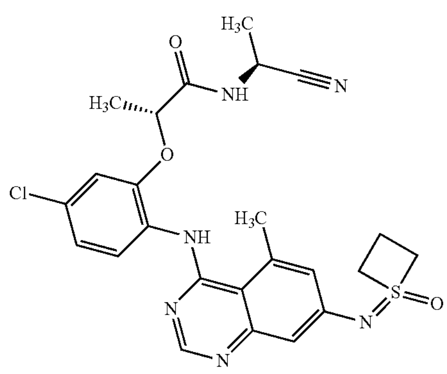 [SMILES: Cc1cc(N=S2(=O)CCC2)cc2ncnc(Nc3ccc(Cl)cc3O[C@H](C)C(=O)N[C@@H](C)C#N)c12] | VI.9 | 513 | 0.95 min (HPLC-M) | P5 with 2 eq HATU, 7.8 eq DIPEA and (2S)-2-aminopropanenitrile |

General Procedure 11 (P11) for Examples Shown in Table 5:

To a mixture of 1 eq of the corresponding amine, 2.5 eq DIPEA and DCM the given amount of reagent is added slowly and the mixture is stirred at RT over night. The reaction mixture is washed with water, dried and concentrated. If necessary the crude product is purified by HPLC or FC.

General Procedure 12 (P12) for Examples Shown in Table 5:

To a mixture of 1 eq of the corresponding amine, 5 eq DIPEA and acetonitrile the given amount of reagent is added slowly and the mixture is stirred at RT for 2 h. Subsequently aqueous 2 mol/l $K_2CO_3$ solution is added and the reaction mixture is passed through a short column of Alox B and concentrated. If necessary the crude product is purified by HPLC or FC.

The following examples in table 5 (example number given in column #) are prepared according to P11 or P12, details are given in the column synthesis comment, the retention-time and mass (ESI-MS m/z M+H⁺) determined by HPLC-MS are given in the columns MS and RT.

TABLE 5

| # | Structure | SM | MS | RT | Synthesis Comment |
|---|---|---|---|---|---|
| 5.001 | 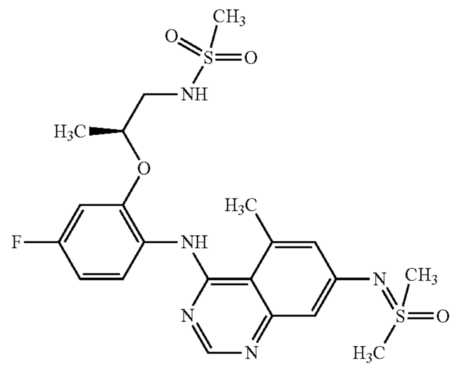 | 3.024 | 496 | 0.65 min (HPLC-B) | P11 with 1.0 eq. methanesulfonyl chloride |
| 5.002 | 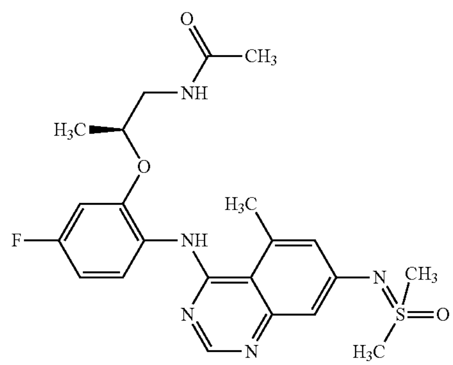 [SMILES: CC(=O)NC[C@H](C)Oc1cc(F)ccc1Nc1ncnc2cc(N=S(C)(C)=O)cc(C)c12] | 3.024 | 460 | 0.64 min (HPLC-B) | P11 with 1.0 eq. acetyl chloride |
| 5.003 | 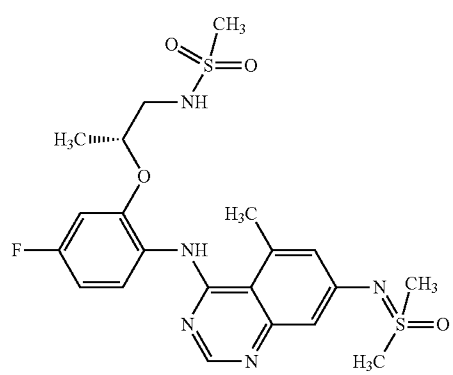 [SMILES: Cc1cc(N=S(C)(C)=O)cc2ncnc(Nc3ccc(F)cc3O[C@H](C)CNS(C)(=O)=O)c12] | 3.018 | 496 | 0.65 min (HPLC-B) | P11 with 1.0 eq. methanesulfonyl chloride |
| 5.004 | 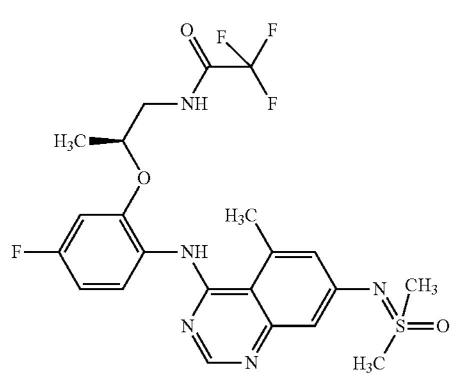 [SMILES: Cc1cc(N=S(C)(C)=O)cc2ncnc(Nc3ccc(F)cc3O[C@@H](C)CNC(=O)C(F)(F)F)c12] | 3.024 | 514 | 0.71 min (HPLC-B) | P11 with 1.0 eq. trifluoracetic acid anhydride |

TABLE 5-continued
| # | Structure | SM | MS | RT | Synthesis Comment |
|---|---|---|---|---|---|
| 5.005 | 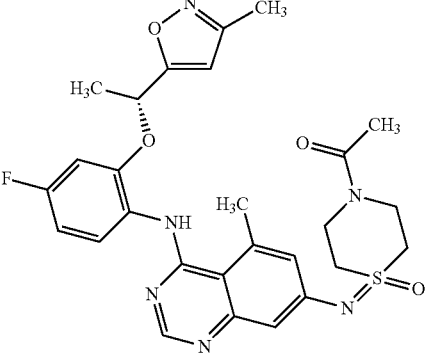 | 2.016 | 553 | 0.72 min (HPLC-B) | P12 with 2.0 eq acetic acid and 1.1 eq HATU |
| 5.006 | 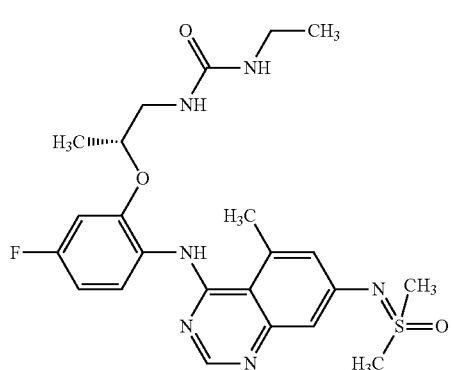 | 3.018 | 489 | 0.66 min (HPLC-B) | P11 with 1.0 eq ethyl isocyanate |
| 5.007 | 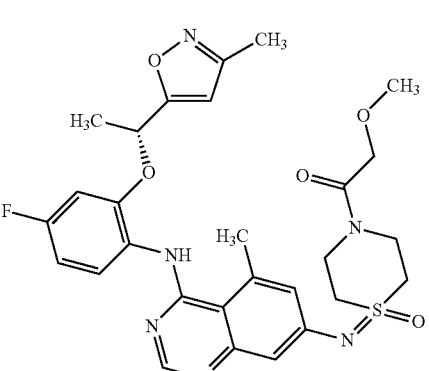 | 2.016 | 583 | 0.72 min (HPLC-B) | P12 with 2.0 eq methoxyacetic acid and 1.1 eq HATU |
| 5.008 | 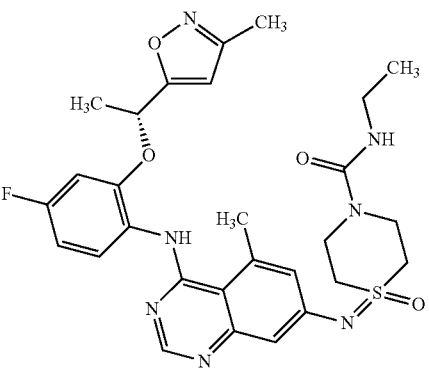 [SMILES: CCNC(=O)N1CCS(=O)(=Nc2cc(C)c3c(Nc4ccc(F)cc4O[C@H](C)c4cc(C)no4)ncnc3c2)CC1] | 2.016 | 582 | 0.73 min (HPLC-B) | P12 with 1.0 eq ethyl isocyanate |

TABLE 5-continued

| # | Structure | SM | MS | RT | Synthesis Comment |
|---|---|---|---|---|---|
| 5.009 | 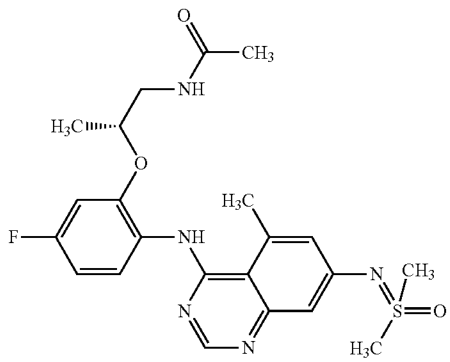 [SMILES: CC(=O)NC[C@@H](C)Oc1cc(F)ccc1Nc1ncnc2cc(N=S(C)(C)=O)cc(C)c12] | 3.018 | 460 | 0.64 min (HPLC-B) | P11 with 1.0 eq. acetyl chloride |
| 5.010 | 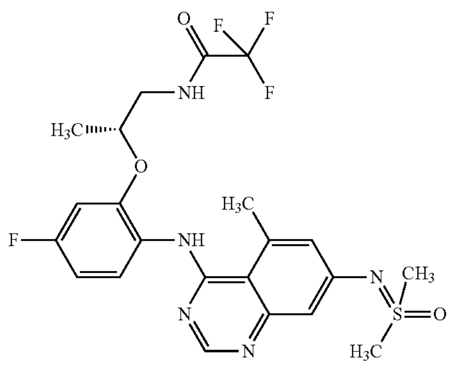 [SMILES: Cc1cc(N=S(C)(C)=O)cc2ncnc(Nc3ccc(F)cc3O[C@H](C)CNC(=O)C(F)(F)F)c12] | 3.018 | 514 | 0.71 min (HPLC-B) | P11 with 1.0 eq. trifluoracetic acid anhydride |
| 5.011 | 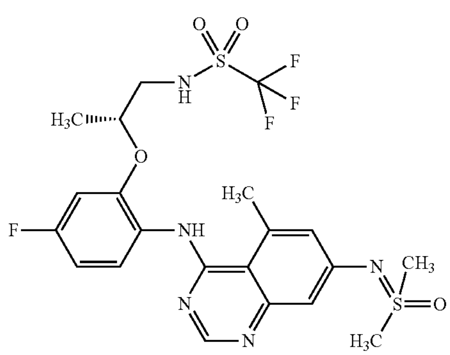 [SMILES: Cc1cc(N=S(C)(C)=O)cc2ncnc(Nc3ccc(F)cc3O[C@H](C)CNS(=O)(=O)C(F)(F)F)c12] | 3.018 | 550 | 0.74 min (HPLC-B) | P11 with 1.0 eq. trifluoro-methanesulfonyl chloride |
| 5.012 | 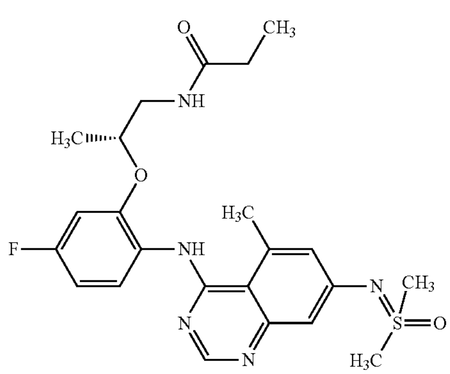 [SMILES: CCC(=O)NC[C@@H](C)Oc1cc(F)ccc1Nc1ncnc2cc(N=S(C)(C)=O)cc(C)c12] | 3.018 | 474 | 0.66 min (HPLC-B) | P11 with 1.0 eq. propionyl chloride |

TABLE 5-continued

| # | Structure | SM | MS | RT | Synthesis Comment |
|---|---|---|---|---|---|
| 5.013 | 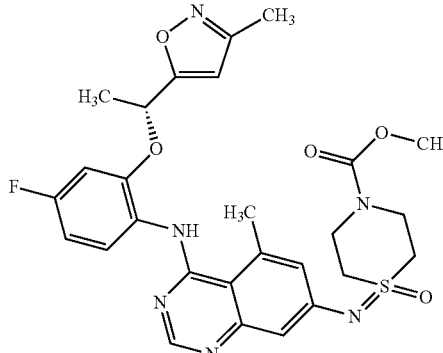 | 2.016 | 569 | 0.74 min (HPLC-B) | P12 with 1.0 eq methyl chloroformate |

General Procedure 13 (P13) for Examples Shown in Table 6:

1 eq of the corresponding aryl fluoride 1.3 eq $Cs_2CO_3$ in a mixture of the respective alcohol and dioxane with the ratio 1:4 is stirred at 120° C. in a pressure vessel for the given time. If necessary, additional $Cs_2CO_3$ and alcohol are added and the reaction is continued at 120° C. for the given time. The reaction mixture is diluted with water and extracted with EtOAc. The organic layers are pooled dried and evaporated. If required, the crude product is further purified by FC or HPLC. Another example for the reaction and work-up is the synthesis of VII.3.

To obtain the following examples (example number given in column #) shown in table 5, the corresponding compounds (example number given in column SM) are transformed according to P13. Details are given in the column synthesis comment, the retention-time and mass (ESI-MS m/z M+H⁺) determined by HPLC-MS are given in the columns MS and RT.

TABLE 6

| # | Structure | SM | MS | RT | Synthesis Comment |
|---|---|---|---|---|---|
| 6.001 | 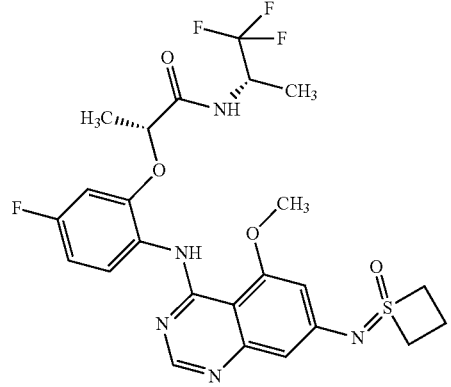 [SMILES: COc1cc(N=S2(=O)CCC2)cc2ncnc(Nc3ccc(F)cc3O[C@H](C)C(=O)N[C@@H](C)C(F)(F)F)c12] | 4.136 | 556 | 0.87 min (HPLC-A) | P13 100° C. with MeOH |
| 6.002 | 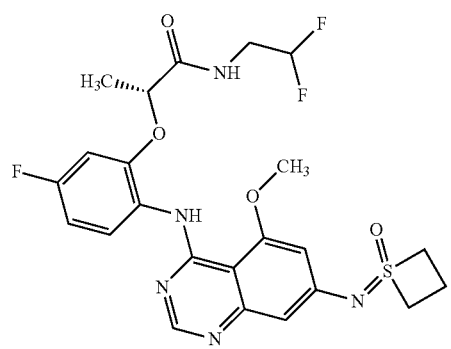 [SMILES: COc1cc(N=S2(=O)CCC2)cc2ncnc(Nc3ccc(F)cc3O[C@H](C)C(=O)NCC(F)F)c12] | 4.123 | 524 | 0.69 min (HPLC-B) | P13 90° C. with MeOH and Dioxane as cosolvent |

TABLE 6-continued

| # | Structure | SM | MS | RT | Synthesis Comment |
|---|---|---|---|---|---|
| 6.003 | 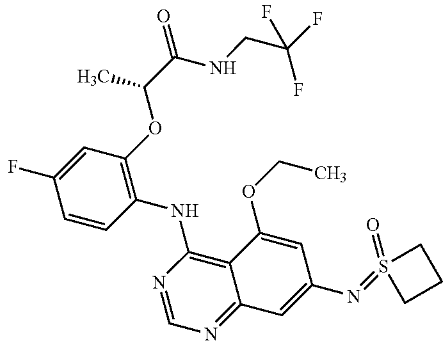 [SMILES: CCOc1cc(N=S2(=O)CCC2)cc2ncnc(Nc3ccc(F)cc3O[C@H](C)C(=O)NCC(F)(F)F)c12] | 4.1 | 556 | 0.86 min (HPLC-B) | P13 90° C. with EtOH and Dioxane as cosolvent |
| 6.004 | 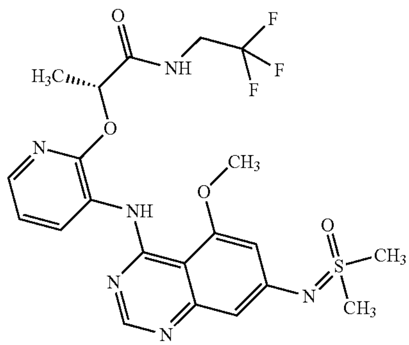 [SMILES: COc1cc(N=S(C)(C)=O)cc2ncnc(Nc3cccnc3O[C@H](C)C(=O)NCC(F)(F)F)c12] | 2.031 | 513 | 0.67 min (HPLC-B) | P13 90° C. with MeOH and Dioxane as cosolvent |

Example 7.005

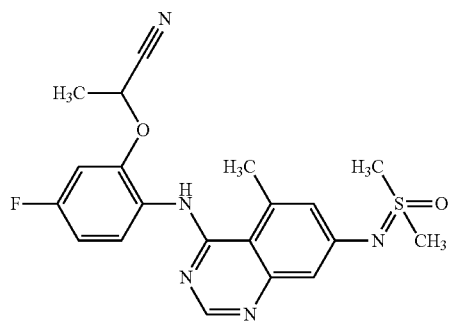 [SMILES: Cc1cc(N=S(C)(C)=O)cc2ncnc(Nc3ccc(F)cc3OC(C)C#N)c12]

Example 7.008

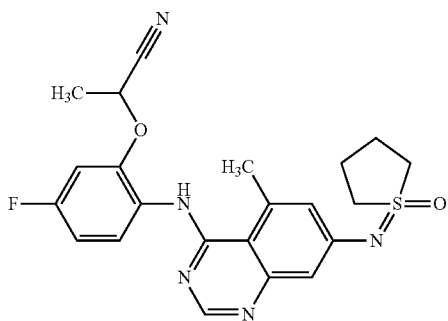 [SMILES: Cc1cc(N=S2(=O)CCCC2)cc2ncnc(Nc3ccc(F)cc3OC(C)C#N)c12]

0.2 g (0.56 mmol) Intermediate V.1, 0.2 g (1.67 mmol) K$_2$CO$_3$ and 0.1 g (0.83 mmol) 2-bromo-propionitrile and a catalytic amount of sodium iodide in dimethylacetamide are stirred at RT for 2 days. The mixture is diluted with brine and extracted with EtOAc. The organic layers are dried and evaporated. The residue is purified by FC.

Yield: 0.2 g (70%), ESI-MS: m/z=414 (M+H)+; R$_f$(HPLC): 0.65 min (HPLC-B)

30.0 mg (0.08 mmol) Intermediate V.2, 70.0 mg (0.21 mmol) Cs$_2$CO$_3$ and 0.01 mL (12.0 mmol) 2-bromo-propionitrile in 1 mL ACN are stirred 60° C. for 2 h. The mixture is diluted with water and extracted with DCM. The organic layer is separated, dried and evaporated. The residue is purified by HPLC.

Yield: 15.4 mg (45%), ESI-MS: m/z=440 (M+H)$^+$; R$_f$(HPLC): 0.50 min (HPLC-K)

Example 7.010 and Example 7.002

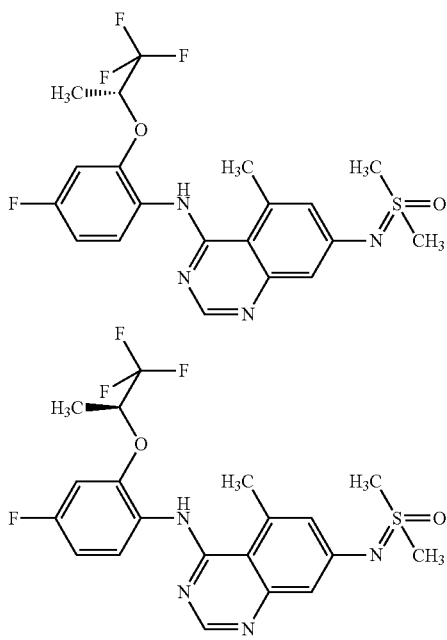

Separation of the enantiomeres obtained in example 15 (0.04 g; 0.08 mmol), the absolute configuration is not determined. HPLC: Agilent 1260 with Aurora A5 Fusion and DA-detector, Chiralcel OZ-H 4.6×250 mm, 5 μm (Daicel), 40° C., 150 bar backpressure, 75% scCO$_2$, 25% MeOH+0.2% DEA, 4 ml/min
Isomer 1, Example 7.010: Yield: 0.01 g (41%), R$_t$(HPLC): 4.07 min
Isomer 2, Example 7.002: Yield: 0.01 g (39%), R$_t$(HPLC): 4.62 min Example 7.006 and Example 7.007

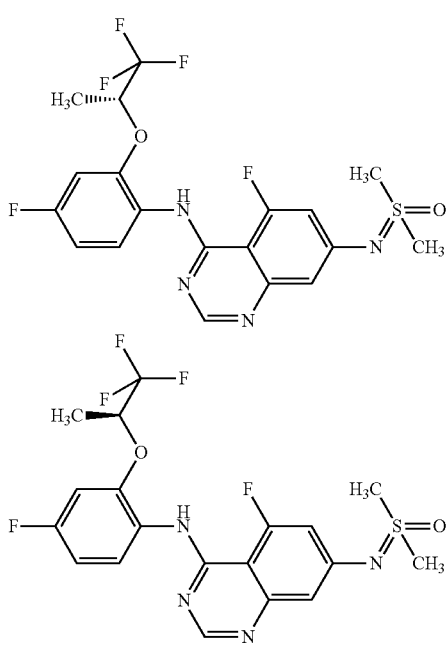

Separation of the enantiomeres obtained in example 13 (0.03 g; 0.07 mmol), the absolute configuration is not determined. HPLC: Agilent 1260 with Aurora A5 Fusion and DA-detector, Chiralpak AS-H 4.6×250 mm, 5 μm (Daicel), 40° C., 150 bar backpressure, 85% scCO$_2$, 15% iPrOH+0.2% DEA, 4 ml/min
Isomer 1, Example 7.006: Yield: 0.01 g (30%), R$_t$(HPLC): 3.94 min
Isomer 2, Example 7.007: Yield: 0.01 g (29%), R$_t$(HPLC): 4.49 min Example 7.004 and Example 7.009

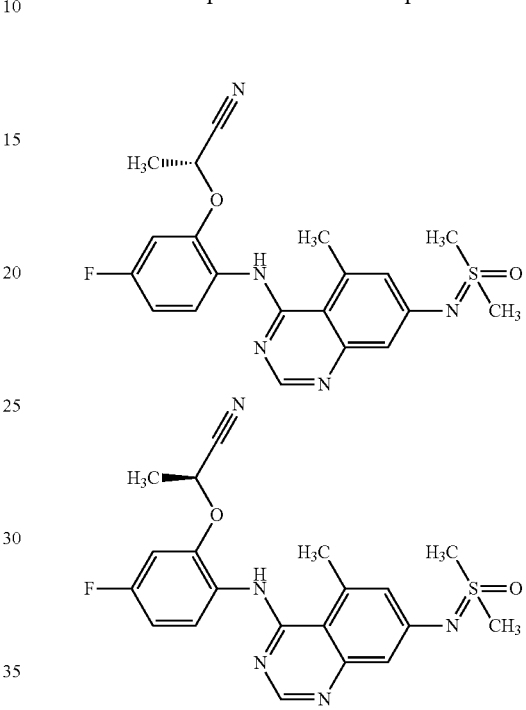

Separation of the enantiomeres obtained in example 175 (0.1 g; 0.31 mmol), the absolute configuration is not determined. HPLC: Agilent 1260 with Aurora A5 Fusion and DA-detector, Chiralcel OZ—H 4.6×250 mm, 5 μm (Daicel), 40° C., 150 bar backpressure, 70% scCO$_2$, 30% MeOH+ 0.2% DEA, 4 ml/min
Isomer 1, Example 7.004: Yield: 0.04 g (31%), R$_t$(HPLC): 4.47 min
Isomer 2, Example 7.009: Yield: 0.03 g (22%), R$_t$(HPLC): 5.14 min Example 7.003

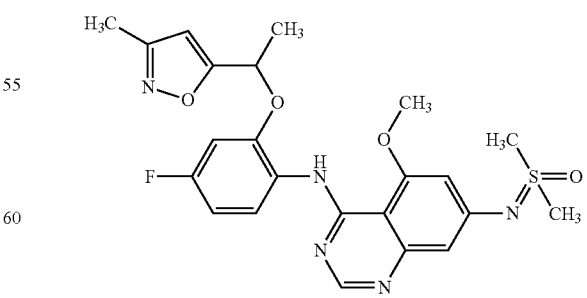

50.0 mg (0.11 mmol) example 21, 40.0 mg (0.13 mmol) Cs$_2$CO$_3$ and 0.11 mL (26.0 mmol) methanol in 1 mL dioxane are stirred in a sealed flask at 120° C. for 3 days. Additional Cs₂CO₃ and MeOH are added and the mixture is stirred at 120° C. over night. The mixture is poured on ice water and extracted with DCM. The aqueous layer is extracted with EtOAc. The combined organic layers are dried and evaporated.

Yield: 17.0 mg (33%), ESI-MS: m/z=486 (M+H)⁺; R_t (HPLC): 1.12 min (HPLC-J)

Example 7.001

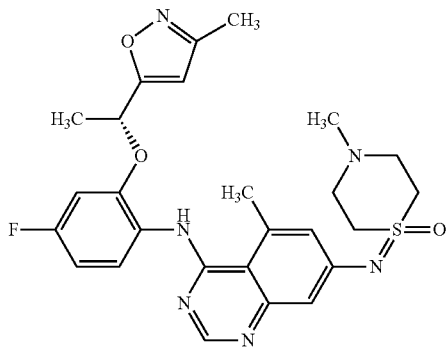 [SMILES: Cc1cc([C@@H](C)Oc2cc(F)ccc2Nc2ncnc3cc(N=S4(=O)CCN(C)CC4)cc(C)c23)on1]

A mixture of 26.6 mg (0.043 mmol) example 34, 7 µl (0.086 mmol) formaldehyde, 3 µl (0.052 mmol) actic acid, 8 µl N,N-Diisopropylethylamine and 28 mg (0.128 mmol) NaBH₄ in 0.5 mL DMF are stirred at RT over night. The reaction mixture is purified by HPLC.

Yield: 12.0 mg (54%), ESI-MS: m/z=525 (M+H)⁺; R_t (HPLC): 0.85 min (HPLC-M)

Example 7.011

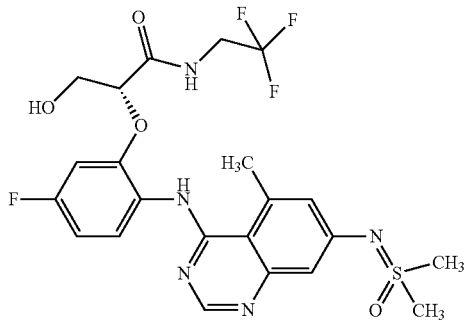 [SMILES: Cc1cc(N=S(C)(C)=O)cc2ncnc(Nc3ccc(F)cc3O[C@H](CO)C(=O)NCC(F)(F)F)c12]

Step 1:
methyl (2R)-3-benzyloxy-2-[2-[(7-bromo-5-methyl-quinazolin-4-yl)amino]-5-fluoro-phenoxy]propanoate was prepared according to P3 from 2-[(7-bromo-5-methyl-quinazolin-4-yl)amino]-5-fluoro-phenol (intermediate V.9 step 1) and (S)-3-Benzyloxy-2-hydroxy-propionic acid methyl ester.

ESI-MS: m/z=540 (M+H)⁺; R_t (HPLC): 1.02 min (HPLC-E)
Step 2:
(2R)-3-benzyloxy-2-[2-[[7-[[dimethyl(oxo)-λ⁶-sulfanylidene]amino]-5-methyl-quinazolin-4-yl]amino]-5-fluoro-phenoxy]propanoic acid was prepared according to P2 (3 h 80° C.) from methyl (2R)-3-benzyloxy-2-[2-[(7-bromo-5-methyl-quinazolin-4-yl)amino]-5-fluoro-phenoxy]propanoate and dimethyl sulfoximine (IV.1).

ESI-MS: m/z=539 (M+H)⁺; R_t (HPLC): 0.89 min (HPLC-E)
Step 3:
(2R)-3-benzyloxy-2-[2-[[7-[[dimethyl(oxo)-λ⁶-sulfanylidene]amino]-5-methyl-quinazolin-4-yl]amino]-5-fluoro-phenoxy]-N-(2,2,2-trifluoroethyl)propanamide was prepared according to P5 from (2R)-3-benzyloxy-2-[2-[[7-[[dimethyl(oxo)-λ⁶-sulfanylidene]amino]-5-methyl-quinazolin-4-yl]amino]-5-fluoro-phenoxy]propanoic acid and 2,2,2-trifluoroethanamine.

ESI-MS: m/z=620 (M+H)⁺; R_t (HPLC): 0.95 min (HPLC-E)
Step 4:
A mixture of 50 mg (0.08 mmol) (2R)-3-benzyloxy-2-[2-[[7-[[dimethyl(oxo)-λ⁶-sulfanylidene]amino]-5-methyl-quinazolin-4-yl]amino]-5-fluoro-phenoxy]-N-(2,2,2-trifluoroethyl)propanamide and DCM was cooled to 5° C. and 0.1 ml (0.08 mmol) 1 mol/l solution of BBr₃ in DCM was added dropwise. The reaction mixture was slowly warmed to RT and stirred over night. Aq. NaHCO₃ solution is added carefully and the solvent evaporated. The crude product is purified via HPLC.

Yield: 27 mg (63%), ESI-MS: m/z=530 (M+H)⁺; R_t (HPLC): 0.81 min (HPLC-E)

Example 7.012

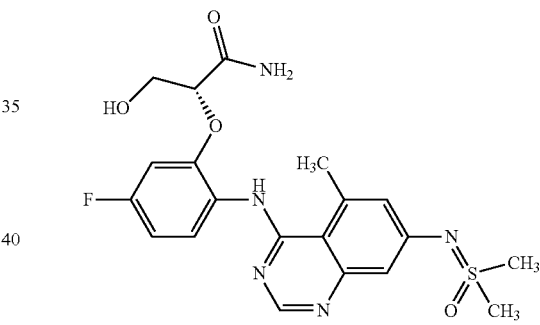

Is prepared in a similar manner as example 7.011 using ammonia instead of 2,2,2-trifluoroethanamine.

ESI-MS: m/z=448 (M+H)⁺; R_t (HPLC): 0.70 min (HPLC-E)

Example 7.013

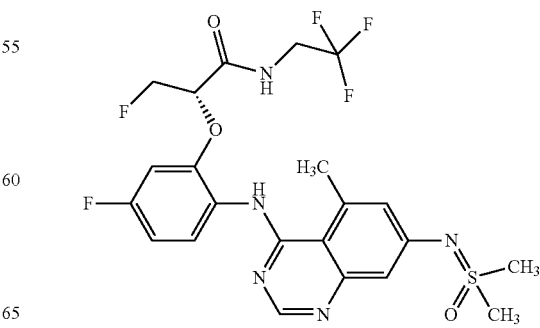

To a mixture of 25 mg (0.05 mmol) of example 7.011 and DCM 11 mg (0.07 mmol) diethylaminosulfur trifluoride is added and the mixture is stirred over night. Aq. NaHCO$_3$ solution is added carefully and the mixture is extracted with DCM. The organic phases are pooled and evaporated. The crude product is purified via HPLC Yield: 13 mg (50%), ESI-MS: m/z=532 (M+H)$^+$; R$_t$ (HPLC): 0.55 min (HPLC-V)

The invention claimed is:

1. A compound of formula I:

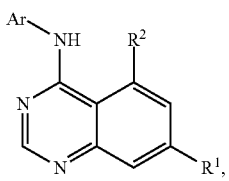

I wherein
Ar is selected from a group consisting of:

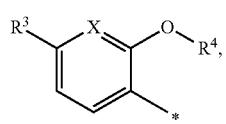

wherein X is N;
R$^3$ is H, halogen, CN or C(=O)—NH$_2$; and
R$^4$ is selected from a group consisting of:

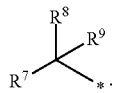

wherein R$^7$ is selected from a group consisting of H, CN, C$_{1-6}$-alkyl, —O—(C$_{1-3}$-alkyl), C$_{2-4}$-alkynyl, C$_{3-7}$-cycloalkyl, heterocyclyl, —(C$_{1-3}$-alkyl)-heterocyclyl, —(C$_{1-3}$-alkyl)-O-heterocyclyl, aryl, —(C$_{1-3}$-alkyl)-aryl, 5- or 6-membered heteroaryl, —(C$_{1-3}$-alkyl)-heteroaryl, —COOH, —(C=O)—O—(C$_{1-6}$-alkyl), —(C=O)—N=S(=O)(C$_{1-3}$-alkyl)$_2$ and —(C=O)—NR$^{N1}$R$^{N2}$;
wherein R$^{N1}$ is H or C$_{1-3}$-alkyl; and
R$^{N2}$ is selected from a group consisting of H, C$_{1-6}$-alkyl, C$_{2-5}$-alkynyl, C$_{3-7}$-cycloalkyl, heterocyclyl, —(C$_{1-3}$-alkyl)-heterocyclyl, —(C$_{1-3}$-alkyl)-aryl and —SO$_2$—(C$_{1-3}$-alkyl);
or R$^{N1}$ and R$^{N2}$ together with the N-atom to which they are attached form a azetidinyl, pyrrolidinyl, piperidinyl, 4-oxo-piperidinyl, piperazinyl, morpholinyl, thiomorpholinyl, 1-oxo-thiomorpholinyl, 1,1-dioxo-thiomorpholinyl or 1-imino-1,4-thiazinane-1-oxide ring, which may be substituted with one OH, C$_{1-3}$-alkyl or —O—C$_{1-3}$-alkyl; and
wherein in R$^4$, each heterocyclyl is selected from a group consisting of 4-, 5- or 6-membered saturated monocyclic ring systems containing 1, 2 or 3 heteroatoms independently of each other selected from the group consisting on O, S, N and NH, wherein one —CH$_2$— group may be replaced by a —C(=O)— group and wherein each heterocyclyl group is optionally substituted with C$_{1-3}$-alkyl;
wherein in R$^4$, each aryl is phenyl or naphthyl;
wherein in R$^4$, each heteroaryl is selected from a group consisting of 5- or 6-membered monocyclic heteroaromatic ring systems containing 1, 2 or 3 heteroatoms independently of each other selected from the group consisting of O, S, N and NH and is optionally substituted with $C_{1-3}$-alkyl;

wherein in $R^4$, each alkyl is optionally substituted with 1 or more F or with one or two substituents independently selected from the group consisting of CN, OH, —O—($C_{1-3}$-alkyl), —O-tetrahydrofuranyl, $NH_2$, —NH—(C=O)—($C_{1-3}$-alkyl), —NH—(C=O)—NH—($C_{1-3}$-alkyl) or —NH—$SO_2$—($C_{1-3}$-alkyl); and wherein in $R^4$, each cycloalkyl is optionally substituted with 1 or more F or one CN, OH, $CF_3$, —O—($C_{1-3}$-alkyl) or =O; and $R^8$ and $R^9$ are independently of each other selected from the group consisting of:

H and $C_{1-3}$-alkyl optionally substituted with 1-3 F or one OH or $NH_2$;

$R^1$ is selected from a group consisting of:

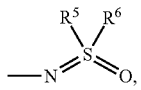

wherein $R^5$ is selected from the group consisting of:
a) $C_{1-3}$-alkyl, which is optionally substituted with a substituent selected from the group consisting of —O—($C_{1-3}$-alkyl), —O—$C_{3-7}$-cycloalkyl, —O-heterocyclyl, $C_{3-7}$-cycloalkyl, heterocyclyl and phenyl, wherein each alkyl group is optionally substituted with one or more F; and
b) $C_{2-3}$-alkenyl, $C_{2-3}$-alkynyl, $C_{3-7}$-cycloalkyl, heterocyclyl, heteroaryl, and aryl; wherein in $R^5$ heteroaryl is a mono- or bicyclic ring system containing 1, 2, 3 or 4 heteroatoms selected from N, O or S(O)$_r$ with r=0, 1 or 2 wherein at least one of the heteroatoms is part of an aromatic ring, and wherein said ring system may have a carbonyl group, where each heterocyclyl is a saturated or unsaturated mono-, bi-, tri- or spirocarbocyclic ring system containing one or more heteroatoms selected from N, O or S(O)$_r$ with r=0, 1 or 2, which in addition may have a carbonyl group and where aryl is a carbocyclic aromatic monocyclic group containing 6 carbon atoms which may be further fused to a second 5- or 6-membered carbocyclic group which may be aromatic, saturated or unsaturated and $R^6$ is $C_{1-3}$-alkyl which is optionally substituted with one or more F, or wherein $R^5$ and $R^6$ together with the sulfur atom to which they are attached form a 4 to 7-membered saturated or partly unsaturated heterocycle that further to the sulfur atom may contain one additional heteroatom selected from the group consisting of O, S and $NR^N$, wherein $R^N$ is H, $C_{1-3}$alkyl, —C(=O)—($C_{1-3}$-alkyl), —C(=O)—O—($C_{1-4}$-alkyl), —C(=O)—($C_{1-3}$-alkyl)-O—($C_{1-4}$-alkyl), —C(=O)—$NH_2$, —C(=O)—NH($C_{1-3}$-alkyl), —C(=O)—N($C_{1-3}$-alkyl)$_2$ or —$SO_2$($C_{1-4}$-alkyl);

and wherein $R^5$, $R^6$ and the heterocycles formed by $R^5$ and $R^6$ together with the sulfur atom to which they are attached may each be independently substituted with halogen, CN, OH, $NH_2$, —NH($C_{1-4}$-alkyl), —N($C_{1-4}$-alkyl)$_2$, —NH—C(=O)—($C_{1-4}$-alkyl), —NH—C(=O)—O—($C_{1-4}$-alkyl), —NH—C(=O)—$NH_2$, —NH—C(=O)—NH—($C_{1-4}$-alkyl), —NH—C(=O)—N($C_{1-4}$-alkyl)$_2$, —N($C_{1-4}$-alkyl)-C(=O)—($C_{1-4}$-alkyl), —N($C_{1-4}$-alkyl)-C(=O)—O—($C_{1-4}$-alkyl), —N($C_{1-4}$-alkyl)-C(=O)—$NH_2$, —N($C_{1-4}$-alkyl)-C(=O)—NH—($C_{1-4}$-alkyl), —N($C_{1-4}$-alkyl)-C(=O)—N($C_{1-4}$-alkyl)$_2$, —O—($C_{1-4}$-alkyl), $C_{1-6}$-alkyl, $C_{3-7}$-cycloalkyl, heterocylcyl, where heterocyclyl refers to a saturated or unsaturated mono-, bi-, tri- or spirocarbocyclic ring system containing one or more heteroatoms selected from N, O or S(O)$_r$ with r=0, 1 or 2, which in addition may have a carbonyl group, heteroaryl, where heteroaryl refers to a mono- or bicyclic ring system containing 1, 2, 3 or 4 heteroatoms selected from N, O or S(O)$_r$ with r=0, 1 or 2 wherein at least one of the heteroatoms is part of an aromatic ring, and wherein said ring system may have a carbonyl group, —C(=O)—$NH_2$, —C(=O)—NH($C_{1-4}$-alkyl), —C(=O)—N($C_{1-4}$-alkyl)$_2$, —COOH, —C(=O)—O—($C_{1-4}$-alkyl), —($C_{1-4}$-alkyl)-NH—C(=O)—($C_{1-4}$-alkyl); —SO—($C_{1-4}$-alkyl) or —$SO_2$—($C_{1-4}$-alkyl); and $R^2$ is selected from a group consisting of halogen, CN, OH, $NH_2$, $C_{1-3}$-alkyl, $C_{2-3}$-alkenyl, $C_{2-3}$-alkynyl, $C_{3-5}$-cycloalkyl, —O-cyclopropyl and —S—$C_{1-3}$-alkyl, wherein each alkyl group is optionally substituted with one or more F; and wherein, if not otherwise specified, each alkyl group in the above definitions is linear or branched and may be substituted with one to three F;

or a stereoisomer or salt thereof.

2. The compound according to claim 1, wherein $R^1$ is selected from a group consisting of:

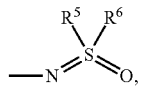

wherein $R^5$ is selected from the group consisting of:
a) $C_{1-3}$-alkyl, which is optionally substituted with —O—($C_{1-3}$-alkyl), —O—$C_{3-7}$-cycloalkyl, $C_{3-7}$-cycloalkyl, or phenyl,
  wherein each alkyl group is optionally substituted with one or more F; and
b) $C_{3-7}$-cycloalkyl, pyridinyl, and phenyl; and $R^6$ is $C_{1-3}$-alkyl which is optionally substituted with one or more F;

or wherein $R^5$ and $R^6$ together with the sulfur atom to which they are attached form a 4- to 7-membered saturated or partly unsaturated heterocycle that further to the sulfur atom may contain one additional heteroatom selected from the group consisting of O, S and $NR^N$, wherein $R^N$ is H, $C_{1-3}$alkyl, —C(=O)—($C_{1-3}$-alkyl), —C(=O)—O—($C_{1-4}$-alkyl), —C(=O)—($C_{1-3}$-alkyl)-O—($C_{1-4}$-alkyl), —C(=O)—$NH_2$, —C(=O)—NH($C_{1-3}$-alkyl), —C(=O)—N($C_{1-3}$-alkyl)$_2$ or —$SO_2$($C_{1-4}$-alkyl);

or a salt thereof.

3. The compound according to claim 1, wherein $R^2$ is selected from a group consisting of F, Cl, Br, $CH_3$, $CF_3$, cyclopropyl and —O—$CH_3$, or a salt thereof.

4. The compound according to claim 1, wherein Ar is selected from a group consisting of:

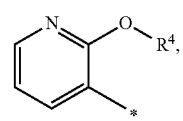

or a salt thereof.

5. The compound according to claim 1, wherein $R^4$ is selected from a group consisting of:

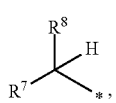

wherein $R^7$ is selected from a group consisting of CN, $C_{1-6}$-alkyl, —O—($C_{1-3}$-alkyl), $C_{2-4}$-alkynyl, $C_{3-7}$-cycloalkyl, heterocyclyl, —($C_{1-3}$-alkyl)-heterocyclyl, —($C_{1-3}$-alkyl)-O-heterocyclyl, aryl, —($C_{1-3}$-alkyl)-aryl, 5- or 6-membered heteroaryl, —($C_{1-3}$-alkyl)-heteroaryl, —COOH, —(C=O)—O—($C_{1-6}$-alkyl), —(C=O)—N=S(=O)($C_{1-3}$-alkyl)$_2$ and —(C=O)—$NR^{N1}R^{N2}$;
wherein $R^{N1}$ is H or $C_{1-3}$-alkyl; and
$R^{N2}$ is selected from a group consisting of H, $C_{1-6}$-alkyl, $C_{2-5}$-alkynyl, $C_{3-7}$-cycloalkyl, heterocyclyl, —($C_{1-3}$-alkyl)-heterocyclyl, —($C_{1-3}$-alkyl)-aryl, —SO$_2$—($C_{1-3}$-alkyl);
or $R^{N1}$ and $R^{N2}$ together with the N-atom to which they are attached form a azetidinyl, pyrrolidinyl, piperidinyl, 4-oxo-piperidinyl, piperazinyl, morpholinyl, thiomorpholinyl or 1-oxo-thiomorpholinyl ring, which may be substituted with one OH, $C_{1-3}$-alkyl or —O—$C_{1-3}$-alkyl; and
wherein in the definition of $R^4$, each heterocyclyl is selected from a group consisting of 2-oxo-pyrrolidinyl, 2-oxo-piperidinyl, 2-oxo-oxazolidinyl, oxetanyl, tetrahydrofuranyl, tetrahydropyranyl and [1,4]-dioxanyl and is optionally substituted with $C_{1-3}$-alkyl;
wherein in the definition of $R^4$, each aryl is phenyl;
wherein in the definition of $R^4$, each heteroaryl is selected from a group consisting of pyrazolyl, imidazolyl, oxazolyl, isoxazolyl, oxadiazolyl, thiazolyl, thiadiazolyl, pyridinyl, pyrimidinyl, pyrazinyl and pyridazinyl and is optionally substituted with $C_{1-3}$-alkyl;
wherein in the definition of $R^4$, each alkyl is optionally substituted with 1-3 F or with one or two substituents independently selected from the group consisting of CN, OH, —O—($C_{1-3}$-alkyl), —O-tetrahydrofuranyl, NH$_2$, —NH—(C=O)—($C_{1-3}$-alkyl), —NH—(C=O)—NH—($C_{1-3}$-alkyl) or —NH—SO$_2$—($C_{1-3}$-alkyl); and
wherein in the definition of $R^4$, each cycloalkyl is optionally substituted with 1-3 F or one CN, OH, CF$_3$ or =O; and
$R^8$ is selected from the group consisting of H and $C_{1-3}$-alkyl optionally substituted with 1-3 F or one OH or NH$_2$;
or a salt thereof.

6. The compound according to claim 1, wherein
Ar is selected from a group consisting of:

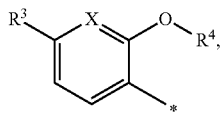

wherein X is N;
$R^3$ is H, F, Cl, Br, CN or —C(=O)—NH$_2$; and $R^4$ is selected from a group consisting of:

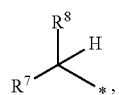

wherein $R^7$ is selected from a group consisting of CN, $C_{1-6}$ alkyl, $C_{3-7}$-cycloalkyl heterocyclyl, phenyl, 5- or 6-membered heteroaryl, —(C=O)—N=S(=O)($C_{1-3}$-alkyl)$_2$ and —(C=O)—$NR^{N1}R^{N2}$;
wherein $R^{N1}$ is H or $C_{1-3}$-alkyl; and
$R^{N2}$ is selected from a group consisting of H, $C_{1-6}$-alkyl, $C_{2-5}$-alkynyl, $C_{3-7}$-cycloalkyl, heterocyclyl, —($C_{1-3}$-alkyl)-heterocyclyl, —($C_{1-3}$-alkyl)-phenyl, —SO$_2$—($C_{1-3}$-alkyl);
or $R^{N1}$ and $R^{N2}$ together with the N-atom to which they are attached form a azetidinyl, pyrrolidinyl, piperidinyl, 4-oxo-piperidinyl, piperazinyl, morpholinyl, thiomorpholinyl or 1-oxo-thiomorpholinyl ring, which may be substituted with one OH, $C_{1-3}$-alkyl or —O—$C_{1-3}$-alkyl; and
wherein in the definition of $R^4$, each heterocyclyl is selected from a group consisting of 2-oxo-pyrrolidinyl, 2-oxo-piperidinyl, 2-oxo-oxazolidinyl, oxetanyl, tetrahydrofuranyl, tetrahydropyranyl and [1,4]-dioxanyl and is optionally substituted with $C_{1-3}$-alkyl;
wherein in the definition of $R^4$, each heteroaryl is selected from a group consisting of pyrazolyl, imidazolyl, oxazolyl, isoxazolyl, oxadiazolyl, thiazolyl, thiadiazolyl, pyridinyl, pyrimidinyl, pyrazinyl and pyridazinyl and is optionally substituted with $C_{1-3}$-alkyl;
wherein in the definition of $R^4$, each alkyl is optionally substituted with 1-3 F or with one or two substituents independently selected from the group consisting of CN, OH, —O—($C_{1-3}$-alkyl), —O-tetrahydrofuranyl, NH$_2$, —NH—(C=O)—($C_{1-3}$-alkyl), —NH—(C=O)—NH—($C_{1-3}$-alkyl) or —NH—SO$_2$—($C_{1-3}$-alkyl); and
wherein in the definition of $R^4$, each cycloalkyl is optionally substituted with 1-3 F or one CN, OH, CF$_3$ or =O; and
$R^8$ is selected from a group consisting of H, CH$_3$, CH$_2$F, CF$_3$ and CH$_2$CH$_3$;
$R^1$ is selected from a group consisting of:

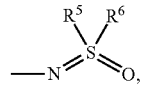

wherein $R^5$ is methyl or ethyl; and
$R^6$ is methyl or ethyl;
or wherein $R^5$ and $R^6$ together with the sulfur atom to which they are attached form a 5- or 6-membered saturated heterocycle that in addition to the sulfur atom may contain one additional heteroatom selected from the group consisting of O and —$NR^N$—,
wherein $R^N$ is H, CH$_3$, —C(=O)—CH$_3$, —C(=O)—OCH$_3$, —C(=O)—CH$_2$—OCH$_3$ or —C(=O)—NH—CH$_2$CH$_3$; and
$R^2$ is selected from a group consisting of F, Cl, Br, CH$_3$, CF$_3$, cyclopropyl and —O—CH$_3$;
and the pharmaceutically acceptable salts thereof.

7. A pharmaceutically acceptable salt of a compound according to claim 1.

8. A pharmaceutical composition comprising a compound according to claim 1 or a pharmaceutically acceptable salt thereof and optionally a pharmaceutically acceptable carrier.

9. The pharmaceutical composition according to claim 8 further comprising an additional therapeutic agent.

10. The pharmaceutical composition according to claim 9 wherein the additional therapeutic agent is selected from an antidiabetic agent, a lipid lowering agent, a cardiovascular agent, an antihypertensive agent, a diuretic agent, a thrombocyte aggregation inhibitor, an antineoplastic agent or an anti-obesity agent.

* * * * *